(12) United States Patent
Ding et al.

(10) Patent No.: US 12,302,753 B2
(45) Date of Patent: May 13, 2025

(54) ORGANIC ELECTROLUMINESCENT MATERIALS AND DEVICES

(71) Applicant: BEIJING SUMMER SPROUT TECHNOLOGY CO., LTD., Beijing (CN)

(72) Inventors: Hualong Ding, Beijing (CN); Chi Yuen Raymond Kwong, Beijing (CN); Chuanjun Xia, Beijing (CN)

(73) Assignee: BEIJING SUMMER SPROUT TECHNOLOGY CO., LTD., Beijing (CN)

( * ) Notice: Subject to any disclaimer, the term of this patent is extended or adjusted under 35 U.S.C. 154(b) by 788 days.

(21) Appl. No.: 17/577,924

(22) Filed: Jan. 18, 2022

(65) Prior Publication Data
US 2022/0140252 A1    May 5, 2022

Related U.S. Application Data

(63) Continuation-in-part of application No. 17/378,429, filed on Jul. 16, 2021.

(30) Foreign Application Priority Data

Jul. 20, 2020  (CN) .......................... 202010698126.6
Jun. 30, 2021  (CN) .......................... 202110716169.7

(51) Int. Cl.
H01L 51/50    (2006.01)
C07D 413/14    (2006.01)
(Continued)

(52) U.S. Cl.
CPC ......... H10K 85/656 (2023.02); C07D 413/14 (2013.01); C09K 11/06 (2013.01);
(Continued)

(58) Field of Classification Search
None
See application file for complete search history.

(56) References Cited

U.S. PATENT DOCUMENTS 5,703,436 A    12/1997  Forrest et al.
5,707,745 A     1/1998  Forrest et al.
(Continued)

FOREIGN PATENT DOCUMENTS

CN    105176519 A    12/2015
CN    107629034 A     1/2018
(Continued)

OTHER PUBLICATIONS

Al-Ahmad et al., "New Family of Redox-Active Heterocycles," J. Amer. Chem. Soc. 117(3), pp. 1145-1146, DOI:10.1021/ja00108a038 (1995).
(Continued)

*Primary Examiner* — Gregory D Clark
(74) *Attorney, Agent, or Firm* — ArentFox Schiff LLP; Joseph M. Maraia; Marlo Schepper Grolnic

(57) ABSTRACT

Disclosed are a novel organic electroluminescent material and a device thereof. The organic electroluminescent material is a novel compound having the structure in Formula 1. The organic electroluminescent material has LUMO energy levels of different depths, can be used as a single hole injection material, and is also an excellent p-type dopant material, which is of great significance for the development of new high-performance hole injection materials. Also disclosed are an organic electroluminescent device comprising the novel compound and a compound composition comprising the novel compound.

22 Claims, 2 Drawing Sheets

(51) Int. Cl.
   *C09K 11/06*   (2006.01)
   *H10K 85/60*   (2023.01)
   *H10K 50/15*   (2023.01)
   *H10K 50/17*   (2023.01)
   *H10K 50/19*   (2023.01)

(52) U.S. Cl.
   CPC .... *H10K 85/653* (2023.02); *C09K 2211/1018* (2013.01); *H10K 50/15* (2023.02); *H10K 50/17* (2023.02); *H10K 50/19* (2023.02)

(56) References Cited

U.S. PATENT DOCUMENTS

| | | | |
|---|---|---|---|
| 5,844,363 | A | 12/1998 | Gu et al. |
| 6,097,147 | A | 8/2000 | Baldo et al. |
| 6,303,238 | B1 | 10/2001 | Thompson et al. |
| 7,279,704 | B2 | 10/2007 | Walters et al. |
| 7,968,146 | B2 | 6/2011 | Wagner et al. |
| 2003/0230980 | A1 | 12/2003 | Forrest et al. |
| 2004/0174116 | A1 | 9/2004 | Lu et al. |
| 2015/0349273 | A1 | 12/2015 | Hung et al. |
| 2016/0359122 | A1 | 12/2016 | Boudreault et al. |
| 2017/0012215 | A1 | 1/2017 | Miyashita et al. |
| 2019/0181349 | A1 | 6/2019 | Xia |
| 2020/0062778 | A1 | 2/2020 | Cui et al. |
| 2021/0167298 | A1 | 6/2021 | Pang et al. |
| 2022/0020935 | A1 | 1/2022 | Ding et al. |

FOREIGN PATENT DOCUMENTS

| | | | | |
|---|---|---|---|---|
| JP | H0338578 | A | | 2/1991 |
| JP | 2005-123033 | | * 5/2005 | ............. H01L 31/04 |
| JP | 2008169125 | A | | 7/2008 |
| JP | 2021070681 | A | | 5/2021 |
| KR | 1020170003472 | A | | 1/2017 |
| KR | 1020170079357 | A | | 7/2017 |
| KR | 1020230010023 | A | | 1/2023 |
| WO | 2016124694 | A1 | | 8/2016 |

OTHER PUBLICATIONS

Notice of Second Review Opinion in CN Application No. 202110716169.7 dated Jul. 6, 2023, with English translation, 8 pages.
Written Decision on Registration in KR Application No. 10-2021-0094718 dated Aug. 22, 2023, with English translation, 6 pages.
Albert et al., "Rational Design of Molecules with Large Hyperpolarizabilities. Electric Field, Solvent Polarity, and Bond Length Alternation Effects on Merocyanine Dye Linear and Nonlinear Optical Properties," J. Phys. Chem. 100, pp. 9714-9725 (1996).
English translation and German language version of Office Action in DE Application No. 10 2021 118 596.3, dated Apr. 28, 2022 (14 pps.).
Ishida et al., "Novel Electron Acceptors Bearing a Heteroquinonoid System III: 2,5-Bis(dicyanomethylene)-2,5-dihydrofuran and Its Conjugated Homologues as Novel Oxygen-Containing Electron Acceptors," Bull. Chem. Soc. Jpn. 63(10), pp. 2828-2835 (1990).
Khodair et al., "A new approach to the synthesis of substituted 4-imidazolidinones as potential antiviral and antitumor agents," Tetrahedron 54(19), pp. 4859-4872 (1998).
Koyioni et al., "Synthesis of 5,5'-Diaryliminio Quinoidal 2,2'-Bithiazoles," Org. Lett. 19, pp. 174-177, DOI:10.1021/acs.orglett. 6b03474 (2017).
Machine Translation and German-language version of Wikipedia entry "Nucleophilia," dated Apr. 9, 2020 (8 pps.).
Nandi et al., "Theoretical study of static second-order nonlinear optical properties of push-pull heteroquinonoid dimers," J. Mol. Structure: THEOCHEM 760, pp. 235-244 (2006).
Suzuki, K. et al., "Synthesis and characterization of novel strong electron acceptors: bithiazole analogues of tetracyanodiphenoquinodimethane (TCNDQ)," Tetrahedron Letters 41, pp. 8359-8364 (2000).
Tang et al., "Organic electroluminescent diodes," Appl. Phys. Lett. 51(12), pp. 913-915 (1987).
Turkevich et al., "[Synthesis of an] Asymmetric Thiazolidine-2,4-dione azine," Khimiya ta Biologiya 32(6), 7 pps. (1970).
Uoyama et al., "Highly efficient organic light-emitting diodes from delayed fluorescence," Nature 492, pp. 234-240 (Dec. 2012).
Wang et al., "Conjugated electron donor-acceptor molecules with (E)-[4,40-biimidazolylidene]-5,50(1H, 10H)-dione for new organic semiconductors," J. Mater. Chem. C. 2, pp. 1149-1157 (2014).
Wang et al., "New alternating electron donor-acceptor conjugated polymers entailing (E)-[4,40-biimidazolylidene]-5,50(1H, 10H)-dione moieties," Polym. Chem. vol. 4, iss. 20, pp. 5283-5290, DOI:10.1039/C3PY00129F (2013).
English translation of Office Action in JP Application No. 2021-119068, dated Sep. 2, 2022 (6 pgs.).
Kaepplinger et al., "Barton-Kellogg Olefination of Conjugated Dithioxo Compounds," Sulfur Letters, vol. 26, pp. 141-147, 2003.
Office Action dated Dec. 23, 2022, for related CN Application No. 202110716169.7 (24 Pages).
Office Action dated Feb. 3, 2023, for related JP Application No. 2021-119068 (12 Pages).
Office Action dated Apr. 3, 2023, for related KR Application No. 10-2021-0094718 (16 Pages).
RN 115606-23-0, Registry, STN Columbus (2 Pages).
RN 116153-37-8, Registry, STN Columbus (3 Pages).

* cited by examiner

ORGANIC ELECTROLUMINESCENT MATERIALS AND DEVICES

CROSS-REFERENCE TO RELATED APPLICATION(S)

This application is a Continuation-in-Part of U.S. application Ser. No. 17/378,429, filed on Jul. 16, 2021, which claims priority to Chinese Patent Application No. CN202010698126.6 filed on Jul. 20, 2020 and Chinese Patent Application No. CN202110716169.7 filed on Jun. 30, 2021, and the entirety of each of which is incorporated herein by reference.

TECHNICAL FIELD

The present disclosure relates to a novel compound and an organic electroluminescent device thereof. More particularly, the present disclosure relates to a novel compound having a structure of Formula 1, an electroluminescent device containing the compound, and a compound composition containing the compound.

BACKGROUND

Organic electronic devices include, but are not limited to, the following types: organic light-emitting diodes (OLEDs), organic field-effect transistors (O-FETs), organic light-emitting transistors (OLETs), organic photovoltaic devices (OPVs), dye-sensitized solar cells (DSSCs), organic optical detectors, organic photoreceptors, organic field-quench devices (OFQDs), light-emitting electrochemical cells (LECs), organic laser diodes and organic plasmon emitting devices.

In 1987, Tang and Van Slyke of Eastman Kodak reported a bilayer organic electroluminescent device, which comprises an arylamine hole transporting layer and a tris-8-hydroxyquinolato-aluminum layer as the electron and emitting layer (Applied Physics Letters, 1987, 51 (12): 913-915). Once a bias is applied to the device, green light was emitted from the device. This device laid the foundation for the development of modern organic light-emitting diodes (OLEDs). State-of-the-art OLEDs may comprise multiple layers such as charge injection and transporting layers, charge and exciton blocking layers, and one or multiple emissive layers between the cathode and anode. Since the OLED is a self-emitting solid state device, it offers tremendous potential for display and lighting applications. In addition, the inherent properties of organic materials, such as their flexibility, may make them well suited for particular applications such as fabrication on flexible substrates.

The OLED can be categorized as three different types according to its emitting mechanism. The OLED invented by Tang and van Slyke is a fluorescent OLED. It only utilizes singlet emission. The triplets generated in the device are wasted through nonradiative decay channels. Therefore, the internal quantum efficiency (IQE) of the fluorescent OLED is only 25%. This limitation hindered the commercialization of OLED. In 1997, Forrest and Thompson reported phosphorescent OLED, which uses triplet emission from heavy metal containing complexes as the emitter. As a result, both singlet and triplets can be harvested, achieving 100% IQE. The discovery and development of phosphorescent OLED contributed directly to the commercialization of active-matrix OLED (AMOLED) due to its high efficiency. Recently, Adachi achieved high efficiency through thermally activated delayed fluorescence (TADF) of organic compounds. These emitters have small singlet-triplet gap that makes the transition from triplet back to singlet possible. In the TADF device, the triplet excitons can go through reverse intersystem crossing to generate singlet excitons, resulting in high IQE.

OLEDs can also be classified as small molecule and polymer OLEDs according to the forms of the materials used. A small molecule refers to any organic or organometallic material that is not a polymer. The molecular weight of the small molecule can be large as long as it has well defined structure. Dendrimers with well-defined structures are considered as small molecules. Polymer OLEDs include conjugated polymers and non-conjugated polymers with pendant emitting groups. Small molecule OLED can become the polymer OLED if post polymerization occurred during the fabrication process.

There are various methods for OLED fabrication. Small molecule OLEDs are generally fabricated by vacuum thermal evaporation. Polymer OLEDs are fabricated by solution process such as spin-coating, inkjet printing, and slit printing. If the material can be dissolved or dispersed in a solvent, the small molecule OLED can also be produced by solution process.

The emitting color of the OLED can be achieved by emitter structural design. An OLED may comprise one emitting layer or a plurality of emitting layers to achieve desired spectrum. In the case of green, yellow, and red OLEDs, phosphorescent emitters have successfully reached commercialization. Blue phosphorescent device still suffers from non-saturated blue color, short device lifetime, and high operating voltage. Commercial full-color OLED displays normally adopt a hybrid strategy, using fluorescent blue and phosphorescent yellow, or red and green. At present, efficiency roll-off of phosphorescent OLEDs at high brightness remains a problem. In addition, it is desirable to have more saturated emitting color, higher efficiency, and longer device lifetime.

Organic electroluminescent devices convert electrical energy into light by applying voltage across the device. Generally, an organic electroluminescent device includes an anode, a cathode, and organic layer between the anode and the cathode. The organic layer of an electroluminescent device includes a hole injection layer, a hole transporting layer, an electron blocking layer, a light-emitting layer (including host materials and dopant materials), an electron buffer layer, a hole blocking layer, an electron transport layer, and an electron injection layer etc. According to different function of the materials, the materials that consist of the organic layer can be divided into hole injection materials, hole transporting materials, electron blocking materials, host materials, luminescent materials, electron buffer materials, hole blocking materials, electron transporting materials, and electron injection materials, etc. When a bias is applied to the device, holes are injected from the anode to the light-emitting layer, and electrons are injected from the cathode to the light-emitting layer. The holes and electrons meet each other to form excitons, and the excitons recombine and emit light. Among them, the hole injection layer is one of the important functional layers that affect the performance of the organic electroluminescent device. The selection and matching of materials can have an important impact on the performance of the organic electroluminescent device, such as driving voltage, efficiency, and lifetime. Commercially, it is expected to obtain organic electroluminescent devices with low driving voltage, high efficiency, long lifetime and other characteristics. Therefore, it is very critical to develop a novel hole injection layer.

Currently, the hole injection layer is generally composed of a single material or multiple materials. The single material is generally a material with a deep LUMO, such as HATCN. The multiple materials refer to doping a p-type, deep-LUMO material with a hole transporting material. This mode can generate migrated holes (free carriers) by doping matrix materials (generally hole transporting materials) with a dopant, and can improve the hole injection ability of the anode and change the Fermi level of the device. Because the LUMO of HATCN is not deep enough, it cannot be used as a p-type dopant. The deep-LUMO material is generally a conjugated system compound with one or more strong electron-withdrawing substituents, the use of deep LUMO material doped in the hole injection layer formed by the hole transport material can increase the hole mobility of the hole injection layer, reduce the voltage of the organic electroluminescent device, and thereby improve the efficiency and lifetime of the device. It is difficult to synthesize the deep-LUMO material because the material has strong electron-withdrawing substituents, and meanwhile, it is difficult for the deep-LUMO material to have properties of deep LUMO, high stability, and high film formation together. For example, F4-TCNQ (a p-type hole injection material) has a deep LUMO, but its evaporation temperature is too low, which affects the deposition control, the reproducibility of production performance, and the thermal stability of devices.

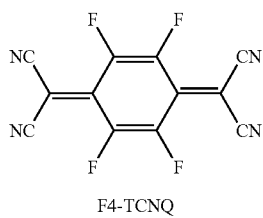

F4-TCNQ

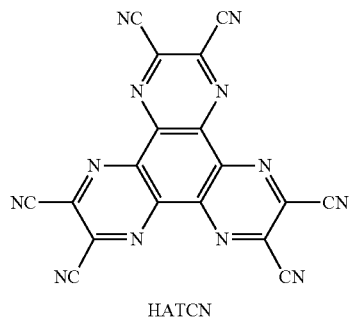

HATCN

CN105176519 discloses a radialene compound containing a structure of thiazole, wherein the general structure formula of the compound is

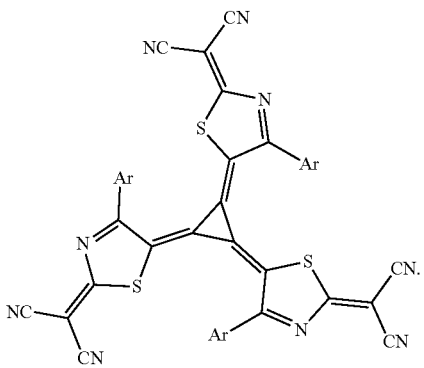

This application is concerned with the properties of compounds having the radialene structure but does not disclose or teach the properties and applications of any compound having a parent core structure similar to the parent core structure of the present application.

JPH0338578 discloses a class of compounds containing structures of bifuran, bithiophene, and the like as electron acceptors, it contains the following general structural formula:

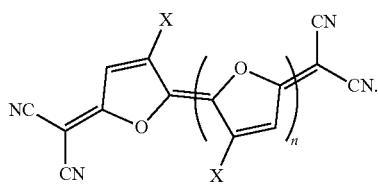

However, this application does not disclose or teach the properties and applications of any compound having a parent core structure similar to the parent core structure of the present application.

Since the hole injection layer has a great impact on the voltage, efficiency, and lifetime of the OLED device, it is necessary to develop a deep-LUMO hole injection material with high stability and high film formation in organic electroluminescent materials, such materials have a deeper LUMO energy level, which can improve the transport balance of electrons and holes and improve the device performance, and thus it is very important to develop novel high-performance hole injection materials.

SUMMARY

The present disclosure aims to provide a series of compounds having a structure of Formula 1 to solve at least part of the preceding problems.

According to an embodiment of the present disclosure, disclosed is a compound which has a structure represented by Formula 1:

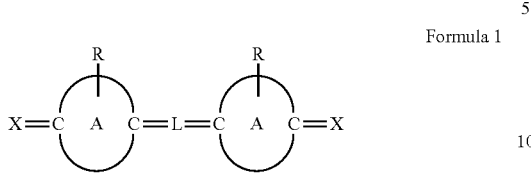

Formula 1 wherein,

L is, at each occurrence identically or differently, selected from

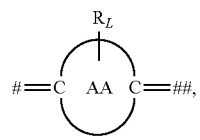

or any combination thereof;

ring AA is a conjugated structure having 4 to 30 ring atoms and comprising at least one intra-ring double bond;

ring A is, at each occurrence identically or differently, a 5-membered heterocyclic ring, and the 5-membered heterocyclic ring comprises an intra-ring double bond, three C atoms, one N atom, and one W; the W is, at each occurrence identically or differently, selected from the group consisting of O, S, Se, and $NR_N$;

X is, at each occurrence identically or differently, selected from the group consisting of Se, NR', and CR"R'";

$R_L$ represents, at each occurrence identically or differently, mono-substitution, multiple substitutions or non-substitution;

R, R', R", R'", $R_L$, and $R_N$ are, at each occurrence identically or differently, selected from the group consisting of: hydrogen, deuterium, halogen, a nitroso group, a nitro group, an acyl group, a carbonyl group, a carboxylic acid group, an ester group, a cyano group, an isocyano group, SCN, OCN, $SF_5$, a boranyl group, a sulfinyl group, a sulfonyl group, a phosphoroso group, a hydroxyl group, a sulfanyl group, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted aralkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted alkynyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted alkylgermanyl having 3 to 20 carbon atoms, substituted or unsubstituted arylgermanyl having 6 to 20 carbon atoms, and combinations thereof;

when X is selected from NR' or CR"R'", at least one of R', R", and R'" is a group having at least one electron-withdrawing group;

adjacent substituents R", R'" can be optionally joined to form a ring; and adjacent substituents R, $R_L$ can be optionally joined to form a ring;

wherein "#" and "##" represent positions where L is connected to ring A.

According to another embodiment of the present disclosure, further disclosed is an electroluminescent device which includes an anode, a cathode, and organic layer disposed between the anode and the cathode, at least one of the organic layers comprises the compound described in the preceding embodiment.

According to another embodiment of the present disclosure, further disclosed is a compound composition which includes the compound described in the preceding embodiment.

The present application discloses a series of novel compounds of formula 1 with a novel dehydrogenation linking skeleton. These compounds have a deep LUMO energy level and can be used as a single hole injection material or as a very excellent p-type dopant applied to the hole injection layer, and this is very important for developing novel high-performance hole injection materials.

DETAILED DESCRIPTION

Figure 1:
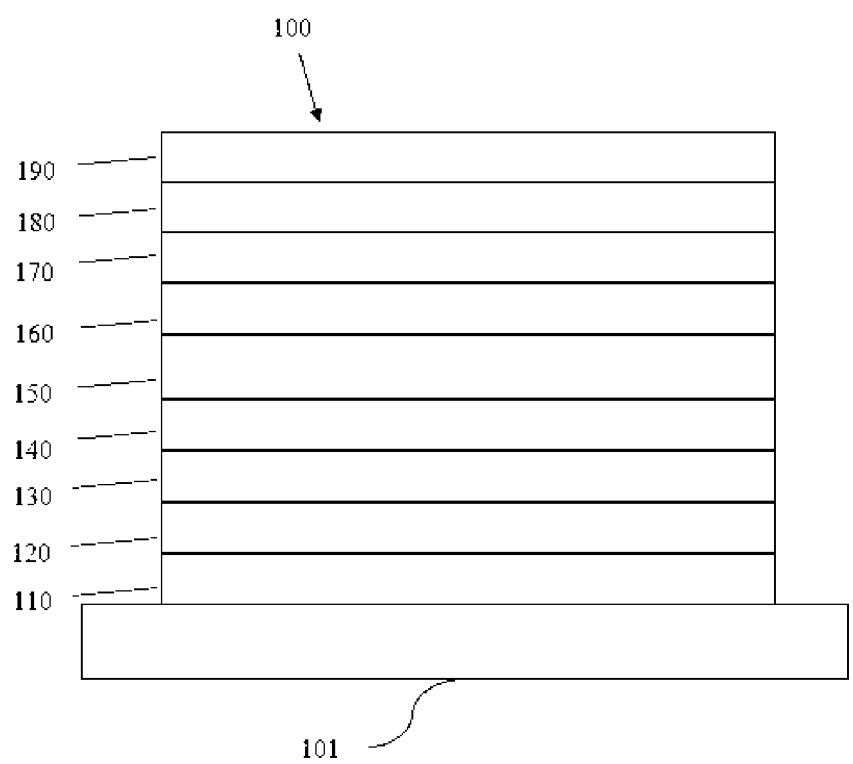
FIG. 1 is a schematic diagram of an organic light-emitting apparatus that may include a compound and a compound composition disclosed by the present disclosure.

OLEDs can be fabricated on various types of substrates such as glass, plastic, and metal foil. FIG. 1 schematically shows an organic light emitting device 100 without limitation. The figures are not necessarily drawn to scale. Some of the layers in the figures can also be omitted as needed. Device 100 may include a substrate 101, an anode 110, a hole injection layer 120, a hole transport layer 130, an electron blocking layer 140, an emissive layer 150, a hole blocking layer 160, an electron transport layer 170, an electron injection layer 180 and a cathode 190. Device 100 may be fabricated by depositing the layers described in order. The properties and functions of these various layers, as well as example materials, are described in more detail in U.S. Pat. No. 7,279,704 at cols. 6-10, the contents of which are incorporated by reference herein in its entirety.

More examples for each of these layers are available. For example, a flexible and transparent substrate-anode combination is disclosed in U.S. Pat. No. 5,844,363, which is incorporated by reference herein in its entirety. An example of a p-doped hole transport layer is m-MTDATA doped with F4-TCNQ at a molar ratio of 50:1, as disclosed in U.S. Patent Application Publication No. 2003/0230980, which is incorporated by reference herein in its entirety. Examples of host materials are disclosed in U.S. Pat. No. 6,303,238 to Thompson et al., which is incorporated by reference herein in its entirety. An example of an n-doped electron transport layer is BPhen doped with Li at a molar ratio of 1:1, as disclosed in U.S. Patent Application Publication No. 2003/0230980, which is incorporated by reference herein in its entirety. U.S. Pat. Nos. 5,703,436 and 5,707,745, which are incorporated by reference herein in their entireties, disclose examples of cathodes including composite cathodes having a thin layer of metal such as Mg:Ag with an overlying transparent, electrically-conductive, sputter-deposited ITO layer. The theory and use of blocking layers are described in more detail in U.S. Pat. No. 6,097,147 and U.S. Patent Application Publication No. 2003/0230980, which are incorporated by reference herein in their entireties. Examples of injection layers are provided in U.S. Patent Application Publication No. 2004/0174116, which is incorporated by reference herein in its entirety. A description of protective layers may be found in U.S. Patent Application Publication No. 2004/0174116, which is incorporated by reference herein in its entirety.

The layered structure described above is provided by way of non-limiting examples. Functional OLEDs may be achieved by combining the various layers described in different ways, or layers may be omitted entirely. It may also include other layers not specifically described. Within each layer, a single material or a mixture of multiple materials can be used to achieve optimum performance. Any functional layer may include several sublayers. For example, the emissive layer may have two layers of different emitting materials to achieve desired emission spectrum.

In one embodiment, an OLED may be described as having an "organic layer" disposed between a cathode and an anode. This organic layer may comprise a single layer or multiple layers.

Figure 2:
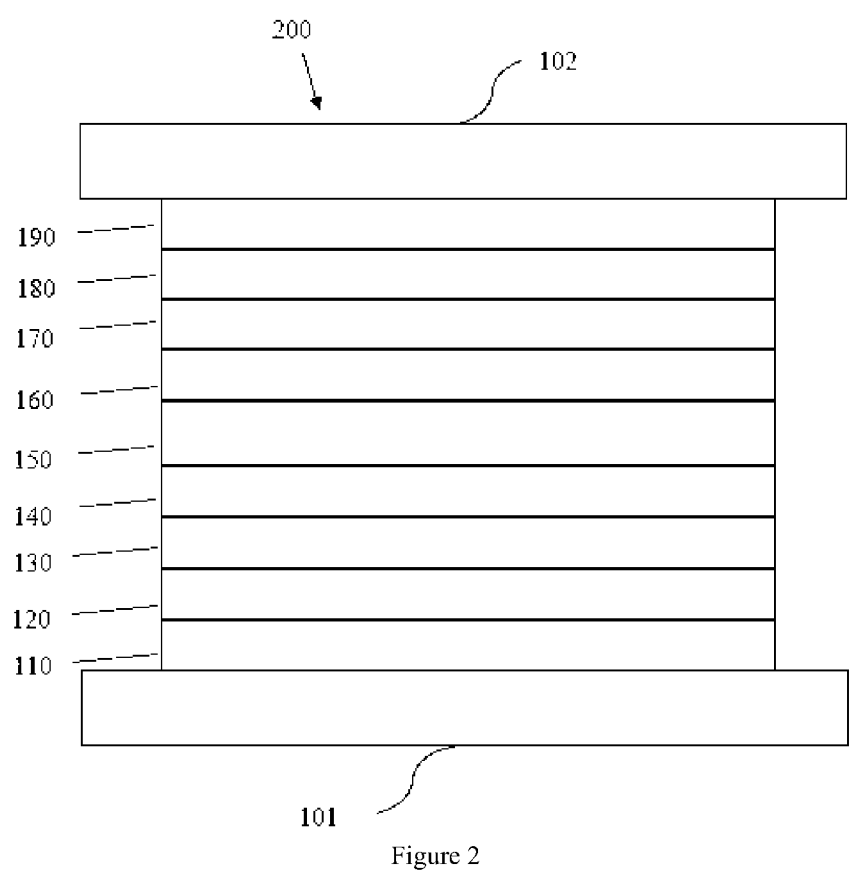
FIG. 2 is a schematic diagram of another organic light-emitting apparatus that may include a compound and a compound composition disclosed by the present disclosure.

An OLED can be encapsulated by a barrier layer. FIG. 2 schematically shows an organic light emitting device 200 without limitation. FIG. 2 differs from FIG. 1 in that the organic light emitting device include a barrier layer 102, which is above the cathode 190, to protect it from harmful species from the environment such as moisture and oxygen. Any material that can provide the barrier function can be used as the barrier layer such as glass or organic-inorganic hybrid layers. The barrier layer should be placed directly or indirectly outside of the OLED device. Multilayer thin film encapsulation was described in U.S. Pat. No. 7,968,146, which is incorporated by reference herein in its entirety.

Devices fabricated in accordance with embodiments of the present disclosure can be incorporated into a wide variety of consumer products that have one or more of the electronic component modules (or units) incorporated therein. Some examples of such consumer products include flat panel displays, monitors, medical monitors, televisions, billboards, lights for interior or exterior illumination and/or signaling, heads-up displays, fully or partially transparent displays, flexible displays, smart phones, tablets, phablets, wearable devices, smart watches, laptop computers, digital cameras, camcorders, viewfinders, micro-displays, 3-D displays, vehicles displays, and vehicle tail lights.

The materials and structures described herein may be used in other organic electronic devices listed above.

As used herein, "top" means furthest away from the substrate, while "bottom" means closest to the substrate. Where a first layer is described as "disposed over" a second layer, the first layer is disposed further away from the substrate. There may be other layers between the first and second layers, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

It is believed that the internal quantum efficiency (IQE) of fluorescent OLEDs can exceed the 25% spin statistics limit through delayed fluorescence. As used herein, there are two types of delayed fluorescence, i.e., P-type delayed fluorescence and E-type delayed fluorescence. P-type delayed fluorescence is generated from triplet-triplet annihilation (TTA).

On the other hand, E-type delayed fluorescence does not rely on the collision of two triplets, but rather on the transition between the triplet states and the singlet excited states. Compounds that are capable of generating E-type delayed fluorescence are required to have very small singlet-triplet gaps to convert between energy states. Thermal energy can activate the transition from the triplet state back to the singlet state. This type of delayed fluorescence is also known as thermally activated delayed fluorescence (TADF). A distinctive feature of TADF is that the delayed component increases as temperature rises. If the reverse intersystem crossing (RISC) rate is fast enough to minimize the non-radiative decay from the triplet state, the fraction of back populated singlet excited states can potentially reach 75%. The total singlet fraction can be 100%, far exceeding 25% of the spin statistics limit for electrically generated excitons.

E-type delayed fluorescence characteristics can be found in an exciplex system or in a single compound. Without being bound by theory, it is believed that E-type delayed fluorescence requires the luminescent material to have a small singlet-triplet energy gap ($\Delta E_{S-T}$). Organic, non-metal containing, donor-acceptor luminescent materials may be able to achieve this. The emission in these materials is generally characterized as a donor-acceptor charge-transfer (CT) type emission. The spatial separation of the HOMO and LUMO in these donor-acceptor type compounds generally results in small $\Delta E_{S-T}$. These states may involve CT states. Generally, donor-acceptor luminescent materials are constructed by connecting an electron donor moiety such as amino- or carbazole-derivatives and an electron acceptor moiety such as N-containing six-membered aromatic rings.

Definition of Terms of Substituents

Halogen or halide—as used herein includes fluorine, chlorine, bromine, and iodine.

Alkyl—as used herein includes both straight and branched chain alkyl groups. Alkyl may be alkyl having 1 to 20 carbon atoms, preferably alkyl having 1 to 12 carbon atoms, and more preferably alkyl having 1 to 6 carbon atoms. Examples of alkyl groups include a methyl group, an ethyl group, a propyl group, an isopropyl group, a n-butyl group, an s-butyl group, an isobutyl group, a t-butyl group, an n-pentyl group, an n-hexyl group, an n-heptyl group, an n-octyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, an n-octadecyl group, a neopentyl group, a 1-methylpentyl group, a 2-methylpentyl group, a 1-pentylhexyl group, a 1-butylpentyl group, a 1-heptyloctyl group, and a 3-methylpentyl group. Of the above, preferred are a methyl group, an ethyl group, a propyl group, an isopropyl group, a n-butyl group, an s-butyl group, an isobutyl group, a t-butyl group, an n-pentyl group, a neopentyl group, and an n-hexyl group. Additionally, the alkyl group may be optionally substituted.

Cycloalkyl—as used herein includes cyclic alkyl groups. The cycloalkyl groups may be those having 3 to 20 ring carbon atoms, preferably those having 4 to 10 carbon atoms. Examples of cycloalkyl include cyclobutyl, cyclopentyl, cyclohexyl, 4-methylcyclohexyl, 4,4-dimethylcylcohexyl, 1-adamantyl, 2-adamantyl, 1-norbornyl, 2-norbornyl, and the like. Of the above, preferred are cyclopentyl, cyclohexyl, 4-methylcyclohexyl, and 4,4-dimethylcylcohexyl. Additionally, the cycloalkyl group may be optionally substituted.

Heteroalkyl—as used herein, includes a group formed by replacing one or more carbons in an alkyl chain with a hetero-atom(s) selected from the group consisting of a nitrogen atom, an oxygen atom, a sulfur atom, a selenium atom, a phosphorus atom, a silicon atom, a germanium atom, and a boron atom. Heteroalkyl may be those having 1 to 20 carbon atoms, preferably those having 1 to 10 carbon atoms, and more preferably those having 1 to 6 carbon atoms. Examples of heteroalkyl include methoxymethyl, ethoxymethyl, ethoxyethyl, methylthiomethyl, ethylthiomethyl, ethylthioethyl, methoxymethoxymethyl, ethoxymethoxymethyl, ethoxyethoxyethyl, hydroxymethyl, hydroxyethyl, hydroxypropyl, mercaptomethyl, mercaptoethyl, mercaptopropyl, aminomethyl, aminoethyl, aminopropyl, dimethylaminomethyl, trimethylgermanylmethyl, trimethylgermanylethyl, trimethylgermanylisopropyl, dimethylethylgermanylmethyl, dimethylisopropylgermanylmethyl, tert-butyldimethylgermanylmethyl, triethylgermanylmethyl, triethylgermanylethyl, triisopropylgermanylmethyl, triisopropylgermanylethyl, trimethylsilylmethyl, trimethylsilylethyl, trimethylsilylisopropyl, triisopropylsilylmethyl and triisopropylsilylethyl. Additionally, the heteroalkyl group may be optionally substituted.

Alkenyl—as used herein includes straight chain, branched chain, and cyclic alkene groups. Alkenyl may be those having 2 to 20 carbon atoms, preferably those having 2 to 10 carbon atoms. Examples of alkenyl include vinyl, 1-propenyl group, 1-butenyl, 2-butenyl, 3-butenyl, 1,3-butanedienyl, 1-methylvinyl, styryl, 2,2-diphenylvinyl, 1,2-diphenylvinyl, 1-methylallyl, 1,1-dimethylallyl, 2-methylallyl, 1-phenylallyl, 2-phenylallyl, 3-phenylallyl, 3,3-diphenylallyl, 1,2-dimethylallyl, 1-phenyl-1-butenyl, 3-phenyl-1-butenyl, cyclopentenyl, cyclopentadienyl, cyclohexenyl, cycloheptenyl, cycloheptatrienyl, cyclooctenyl, cyclooctatetraenyl, and norbornenyl. Additionally, the alkenyl group may be optionally substituted.

Alkynyl—as used herein includes straight chain alkynyl groups. Alkynyl may be those having 2 to 20 carbon atoms, preferably those having 2 to 10 carbon atoms. Examples of alkynyl groups include ethynyl, propynyl, propargyl, 1-butynyl, 2-butynyl, 3-butynyl, 1-pentynyl, 2-pentynyl, 3,3-dimethyl-1-butynyl, 3-ethyl-3-methyl-1-pentynyl, 3,3-diisopropyl-1-pentynyl, phenylethynyl, phenylpropynyl, etc. Of the above, preferred are ethynyl, propynyl, propargyl, 1-butynyl, 2-butynyl, 3-butynyl, 1-pentynyl, and phenylethynyl. Additionally, the alkynyl group may be optionally substituted.

Aryl or an aromatic group—as used herein includes non-condensed and condensed systems. Aryl may be those having 6 to 30 carbon atoms, preferably those having 6 to 20 carbon atoms, and more preferably those having 6 to 12 carbon atoms. Examples of aryl groups include phenyl, biphenyl, terphenyl, triphenylene, tetraphenylene, naphthalene, anthracene, phenalene, phenanthrene, fluorene, pyrene, chrysene, perylene, and azulene, preferably phenyl, biphenyl, terphenyl, triphenylene, fluorene, and naphthalene. Examples of non-condensed aryl groups include phenyl, biphenyl-2-yl, biphenyl-3-yl, biphenyl-4-yl, p-terphenyl-4-yl, p-terphenyl-3-yl, p-terphenyl-2-yl, m-terphenyl-4-yl, m-terphenyl-3-yl, m-terphenyl-2-yl, o-tolyl, m-tolyl, p-tolyl, p-(2-phenylpropyl)phenyl, 4'-methylbiphenylyl, 4"-t-butyl-p-terphenyl-4-yl, o-cumenyl, m-cumenyl, p-cumenyl, 2,3-xylyl, 3,4-xylyl, 2,5-xylyl, mesityl, and m-quarterphenyl. Additionally, the aryl group may be optionally substituted.

Heterocyclic groups or heterocycle—as used herein include non-aromatic cyclic groups. Non-aromatic heterocyclic groups include saturated heterocyclic groups having 3 to 20 ring atoms and unsaturated non-aromatic heterocyclic groups having 3 to 20 ring atoms, where at least one ring atom is selected from the group consisting of a nitrogen atom, an oxygen atom, a sulfur atom, a selenium atom, a silicon atom, a phosphorus atom, a germanium atom, and a boron atom. Preferred non-aromatic heterocyclic groups are those having 3 to 7 ring atoms, each of which includes at least one hetero-atom such as nitrogen, oxygen, silicon, or sulfur. Examples of non-aromatic heterocyclic groups include oxiranyl, oxetanyl, tetrahydrofuranyl, tetrahydropyranyl, dioxolanyl, dioxanyl, aziridinyl, dihydropyrrolyl, tetrahydropyrrolyl, piperidinyl, oxazolidinyl, morpholinyl, piperazinyl, oxepinyl, thiepinyl, azepinyl, and tetrahydrosilolyl. Additionally, the heterocyclic group may be optionally substituted.

Heteroaryl—as used herein, includes non-condensed and condensed hetero-aromatic groups having 1 to 5 hetero-atoms, where at least one hetero-atom is selected from the group consisting of a nitrogen atom, an oxygen atom, a sulfur atom, a selenium atom, a silicon atom, a phosphorus atom, a germanium atom, and a boron atom. A heteroaromatic group is also referred to as heteroaryl. Heteroaryl may be those having 3 to 30 carbon atoms, preferably those having 3 to 20 carbon atoms, and more preferably those having 3 to 12 carbon atoms. Suitable heteroaryl groups include dibenzothiophene, dibenzofuran, dibenzoselenophene, furan, thiophene, benzofuran, benzothiophene, benzoselenophene, carbazole, indolocarbazole, pyridoindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, benzofuropyridine, furodipyridine, benzothienopyridine, thienodipyridine, benzoselenophenopyridine, and selenophenodipyridine, preferably dibenzothiophene, dibenzofuran, dibenzoselenophene, carbazole, indolocarbazole, imidazole, pyridine, triazine, benzimidazole, 1,2-azaborine, 1,3-azaborine, 1,4-azaborine, borazine, and aza-analogs thereof. Additionally, the heteroaryl group may be optionally substituted.

Alkoxy—as used herein, is represented by —O-alkyl, —O-cycloalkyl, —O-heteroalkyl, or —O-heterocyclic group. Examples and preferred examples of alkyl, cycloalkyl, heteroalkyl, and heterocyclic groups are the same as those described above. Alkoxy groups may be those having 1 to 20 carbon atoms, preferably those having 1 to 6 carbon atoms. Examples of alkoxy groups include methoxy, ethoxy, propoxy, butoxy, pentyloxy, hexyloxy, cyclopropyloxy, cyclobutyloxy, cyclopentyloxy, cyclohexyloxy, tetrahydrofuranyloxy, tetrahydropyranyloxy, methoxypropyloxy, ethoxyethyloxy, methoxymethyloxy, and ethoxymethyloxy. Additionally, the alkoxy group may be optionally substituted.

Aryloxy—as used herein, is represented by —O-aryl or —O-heteroaryl. Examples and preferred examples of aryl and heteroaryl are the same as those described above. Aryloxy groups may be those having 6 to 30 carbon atoms, preferably those having 6 to 20 carbon atoms. Examples of aryloxy groups include phenoxy and biphenyloxy. Additionally, the aryloxy group may be optionally substituted.

Arylalkyl—as used herein, contemplates alkyl substituted with an aryl group. Arylalkyl may be those having 7 to 30 carbon atoms, preferably those having 7 to 20 carbon atoms, and more preferably those having 7 to 13 carbon atoms. Examples of arylalkyl groups include benzyl, 1-phenylethyl, 2-phenylethyl, 1-phenylisopropyl, 2-phenylisopropyl, phenyl-t-butyl, alpha-naphthylmethyl, 1-alpha-naphthylethyl, 2-alpha-naphthylethyl, 1-alpha-naphthylisopropyl, 2-alpha-naphthylisopropyl, beta-naphthylmethyl, 1-beta-naphthylethyl, 2-beta-naphthylethyl, 1-beta-naphthylisopropyl, 2-beta-naphthylisopropyl, p-methylbenzyl, m-methylbenzyl, o-methylbenzyl, p-chlorobenzyl, m-chlorobenzyl, o-chlorobenzyl, p-bromobenzyl, m-bromobenzyl, o-bromobenzyl, p-iodobenzyl, m-iodobenzyl, o-iodobenzyl, p-hydroxybenzyl, m-hydroxybenzyl, o-hydroxybenzyl, p-aminobenzyl, m-aminobenzyl, o-aminobenzyl, p-nitrobenzyl, m-nitrobenzyl, o-nitrobenzyl, p-cyanobenzyl, m-cyanobenzyl, o-cyanobenzyl, 1-hydroxy-2-phenylisopropyl, and 1-chloro-2-phenylisopropyl. Of the above, preferred are benzyl, p-cyanobenzyl, m-cyanobenzyl, o-cyanobenzyl, 1-phenylethyl, 2-phenylethyl, 1-phenylisopropyl, and 2-phenylisopropyl. Additionally, the arylalkyl group may be optionally substituted.

Alkylsilyl—as used herein, contemplates a silyl group substituted with an alkyl group. Alkylsilyl groups may be those having 3 to 20 carbon atoms, preferably those having 3 to 10 carbon atoms. Examples of alkylsilyl groups include trimethylsilyl, triethylsilyl, methyldiethylsilyl, ethyldimethylsilyl, tripropylsilyl, tributylsilyl, triisopropylsilyl, methyldiisopropylsilyl, dimethylisopropylsilyl, tri-t-butylsilyl, triisobutylsilyl, dimethyl t-butylsilyl, and methyldi-t-butylsilyl. Additionally, the alkylsilyl group may be optionally substituted.

Arylsilyl—as used herein, contemplates a silyl group substituted with at least one aryl group. Arylsilyl groups may be those having 6 to 30 carbon atoms, preferably those having 8 to 20 carbon atoms. Examples of arylsilyl groups include triphenylsilyl, phenyldibiphenylylsilyl, diphenylbiphenylsilyl, phenyldiethylsilyl, diphenylethylsilyl, phenyldimethylsilyl, diphenylmethylsilyl, phenyldiisopropylsilyl, diphenylisopropylsilyl, diphenylbutylsilyl, diphenylisobutylsilyl, diphenyl t-butylsilyl. Additionally, the arylsilyl group may be optionally substituted.

Alkylgermanyl group—as used herein contemplates a germanium group substituted with an alkyl group. Alkylgermanyl groups may be those having 3 to 20 carbon atoms, preferably those having 3 to 10 carbon atoms. Examples of alkylgermanyl groups include trimethylgermanyl, triethylgermanyl, methyldiethylgermanyl, ethyldimethylgermane, tripropylgermanyl, tributylgermanyl, triisopropylgermanyl, methyldiisopropylgermanyl, dimethylisopropylgermanyl, tri-t-butylgermanyl, triisobutylgermanyl, dimethyl-t-butylgermanyl, and methyldi-t-butylgermanyl. Additionally, the alkylgermanyl group may be optionally substituted.

Arylgermanyl group—as used herein contemplates a germanium group substituted with at least one aryl group or heteroaryl group. Arylgermanyl groups may be those having 6 to 30 carbon atoms, preferably those having 8 to 20 carbon atoms. Examples of arylgermanyl groups include triphenylgermanyl, phenyldibiphenylylgermanyl, diphenylbiphenylgermanyl, phenyldiethylgermanyl, diphenylethylgermanyl, phenyldimethylgermanyl, diphenylmethylgermanyl, phenyldiisopropylgermanyl, diphenylisopropylgermanyl, diphenylbutylgermanyl, diphenylisobutylgermanyl, and diphenyl-t-butylgermanyl. Additionally, the aryl germanium group may be optionally substituted.

The term "aza" in azadibenzofuran, azadibenzothiophene, etc. means that one or more of C—H groups in the respective aromatic fragment are replaced by a nitrogen atom. For example, azatriphenylene encompasses dibenzo[f,h]quinoxaline, dibenzo[f,h]quinoline and other analogs with two or more nitrogens in the ring system. One of ordinary skill in the art can readily envision other nitrogen analogs of the aza-derivatives described above, and all such analogs are intended to be encompassed by the terms as set forth herein.

In the present disclosure, unless otherwise defined, when any term of the group consisting of substituted alkyl, substituted cycloalkyl, substituted heteroalkyl, substituted heterocyclic group, substituted arylalkyl, substituted alkoxy, substituted aryloxy, substituted alkenyl, substituted alkynyl, substituted aryl, substituted heteroaryl, substituted alkylsilyl, substituted arylsilyl, substituted alkylgermanyl, substituted arylgermanyl, substituted amino, substituted acyl, substituted carbonyl, a substituted carboxylic acid group, a substituted ester group, substituted sulfinyl, substituted sulfonyl, and substituted phosphino is used, it means that any group of alkyl, cycloalkyl, heteroalkyl, heterocyclic group, arylalkyl, alkoxy, aryloxy, alkenyl, alkynyl, aryl, heteroaryl, alkylsilyl, arylsilyl, amino, acyl, carbonyl, a carboxylic acid group, an ester group, sulfinyl, sulfonyl, and phosphino may be substituted with one or more moieties selected from the group consisting of deuterium, halogen, unsubstituted alkyl having 1 to 20 carbon atoms, unsubstituted cycloalkyl having 3 to 20 ring carbon atoms, unsubstituted heteroalkyl having 1 to 20 carbon atoms, an unsubstituted heterocyclic group having 3 to 20 ring atoms, unsubstituted arylalkyl having 7 to 30 carbon atoms, unsubstituted alkoxy having 1 to 20 carbon atoms, unsubstituted aryloxy having 6 to 30 carbon atoms, unsubstituted alkenyl having 2 to 20 carbon atoms, unsubstituted alkynyl having 2 to 20 carbon atoms, unsubstituted aryl having 6 to 30 carbon atoms, unsubstituted heteroaryl having 3 to 30 carbon atoms, unsubstituted alkylsilyl having 3 to 20 carbon atoms, unsubstituted arylsilyl group having 6 to 20 carbon atoms, unsubstituted alkylgermanyl having 3 to 20 carbon atoms, unsubstituted arylgermanyl group having 6 to 20 carbon atoms, unsubstituted amino having 0 to 20 carbon atoms, an acyl group, a carbonyl group, a carboxylic acid group, an ester group, a cyano group, an isocyano group, a hydroxyl group, a sulfanyl group, a sulfinyl group, a sulfonyl group, a phosphino group, and combinations thereof.

It is to be understood that when a molecular fragment is described as being a substituent or otherwise attached to another moiety, its name may be written as if it were a fragment (e.g. phenyl, phenylene, naphthyl, dibenzofuryl) or as if it were the whole molecule (e.g. benzene, naphthalene, dibenzofuran). As used herein, these different ways of designating a substituent or an attached fragment are considered to be equivalent.

In the compounds mentioned in the present disclosure, hydrogen atoms may be partially or fully replaced by deuterium. Other atoms such as carbon and nitrogen may also be replaced by their other stable isotopes. The replacement by other stable isotopes in the compounds may be preferred due to its enhancements of device efficiency and stability.

In the compounds mentioned in the present disclosure, multiple substitution refers to a range that includes a di-substitution, up to the maximum available substitution. When substitution in the compounds mentioned in the present disclosure represents multiple substitution (including di-, tri-, and tetra-substitutions etc.), that means the substituent may exist at a plurality of available substitution positions on its linking structure, the substituents present at a plurality of available substitution positions may have the same structure or different structures.

In the compounds mentioned in the present disclosure, adjacent substituents in the compounds cannot be joined to form a ring unless otherwise explicitly defined, for example, adjacent substituents can be optionally joined to form a ring. In the compounds mentioned in the present disclosure, the expression that adjacent substituents can be optionally joined to form a ring includes a case where adjacent substituents may be joined to form a ring and a case where adjacent substituents are not joined to form a ring. When adjacent substituents can be optionally joined to form a ring, the ring formed may be monocyclic or polycyclic, as well as alicyclic, heteroalicyclic, aromatic, or heteroaromatic. In such expression, adjacent substituents may refer to substituents bonded to the same atom, substituents bonded to carbon atoms which are directly bonded to each other, or substituents bonded to carbon atoms which are more distant from each other. Preferably, adjacent substituents refer to substituents bonded to the same carbon atom and substituents bonded to carbon atoms which are directly bonded to each other.

In the present disclosure, the number of ring atoms represents the number of atoms constituting a ring itself of a compound having a structure in which atoms are bonded in the form of a ring (for example, a monocyclic compound, a fused ring compound, a crosslinked compound, a carbocyclic compound, and a heterocyclic compound). When the ring is substituted by a substituent, the atoms contained in the substituent are not included in the number of ring atoms. The "number of ring atoms" recorded herein has the same meaning unless otherwise stated. For example, the number of ring atoms of

is 4, where • is the position where ring A is connected. The number of ring atoms of

is 5. The number of ring atoms of

is 6. The number of ring atoms of

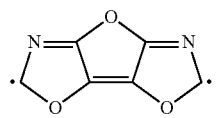

is 11.

The expression that adjacent substituents can be optionally joined to form a ring is also intended to mean that two substituents bonded to the same carbon atom are joined to each other via a chemical bond to form a ring, which can be exemplified by the following formula:

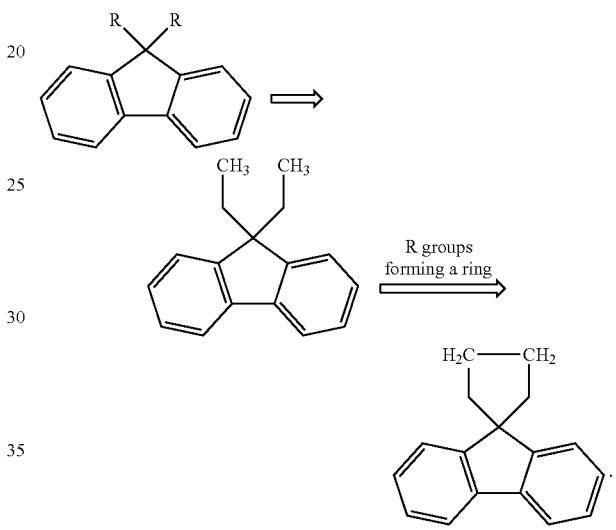

The expression that adjacent substituents can be optionally joined to form a ring is also intended to mean that two substituents bonded to carbon atoms which are directly bonded to each other are joined to each other via a chemical bond to form a ring, which can be exemplified by the following formula:

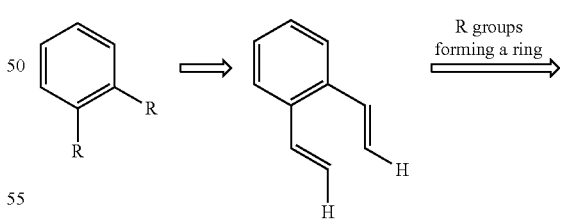

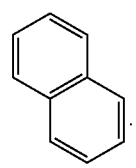

The expression that adjacent substituents can be optionally joined to form a ring is also intended to mean that two substituents bonded to a further distant carbon atom are joined to each other via a chemical bond to form a ring, which can be exemplified by the following formula:

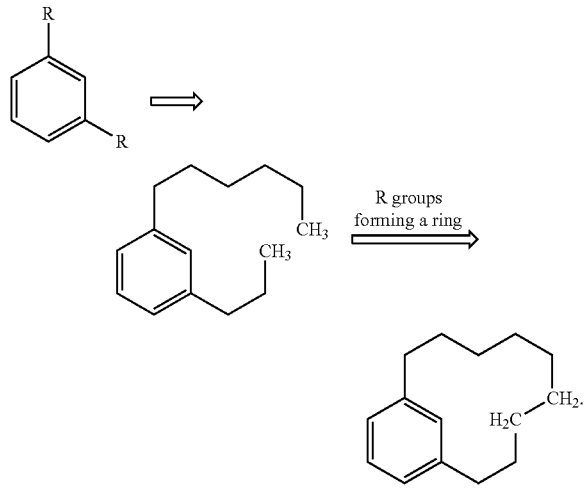

Furthermore, the expression that adjacent substituents can be optionally joined to form a ring is also intended to mean that, in the case where one of the two substituents bonded to carbon atoms which are directly bonded to each other represents hydrogen, the second substituent is bonded at a position at which the hydrogen atom is bonded, thereby forming a ring. This is exemplified by the following formula:

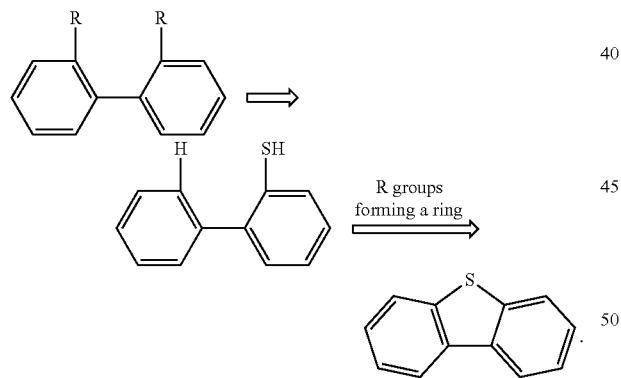

According to an embodiment of the present disclosure, disclosed is a compound which has a structure represented by Formula 1:

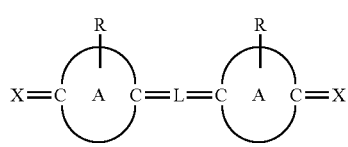

Formula 1 wherein,

L is, at each occurrence identically or differently, selected from

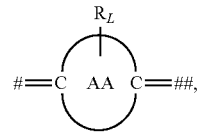

or any combination thereof;

ring AA is a conjugated structure having 4 to 30 ring atoms and comprising at least one intra-ring double bond;

ring A is, at each occurrence identically or differently, a 5-membered heterocyclic ring, and the 5-membered heterocyclic ring comprises an intra-ring double bond, three C atoms, one N atom, and one W; the W is, at each occurrence identically or differently, selected from the group consisting of O, S, Se, and $NR_N$;

X is, at each occurrence identically or differently, selected from the group consisting of Se, NR', and CR"R'";

$R_L$ represents, at each occurrence identically or differently, mono-substitution, multiple substitutions or non-substitution;

R, R', R", R'", $R_L$, and $R_N$ are, at each occurrence identically or differently, selected from the group consisting of: hydrogen, deuterium, halogen, a nitroso group, a nitro group, an acyl group, a carbonyl group, a carboxylic acid group, an ester group, a cyano group, an isocyano group, SCN, OCN, $SF_5$, a boranyl group, a sulfinyl group, a sulfonyl group, a phosphoroso group, a hydroxyl group, a sulfanyl group, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted aralkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted alkynyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted alkylgermanyl having 3 to 20 carbon atoms, substituted or unsubstituted arylgermanyl having 6 to 20 carbon atoms, and combinations thereof;

when X is selected from NR' or CR"R'", at least one of R', R", and R'" is a group having at least one electron-withdrawing group;

adjacent substituents R", R'" can be optionally joined to form a ring; and adjacent substituents R, $R_L$ can be optionally joined to form a ring;

wherein "#" and "##" represent positions where L is connected to ring A.

In this embodiment, "L is, at each occurrence identically or differently, selected from

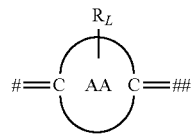

or any combination thereof", is intended to mean that L is, at each occurrence identically or differently, selected from

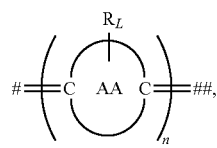

n is selected from an integer from 1 to 10; preferably, n is selected from an integer from 1 to 5; and more preferably, n is selected from an integer from 1 to 3; when n is equal to 1, L is selected from

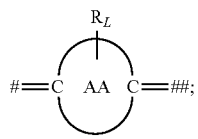

when n is greater than or equal to 2, multiple L are, at each occurrence identically or differently, selected from

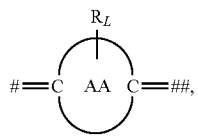

and the multiple L are arbitrarily combined through "#" or

In this disclosure, "adjacent substituents R, $R_L$ can be optionally joined to form a ring" is intended to mean that for groups of adjacent substituents, for example, two substituents R, two substituents $R_L$, and substituents R and $R_L$, any one or more of these substituent groups can be joined to form a ring. Obviously, it is possible that none of these substituents are joined to form a ring.

In the group with structure

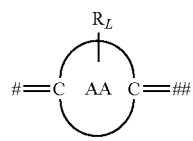

mentioned in this disclosure, ring AA is a conjugated structure having 4-30 ring atoms; ring AA has the structural characteristics of at least one intra-ring double bond and conjugated structure, wherein ring AA can be a monocyclic structure, a fused ring structure or a condensed ring structure; the ring AA can be a heterocyclic structure or a carbocyclic structure. The group having the

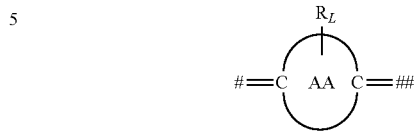

structure used herein includes, but is not limited to, the structures shown in Formula 6 to Formula 41 mentioned herein.

According to an embodiment of the present disclosure, wherein in Formula 1, at least one of substituents R, $R_L$, and $R_N$ is a group having at least one electron-withdrawing group.

According to an embodiment of the present disclosure, wherein in Formula 1, at least one of substituents R, and $R_L$ is a group having at least one electron-withdrawing group.

According to an embodiment of the present disclosure, wherein the structure of

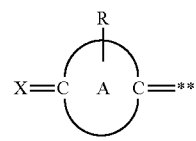

connected to both sides of L in Formula 1 is, at each occurrence identically or differently, selected from any one of the structures represented by Formula 2 to Formula 5:

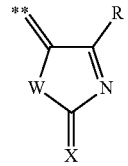

Formula 2

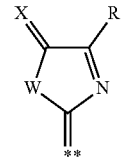

Formula 3

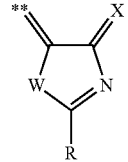

Formula 4

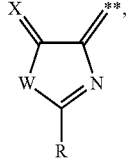

Formula 5 wherein in Formula 2 to Formula 5,

W is, at each occurrence identically or differently, selected from the group consisting of O, S, Se, and $NR_N$;

X is, at each occurrence identically or differently, selected from the group consisting of Se, NR', and CR"R'";

R, R', R", R'" and $R_N$ are, at each occurrence identically or differently, selected from the group consisting of: hydrogen, deuterium, halogen, a nitroso group, a nitro group, an acyl group, a carbonyl group, a carboxylic acid group, an ester group, a cyano group, an isocyano group, SCN, OCN, $SF_5$, a boranyl group, a sulfinyl group, a sulfonyl group, a phosphoroso group, a hydroxyl group, a sulfanyl group, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted aralkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted alkynyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted alkylgermanyl having 3 to 20 carbon atoms, substituted or unsubstituted arylgermanyl having 6 to 20 carbon atoms, and combinations thereof;

"**" represents positions where Formula 2 to Formula 5 are connected to L in Formula 1.

According to an embodiment of the present disclosure, wherein, the ring AA is a conjugated structure having 5-30 ring atoms and comprising at least one five-membered ring or six-membered ring.

According to an embodiment of the present disclosure, wherein, the ring AA is a conjugated structure having 5-30 ring atoms and comprising at least one five-membered ring.

According to an embodiment of the present disclosure, wherein, L in Formula 1 is, at each occurrence identically or differently, selected from structures represented by Formula 6 to Formula 41, or combinations thereof:

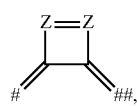

Formula 6

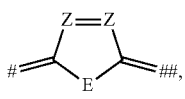

Formula 7

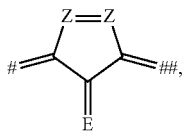

Formula 8

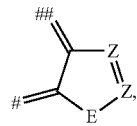

Formula 9

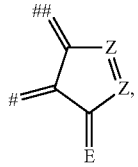

Formula 10

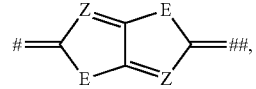

Formula 11

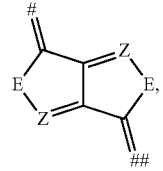

Formula 12

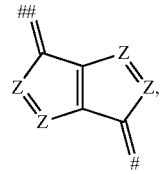

Formula 13

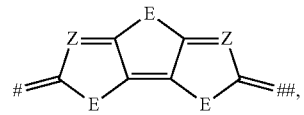

Formula 14

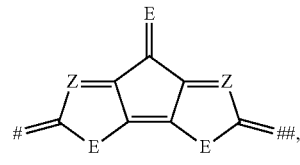

Formula 15

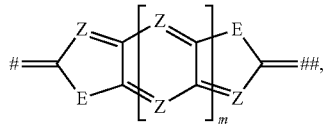

Formula 16

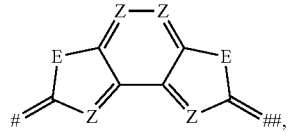

Formula 17

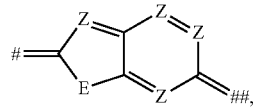

Formula 18

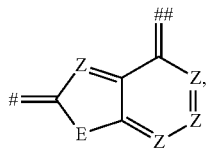

Formula 19

Formula 20
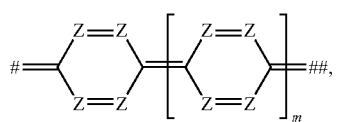
Formula 21
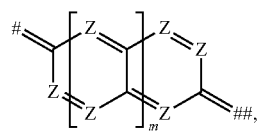
Formula 22
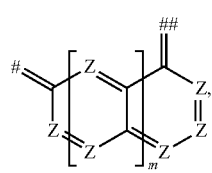
Formula 23
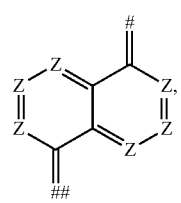
Formula 24
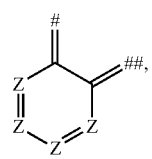
Formula 25
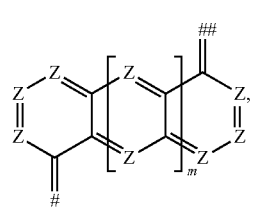
Formula 26
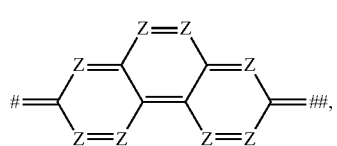
Formula 27
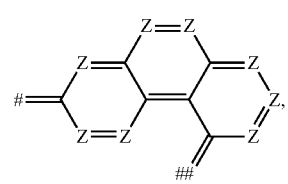
Formula 28
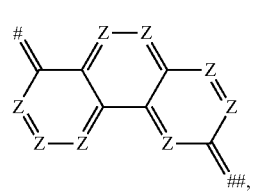
Formula 29
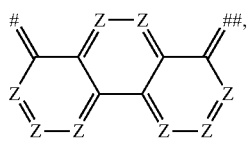
Formula 30
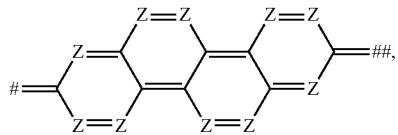
Formula 31
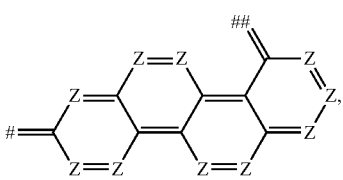
Formula 32
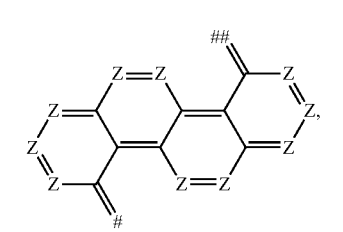
Formula 33
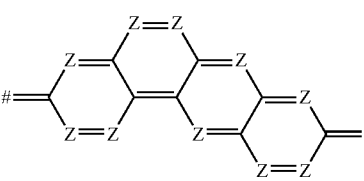
Formula 34
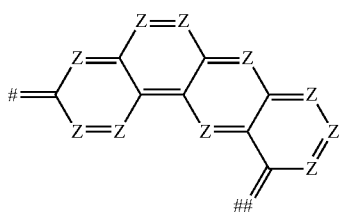
Formula 35
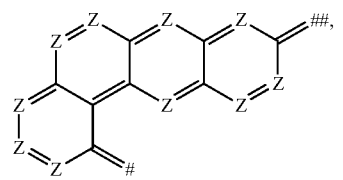
Formula 36
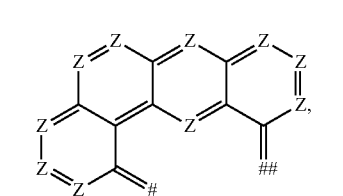

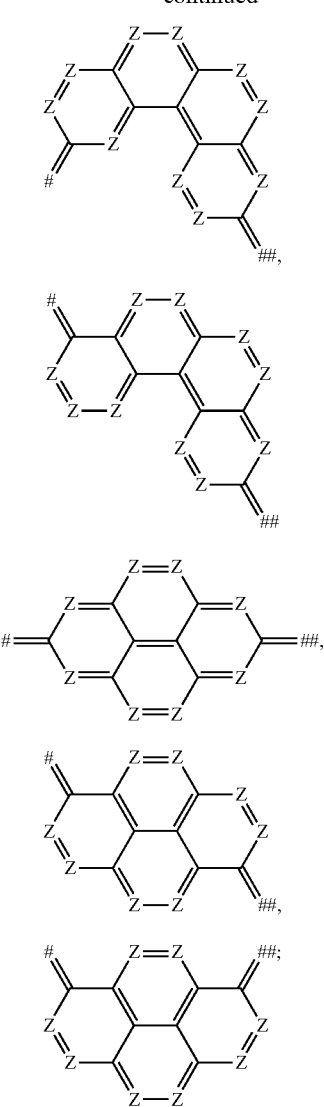

Formula 37

Formula 38

Formula 39

Formula 40

Formula 41 wherein, in Formula 6 to Formula 41, m is, at each occurrence identically or differently, selected from an integer from 1 to 4;

E is, at each occurrence identically or differently, selected from the group consisting of O, S, Se and $CR_AR_B$;

Z is, at each occurrence identically or differently, selected from the group consisting of $CR_L$ or N;

$R_A$, $R_B$, $R_L$ are, at each occurrence identically or differently, selected from the group consisting of: hydrogen, deuterium, halogen, a nitroso group, a nitro group, an acyl group, a carbonyl group, a carboxylic acid group, an ester group, a cyano group, an isocyano group, SCN, OCN, $SF_5$, a boranyl group, a sulfinyl group, a sulfonyl group, a phosphoroso group, a hydroxyl group, a sulfanyl group, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted aralkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted alkynyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted alkylgermanyl having 3 to 20 carbon atoms, substituted or unsubstituted arylgermanyl having 6 to 20 carbon atoms, and combinations thereof;

adjacent substituents $R_A$ and $R_B$ can be optionally joined to form a ring;

adjacent substituents $R_L$ can be optionally joined to form a ring;

"#" and "##" represent positions where Formula 6 to Formula 41 are connected to ring A or L in Formula 1.

According to an embodiment of the present disclosure, wherein L in Formula 1 is, at each occurrence identically or differently, selected from structures represented by Formula 7 to Formula 19.

In this embodiment, "L is, at each occurrence identically or differently, selected from structures represented by Formula 6 to Formula 41" is intended to mean that L can be selected from any structure represented by formula 6 to formula 41, and can also be selected from any structure formed by connecting any two or more structure from formula 6 to formula 41 through positions "#" or "##", for example, formula 8 is connected to formula 8 itself:

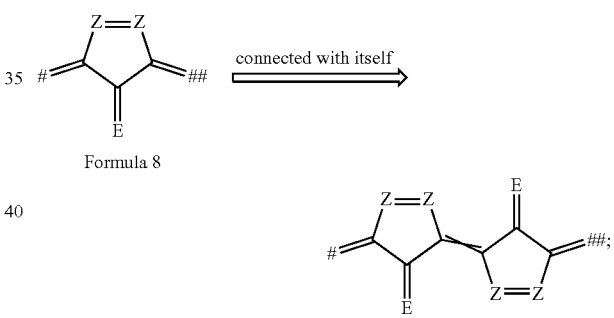

Formula 8

For another example, formula 7 is connected to formula 8:

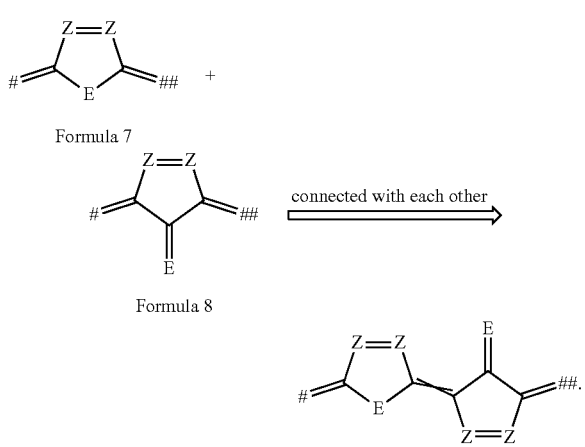

Formula 7

Formula 8

In this embodiment, "# and ## represent positions where Formula 6 to Formula 41 are connected to ring A or L in Formula 1" including the following situations: any one of structure in formula 6 to formula 41 is connected to ring A in formula 1 through "#" and "##", for example, in formula 7, "#" and "##" are connected to ring A to obtain the structure:

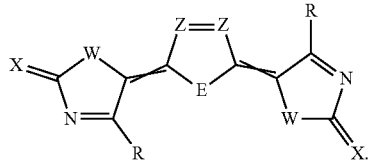

In addition, any two or more structure from formula 6 to formula 41 can also connected with each other through "#" or "##", for example, the structure formed by connecting formula 8 with itself:

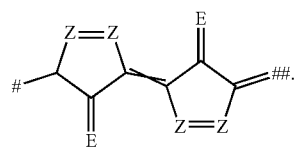

According to an embodiment of the present disclosure, wherein, the compound has any one of the structures represented by Formula LI to Formula LXXXV, Formula LVI-I and Formula LXV-1:

Formula LI

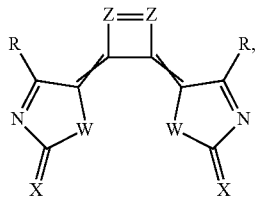

Formula LII

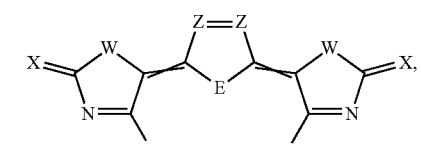

Formula LIII

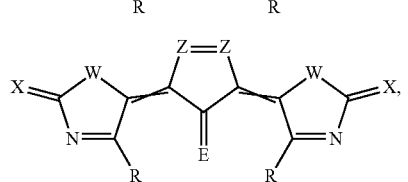

Formula LIV

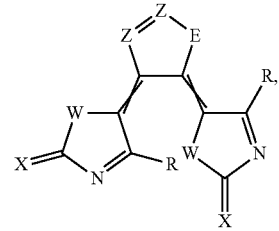

Formula LV

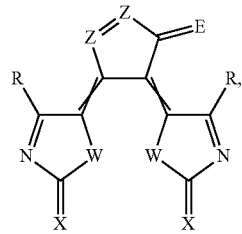

Formula LVI

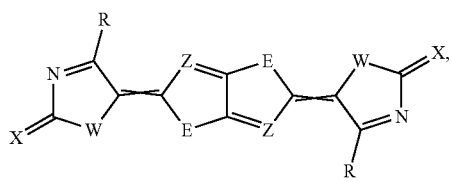

Formula LVII

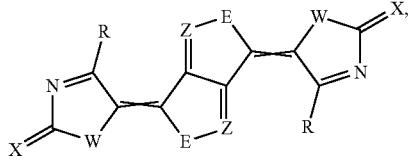

Formula LVIII

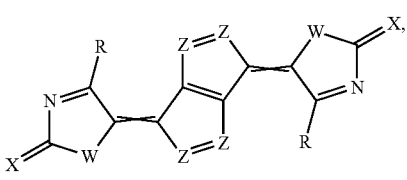

Formula LIX

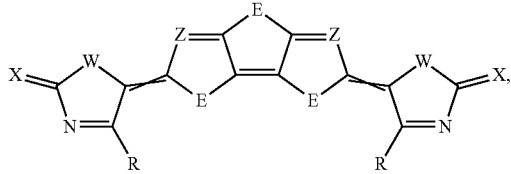

Formula LX

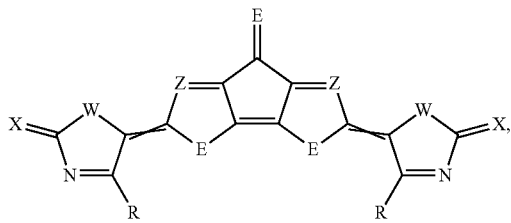

Formula LXI

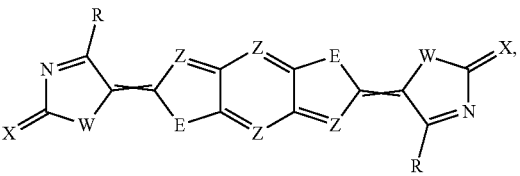

Formula LXII
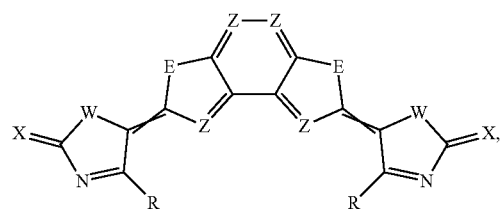
Formula LXIII
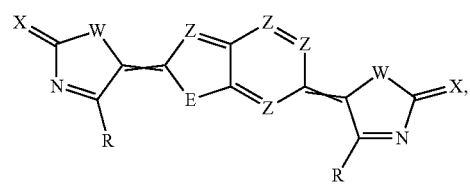
Formula LXIV
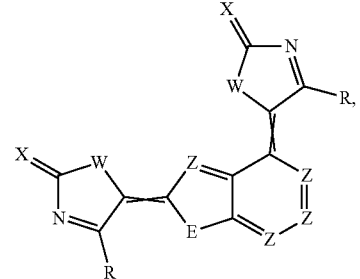
Formula LXV
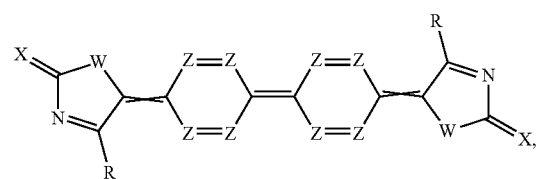
Formula LXVI
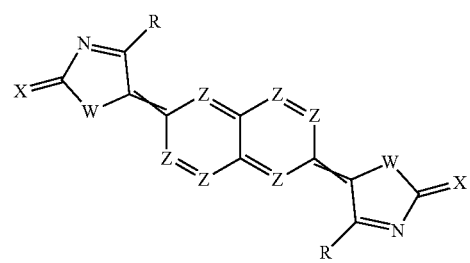
Formula LXVII
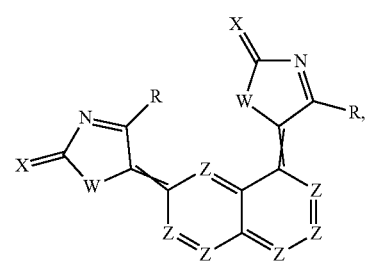
Formula LXVIII
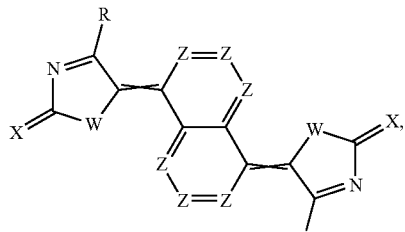
Formula LXIX
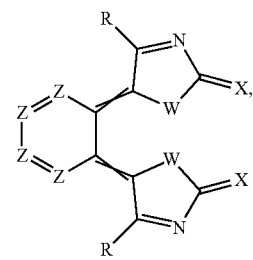
Formula LXX
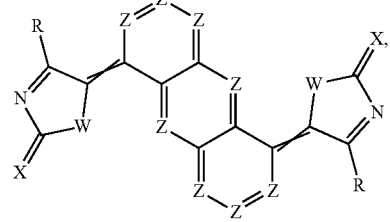
Formula LXXI
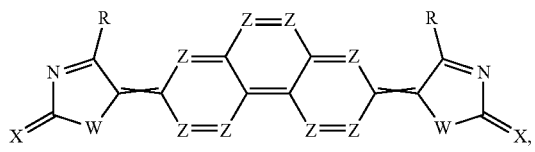
Formula LXXII
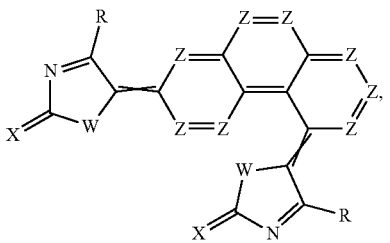
Formula LXXIII
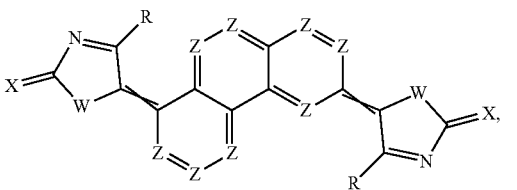
Formula LXXIV -continued
Formula LXXV
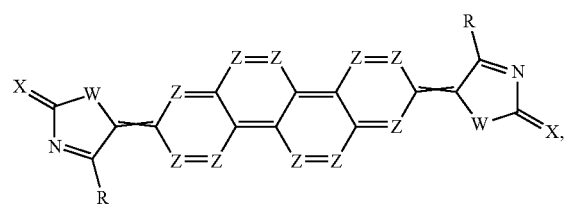
Formula LXXVI
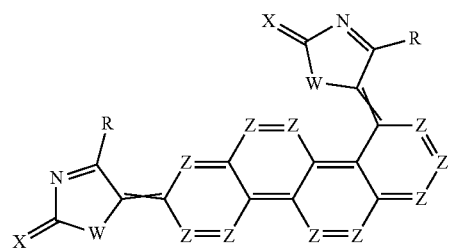
Formula LXXVII
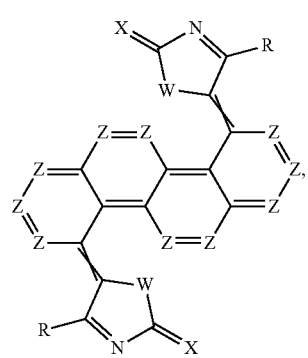
Formula LXXVIII
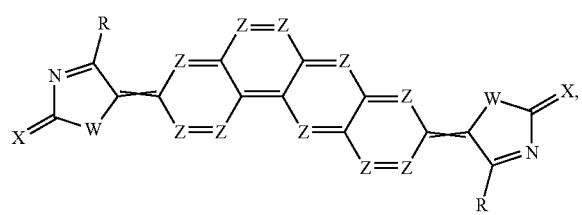
Formula LXXIX
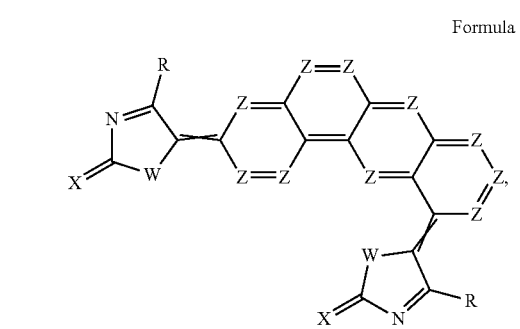
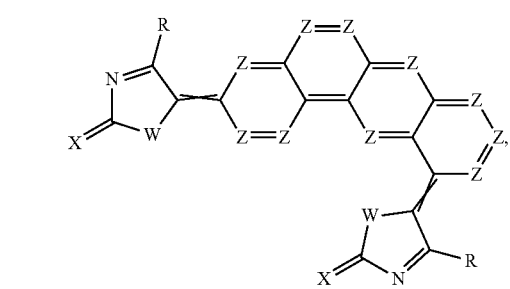
-continued
Formula LXXX
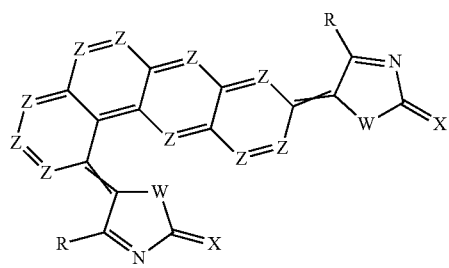
Formula LXXXI
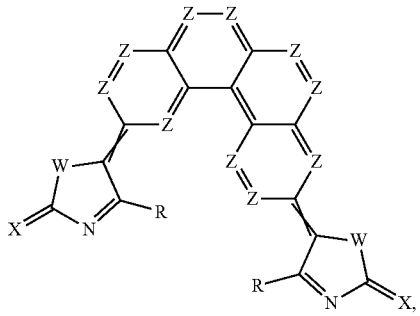
Formula LXXXII
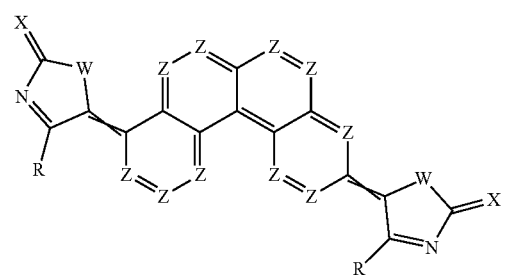
Formula LXXXIII
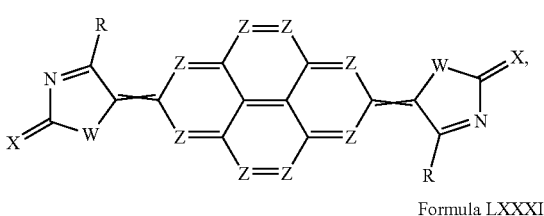
Formula LXXXIV
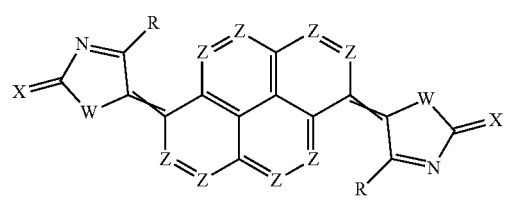
Formula LXXXV
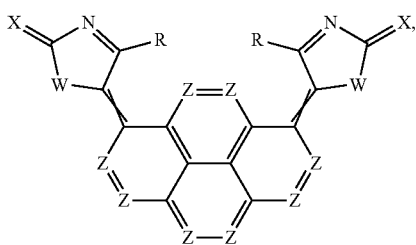

Formula LVI-I

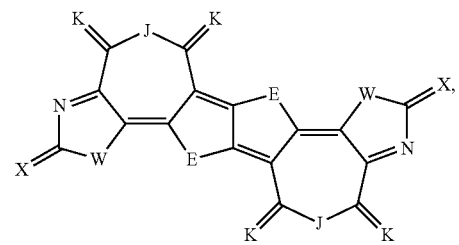

Formula LXV-I

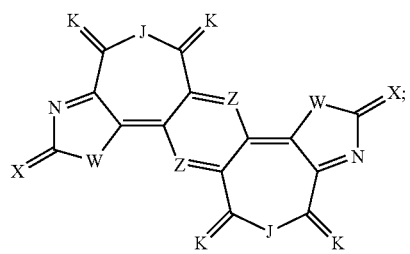

wherein, in Formula LI to Formula LXXXV, Formula LVI-I and Formula LXV-1,

K and E are, at each occurrence identically or differently, selected from the group consisting of O, S, Se, and $CR_AR_B$;

Z is, at each occurrence identically or differently, selected from the group consisting of $CR_L$ and N;

X is, at each occurrence identically or differently, selected from the group consisting of Se, NR' and CR"R'";

W is, at each occurrence identically or differently, selected from the group consisting of O, S, Se, and $NR_N$;

J is, at each occurrence identically or differently, selected from the group consisting of O, S, Se, and $NR_{NJ}$;

$R_A$, $R_B$, R, R', R", R'", $R_L$, $R_N$ and $R_{NJ}$ are, at each occurrence identically or differently, selected from the group consisting of: hydrogen, deuterium, halogen, a nitroso group, a nitro group, an acyl group, a carbonyl group, a carboxylic acid group, an ester group, a cyano group, an isocyano group, SCN, OCN, $SF_5$, a boranyl group, a sulfinyl group, a sulfonyl group, a phosphoroso group, a hydroxyl group, a sulfanyl group, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted aralkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted alkynyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted alkylgermanyl having 3 to 20 carbon atoms, substituted or unsubstituted arylgermanyl having 6 to 20 carbon atoms, and combinations thereof;

adjacent substituents $R_A$ and $R_B$ can be optionally joined to form a ring;

when X is selected from NR' or CR"R'", at least one of R', R", and R'" is a group having at least one electron-withdrawing group;

adjacent substituents R", R'" can be optionally joined to form a ring; and adjacent substituents R, $R_L$ can be optionally joined to form a ring.

According to an embodiment of the present disclosure, wherein, at least one of substituents R, $R_L$, $R_N$ and $R_{NJ}$ is a group having at least one electron-withdrawing group.

According to an embodiment of the present disclosure, wherein, the compound has any one of the structures represented by Formula LII to Formula LXIV.

Herein, "⋈" in the above structure formula indicates that the structure has a cis-configuration and a trans-configuration. Taking Formula LII

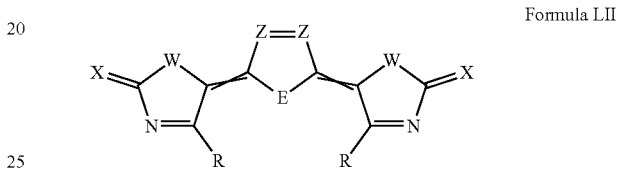

as an example, when two R are identical, two Y are identical, and two X are identical in Formula LII, the following structures are included:

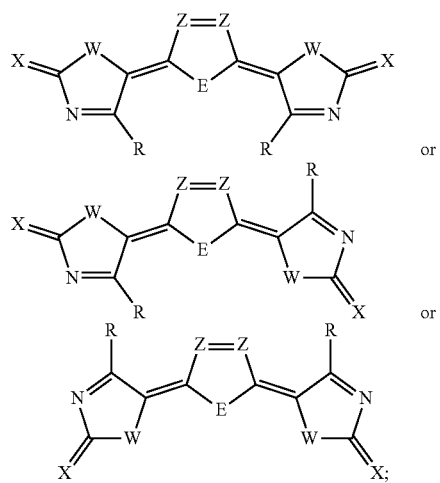

and when at least one pair of two R (referred as $R^1$ and $R^2$; $R^1$ and $R^2$ may be identical or different), and/or two Z (referred as $Z_1$ and $Z_2$; $Z_1$ and $Z_2$ may be identical or different), and/or two W (referred as $W_1$ and $W_2$; $W_1$ and $W_2$ may be identical or different), and/or two X (referred as $X_1$ and $X_2$; $X_1$ and $X_2$ may be identical or different) are different in Formula LII, the following structures are included:

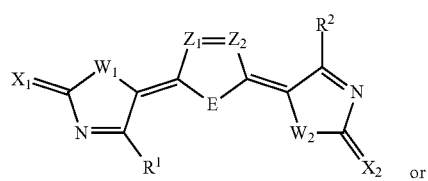

or

-continued

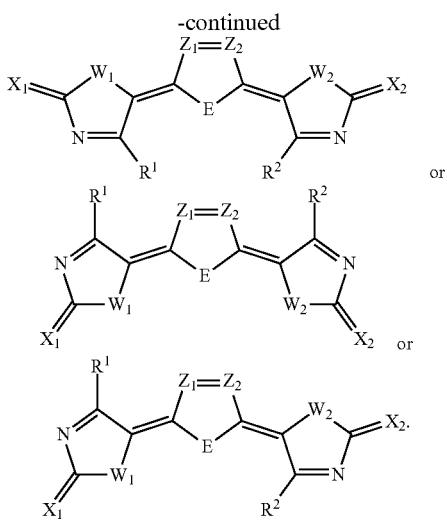

According to an embodiment of the present disclosure, wherein X is, at each occurrence identically or differently, selected from CR"R'".

According to an embodiment of the present disclosure, wherein W is, at each occurrence identically or differently, selected from O, S or Se.

According to an embodiment of the present disclosure, wherein W is, at each occurrence identically or differently, selected from O or S.

According to an embodiment of the present disclosure, wherein W is O.

According to an embodiment of the present disclosure, wherein W is, at each occurrence identically or differently, selected from $NR_N$, and $R_N$ is, at each occurrence identically or differently, selected from the group consisting of: substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted aralkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted alkynyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, and combinations thereof.

According to an embodiment of the present disclosure, wherein $R_N$ is, at each occurrence identically or differently, selected from the group consisting of: substituted or unsubstituted alkyl having 1 to 20 carbon atoms, substituted or unsubstituted cycloalkyl having 3 to 20 ring carbon atoms, substituted or unsubstituted aryl having 6 to 30 carbon atoms, substituted or unsubstituted heteroaryl having 3 to 30 carbon atoms, and combinations thereof.

According to an embodiment of the present disclosure, wherein R is, at each occurrence identically or differently, a group having at least one electron-withdrawing group.

According to an embodiment of the present disclosure, wherein each of R', R", R''', $R_L$, $R_N$ is a group having at least one electron-withdrawing group.

According to an embodiment of the present disclosure, wherein at least one of R is a group having an electron-withdrawing group; and/or each of R', R", R''', $R_L$, $R_N$ and $R_{NJ}$ is a group having at least one electron-withdrawing group.

According to an embodiment of the present disclosure, wherein R is, at each occurrence identically or differently, selected from substituted or unsubstituted aryl having 6 to 30 carbon atoms, substituted or unsubstituted heteroaryl having 3 to 30 carbon atoms, or combinations thereof.

According to an embodiment of the present disclosure, wherein R is, at each occurrence identically or differently, selected from aryl having 6 to 30 carbon atoms with at least one electron-withdrawing group substitute, heteroaryl having 3 to 30 carbon atoms with at least one electron-withdrawing group substitute, or combinations thereof.

According to an embodiment of the present disclosure, wherein the Hammett constant of the electron-withdrawing group is greater than or equal to 0.05.

According to an embodiment of the present disclosure, wherein the Hammett constant of the electron-withdrawing group is greater than or equal to 0.3.

According to an embodiment of the present disclosure, wherein the Hammett constant of the electron-withdrawing group is greater than or equal to 0.5.

In the present disclosure, the Hammett substituent constant value of the electron-withdrawing group is greater than or equal to 0.05, the electron-withdrawing ability is strong, which can significantly reduce the LUMO energy level of the compound of the present disclosure and achieve the effect of improving the charge mobility.

It is to be noted that the Hammett substituent constant value includes para- and/or meta-Hammett substituent constants. As long as one of the para constant and meta constant is greater than or equal to 0.05, the substituent can be used as the group selected in the present disclosure.

According to an embodiment of the present disclosure, wherein the electron-withdrawing group is selected from the group consisting of: halogen, a nitroso group, a nitro group, an acyl group, a carbonyl group, a carboxylic acid group, an ester group, a cyano group, an isocyano group, SCN, OCN, $SF_5$, a boranyl group, a sulfinyl group, a sulfonyl group, a phosphoroso group, an aza-aromatic ring group, or any one of the following groups substituted by one or more of halogen, a nitroso group, a nitro group, an acyl group, a carbonyl group, a carboxylic acid group, an ester group, a cyano group, an isocyano group, SCN, OCN, $SF_5$, a boranyl group, a sulfinyl group, a sulfonyl group, a phosphoroso group, and an aza-aromatic ring group: alkyl having 1 to 20 carbon atoms, cycloalkyl having 3 to 20 ring carbon atoms, heteroalkyl having 1 to 20 carbon atoms, a heterocyclic group having 3 to 20 ring atoms, aralkyl having 7 to 30 carbon atoms, alkoxy having 1 to 20 carbon atoms, aryloxy having 6 to 30 carbon atoms, alkenyl having 2 to 20 carbon atoms, alkynyl having 2 to 20 carbon atoms, aryl having 6 to 30 carbon atoms, heteroaryl having 3 to 30 carbon atoms, alkylsilyl having 3 to 20 carbon atoms, arylsilyl having 6 to 20 carbon atoms, substituted or unsubstituted alkylgermanyl having 3 to 20 carbon atoms, substituted or unsubstituted arylgermanyl having 6 to 20 carbon atoms, and combinations thereof.

According to an embodiment of the present disclosure, wherein the electron-withdrawing group is selected from a group consisting of: F, $CF_3$, $CHF_2$, $OCF_3$, $SF_5$, $SO_2CF_3$, a cyano group, an isocyano group, SCN, OCN, a pyrimidinyl group, a triazinyl group, and combinations thereof.

According to an embodiment of the present disclosure, wherein X is, at each occurrence identically or differently, selected from the group consisting of the following structures:
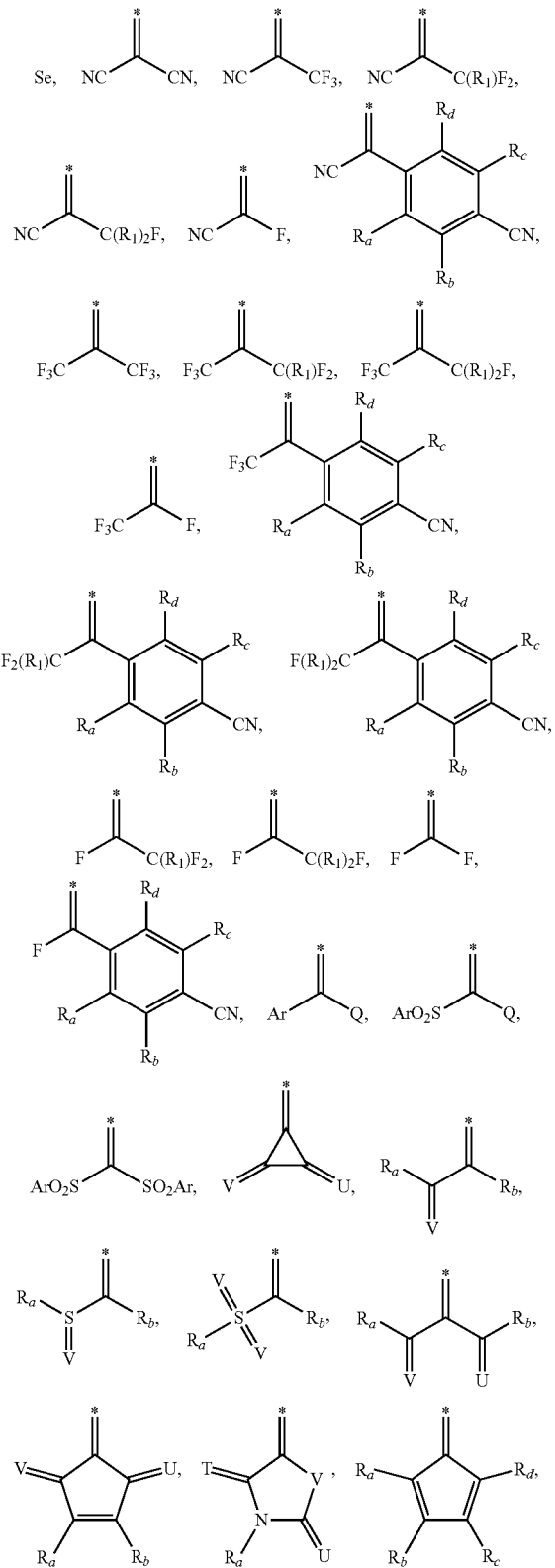
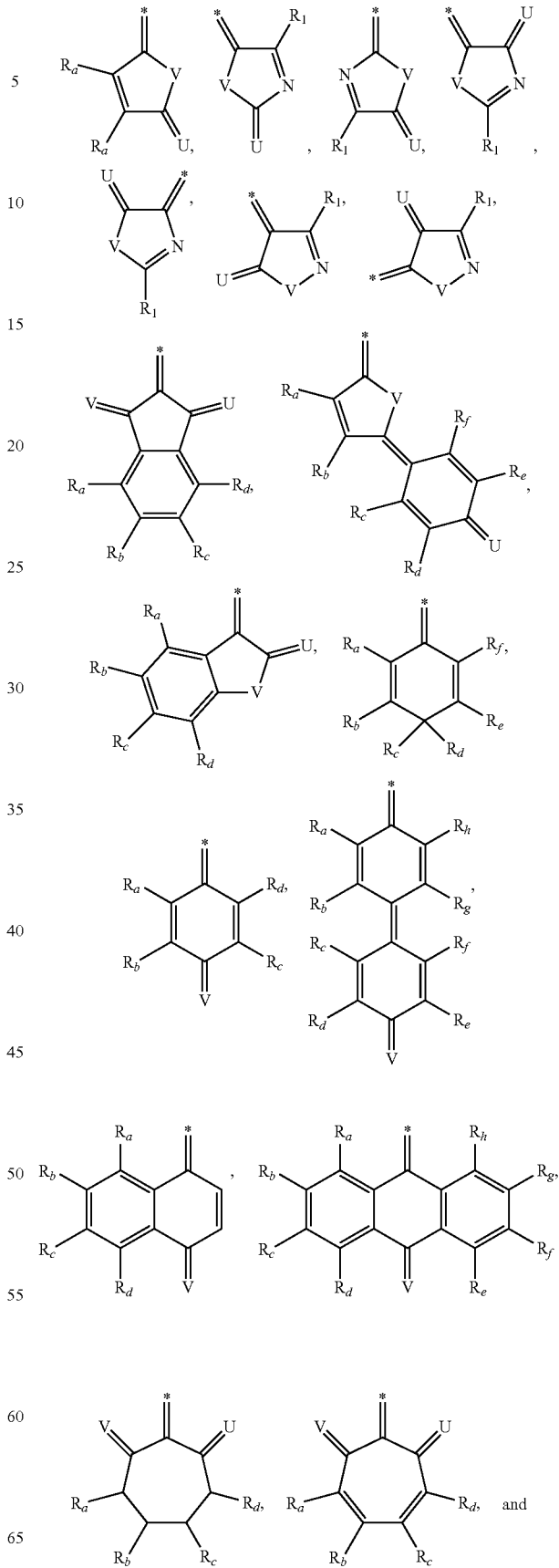

-continued

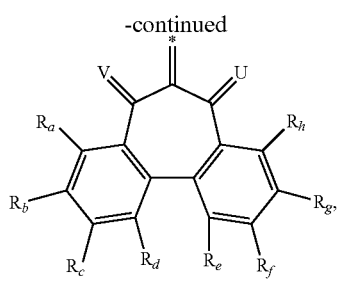

wherein V, U, and T are, at each occurrence identically or differently, selected from the group consisting of $CR_vR_u$, $NR_v$, O, S, and Se;

wherein Ar is, at each occurrence identically or differently, selected from substituted or unsubstituted aryl having 6 to 30 carbon atoms or substituted or unsubstituted heteroaryl having 3 to 30 carbon atoms;

wherein $R_1$, Q, $R_a$, $R_b$, $R_c$, $R_d$, $R_e$, $R_f$, $R_g$, $R_h$, $R_v$, and $R_u$ are, at each occurrence identically or differently, selected from the group consisting of: hydrogen, deuterium, halogen, a nitroso group, a nitro group, an acyl group, a carbonyl group, a carboxylic acid group, an ester group, a cyano group, an isocyano group, SCN, OCN, $SF_5$, a boranyl group, a sulfinyl group, a sulfonyl group, a phosphoroso group, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted aralkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted alkynyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted alkylgermanyl having 3 to 20 carbon atoms, substituted or unsubstituted arylgermanyl having 6 to 20 carbon atoms, and combinations thereof;

preferably, $R_1$ is, at each occurrence identically or differently, selected from the group consisting of: F, $CF_3$, $OCF_3$, $SF_5$, $SO_2CF_3$, a cyano group, an isocyano group, SCN, OCN, pentafluorophenyl, 4-cyanotetrafluorophenyl, tetrafluoropyridyl, a pyrimidinyl group, a triazinyl group, and combinations thereof;

wherein Q is a group having at least one electron-withdrawing group, and for any one of the preceding structures, when one or more of $R_a$, $R_b$, $R_c$, $R_d$, $R_e$, $R_f$, $R_g$, $R_h$, $R_v$, and $R_u$ occur, at least one of $R_a$, $R_b$, $R_c$, $R_d$, $R_e$, $R_f$, $R_g$, $R_h$, $R_v$, and $R_u$ is a group having at least one electron-withdrawing group; preferably, the group having at least one electron-withdrawing group is selected from the group consisting of: F, $CF_3$, $OCF_3$, $SF_5$, $SO_2CF_3$, a cyano group, an isocyano group, SCN, OCN, pentafluorophenyl, 4-cyanotetrafluorophenyl, tetrafluoropyridyl, a pyrimidinyl group, a triazinyl group, and combinations thereof;

adjacent substituents $R_1$, $R_a$, $R_b$, $R_c$, $R_d$, $R_e$, $R_f$, $R_g$, $R_h$, $R_v$, and $R_u$ can be optionally joined to form a ring;

"*" represents a position where X having the preceding structures is connected to ring A in Formula 1.

According to an embodiment of the present disclosure, wherein X is, at each occurrence identically or differently, selected from the group consisting of the following structures:

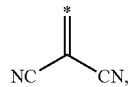 A1

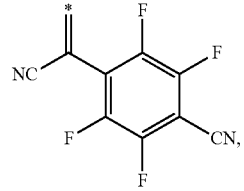 A2

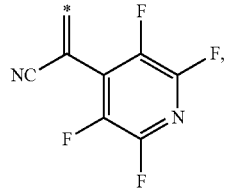 A3

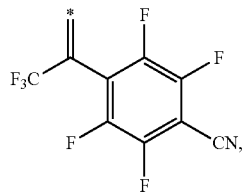 A4

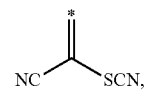 A5

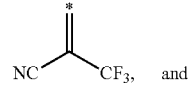 A6

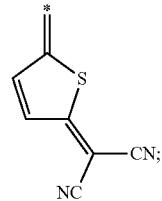 A7

"*" represents a position where X having the preceding structures is connected to five-membered ring in Formula 1.

According to an embodiment of the present disclosure, wherein X is selected from

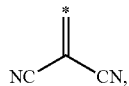   A1

"*" represents a position where X having the preceding structures is connected to five-membered ring in Formula 1.

According to an embodiment of the present disclosure, wherein R, $R_L$, $R_N$, and $R_{NJ}$ are, at each occurrence identically or differently, selected from the group consisting of: hydrogen, deuterium, halogen, a nitroso group, a nitro group, an acyl group, a carbonyl group, a carboxylic acid group, an ester group, a cyano group, an isocyano group, SCN, OCN, $SF_5$, a boranyl group, a sulfinyl group, a sulfonyl group, a phosphoroso group, a hydroxyl group, a sulfanyl group, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted aralkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted alkynyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted alkylgermanyl having 3 to 20 carbon atoms, substituted or unsubstituted arylgermanyl having 6 to 20 carbon atoms, and combinations thereof.

According to an embodiment of the present disclosure, wherein R, $R_L$, $R_N$, and $R_{NJ}$ are, at each occurrence identically or differently, selected from the group consisting of: hydrogen, deuterium, a methyl group, an isopropyl group, $NO_2$, $SO_2CH_3$, $SCF_3$, $C_2F_5$, $OC_2F_5$, diphenylmethylsilyl, a phenyl group, methoxyphenyl, p-methylphenyl, 2,6-diisopropylphenyl, a biphenylyl group, polyfluorophenyl, difluopyridyl, nitrophenyl, dimethylthiazolyl, CN, a vinyl group substituted by one or more of CN or $CF_3$, an acetenyl group substituted by one of CN or $CF_3$, dimethylphosphoryl, diphenylphosphoryl, F, $CF_3$, $OCF_3$, $SF_5$, $SO_2CF_3$, a cyano group, an isocyano group, SCN, OCN, trifluoromethylphenyl, trifluoromethoxyphenyl, bis(trifluoromethyl)phenyl, bis(trifluoromethoxy)phenyl, 4-cyanotetrafluorophenyl, a phenyl or biphenylyl group substituted by one or more of F, CN or $CF_3$, tetrafluoropyridyl, a pyrimidinyl group, a triazinyl group, a pyridyl group, diphenylboryl, phenoxaborin, and combinations thereof.

According to an embodiment of the present disclosure, wherein R, $R_L$, $R_N$, and $R_{NJ}$ are, at each occurrence identically or differently, selected from the group consisting of the following structures:

   B1

   B2

   B3

   B4

   B5

   B6

   B7

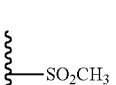   B8

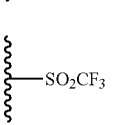   B9

   B10

   B11

   B12

   B13

   B14

   B15

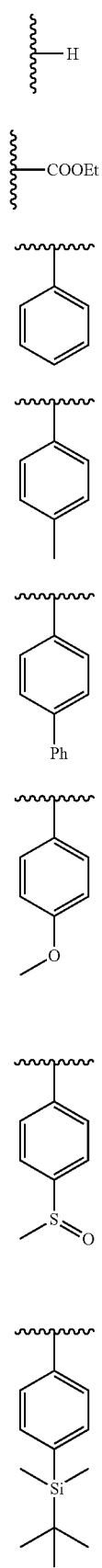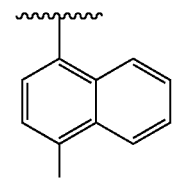

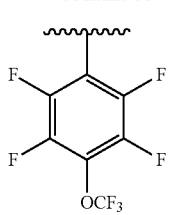 B33
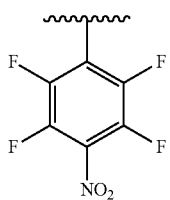 B34
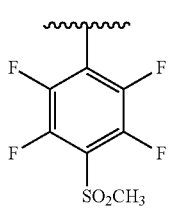 B35
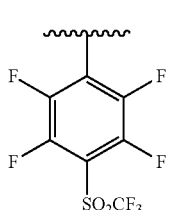 B36
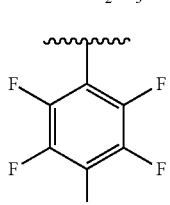 B37
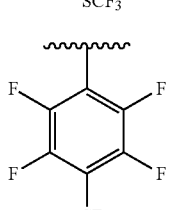 B38
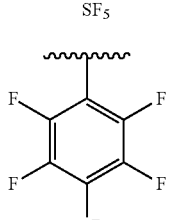 B39
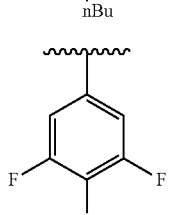 B40
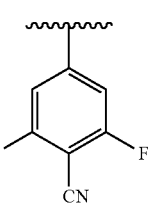 B41
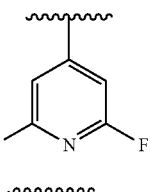 B42
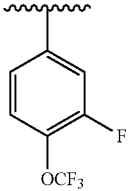 B43
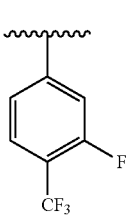 B44
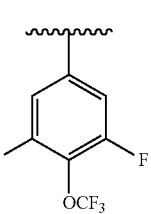 B45
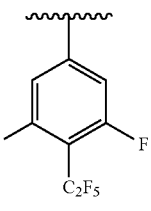 B46
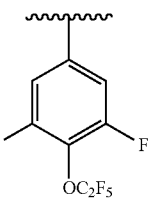 B47
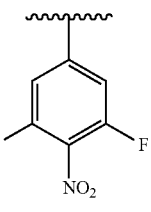 B48

-continued
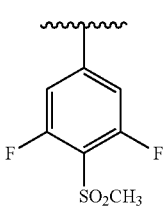 B49
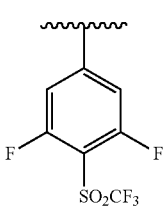 B50
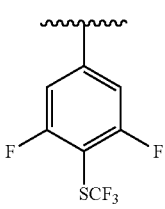 B51
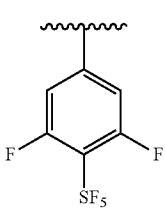 B52
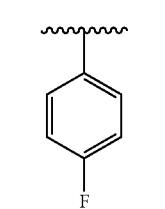 B53
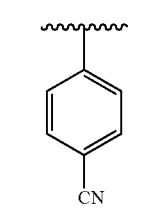 B54
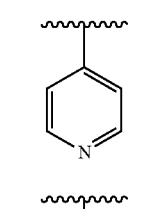 B55
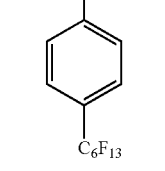 B56
-continued
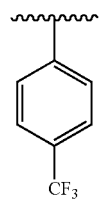 B57
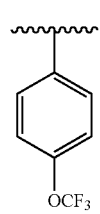 B58
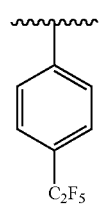 B59
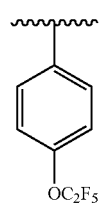 B60
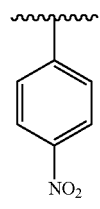 B61
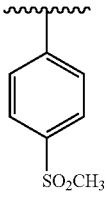 B62
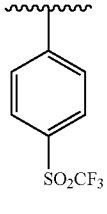 B63
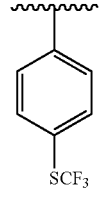 B64

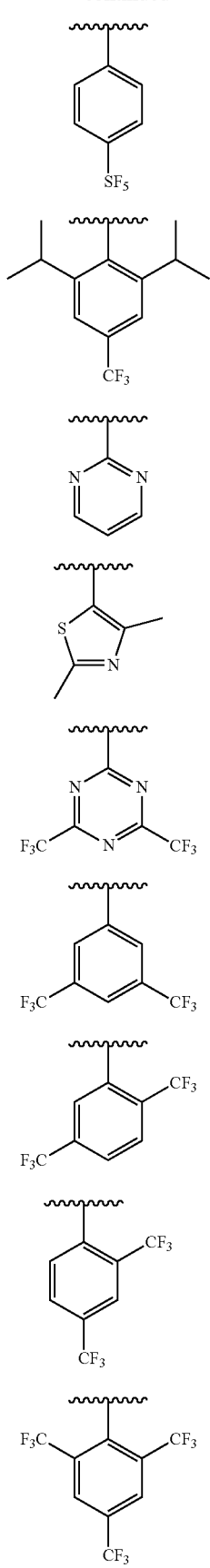
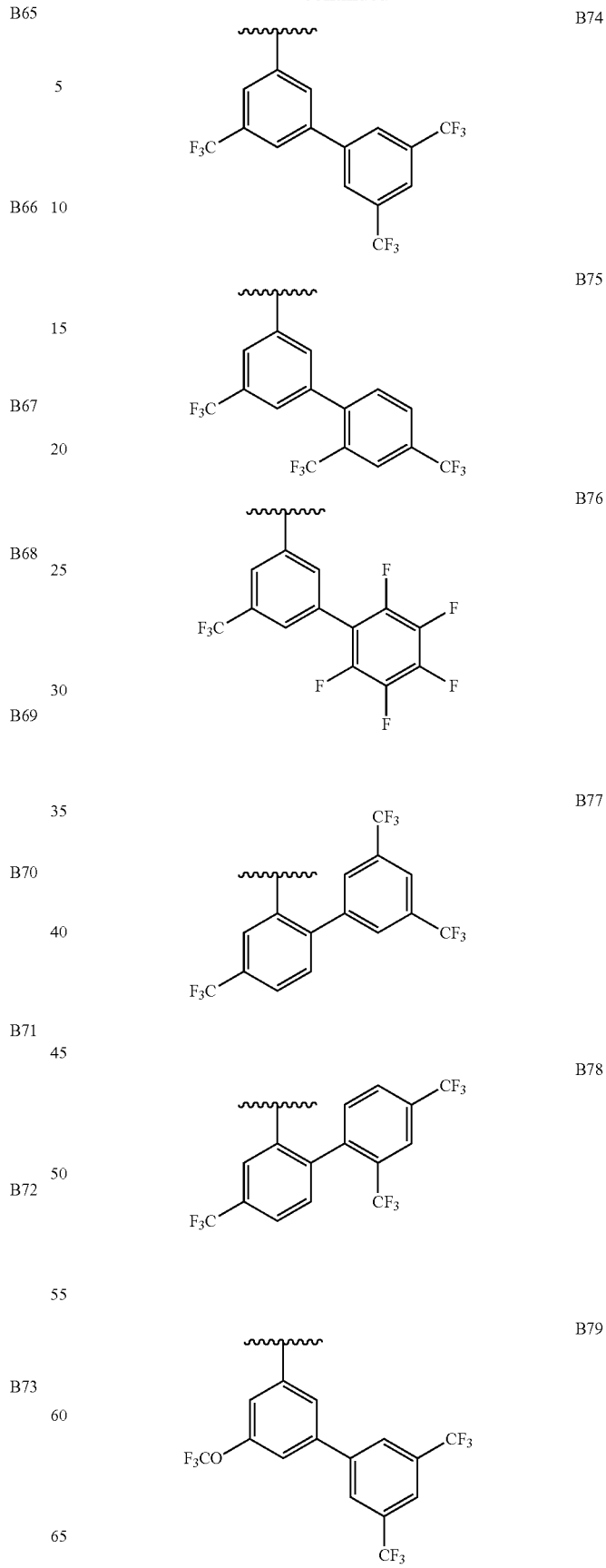

| | |
|---|---|
| 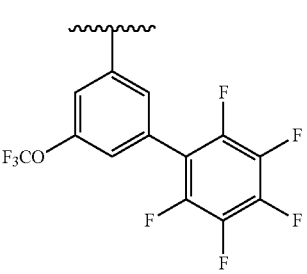 B80 | 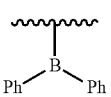 B89 |
| 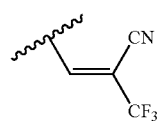 B81 | 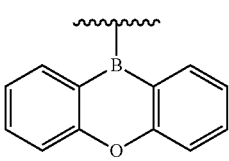 B90 |
| 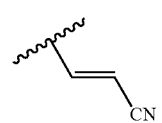 B82 | 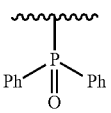 B91 |
| 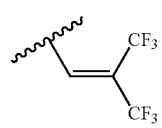 B83 | 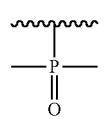 B92 |
| 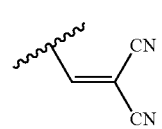 B84 | 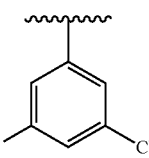 B93 |
| 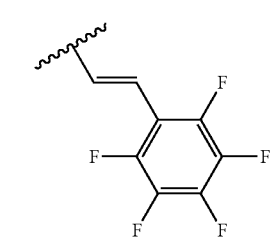 B85 | 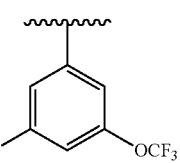 B94 |
| 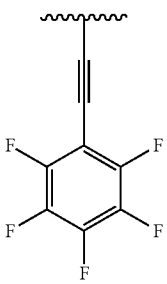 B86 | 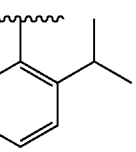 B95 |
| 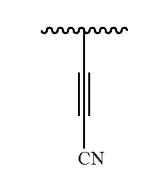 B87 | 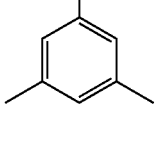 B96 |
| 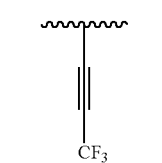 B88 | 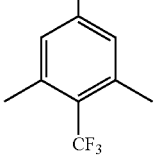 B97 |
| | 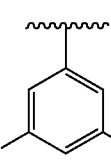 B98 |

-continued
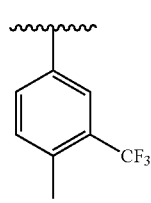 B99
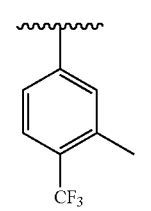 B100
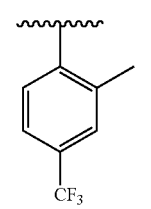 B101
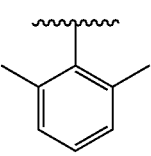 B102
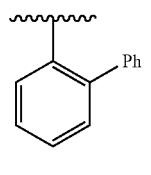 B103
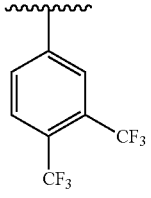 B104
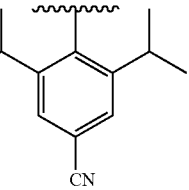 B105
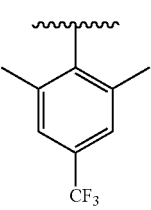 B106
-continued
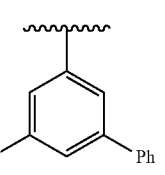 B107
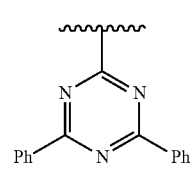 B108
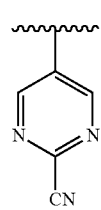 B109
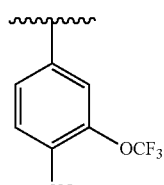 B110
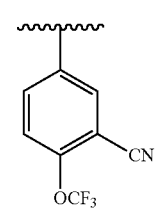 B111
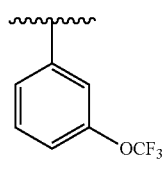 B112
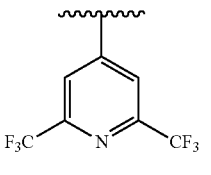 B113
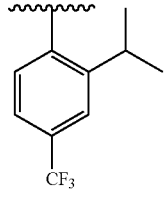 B114

B115 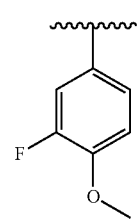

B116 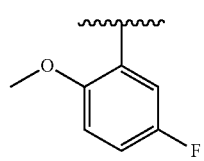

B117 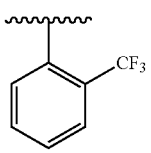

B118 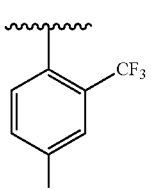

B119 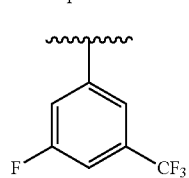

B120 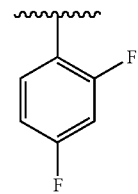

B121 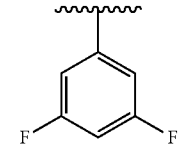

B122 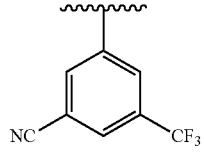

B123 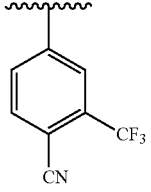

B124 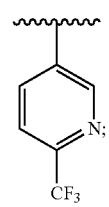

in the above structure, Ph represents phenyl;

wherein "—" represents a position where R having the preceding structures is connected to Formula 1 and a position where $R_L$ having the preceding structures is connected to L; "—" further represents a position where $R_{NJ}$ is connected to N when J is selected from $NR_{NJ}$; and "—" further represents a position where $R_N$ is connected to N when W is selected from $NR_N$.

According to an embodiment of the present disclosure, wherein R, $R_L$, $R_N$, and $R_{NJ}$ are, at each occurrence identically or differently, selected from the group consisting of the following:

B6 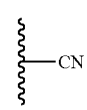

B13 

B14 

B16 

B17 

B18 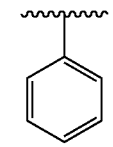

B25 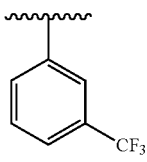

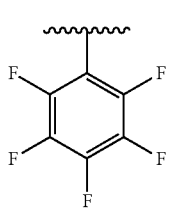 B27
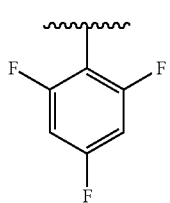 B28
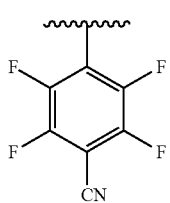 B30
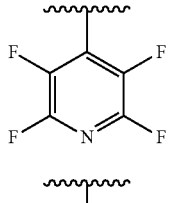 B31
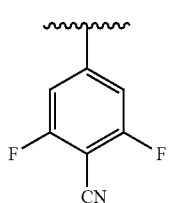 B40
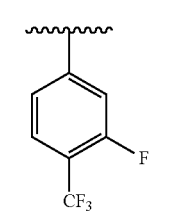 B41
B42
B44
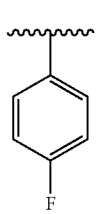 B53
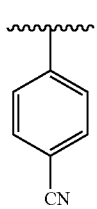 B54
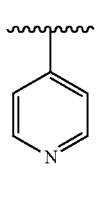 B55
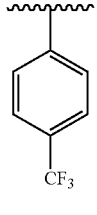 B57
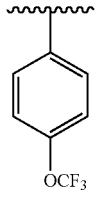 B58
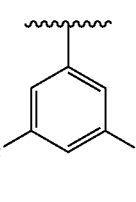 B70
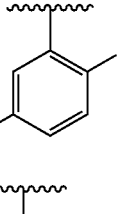 B71
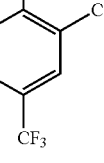 B72

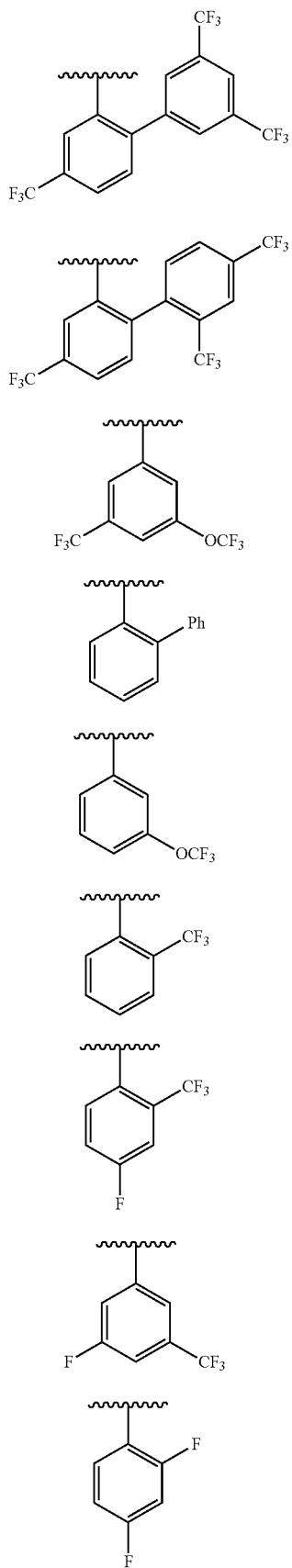
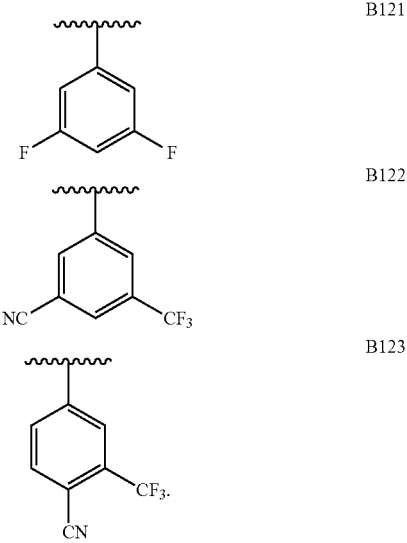

According to an embodiment of the present disclosure, wherein X is selected from NR' or CR"R'", at least one of R', R" and R'" is a group having at least one electron-withdrawing group; adjacent substituents R" and R'" are not connected to form a ring.

According to an embodiment of the present disclosure, wherein the compound is selected from the group consisting of: Compound LIO-1 to Compound LIO-108, Compound LIIO-1 to Compound LIIO-396, Compound LIIIO-1 to Compound LIIIO-298, Compound LIVO-1 to Compound LIVO-108, Compound LVO-1 to Compound LVO-108, Compound LVIO-1 to Compound LVIO-298, Compound LVIIO-1 to Compound LVIIO-298, Compound LVIIIO-1 to Compound LVIIIO-108, Compound LIXO-1 to Compound LIXO-298, Compound LXO-1 to Compound LXO-298, Compound LXIO-1 to Compound LXIO-66, Compound LXIA-1 to Compound LXIA-42, Compound LXIIO-1 to Compound LXIIO-66, Compound LXIIA-1 to Compound LXIIA-42, Compound LXIIIO-1 to Compound LXIIIO-66, and Compound LXIIIA-1 to Compound LXIIIA-42, Compound LXIVO-1 to Compound LXIVO-66, Compound LXIVA-1 to Compound LXIVA-42, Compound LXVO-1 to Compound LXVO-66, Compound LXVA-1 to Compound LXVA-42, Compound LXVIO-1 to Compound LXVIO-66, Compound LXVIA-1 to Compound LXVIA-42, Compound LXVIIO-1 to Compound LXVIIO-66, Compound LXVIIA-1 to Compound LXVIIA-42, Compound LXVIIIO-1 to Compound LXVIIIO-66, Compound LXVIIIA-1 to Compound LXVIIIA-42, Compound LXIXO-1 to Compound LXIXO-66, Compound LXIXA-1 to Compound LXIXA-42, Compound LXXO-1 to Compound LXXO-66, Compound LXXA-1 to Compound LXXA-42, Compound LXXIO-1 to Compound LXXIO-66, Compound LXXIA-1 to Compound LXXIA-42, Compound LXXIIO-1 to Compound LXXIIO-66, Compound LXXIIA-1 to Compound LXXIIA-42, Compound LXXIIIO-1 to Compound LXXIIIO-66, Compound LXXIIIA-1 to Compound LXXIIIA-42, Compound LXXIVO-1 to Compound LXXIVO-66, Compound LXXIVA-1 to Compound LXXIVA-42, Compound LXXVO-1 to Compound LXXVO-66, Compound LXXVA-1 to Compound LXXVA-42, Compound LXXVIO-1 to Compound LXXVIO-66, Compound LXXVIA-1 to Compound LXXVIA-42, Compound LXXVIIO-1 to Compound LXXVIIO-66, Compound LXXVIIA-1 to Compound LXXVIIA-42, Compound LXXVIIIO-1 to Compound LXXVIIIO-66, Compound LXXVIIIA-1 to Compound LXXVIIIA-42, Compound LXXIXO-1 to Compound LXXIXO-66, Compound LXXIXA-1 to Compound LXXIXA-42, Compound LXXXO-1 to Compound LXXXO-66, Compound LXXXA-1 to Compound LXXXA-42, Compound LXXXIO-1 to Compound LXXXIO-66, Compound LXXXIA-1 to Compound LXXXIA-42, Compound LXXXIIO-1 to Compound LXXXIIO-66, Compound LXXXIIA-1 to Compound LXXXIIA-42, Compound LXXXIIIO-1 to Compound LXXXIIIO-66, Compound LXXXIIIA-1 to Compound LXXXIIIA-42, Compound LXXXIVO-1 to Compound LXXXIVO-66, Compound LXXXIVA-1 to Compound LXXXIVA-42, Compound LXXXVO-1 to Compound LXXXVO-66, Compound LXXXVA-1 to Compound LXXXVA-42, Compound LVI-IO-1 to Compound LVI-IO-138 and Compound LXV-IO-1 to Compound LXV-IO-60, the specific structures of above compounds are shown in claim 16.

According to an embodiment of the present disclosure, disclosed is an organic electronic device which includes:
an anode,
a cathode, and
an organic layer disposed between the anode and the cathode, wherein the organic layer includes the compound described in any one of the preceding embodiments.

According to an embodiment of the present disclosure, wherein the organic layer is a hole injection layer or a hole transporting layer, and the hole injection layer or the hole transporting layer is formed by the compound alone.

According to an embodiment of the present disclosure, wherein the organic layer is a hole injection layer or a hole transporting layer, and the hole injection layer or the hole transporting layer further includes at least one hole transporting material; wherein the molar doping ratio of the compound to the hole transporting material ranges from 10000:1 to 1:10000.

According to an embodiment of the present disclosure, wherein the molar ratio of the compound to the hole transporting material ranges from 10:1 to 1:100.

According to an embodiment of the present disclosure, wherein the electroluminescent device includes a plurality of stack layers between the anode and the cathode, and the plurality of stack layers include a first emissive layer and a second emissive layer, wherein a first stack layer includes the first emissive layer, a second stack layer includes the second emissive layer, and a charge generation layer is disposed between the first stack layer and the second stack layer, wherein the charge generation layer includes a p-type charge generation layer and an n-type charge generation layer; wherein the p-type charge generation layer includes the compound.

According to an embodiment of the present disclosure, the p-type charge generation layer further includes at least one hole transporting material, wherein the molar doping ratio of the compound to the hole transporting material ranges from 10000:1 to 1:10000.

According to an embodiment of the present disclosure, wherein the molar doping ratio of the compound to the hole transporting material ranges from 10:1 to 1:100.

According to an embodiment of the present disclosure, wherein the hole transporting material includes a compound having a triarylamine unit, a spirobifluorene compound, a pentacene compound, an oligothiophene compound, an oligomeric phenyl compound, an oligomeric phenylenevinyl compound, an oligomeric fluorene compound, a porphyrin complex or a metal phthalocyanine complex.

According to an embodiment of the present disclosure, wherein the charge generation layer further includes a buffer layer disposed between the p-type charge generation layer and the n-type charge generation layer, and the buffer layer includes the compound.

According to an embodiment of the present disclosure, the electroluminescent device is prepared by vacuum evaporation.

According to an embodiment of the present disclosure, further disclosed is a compound composition which includes the compound described in any one of the preceding embodiments.

Combination with Other Materials

The materials described in the present disclosure for a particular layer in an organic light-emitting device can be used in combination with various other materials present in the device. The combinations of these materials are described in more detail in U.S. Pat. App. No. 20160359122 at paragraphs 0132-0161, which is incorporated by reference herein in its entirety. The materials described or referred to the disclosure are non-limiting examples of materials that may be useful in combination with the compounds disclosed herein, and one of skill in the art can readily consult the literature to identify other materials that may be useful in combination.

The materials described herein as useful for a particular layer in an organic light-emitting device may be used in combination with a variety of other materials present in the device. For example, compounds disclosed herein may be used in combination with a wide variety of luminescent dopant, hosts, transport layers, blocking layers, injection layers, electrodes and other layers that may be present. The combination of these materials is described in detail in paragraphs 0080-0101 of U.S. Pat. App. No. 20150349273, which is incorporated by reference herein in its entirety. The materials described or referred to the disclosure are non-limiting examples of materials that may be useful in combination with the compounds disclosed herein, and one of skill in the art can readily consult the literature to identify other materials that may be useful in combination.

In the embodiments of material synthesis, all reactions were performed under nitrogen protection unless otherwise stated. All reaction solvents were anhydrous and used as received from commercial sources. Synthetic products were structurally confirmed and tested for properties using one or more conventional equipment in the art (including, but not limited to, nuclear magnetic resonance instrument produced by BRUKER, liquid chromatograph produced by SHIMADZU, liquid chromatograph-mass spectrometry produced by SHIMADZU, gas chromatograph-mass spectrometry produced by SHIMADZU, differential Scanning calorimeters produced by SHIMADZU, fluorescence spectrophotometer produced by SHANGHAI LENGGUANG TECH., electrochemical workstation produced by WUHAN CORRTEST, and sublimation apparatus produced by ANHUI BEQ, etc.) by methods well known to the persons skilled in the art. As the persons skilled in the art are aware of the above-mentioned equipment use, test methods and other related contents, the inherent data of the sample can be obtained with certainty and without influence, so the above related contents are not further described in this patent.

The measured LUMO energy levels obtained herein were used to determine the electrochemical properties of the compound by cyclic voltammetry. The CorrTest CS120 electrochemical workstation produced by Wuhan Conrtest Instruments Corp., Ltd was used. The three-electrode working system was as follows: the platinum disk electrode was used as the working electrode, the Ag/AgNO$_3$ electrode was used as the reference electrode, and the platinum wire electrode was used as the auxiliary electrode. With anhydrous DCM or DMF as the solvent and 0.1 mol/L tetrabutylammonium hexafluorophosphate as the supporting electrolyte, the target compound was prepared into 10-3 mol/L solution. Before testing, nitrogen was introduced into the solution for 10 minutes to deoxidize. The instrument parameters were as follows: the scanning rate was 100 mV/s, the potential interval was 0.5 mV, and the test window was 1 V to 0.5 V.

MATERIAL SYNTHESIS EXAMPLE

The method for preparing the compound of the present disclosure is not limited herein. Typically, the following compounds are used as examples without limitations, and synthesis routes and preparation methods thereof are described below.

Synthesis Example 1: Synthesis of Compound LIIO-4

Step 1: Synthesis of [Intermediate 1-a]

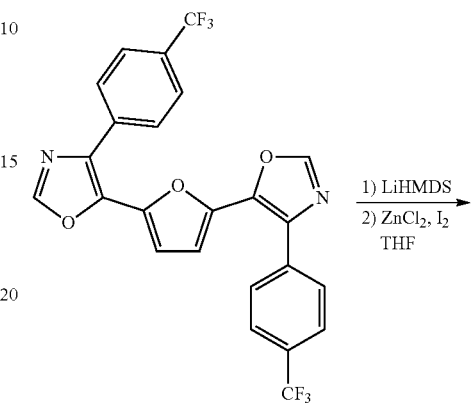

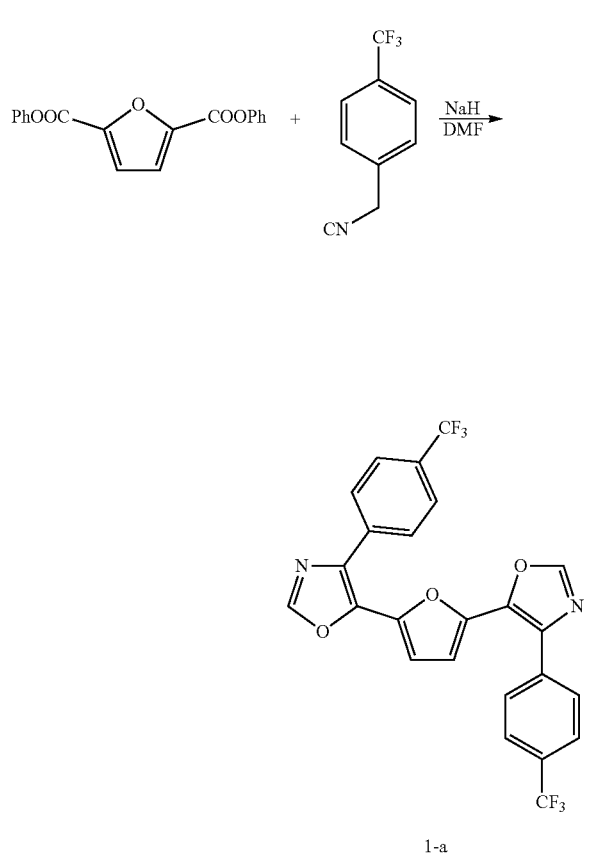

1-a

In a 1 L flask, add diphenyl furandicarboxylate (13.7 g, 44.5 mmol), dissolve it with DMF (320 mL), add 4-trifluoromethylbenzylisocyanide (32.3 g, 175 mmol), and then slowly add NaH (0.26 g, 6.5 mmol, 60% content), and keep reacting in dry air for 4 days. The reaction was tracked and monitored by GC-MS. After the reaction was complete, the solvent was directly spin-dried, and purified by silica gel column chromatography (DCM/PE=1/1 as eluent) to obtain a pale yellow solid product Intermediate 1-a (17.8 g, 82% yield).

Step 2: Synthesis of [Intermediate 1-b]

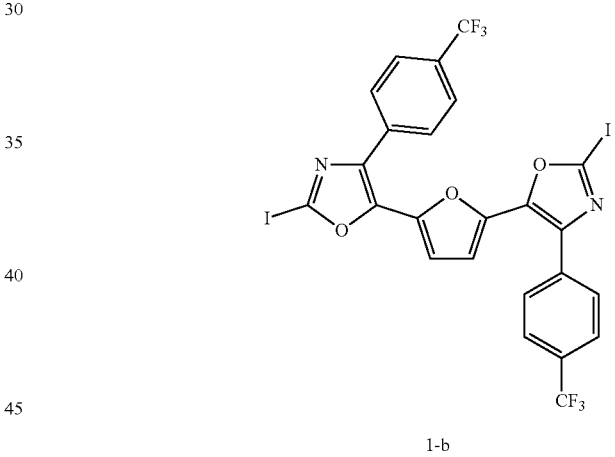

1-b

Under nitrogen protection, Intermediate 1-a (17.8 g, 36.3 mmol) was added to THF (50 mL), the temperature was reduced to −72° C. (by ethanol/dry ice), LiHMDS (lithium bis(trimethylsilyl)amide) solution (1.0 M, 150 mL) was slowly dropped, then the temperature was slowly raised to −30° C., and the reaction proceeded for 0.5 hours. ZnCl$_2$ (2.0 M, 75 mL) solution was dropped at −30° C., the temperature was slowly raised to 0° C., and the reaction proceeded for 10 minutes. Elemental solid iodine (37.2 g, 146 mmol) was added to the reaction solution, and the reaction proceeded at 0° C. for 2 hours. After the reaction was complete, the reaction was quenched with saturated NH$_4$Cl solution. The reaction product was washed with saturated sodium thiosulfate solution, extracted with DCM, dried with anhydrous Na$_2$SO$_4$, and then filtered, and the solvent was removed through rotary evaporation. The product Intermediate Intermediate 1-b (25.3 g, with a yield of 93%) as white solids was obtained by column chromatography on silica gel (with DCM/PE=½ as the eluent).

Step 3: Synthesis of [Intermediate 1-c]

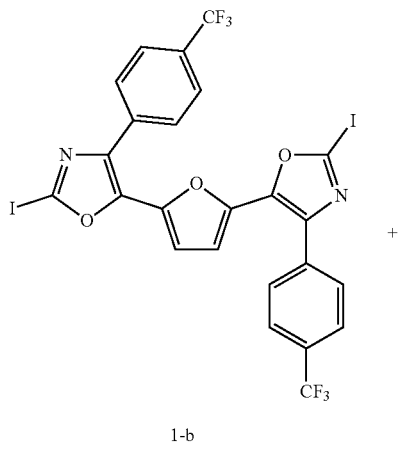

1-b

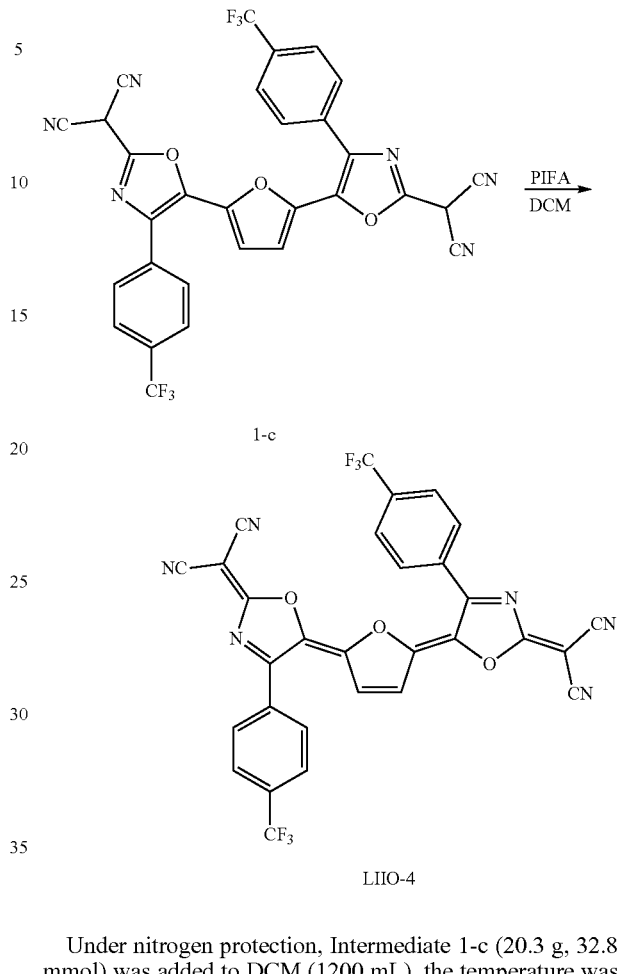

Under nitrogen protection, malononitrile (9.7 g, 147 mmol) was added to anhydrous DMF (360 mL), and K$_2$CO$_3$ (20.5 g, 148 mmol) was added portion-wise at 0° C. and stirred for 30 minutes. Then Intermediate 1-b (25.3 g, 34.0 mmol) and Pd(PPh$_4$)$_3$ (2.94 g, 2.54 mmol) were added, the temperature was raised to 80° C., and the reaction proceeded for 24 hours. After the complete conversion was achieved, the reaction product was poured into ice water, pH was adjusted to be less than 1 with 2N dilute hydrochloric acid, and then a large number of yellow solids were precipitated and then filtered. The filter cake was washed with a large amount of water and petroleum ether. The solid product was dissolved with acetone, rotate and evaporate until about 50 mL of acetone remains, and finally filtered to give yellow solids, the product was recrystallized with CH$_3$CN and DCM, and finally filtered to give a yellow solid Intermediate 1-c (20.3 g, 97% yield).

Step 4: Synthesis of Compound LIIO-4

Under nitrogen protection, Intermediate 1-c (20.3 g, 32.8 mmol) was added to DCM (1200 mL), the temperature was reduced to 0° C., PIFA ([bis(trifluoroacetoxy)iodo]benzene) (28.2 g, 65.6 mmol) was added portion-wise and stirred at room temperature for 3 days, and the solution was dark green, rotary evaporation to remove about 120 mL of DCM, add 100 mL of n-heptane to precipitate solids, and filter to give a black solid, the filtered product was continuously washed twice with DCM/PE=1:1 and finally to give LIIO-4 (9.0 g, with a yield of 44%) as black solids. The product was confirmed as the target product with a molecular weight of 616.1. The CV of Compound LIIO-4 was measured in DCM to obtain the LUMO of the compound, which was −4.79 eV.

Synthesis Example 2: Synthesis of Compound LIIO-5

Step 1: Synthesis of [Intermediate 2-a]

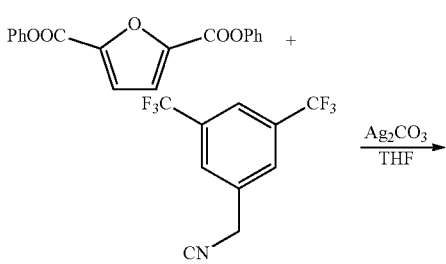

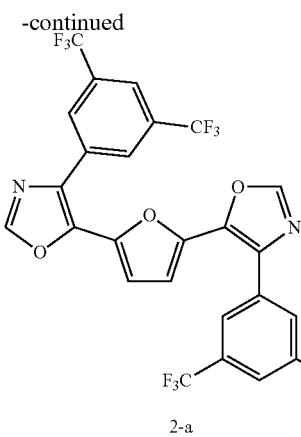

2-a

In a 500 mL flask, add diphenyl furandicarboxylate (6.5 g, 21.1 mmol), dissolve it with THF (240 mL), add 3,5-ditrifluoromethyl benzonitrile (25.5 g, 101 mmol), and then slowly add $Ag_2CO_3$ (0.52 g, 1.9 mmol), and react in dry air for 4 days. The reaction was tracked and monitored by GC-MS. After the reaction was complete, the solvent was directly spin-dried, and purified by silica gel column chromatography (DCM/PE=½ as eluent) to obtain a pale yellow solid product Intermediate 2-a (10.9 g, 82% yield).

Step 2: Synthesis of [Intermediate 2-b]

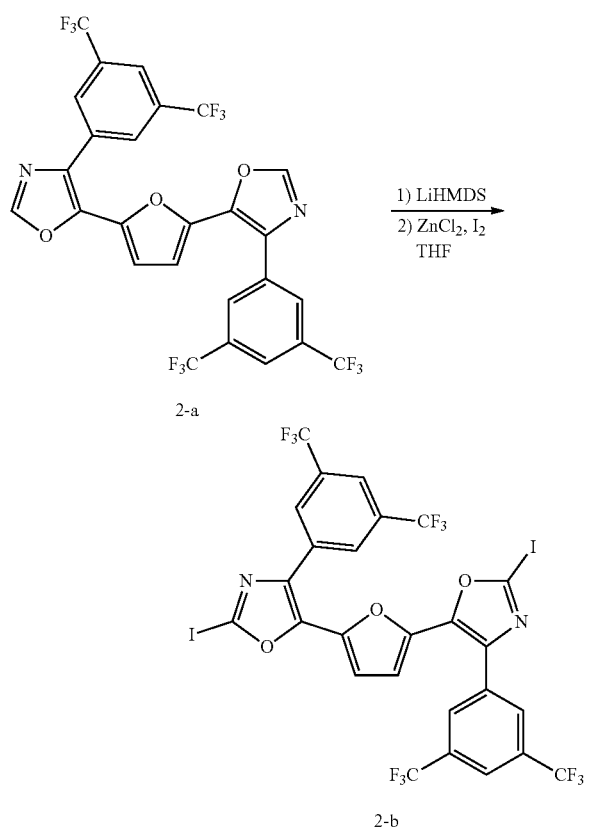

Under nitrogen protection, Intermediate 2-a (10.9 g, 17.4 mmol) was added to THF (180 mL), the temperature was reduced to −72° C. (by ethanol/dry ice), LiHMDS solution (1.0 M, 70 mL) was slowly dropped, then the temperature was slowly raised to −30° C., and the reaction proceeded for 2 hours. $ZnCl_2$ (2.0 M, 35 mL) solution was dropped at −30° C., the temperature was slowly raised to 0° C., and the reaction proceeded for 10 minutes. Elemental solid iodine (17.7 g, 69.7 mmol) was added to the reaction solution, and the reaction proceeded at room temperature for 1 hours. After the reaction was complete, the reaction was quenched with saturated $NH_4Cl$ solution. The reaction product was washed with saturated sodium thiosulfate solution, extracted with DCM, dried with anhydrous $Na_2SO_4$, and then filtered, and the solvent was removed through rotary evaporation. The product Intermediate 2-b (13.7 g, with a yield of 90%) as white solids was obtained by column chromatography on silica gel (with DCM/PE=¼ as the eluent).

Step 3: Synthesis of [Intermediate 2-c]

Under nitrogen protection, malononitrile (4.40 g, 66.7 mmol) was added to anhydrous DMF (180 mL), and $K_2CO_3$ (8.63 g, 62.4 mmol) was added portion-wise at 0° C. and stirred for 30 minutes. Then Intermediate 2-b (13.7 g, 15.6 mmol) and $Pd(PPh_4)_3$ (1.85 g, 1.60 mmol) were added, the temperature was raised to 80° C., and the reaction proceeded for 24 hours. After the complete conversion was achieved, the reaction product was poured into ice water, pH was adjusted to be less than 1 with 2N dilute hydrochloric acid, and then a large number of yellow solids were precipitated and then filtered, the filter cake was washed with a large amount of water and petroleum ether. The solid product was dissolved with acetone, the solvent was removed by rotary evaporation, and then the solid product was dried. Then be slurried twice with acetonitrile and dichloromethane, filtered, and washed with dichloromethane (20 mL) three times, to give yellow solids Intermediate 2-c (9.3 g, 79% yield).

Step 4: Synthesis of Compound LIIO-5

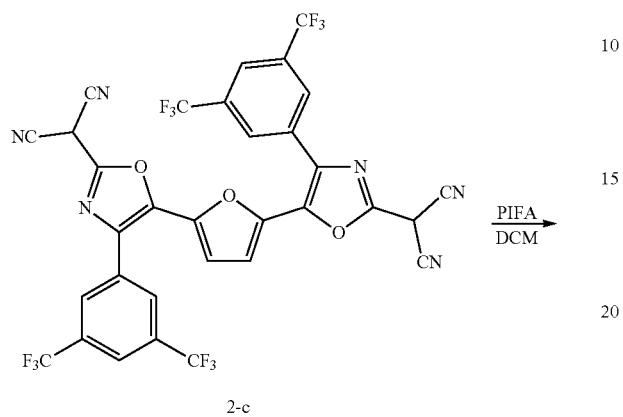

2-c

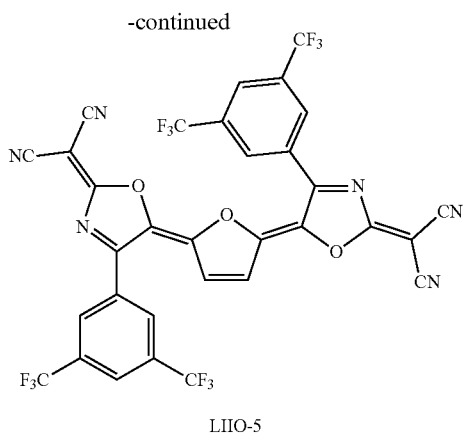

LIIO-5

Under nitrogen protection, Intermediate 2-c (9.3 g, 12.3 mmol) was added to DCM (1200 mL), the temperature was reduced to 0° C., PIFA (10.6 g, 24.7 mmol) was added portion-wise and stirred at room temperature for 2 days, and the solution was dark green, DCM was removed by rotary evaporation until the remaining DCM was about 150 mL, add 100 mL of n-heptane to precipitate solids, and filter to give a black solid, the filtered product was continuously washed twice with DCM/PE=1:1 and finally to give LIIO-5 (5.1 g, with a yield of 55%) as black solids. The product was confirmed as the target product with a molecular weight of 752.1. The CV of Compound LIIO-5 was measured in DCM to obtain the LUMO of the compound, which was −4.89 eV.

The LUMO energy levels of some of the compounds disclosed in the present disclosure were obtained by calculating [GAUSS-09, B3LYP/6-311G (d)] by DFT, and the related compounds and their LUMO values are shown in Tables 1.

TABLE 1

DFT calculation results

| Compound | LUMO(eV) | Compound | LUMO(eV) | Compound | LUMO(eV) |
|---|---|---|---|---|---|
| LIIO-4 | −5.06 | LIIO-5 | −5.17 | LIIO-6 | −5.04 |
| LIIO-16 | −5.18 | LIIO-17 | −5.29 | LIIO-18 | −5.14 |
| LIIO-28 | −5.32 | LIIO-29 | −5.45 | LIIO-40 | −5.66 |
| LIIO-41 | −5.80 | LIIIO-17 | −5.17 | LIVO-23 | −5.28 |
| LVO-23 | −5.29 | LVIO-11 | −5.15 | LVIO-12 | −5.03 |
| LVIO-22 | −5.12 | LVIO-23 | −5.27 | LVIO-24 | −5.14 |
| LVIO-29 | −5.44 | LVIO-34 | −5.27 | LVIO-35 | −5.41 |
| LVIIIO-5 | −5.49 | LIXO-23 | −5.22 | LXO-17 | −5.17 |
| LXIO-23 | −5.50 | LXIIO-23 | −5.55 | LXIIIO-23 | −5.60 |
| LXIVO-23 | −5.63 | LXVO-20 | −5.78 | LXVO-23 | −6.02 |
| LXVIO-5 | −5.37 | LXVIO-20 | −5.54 | LXVIO-6 | −5.25 |
| LXVIO-22 | −5.66 | LXVIO-23 | −5.80 | LXVIO-24 | −5.62 |
| LXVIIO-23 | −5.77 | LXVIIIO-2 | −5.28 | LXVIIIO-5 | −5.48 |
| LXVIIIO-6 | −5.45 | LXVIIIO-20 | −5.57 | LXVIIIO-22 | −5.74 |
| LXVIIIO-23 | −5.86 | LXVIIIO-24 | −5.71 | LXXO-23 | −5.71 |
| LXXIO-23 | −5.92 | LXXXIIIO-23 | −5.94 | LXXXIVO-23 | −5.57 |
| LXXXVO-23 | −5.47 | LVI-IO-64 | −5.69 | LXVI-IO-4 | −5.86 |

From the measured data for LUMO energy levels, it can be seen that the measured LUMO energy levels of the compound LIIO-4 and compound LIIO-5 of the present disclosure are −4.79 eV and −4.89 eV, which are deeper than the LUMO energy level −4.33 eV of HATCN (measured by the method of the present disclosure in DCM solvent), indicating that compound LIIO-4 and compound LIIO-5 have excellent hole injection capabilities.

The LUMO energy levels calculated by DFT of representative compounds with the structure of Formula 1 are shown in Table 1. It can be seen from the data that the compounds with different L structures in the present disclosure all have a deeper LUMO energy level, which is further explained the compounds with the structure of Formula 1 disclosed in the present disclosure all have a relatively deep LUMO energy level, and are potential compounds that can be used as a hole injection material in organic electronic devices.

The LUMO energy levels calculated of some compounds are shown in Table 1. Among them, the compound LXVIIIO-2, which does not have an electron withdrawing group in the substituent R and R$_L$ in the structure of Formula 1, already has a deeper LUMO energy level. However, when one of the substituents R and R$_L$ having at least one electron withdrawing group, the LUMO energy level is deeper, such as compound LXVIIIO-5, compound LXVIIIO-6 and compound LXVIIIO-20. Furthermore, in the compounds with different L structures, the compounds in which substituents R and R$_L$ both have an electron withdrawing group have a deeper LUMO energy level than the compound in which R or R$_L$ has an electron withdrawing group, for example, the compound in which L is five-membered heterocyclic skeleton, compound LIIO-16 vs. compound LIIO-4, compound LIIO-17 vs compound LIIO-5, compound LIIO-18 vs compound LIIO-6; the compound in which L is two-five-membered heterocyclic skeleton, compound LVIO-23 vs compound LVIO-11; the compound in which L is biphenyl skeleton, compound LXVO-23 vs. compound LXVO-20; the compound in which L is naphthalene skeleton, compound LXVIO-23 vs compound LXVIO-5, compound LXVIO-24 vs compound LXVIO-6, compound LXVIIIO-23 vs compound LXVIIIO-5. The above shows that the introduction of electron withdrawing groups in the compound of the present disclosure with the structure of Formula 1 is very important, which can reduce the LUMO energy level of the compound, and is of great significance in the study of hole transporting materials.

In summary, the compounds of the present disclosure have a relatively deep LUMO energy level, are very important charge transfer materials, especially have incomparable advantages in hole transporting, can be applied to organic semiconductor devices, and are suitable for different types of organic electronic devices, including but not limited to fluorescent OLEDs, phosphorescent OLEDs, white OLEDs, laminated OLEDs, OTFTs, OPVs, etc.

It should be understood that various embodiments described herein are examples and not intended to limit the scope of the present disclosure. Therefore, it is apparent to persons skilled in the art that the present disclosure as claimed may include variations of specific embodiments and preferred embodiments described herein. Many of the materials and structures described herein may be replaced with other materials and structures without departing from the spirit of the present disclosure. It should be understood that various theories as to why the present disclosure works are not intended to be limitative.

What is claimed is:

1. A compound, having a structure represented by Formula 1:

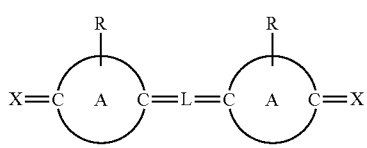

Formula 1 wherein,
L is, at each occurrence identically or differently, selected from

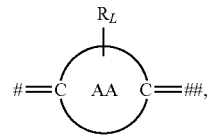

or any combination thereof;
ring AA is a conjugated structure having 4 to 30 ring atoms and comprising at least one intra-ring double bond;
ring A is, at each occurrence identically or differently, a 5-membered heterocyclic ring, and the 5-membered heterocyclic ring comprises an intra-ring double bond, three C atoms, one N atom, and one W; the W is, at each occurrence identically or differently, selected from the group consisting of O, S, Se, and NR$_N$;
X is, at each occurrence identically or differently, selected from the group consisting of Se, NR', and CR"R'";
R$_L$ represents, at each occurrence identically or differently, mono-substitution, multiple substitutions or non-substitution;
R, R', R", R'", R$_L$ and R$_N$ are, at each occurrence identically or differently, selected from the group consisting of: hydrogen, deuterium, halogen, a nitroso group, a nitro group, an acyl group, a carbonyl group, a carboxylic acid group, an ester group, a cyano group, an isocyano group, SCN, OCN, SF$_5$, a boranyl group, a sulfinyl group, a sulfonyl group, a phosphoroso group, a hydroxyl group, a sulfanyl group, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted aralkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted alkynyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted alkylgermanyl having 3 to 20 carbon atoms, substituted or unsubstituted arylgermanyl having 6 to 20 carbon atoms, and combinations thereof;
when X is selected from NR' or CR"R'", at least one of R', R", and R'" is a group having at least one electron-withdrawing group;
adjacent substituents R", R'" can be optionally joined to form a ring; and
adjacent substituents R, R$_L$ can be optionally joined to form a ring;
wherein "#" and "##" represent positions where L is connected to ring A.

2. The compound according to claim 1, wherein at least one of substituents R, R$_L$ and R$_N$ is a group having at least one electron-withdrawing group; preferably, at least one of R and $R_L$ is a group having at least one electron-withdrawing group.

3. The compound according to claim 1, wherein the structure of

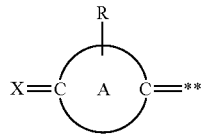

which is connected to both sides of L in Formula 1, at each occurrence identically or differently, selected from any one of the structures represented by Formula 2 to Formula 5:

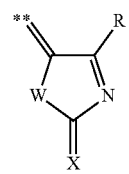

Formula 2

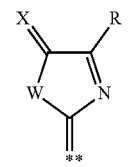

Formula 3

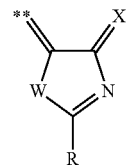

Formula 4

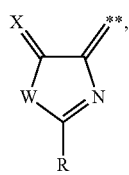

Formula 5 wherein, in Formula 2 to Formula 5,

X, W and R have the same definition as defined in claim 1; and

"**" represents a position where Formula 2 to Formula 5 are connected to L in Formula 1.

4. The compound according to claim 1, wherein, ring AA is a conjugated structure having 5-30 ring atoms and comprising at least one five-membered ring or six-membered ring;

preferably, ring AA is a conjugated structure having 5-30 ring atoms and comprising at least one five-membered ring.

5. The compound according to claim 1, wherein, L is, at each occurrence identically or differently, selected from structures represented by Formula 6 to Formula 41, or combinations thereof:

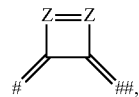

Formula 6

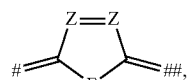

Formula 7

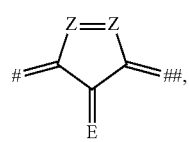

Formula 8

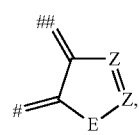

Formula 9

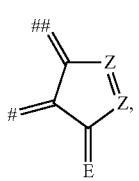

Formula 10

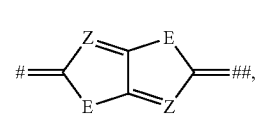

Formula 11

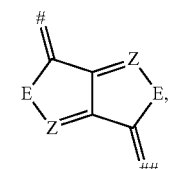

Formula 12

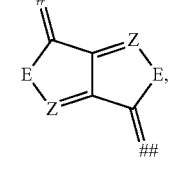

Formula 13

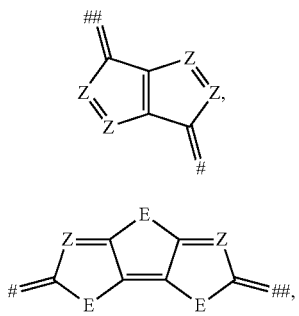

Formula 14

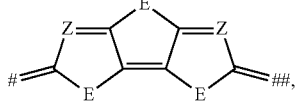

Formula 15

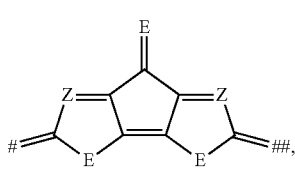

Formula 16

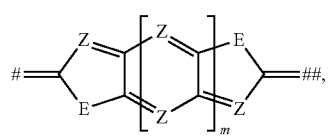

-continued
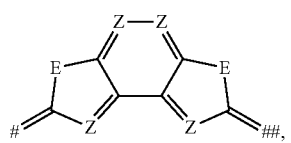
Formula 17
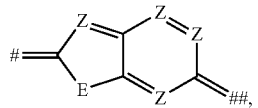
Formula 18
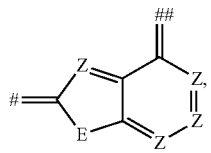
Formula 19
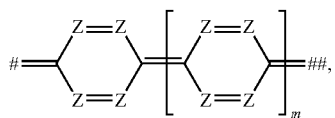
Formula 20
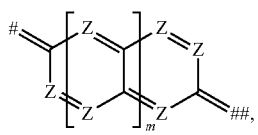
Formula 21
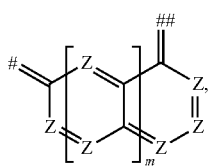
Formula 22
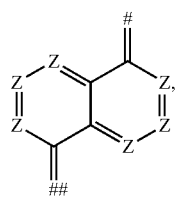
Formula 23
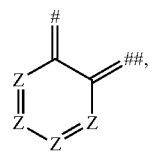
Formula 24
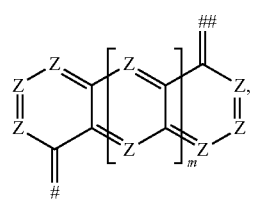
Formula 25
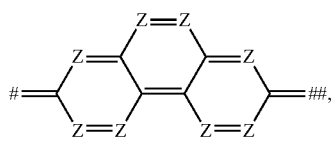
Formula 26
-continued
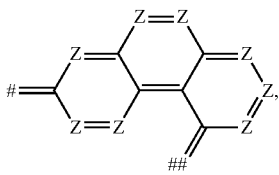
Formula 27
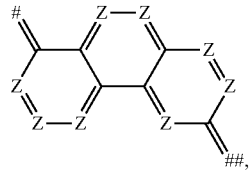
Formula 28
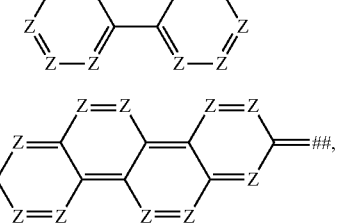
Formula 29
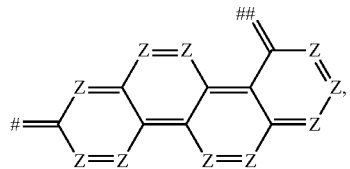
Formula 30
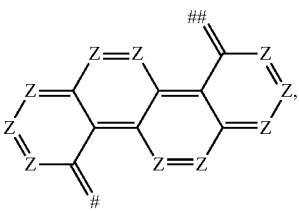
Formula 31
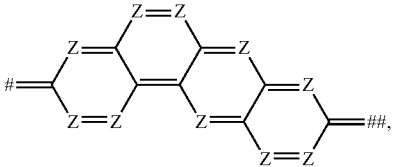
Formula 32
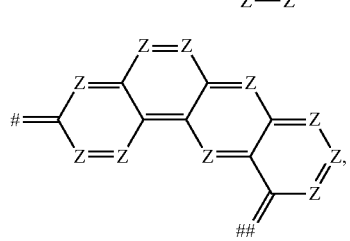
Formula 33
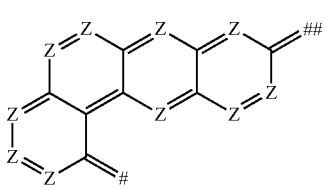
Formula 34
Formula 35

-continued

Formula 36
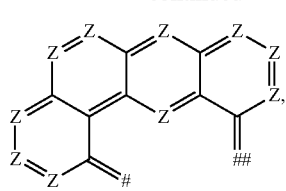

Formula 37
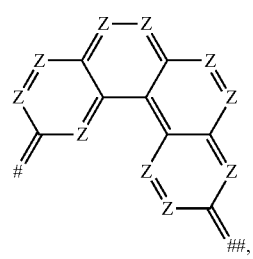

Formula 38
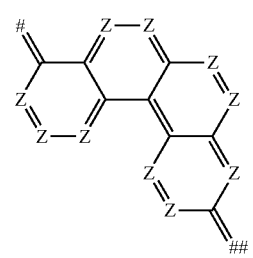

Formula 39
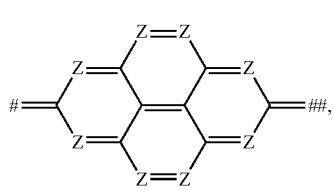

Formula 40
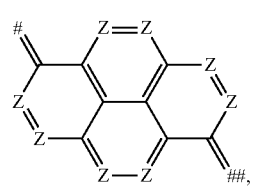

Formula 41
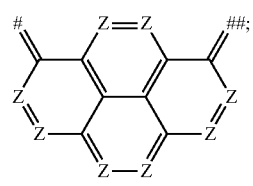

wherein, in Formula 6 to Formula 41, m is, at each occurrence identically or differently, selected from an integer from 1 to 4;

E is, at each occurrence identically or differently, selected from the group consisting of O, S, Se and $CR_AR_B$;

Z is, at each occurrence identically or differently, selected from the group consisting of $CR_L$ or N;

$R_A$, $R_B$, $R_L$ are, at each occurrence identically or differently, selected from the group consisting of: hydrogen, deuterium, halogen, a nitroso group, a nitro group, an acyl group, a carbonyl group, a carboxylic acid group, an ester group, a cyano group, an isocyano group, SCN, OCN, $SF_5$, a boranyl group, a sulfinyl group, a sulfonyl group, a phosphoroso group, a hydroxyl group, a sulfanyl group, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted aralkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted alkynyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted alkylgermanyl having 3 to 20 carbon atoms, substituted or unsubstituted arylgermanyl having 6 to 20 carbon atoms, and combinations thereof;

adjacent substituents $R_A$ and $R_B$ can be optionally joined to form a ring;

adjacent substituents $R_L$ can be optionally joined to form a ring;

"#" and "##" represent positions where Formula 6 to Formula 41 are connected to ring A or L in Formula 1;

preferably, the L is, at each occurrence identically or differently, selected from structures represented by Formula 7 to Formula 19.

6. The compound according to claim 5, the compound has any one of the structures represented by Formula LI to Formula LXXXV, Formula LVI-I and Formula LXV-1:

Formula LI
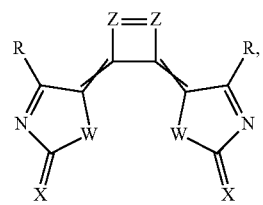

Formula LII
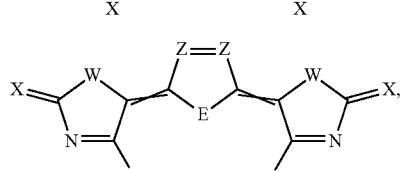

Formula LIII
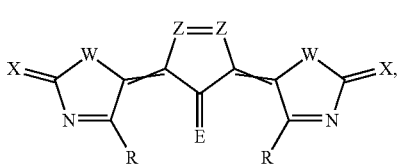

Formula LIV
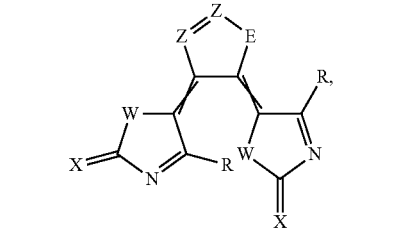

Formula LV
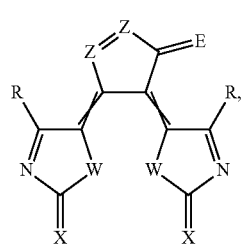
Formula LVI
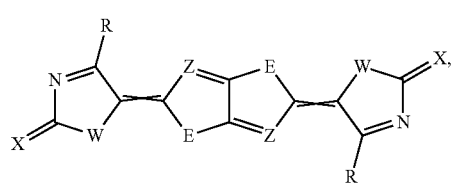
Formula LVII
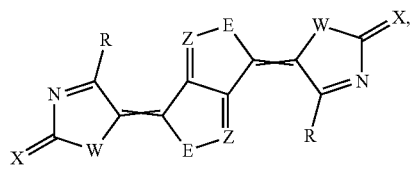
Formula LVIII
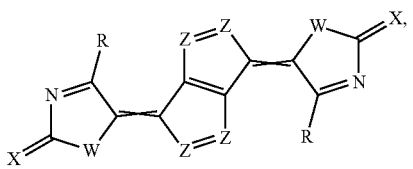
Formula LIX
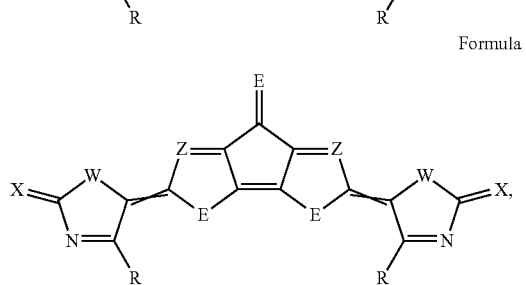
Formula LX
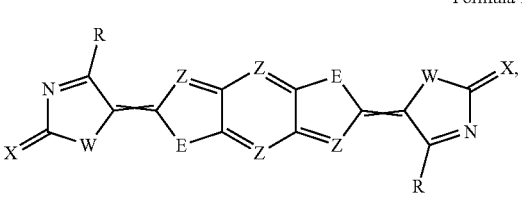
Formula LXI
Formula LXII
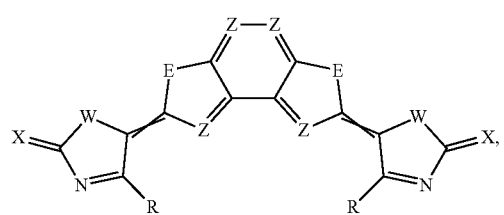
Formula LXIII
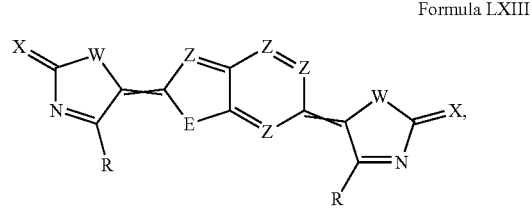
Formula LXIV
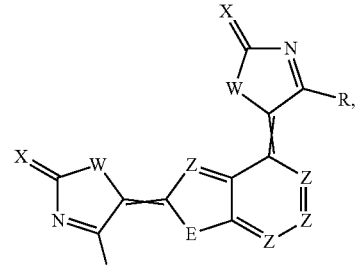
Formula LXV
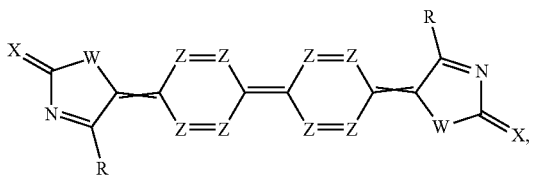
Formula LXVI
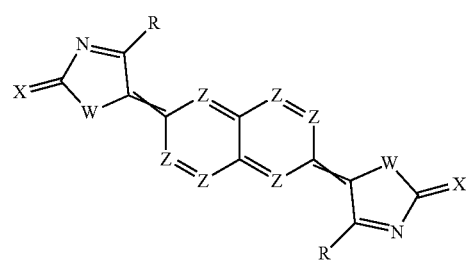
Formula LXVII
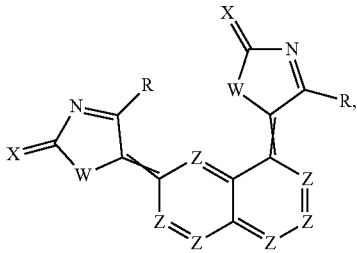

Formula LXVIII
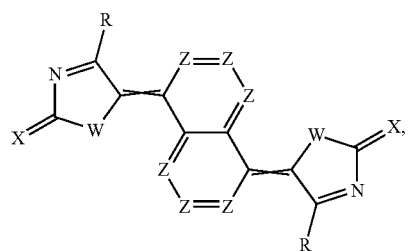
Formula LXIX
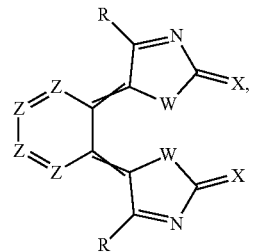
Formula LXX
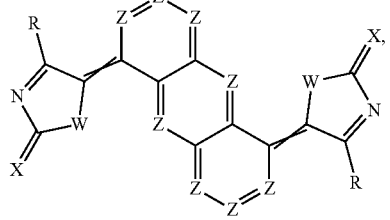
Formula LXXI
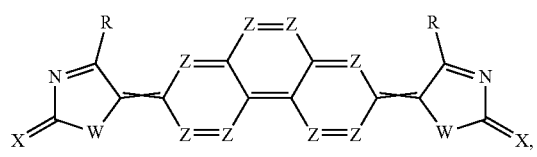
Formula LXXII
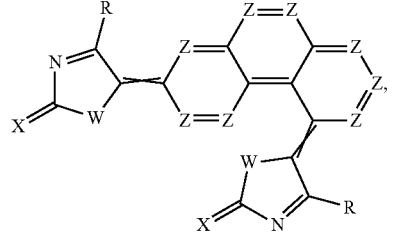
Formula LXXIII
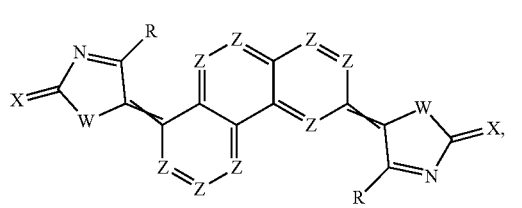
Formula LXXIV
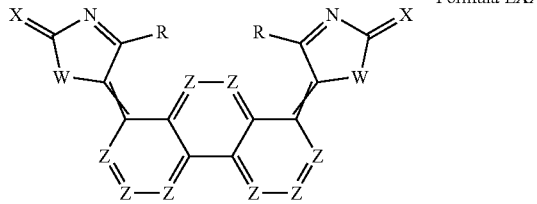
Formula LXXV
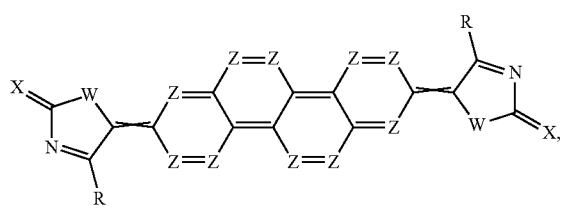
Formula LXXVI
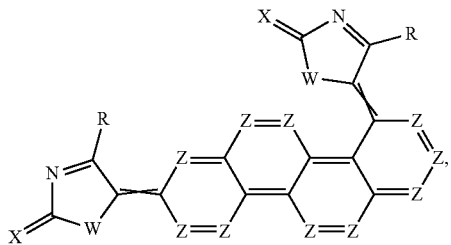
Formula LXXVII
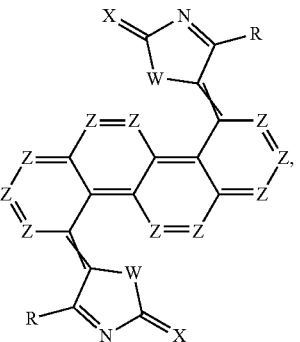
Formula LXXVIII
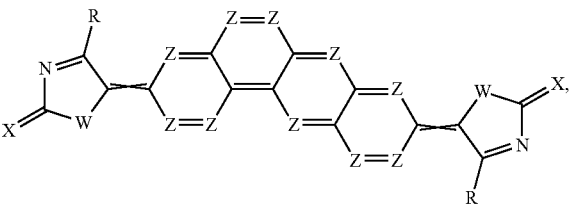
Formula LXXIX
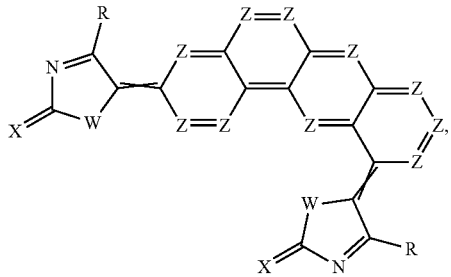

-continued

Formula LXXX

Formula LXXXI

Formula LXXXII

Formula LXXXIII

Formula LXXXIV

Formula LXXXV

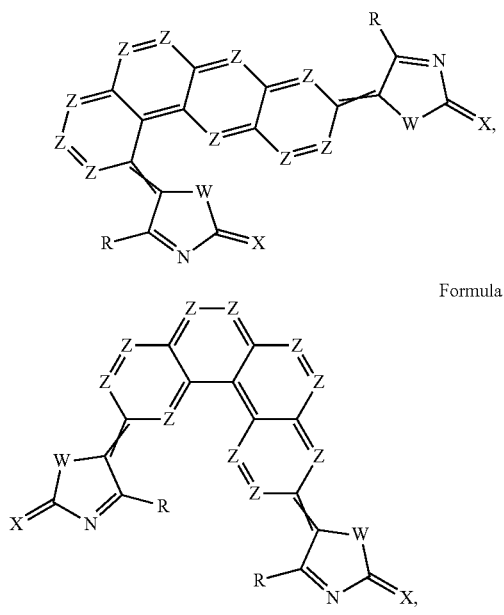

-continued

Formula LVI-I

Formula LXV-I

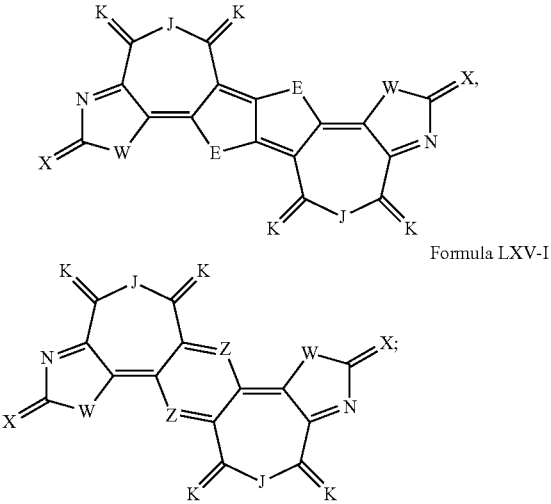

wherein, in Formula LI to Formula LXXXV, Formula LVI-I and Formula LXV-1,

K and E are, at each occurrence identically or differently, selected from the group consisting of O, S, Se, and $CR_AR_B$;

Z is, at each occurrence identically or differently, selected from the group consisting of $CR_L$ and N;

X is, at each occurrence identically or differently, selected from the group consisting of Se, NR' and CR"R'";

W is, at each occurrence identically or differently, selected from the group consisting of O, S, Se, and $NR_N$;

J is, at each occurrence identically or differently, selected from the group consisting of O, S, Se, and $NR_{NJ}$;

$R_A$, $R_B$, R, R', R", R'", $R_L$, $R_N$ and $R_{NJ}$ are, at each occurrence identically or differently, selected from the group consisting of: hydrogen, deuterium, halogen, a nitroso group, a nitro group, an acyl group, a carbonyl group, a carboxylic acid group, an ester group, a cyano group, an isocyano group, SCN, OCN, $SF_5$, a boranyl group, a sulfinyl group, a sulfonyl group, a phosphoroso group, a hydroxyl group, a sulfanyl group, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted aralkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted alkynyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted alkylgermanyl having 3 to 20 carbon atoms, substituted or unsubstituted arylgermanyl having 6 to 20 carbon atoms, and combinations thereof;

adjacent substituents $R_A$ and $R_B$ can be optionally joined to form a ring;

when X is selected from NR' or CR"R'", at least one of R', R", and R'" is a group having at least one electron-withdrawing group;

adjacent substituents R", R'" can be optionally joined to form a ring; and adjacent substituents R, $R_L$ can be optionally joined to form a ring;

preferably, at least one of R, $R_L$, $R_N$ and $R_{NJ}$ is a group having at least one electron-withdrawing group;

preferably, the compound has any one of the structures represented by Formula LII to Formula LXIV.

7. The compound according to claim 1, wherein X is, at each occurrence identically or differently, selected from CR"R'".

8. The compound according to claim 1, wherein W is, at each occurrence identically or differently, selected from O, S or Se; preferably, W is, at each occurrence identically or differently, selected from O or S; and more preferably, W is O.

9. The compound according to claim 1, wherein W is, at each occurrence identically or differently, selected from $NR_N$, and $R_N$ is, at each occurrence identically or differently, selected from the group consisting of: substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted aralkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted alkynyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, and combinations thereof; and preferably, $R_N$ is, at each occurrence identically or differently, selected from the group consisting of: substituted or unsubstituted alkyl having 1 to 20 carbon atoms, substituted or unsubstituted cycloalkyl having 3 to 20 ring carbon atoms, substituted or unsubstituted aryl having 6 to 30 carbon atoms, substituted or unsubstituted heteroaryl having 3 to 30 carbon atoms, and combinations thereof.

10. The compound according to claim 1, wherein R is, at each occurrence identically or differently, a group having at least one electron-withdrawing group; and/or each of R', R", R'", $R_L$ and $R_N$ is a group having at least one electron-withdrawing group.

11. The compound according to claim 1, wherein R is, at each occurrence identically or differently, selected from substituted or unsubstituted aryl having 6 to 30 carbon atoms, substituted or unsubstituted heteroaryl having 3 to 30 carbon atoms, or combinations thereof;

preferably, R is, at each occurrence identically or differently, selected from aryl having 6 to 30 carbon atoms with at least one electron-withdrawing group substitute, heteroaryl having 3 to 30 carbon atoms with at least one electron-withdrawing group substitute, or combinations thereof.

12. The compound according to claim 1, wherein the Hammett constant of the electron-withdrawing group is greater than or equal to 0.05, preferably, is greater than or equal to 0.3, and more preferably, is greater than or equal to 0.5.

13. The compound according to claim 1, wherein the electron-withdrawing group is selected from the group consisting of: halogen, a nitroso group, a nitro group, an acyl group, a carbonyl group, a carboxylic acid group, an ester group, a cyano group, an isocyano group, SCN, OCN, $SF_5$, a boranyl group, a sulfinyl group, a sulfonyl group, a phosphoroso group, an aza-aromatic ring group, or any one of the following groups substituted by one or more of halogen, a nitroso group, a nitro group, an acyl group, a carbonyl group, a carboxylic acid group, an ester group, a cyano group, an isocyano group, SCN, OCN, $SF_5$, a boranyl group, a sulfinyl group, a sulfonyl group, a phosphoroso group, and an aza-aromatic ring group: alkyl having 1 to 20 carbon atoms, cycloalkyl having 3 to 20 ring carbon atoms, heteroalkyl having 1 to 20 carbon atoms, a heterocyclic group having 3 to 20 ring atoms, aralkyl having 7 to 30 carbon atoms, alkoxy having 1 to 20 carbon atoms, aryloxy having 6 to 30 carbon atoms, alkenyl having 2 to 20 carbon atoms, alkynyl having 2 to 20 carbon atoms, aryl having 6 to 30 carbon atoms, heteroaryl having 3 to 30 carbon atoms, alkylsilyl having 3 to 20 carbon atoms, arylsilyl having 6 to 20 carbon atoms, substituted or unsubstituted alkylgermanyl having 3 to 20 carbon atoms, substituted or unsubstituted arylgermanyl having 6 to 20 carbon atoms, and combinations thereof; and preferably, the electron-withdrawing group is selected from the group consisting of: F, $CF_3$, $CHF_2$, $OCF_3$, $SF_5$, $SO_2CF_3$, a cyano group, an isocyano group, SCN, OCN, a pyrimidinyl group, a triazinyl group, and combinations thereof.

14. The compound according to claim 6, wherein X is, at each occurrence identically or differently, selected from the group consisting of the following structures:

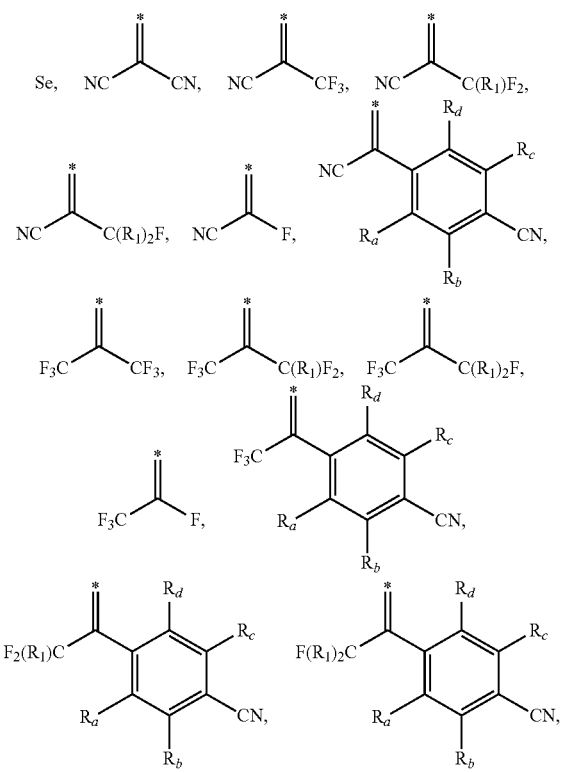

-continued

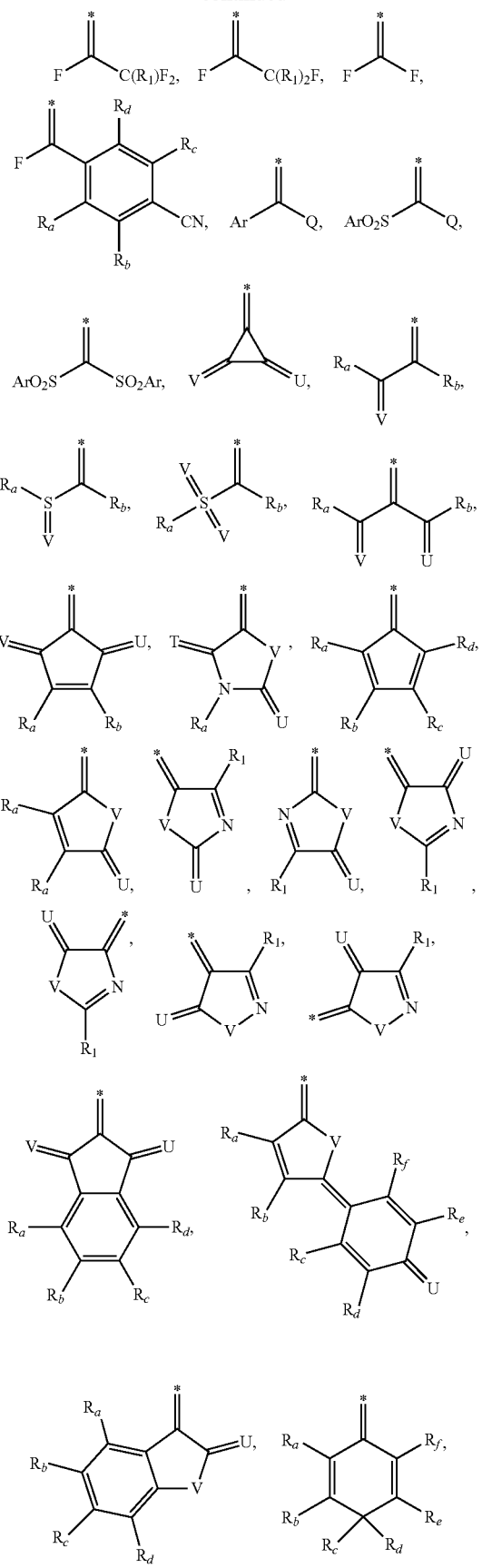

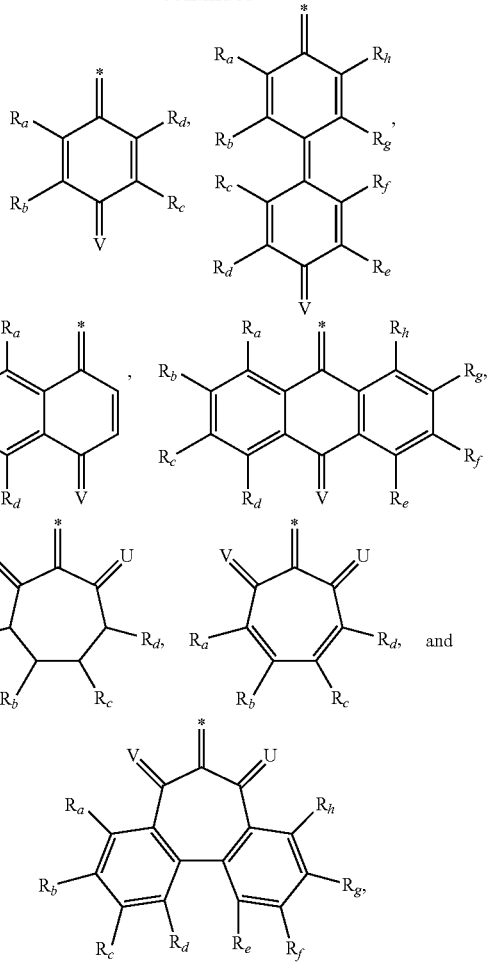

wherein V, U, and T are, at each occurrence identically or differently, selected from the group consisting of $CR_vR_u$, $NR_v$, O, S, and Se;

wherein Ar is, at each occurrence identically or differently, selected from substituted or unsubstituted aryl having 6 to 30 carbon atoms, or substituted or unsubstituted heteroaryl having 3 to 30 carbon atoms;

wherein $R_1$, Q, $R_a$, $R_b$, $R_c$, $R_d$, $R_e$, $R_f$, $R_g$, $R_h$, $R_v$, and $R_u$ are, at each occurrence identically or differently, selected from the group consisting of: hydrogen, deuterium, halogen, a nitroso group, a nitro group, an acyl group, a carbonyl group, a carboxylic acid group, an ester group, a cyano group, an isocyano group, SCN, OCN, $SF_5$, a boranyl group, a sulfinyl group, a sulfonyl group, a phosphoroso group, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted aralkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted alkynyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted alkylgermanyl having 3 to 20 carbon atoms, substituted or unsubstituted arylgermanyl having 6 to 20 carbon atoms, and combinations thereof;

preferably, $R_1$ is, at each occurrence identically or differently, selected from the group consisting of: F, $CF_3$, $OCF_3$, $SF_5$, $SO_2CF_3$, a cyano group, an isocyano group, SCN, OCN, pentafluorophenyl, 4-cyanotetrafluorophenyl, tetrafluoropyridyl, a pyrimidinyl group, a triazinyl group, and combinations thereof;

wherein Q is a group having at least one electron-withdrawing group, and for any one of the preceding structures, when one or more of $R_a$, $R_b$, $R_c$, $R_d$, $R_e$, $R_f$, $R_g$, $R_h$, $R_v$, and $R_u$ occur, at least one of $R_a$, $R_b$, $R_c$, $R_d$, $R_e$, $R_f$, $R_g$, $R_h$, $R_v$, and $R_u$ is a group having at least one electron-withdrawing group; preferably, the group having at least one electron-withdrawing group is selected from the group consisting of: F, $CF_3$, $OCF_3$, $SF_5$, $SO_2CF_3$, a cyano group, an isocyano group, SCN, OCN, pentafluorophenyl, 4-cyanotetrafluorophenyl, tetrafluoropyridyl, a pyrimidinyl group, a triazinyl group, and combinations thereof;

adjacent substituents $R_1$, $R_a$, $R_b$, $R_c$, $R_d$, $R_e$, $R_f$, $R_g$, $R_h$, $R_v$, and $R_u$ can be optionally joined to form a ring; and preferably, wherein X is, at each occurrence identically or differently, selected from the group consisting of the following structures:

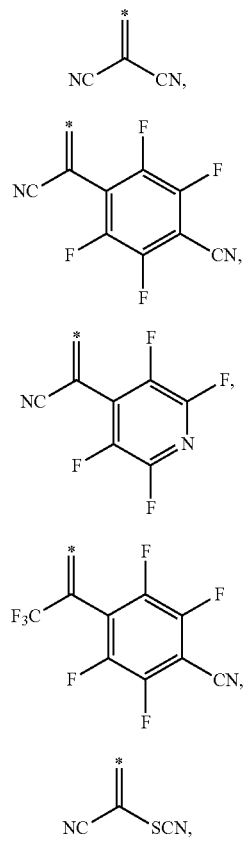

-continued

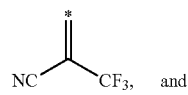

A6

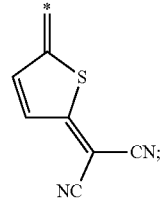

A7 more preferably, wherein X is selected from

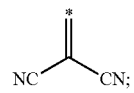

A1

* represents a position where X having the preceding structures is connected to ring A in Formula 1.

15. The compound according to claim 14, wherein R, $R_L$, $R_N$, and $R_{NJ}$ are, at each occurrence identically or differently, selected from the group consisting of: hydrogen, deuterium, halogen, a nitroso group, a nitro group, an acyl group, a carbonyl group, a carboxylic acid group, an ester group, a cyano group, an isocyano group, SCN, OCN, $SF_5$, a boranyl group, a sulfinyl group, a sulfonyl group, a phosphoroso group, a hydroxyl group, a sulfanyl group, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, a substituted or unsubstituted heterocyclic group having 3 to 20 ring atoms, substituted or unsubstituted aralkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted alkynyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, and combinations thereof; and preferably, R, $R_L$, $R_N$, and $R_{NJ}$ are, at each occurrence identically or differently, selected from the group consisting of: hydrogen, deuterium, a methyl group, an isopropyl group, $NO_2$, $SO_2CH_3$, $SCF_3$, $C_2F_5$, $OC_2F_5$, diphenylmethylsilyl, a phenyl group, methoxyphenyl, p-methylphenyl, 2,6-diisopropylphenyl, a biphenylyl group, polyfluorophenyl, difluopyridyl, nitrophenyl, dimethylthiazolyl, CN, a vinyl group substituted by one or more of CN or $CF_3$, an acetenyl group substituted by one of CN or $CF_3$, dimethylphosphoryl, diphenylphosphoryl, F, $CF_3$, $OCF_3$, $SF_5$, $SO_2CF_3$, a cyano group, an isocyano group, SCN, OCN, trifluoromethylphenyl, trifluoromethoxyphenyl, bis(trifluoromethyl)phenyl, bis(trifluoromethoxy)phenyl, 4-cyanotetrafluorophenyl, a phenyl or biphenylyl group substituted by one or more of F, CN or $CF_3$, tetrafluoropyridyl, a pyrimidinyl group, a triazinyl group, a pyridyl group, diphenylboryl, phenoxaborin, and combinations thereof;
more preferably, wherein R, $R_L$, $R_N$, and $R_{NJ}$ are, at each occurrence identically or differently, selected from the group consisting of the following structures:
B1
B2
B3
B4
B5
B6
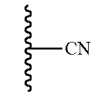
B7
B8
B9
B10
B11
B12
B13
-continued
B14
B15
B16
B17
B18
B19
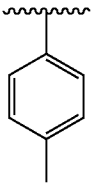
B20
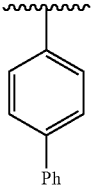
B21
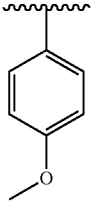
B22
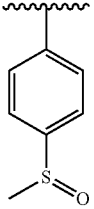

-continued
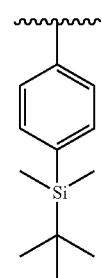
B23
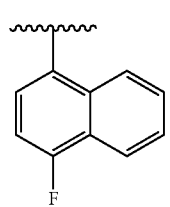
B24
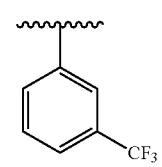
B25
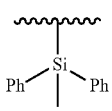
B26
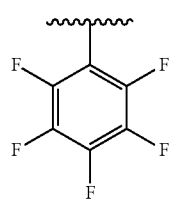
B27
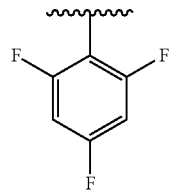
B28
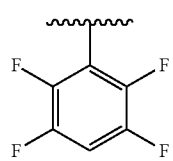
B29
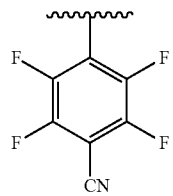
B30
-continued
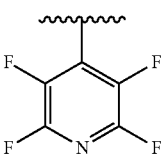
B31
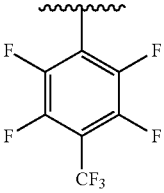
B32
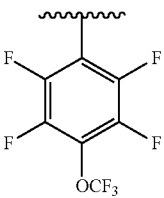
B33
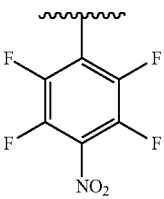
B34
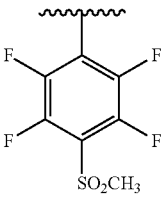
B35
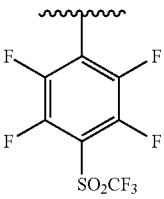
B36
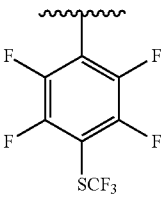
B37
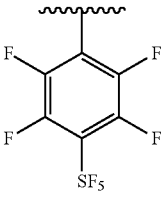
B38

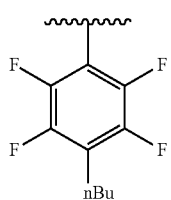 B39
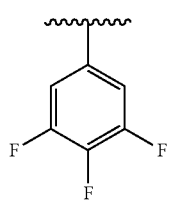 B40
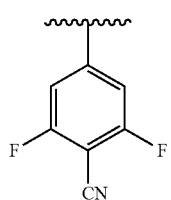 B41
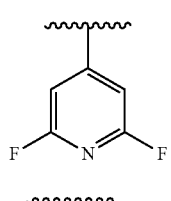 B42
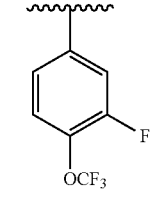 B43
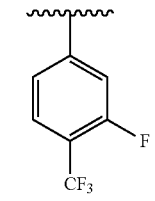 B44
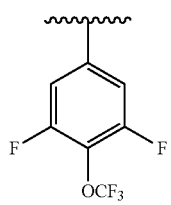 B45
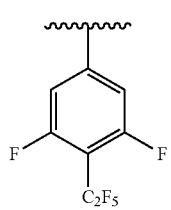 B46
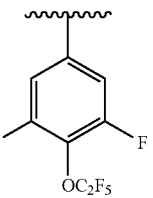 B47
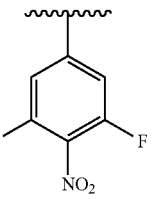 B48
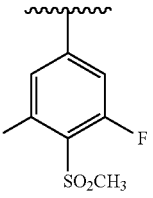 B49
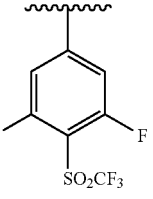 B50
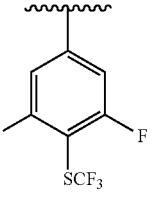 B51
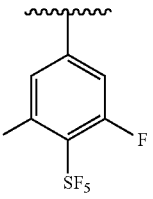 B52
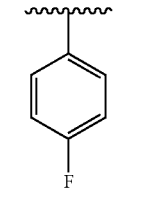 B53
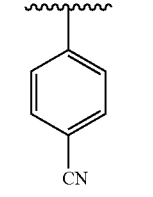 B54

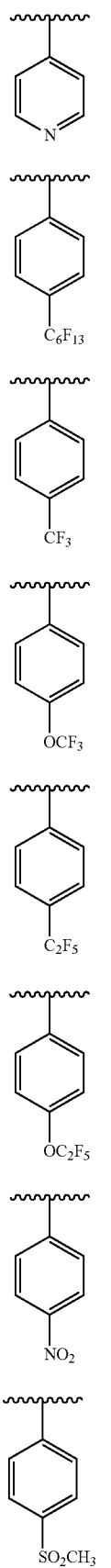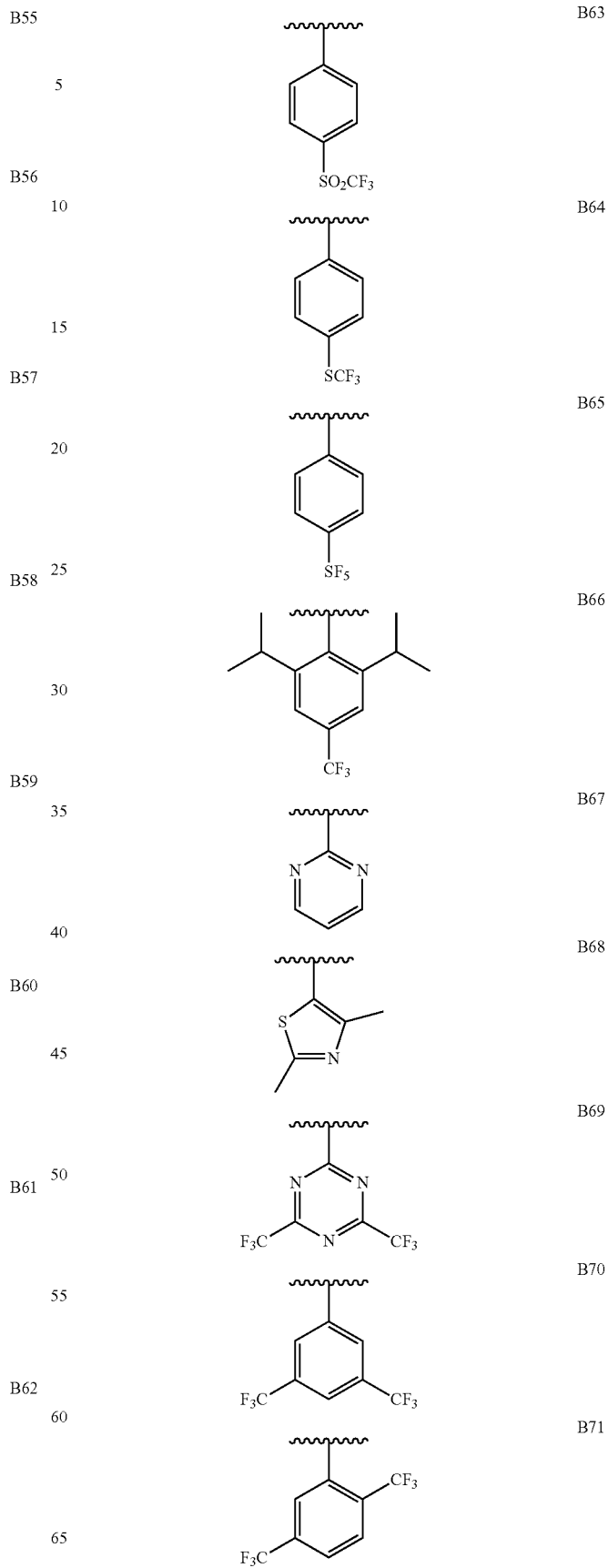

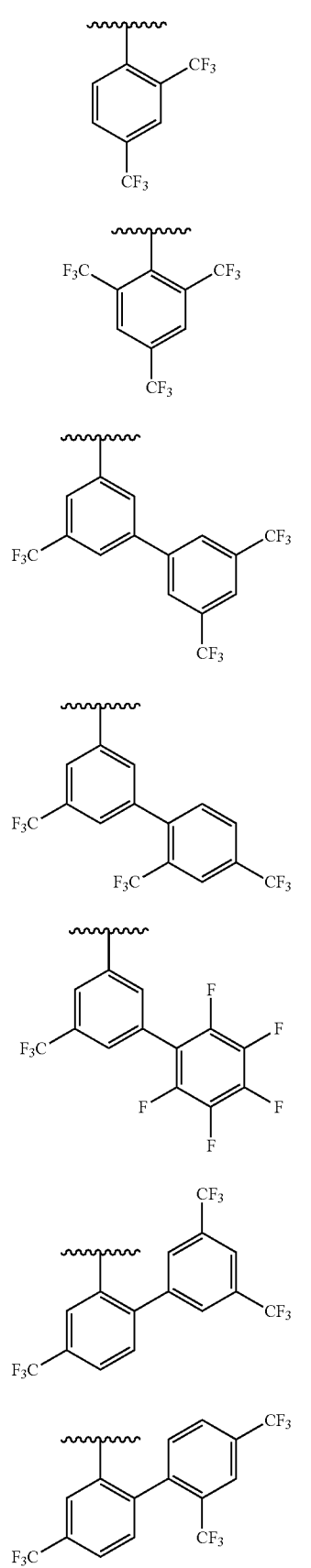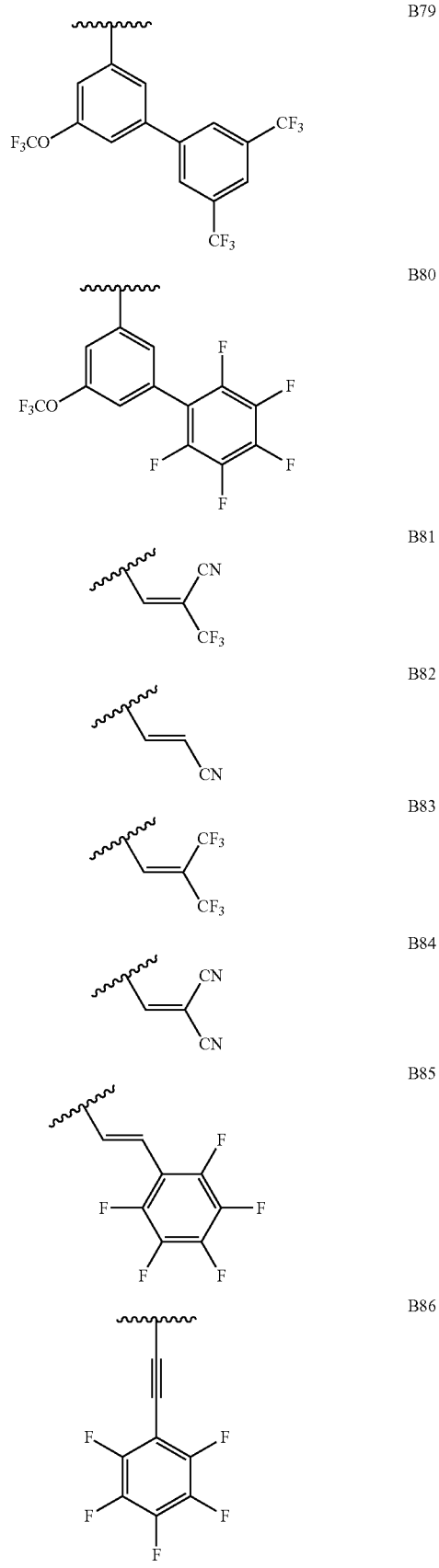

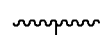 B87
 B88
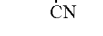 B89
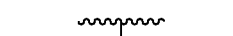 B90
 B91
 B92
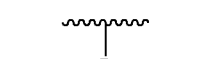 B93
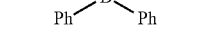 B94
 B95
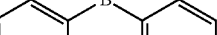 B96
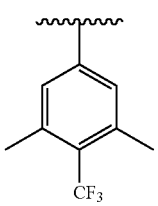 B97
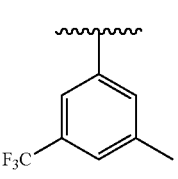 B98
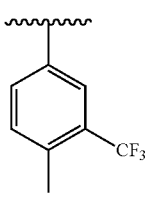 B99
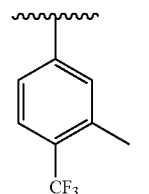 B100
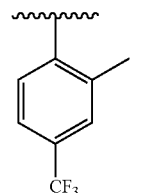 B101
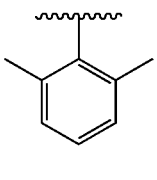 B102
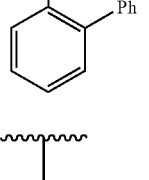 B103
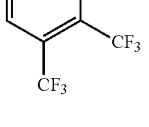 B104

-continued
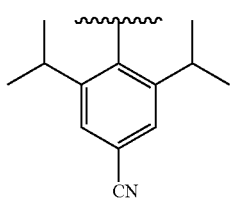 B105
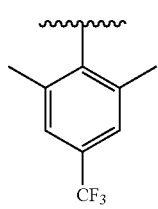 B106
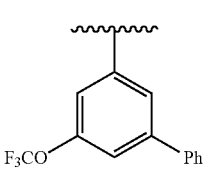 B107
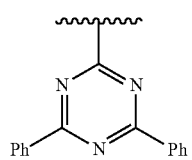 B108
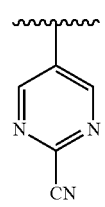 B109
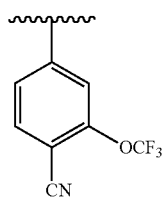 B110
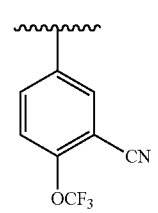 B111
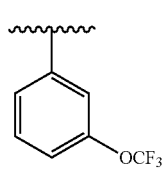 B112
-continued
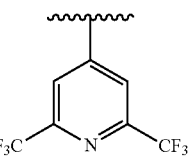 B113
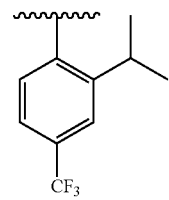 B114
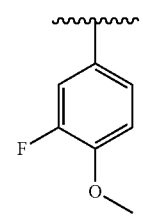 B115
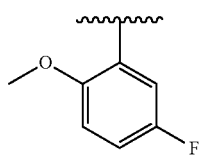 B116
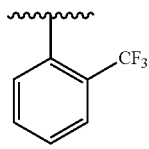 B117
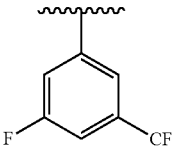 B119
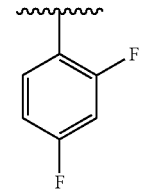 B120
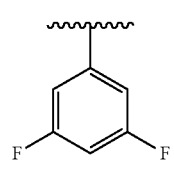 B121
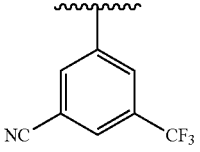 B122

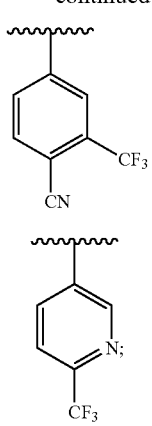

wherein "—" represents a position where R having the preceding structures is connected to Formula 1 and a position where $R_L$ having the preceding structures is connected to L; and "—" further represents a position where $R_N$ is connected to N when W is selected from $NR_N$.

16. The compound according to claim 1, wherein the compound is selected from the group consisting of: Compound LIO-1 to Compound LIO-108, Compound LIIO-1 to Compound LIIO-396, Compound LIIIO-1 to Compound LIIIO-298, Compound LIVO-1 to Compound LIVO-108, Compound LVO-1 to Compound LVO-108, Compound LVIO-1 to Compound LVIO-298, Compound LVIIO-1 to Compound LVIIO-298, Compound LVIIIO-1 to Compound LVIIIO-108, Compound LIXO-1 to Compound LIXO-298, Compound LXO-1 to Compound LXO-298, Compound LXIO-1 to Compound LXIO-66, Compound LXIA-1 to Compound LXIA-42, Compound LXIIO-1 to Compound LXIIO-66, Compound LXIIA-1 to Compound LXIIA-42, Compound LXIIIO-1 to Compound LXIIIO-66, and Compound LXIIIA-1 to Compound LXIIIA-42, wherein specific structures of Compound LXIVO-1 to Compound LXIVO-66, Compound LXIVA-1 to Compound LXIVA-42, Compound LXVO-1 to Compound LXVO-66, Compound LXVA-1 to Compound LXVA-42, Compound LXVIO-1 to Compound LXVIO-66, Compound LXVIA-1 to Compound LXVIA-42, Compound LXVIIO-1 to Compound LXVIIO-66, Compound LXVIIA-1 to Compound LXVIIA-42, Compound LXVIIIO-1 to Compound LXVIIIO-66, Compound LXVIIIA-1 to Compound LXVIIIA-42, Compound LXIXO-1 to Compound LXIXO-66, Compound LXIXA-1 to Compound LXIXA-42, Compound LXXO-1 to Compound LXXO-66, Compound LXXA-1 to Compound LXXA-42, Compound LXXIO-1 to Compound LXXIO-66, Compound LXXIA-1 to Compound LXXIA-42, Compound LXXIIO-1 to Compound LXXIIO-66, Compound LXXIIA-1 to Compound LXXIIA-42, Compound LXXIIIO-1 to Compound LXXIIIO-66, Compound LXXIIIA-1 to Compound LXXIIIA-42, Compound LXXIVO-1 to Compound LXXIVO-66, Compound LXXIVA-1 to Compound LXXIVA-42, Compound LXXVO-1 to Compound LXXVO-66, Compound LXXVA-1 to Compound LXXVA-42, Compound LXXVIO-1 to Compound LXXVIO-66, Compound LXXVIA-1 to Compound LXXVIA-42, Compound LXXVIIO-1 to Compound LXXVIIO-66, Compound LXXVIIA-1 to Compound LXXVIIA-42, Compound LXXVIIIO-1 to Compound LXXVIIIO-66, Compound LXXVIIIA-1 to Compound LXXVIIIA-42, Compound LXXIXO-1 to Compound LXXIXO-66, Compound LXXIXA-1 to Compound LXXIXA-42, Compound LXXXO-1 to Compound LXXXO-66, Compound LXXXA-1 to Compound LXXXA-42, Compound LXXXIO-1 to Compound LXXXIO-66, Compound LXXXIA-1 to Compound LXXXIA-42, Compound LXXXIIO-1 to Compound LXXXIIO-66, Compound LXXXIIA-1 to Compound LXXXIIA-42, Compound LXXXIIIO-1 to Compound LXXXIIIO-66, Compound LXXXIIIA-1 to Compound LXXXIIIA-42, Compound LXXXIVO-1 to Compound LXXXIVO-66, Compound LXXXIVA-1 to Compound LXXXIVA-42, Compound LXXXVO-1 to Compound LXXXVO-66, Compound LXXXVA-1 to Compound LXXXVA-42, Compound LVI-IO-1 to Compound LVI-IO-138 and Compound LXV-IO-1 to Compound LXV-IO-60;

wherein Compound LIO-1 to Compound LIO-108 have a structure represented by Formula LIO:

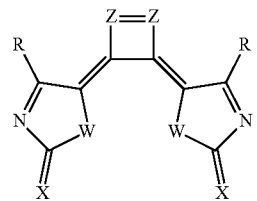

Formula LIO in Formula LIO, two X are identical, two W are identical, two R are identical, two Z are identical and are $CR_L$, and X, W, R and $R_L$ correspond to an atom or a group selected from the following table, respectively:

| NO. | X | W | R | $R_L$ | NO. | X | W | R | $R_L$ | NO. | X | W | R | $R_L$ |
|---|---|---|---|---|---|---|---|---|---|---|---|---|---|---|
| LIO-1 | A1 | O | B1 | H | LIO-2 | A1 | O | B17 | H | LIO-3 | A1 | O | B25 | H |
| LIO-4 | A1 | O | B54 | H | LIO-5 | A1 | O | B70 | H | LIO-6 | A1 | O | B72 | H |
| LIO-7 | A1 | S | B1 | H | LIO-8 | A1 | S | B17 | H | LIO-9 | A1 | S | B25 | H |
| LIO-10 | A1 | S | B54 | H | LIO-11 | A1 | S | B70 | H | LIO-12 | A1 | S | B72 | H |
| LIO-13 | A1 | Se | B54 | H | LIO-14 | A1 | Se | B70 | H | LIO-15 | A1 | Se | B72 | H |
| LIO-16 | A1 | NMe | B54 | H | LIO-17 | A1 | NMe | B70 | H | LIO-18 | A1 | NMe | B72 | H |
| LIO-19 | A1 | O | H | F | LIO-20 | A1 | O | B17 | F | LIO-21 | A1 | O | B25 | F |
| LIO-22 | A1 | O | B54 | F | LIO-23 | A1 | O | B70 | F | LIO-24 | A1 | O | B72 | F |
| LIO-25 | A1 | S | H | F | LIO-26 | A1 | S | B17 | F | LIO-27 | A1 | S | B25 | F |
| LIO-28 | A1 | S | B54 | F | LIO-29 | A1 | S | B70 | F | LIO-30 | A1 | S | B72 | F |
| LIO-31 | A1 | O | H | B6 | LIO-32 | A1 | O | B17 | B6 | LIO-33 | A1 | O | B25 | B6 |
| LIO-34 | A1 | O | B54 | B6 | LIO-35 | A1 | O | B70 | B6 | LIO-36 | A1 | O | B72 | B6 |
| LIO-37 | A1 | S | H | B6 | LIO-38 | A1 | S | B17 | B6 | LIO-39 | A1 | S | B25 | B6 |
| LIO-40 | A1 | S | B54 | B6 | LIO-41 | A1 | S | B70 | B6 | LIO-42 | A1 | S | B72 | B6 |
| LIO-43 | A1 | O | H | B70 | LIO-44 | A1 | O | B17 | B70 | LIO-45 | A1 | O | B25 | B70 |

-continued

| NO. | X | W | R | $R_L$ | NO. | X | W | R | $R_L$ | NO. | X | W | R | $R_L$ |
|---|---|---|---|---|---|---|---|---|---|---|---|---|---|---|
| LIO-46 | A1 | O | B54 | B70 | LIO-47 | A1 | O | B70 | B70 | LIO-48 | A1 | O | B72 | B70 |
| LIO-49 | A1 | S | H | B70 | LIO-50 | A1 | S | B17 | B70 | LIO-51 | A1 | S | B25 | B70 |
| LIO-52 | A1 | S | B54 | B70 | LIO-53 | A1 | S | B70 | B70 | LIO-54 | A1 | S | B70 | B70 |
| LIO-55 | A2 | O | B1 | H | LIO-56 | A2 | O | B17 | H | LIO-57 | A2 | O | B25 | H |
| LIO-58 | A2 | O | B54 | H | LIO-59 | A2 | O | B70 | H | LIO-60 | A2 | O | B72 | H |
| LIO-61 | A2 | S | B1 | H | LIO-62 | A2 | S | B17 | H | LIO-63 | A2 | S | B25 | H |
| LIO-64 | A2 | S | B54 | H | LIO-65 | A2 | S | B70 | H | LIO-66 | A2 | S | B72 | H |
| LIO-67 | A2 | O | B54 | F | LIO-68 | A2 | O | B70 | F | LIO-69 | A2 | O | B72 | F |
| LIO-70 | A2 | S | B54 | F | LIO-71 | A2 | S | B70 | F | LIO-72 | A2 | S | B72 | F |
| LIO-73 | A2 | O | B54 | B6 | LIO-74 | A2 | O | B70 | B6 | LIO-75 | A2 | O | B72 | B6 |
| LIO-76 | A2 | S | B54 | B6 | LIO-77 | A2 | S | B70 | B6 | LIO-78 | A2 | S | B72 | B6 |
| LIO-79 | A2 | O | B54 | B70 | LIO-80 | A2 | O | B70 | B70 | LIO-81 | A2 | O | B72 | B70 |
| LIO-82 | A3 | O | B1 | H | LIO-83 | A3 | O | B17 | H | LIO-84 | A3 | O | B25 | H |
| LIO-85 | A3 | O | B54 | H | LIO-86 | A3 | O | B70 | H | LIO-87 | A3 | O | B72 | H |
| LIO-88 | A3 | S | B1 | H | LIO-89 | A3 | S | B17 | H | LIO-90 | A3 | S | B25 | H |
| LIO-91 | A3 | S | B54 | H | LIO-92 | A3 | S | B70 | H | LIO-93 | A3 | S | B72 | H |
| LIO-94 | A3 | O | B54 | F | LIO-95 | A3 | O | B70 | F | LIO-96 | A3 | O | B72 | F |
| LIO-97 | A3 | S | B54 | F | LIO-98 | A3 | S | B70 | F | LIO-99 | A3 | S | B72 | F |
| LIO-100 | A3 | O | B54 | B6 | LIO-101 | A3 | O | B70 | B6 | LIO-102 | A3 | O | B72 | B6 |
| LIO-103 | A3 | S | B54 | B6 | LIO-104 | A3 | S | B70 | B6 | LIO-105 | A3 | S | B72 | B6 |
| LIO-106 | A3 | O | B54 | B70 | LIO-107 | A3 | O | B70 | B70 | LIO-108 | A3 | O | B72 | B70; | wherein Compound LIIO-1 to Compound LIIO-396 have a structure represented by Formula LIIO:

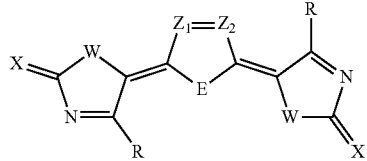

Formula LIIO in Formula LIIO, two X are identical, two W are identical, two R are identical, and X, W, R, $Z_1$, $Z_2$ and E correspond to an atom or a group selected from the following table, respectively:

| NO. | X | W | R | $Z_1$ | $Z_2$ | E | NO. | X | W | R | $Z_1$ | $Z_2$ | E |
|---|---|---|---|---|---|---|---|---|---|---|---|---|---|
| LIIO-1 | A1 | O | B1 | C—H | C—H | O | LIIO-2 | A1 | O | B17 | C—H | C—H | O |
| LIIO-3 | A1 | O | B25 | C—H | C—H | O | LIIO-4 | A1 | O | B57 | C—H | C—H | O |
| LIIO-5 | A1 | O | B70 | C—H | C—H | O | LIIO-6 | A1 | O | B72 | C—H | C—H | O |
| LIIO-7 | A1 | O | B1 | C—H | C—H | S | LIIO-8 | A1 | O | B17 | C—H | C—H | S |
| LIIO-9 | A1 | O | B25 | C—H | C—H | S | LIIO-10 | A1 | O | B57 | C—H | C—H | S |
| LIIO-11 | A1 | O | B70 | C—H | C—H | S | LIIO-12 | A1 | O | B72 | C—H | C—H | S |
| LIIO-13 | A1 | O | B1 | C—F | C—F | O | LIIO-14 | A1 | O | B17 | C—F | C—H | O |
| LIIO-15 | A1 | O | B25 | C—F | C—F | O | LIIO-16 | A1 | O | B57 | C—F | C—F | O |
| LIIO-17 | A1 | O | B70 | C—F | C—F | O | LIIO-18 | A1 | O | B72 | C—F | C—F | O |
| LIIO-19 | A1 | O | B1 | C—F | C—F | S | LIIO-20 | A1 | O | B17 | C—F | C—F | S |
| LIIO-21 | A1 | O | B25 | C—F | C—F | S | LIIO-22 | A1 | O | B57 | C—F | C—F | S |
| LIIO-23 | A1 | O | B70 | C—F | C—F | S | LIIO-24 | A1 | O | B72 | C—F | C—F | S |
| LIIO-25 | A1 | O | B1 | C—H | N |  | O | LIIO-26 | A1 | O | B17 | C—H | N | O |
| LIIO-27 | A1 | O | B25 | C—H | N | O | LIIO-28 | A1 | O | B57 | C—H | N | O |
| LIIO-29 | A1 | O | B70 | C—H | N | O | LIIO-30 | A1 | O | B72 | C—H | N | O |
| LIIO-31 | A1 | O | B1 | C—H | N | S | LIIO-32 | A1 | O | B17 | C—H | N | S |
| LIIO-33 | A1 | O | B25 | C—H | N | S | LIIO-34 | A1 | O | B57 | C—H | N | S |
| LIIO-35 | A1 | O | B70 | C—H | N | S | LIIO-36 | A1 | O | B72 | C—H | N | S |
| LIIO-37 | A1 | O | B1 | N | N | O | LIIO-38 | A1 | O | B17 | N | N | O |
| LIIO-39 | A1 | O | B25 | N | N | O | LIIO-40 | A1 | O | B57 | N | N | O |
| LIIO-41 | A1 | O | B70 | N | N | O | LIIO-42 | A1 | O | B72 | N | N | O |
| LIIO-43 | A1 | O | B1 | N | N | S | LIIO-44 | A1 | O | B17 | N | N | S |
| LIIO-45 | A1 | O | B25 | N | N | S | LIIO-46 | A1 | O | B57 | N | N | S |
| LIIO-47 | A1 | O | B70 | N | N | S | LIIO-48 | A1 | O | B72 | N | N | S |
| LIIO-49 | A1 | S | B1 | C—H | C—H | O | LIIO-50 | A1 | S | B17 | C—H | C—H | O |
| LIIO-51 | A1 | S | B25 | C—H | C—H | O | LIIO-52 | A1 | S | B57 | C—H | C—H | O |
| LIIO-53 | A1 | S | B70 | C—H | C—H | O | LIIO-54 | A1 | S | B72 | C—H | C—H | O |
| LIIO-55 | A1 | S | B1 | C—H | C—H | S | LIIO-56 | A1 | S | B17 | C—H | C—H | S |
| LIIO-57 | A1 | S | B25 | C—H | C—H | S | LIIO-58 | A1 | S | B57 | C—H | C—H | S |

| NO. | X | W | R | $Z_1$ | $Z_2$ | E | NO. | X | W | R | $Z_1$ | $Z_2$ | E |
|---|---|---|---|---|---|---|---|---|---|---|---|---|---|
| LIIO-59 | A1 | S | B70 | C—H | C—H | S | LIIO-60 | A1 | S | B72 | C—H | C—H | S |
| LIIO-61 | A1 | S | B1 | C—F | C—F | O | LIIO-62 | A1 | S | B17 | C—F | C—H | O |
| LIIO-63 | A1 | S | B25 | C—F | C—F | O | LIIO-64 | A1 | S | B57 | C—F | C—F | O |
| LIIO-65 | A1 | S | B70 | C—F | C—F | O | LIIO-66 | A1 | S | B72 | C—F | C—F | O |
| LIIO-67 | A1 | S | B1 | C—F | C—F | S | LIIO-68 | A1 | S | B17 | C—F | C—F | S |
| LIIO-69 | A1 | S | B25 | C—F | C—F | S | LIIO-70 | A1 | S | B57 | C—F | C—F | S |
| LIIO-71 | A1 | S | B70 | C—F | C—F | S | LIIO-72 | A1 | S | B72 | C—F | C—F | S |
| LIIO-73 | A1 | S | B1 | C—H | N | O | LIIO-74 | A1 | S | B17 | C—H | N | O |
| LIIO-75 | A1 | S | B25 | C—H | N | O | LIIO-76 | A1 | S | B57 | C—H | N | O |
| LIIO-77 | A1 | S | B70 | C—H | N | O | LIIO-78 | A1 | S | B72 | C—H | N | O |
| LIIO-79 | A1 | S | B1 | C—H | N | S | LIIO-80 | A1 | S | B17 | C—H | N | S |
| LIIO-81 | A1 | S | B25 | C—H | N | S | LIIO-82 | A1 | S | B57 | C—H | N | S |
| LIIO-83 | A1 | S | B70 | C—H | N | S | LIIO-84 | A1 | S | B72 | C—H | N | S |
| LIIO-85 | A1 | S | B1 | N | N | O | LIIO-86 | A1 | S | B17 | N | N | O |
| LIIO-87 | A1 | S | B25 | N | N | O | LIIO-88 | A1 | S | B57 | N | N | O |
| LIIO-89 | A1 | S | B70 | N | N | O | LIIO-90 | A1 | S | B72 | N | N | O |
| LIIO-91 | A1 | S | B1 | N | N | S | LIIO-92 | A1 | S | B17 | N | N | S |
| LIIO-93 | A1 | S | B25 | N | N | S | LIIO-94 | A1 | S | B57 | N | N | S |
| LIIO-95 | A1 | S | B70 | N | N | S | LIIO-96 | A1 | S | B72 | N | N | S |
| LIIO-97 | A1 | Se | B25 | C—H | C—H | O | LIIO-98 | A1 | Se | B57 | C—H | C—H | O |
| LIIO-99 | A1 | Se | B70 | C—H | C—H | O | LIIO-100 | A1 | Se | B72 | C—H | C—H | O |
| LIIO-101 | A1 | Se | B25 | C—H | C—H | S | LIIO-102 | A1 | Se | B57 | C—H | C—H | S |
| LIIO-103 | A1 | Se | B70 | C—H | C—H | S | LIIO-104 | A1 | Se | B72 | C—H | C—H | S |
| LIIO-105 | A1 | Se | B57 | C—F | C—F | O | LIIO-106 | A1 | Se | B70 | C—F | C—F | O |
| LIIO-107 | A1 | Se | B57 | C—F | C—F | S | LIIO-108 | A1 | Se | B70 | C—F | C—F | S |
| LIIO-109 | A1 | Se | B25 | C—H | N | O | LIIO-110 | A1 | Se | B57 | C—H | N | O |
| LIIO-111 | A1 | Se | B70 | C—H | N | O | LIIO-112 | A1 | Se | B72 | C—H | N | O |
| LIIO-113 | A1 | Se | B25 | C—H | N | S | LIIO-114 | A1 | Se | B57 | C—H | N | S |
| LIIO-115 | A1 | Se | B70 | C—H | N | S | LIIO-116 | A1 | Se | B72 | C—H | N | S |
| LIIO-117 | A1 | Se | B25 | N | N | O | LIIO-118 | A1 | Se | B57 | N | N | O |
| LIIO-119 | A1 | Se | B70 | N | N | O | LIIO-120 | A1 | Se | B72 | N | N | O |
| LIIO-121 | A1 | Se | B25 | N | N | S | LIIO-122 | A1 | Se | B57 | N | N | S |
| LIIO-123 | A1 | Se | B70 | N | N | S | LIIO-124 | A1 | Se | B72 | N | N | S |
| LIIO-125 | A1 | NMe | B25 | C—H | C—H | O | LIIO-126 | A1 | NMe | B57 | C—H | C—H | O |
| LIIO-127 | A1 | NMe | B70 | C—H | C—H | O | LIIO-128 | A1 | NMe | B72 | C—H | C—H | O |
| LIIO-129 | A1 | NMe | B25 | C—H | C—H | S | LIIO-130 | A1 | NMe | B57 | C—H | C—H | S |
| LIIO-131 | A1 | NMe | B70 | C—H | C—H | S | LIIO-132 | A1 | NMe | B72 | C—H | C—H | S |
| LIIO-133 | A1 | NMe | B57 | C—F | C—F | O | LIIO-134 | A1 | NMe | B70 | C—F | C—F | O |
| LIIO-135 | A1 | NMe | B57 | C—F | C—F | S | LIIO-136 | A1 | NMe | B70 | C—F | C—F | S |
| LIIO-137 | A1 | NMe | B25 | C—H | N | O | LIIO-138 | A1 | NMe | B57 | C—H | N | O |
| LIIO-138 | A1 | NMe | B70 | C—H | N | O | LIIO-140 | A1 | NMe | B72 | C—H | N | O |
| LIIO-141 | A1 | NMe | B25 | C—H | N | S | LIIO-142 | A1 | NMe | B57 | C—H | N | S |
| LIIO-143 | A1 | NMe | B70 | C—H | N | S | LIIO-144 | A1 | NMe | B72 | C—H | N | S |
| LIIO-145 | A1 | NMe | B25 | N | N | O | LIIO-146 | A1 | NMe | B57 | N | N | O |
| LIIO-147 | A1 | NMe | B70 | N | N | O | LIIO-148 | A1 | NMe | B72 | N | N | O |
| LIIO-149 | A1 | NMe | B25 | N | N | S | LIIO-150 | A1 | NMe | B57 | N | N | S |
| LIIO-151 | A1 | NMe | B70 | N | N | S | LIIO-152 | A1 | NMe | B72 | N | N | S |
| LIIO-153 | A2 | O | B1 | C—H | C—H | O | LIIO-154 | A2 | O | B17 | C—H | C—H | O |
| LIIO-155 | A2 | O | B25 | C—H | C—H | O | LIIO-156 | A2 | O | B57 | C—H | C—H | O |
| LIIO-157 | A2 | O | B70 | C—H | C—H | O | LIIO-158 | A2 | O | B72 | C—H | C—H | O |
| LIIO-159 | A2 | O | B1 | C—H | C—H | S | LIIO-160 | A2 | O | B17 | C—H | C—H | S |
| LIIO-161 | A2 | O | B25 | C—H | C—H | S | LIIO-162 | A2 | O | B57 | C—H | C—H | S |
| LIIO-163 | A2 | O | B70 | C—H | C—H | S | LIIO-164 | A2 | O | B72 | C—H | C—H | S |
| LIIO-165 | A2 | O | B1 | C—F | C—F | O | LIIO-166 | A2 | O | B17 | C—F | C—H | O |
| LIIO-167 | A2 | O | B25 | C—F | C—F | O | LIIO-168 | A2 | O | B57 | C—F | C—F | O |
| LIIO-169 | A2 | O | B70 | C—F | C—F | O | LIIO-170 | A2 | O | B72 | C—F | C—F | O |
| LIIO-171 | A2 | O | B1 | C—F | C—F | S | LIIO-172 | A2 | O | B17 | C—F | C—F | S |
| LIIO-173 | A2 | O | B25 | C—F | C—F | S | LIIO-174 | A2 | O | B57 | C—F | C—F | S |
| LIIO-175 | A2 | O | B70 | C—F | C—F | S | LIIO-176 | A2 | O | B72 | C—F | C—F | S |
| LIIO-177 | A2 | O | B1 | C—H | N | O | LIIO-178 | A2 | O | B17 | C—H | N | O |
| LIIO-179 | A2 | O | B25 | C—H | N | | LIIO-180 | A2 | O | B57 | C—H | N | O |
| LIIO-181 | A2 | O | B70 | C—H | N | | LIIO-182 | A2 | O | B72 | C—H | N | O |
| LIIO-183 | A2 | O | B1 | C—H | N | | LIIO-184 | A2 | O | B17 | C—H | N | S |
| LIIO-185 | A2 | O | B25 | C—H | N | | LIIO-186 | A2 | O | B57 | C—H | N | S |
| LIIO-187 | A2 | O | B70 | C—H | N | | LIIO-188 | A2 | O | B72 | C—H | N | S |
| LIIO-189 | A2 | O | B1 | N | N | O | LIIO-190 | A2 | O | B17 | N | N | O |
| LIIO-191 | A2 | O | B25 | N | N | O | LIIO-192 | A2 | O | B57 | N | N | O |
| LIIO-193 | A2 | O | B70 | N | N | O | LIIO-194 | A2 | O | B72 | N | N | O |
| LIIO-195 | A2 | O | B1 | N | N | S | LIIO-196 | A2 | O | B17 | N | N | S |
| LIIO-197 | A2 | O | B25 | N | N | S | LIIO-198 | A2 | O | B57 | N | N | S |
| LIIO-199 | A2 | O | B70 | N | N | S | LIIO-200 | A2 | O | B72 | N | N | S |
| LIIO-201 | A2 | S | B1 | C—H | C—H | O | LIIO-202 | A2 | S | B17 | C—H | C—H | O |
| LIIO-203 | A2 | S | B25 | C—H | C—H | O | LIIO-204 | A2 | S | B57 | C—H | C—H | O |
| LIIO-205 | A2 | S | B70 | C—H | C—H | O | LIIO-206 | A2 | S | B72 | C—H | C—H | O |
| LIIO-207 | A2 | S | B1 | C—H | C—H | S | LIIO-208 | A2 | S | B17 | C—H | C—H | S |
| LIIO-209 | A2 | S | B25 | C—H | C—H | S | LIIO-210 | A2 | S | B57 | C—H | C—H | S |
| LIIO-211 | A2 | S | B70 | C—H | C—H | S | LIIO-212 | A2 | S | B72 | C—H | C—H | S |

-continued

| NO. | X | W | R | $Z_1$ | $Z_2$ | E | NO. | X | W | R | $Z_1$ | $Z_2$ | E |
|---|---|---|---|---|---|---|---|---|---|---|---|---|---|
| LIIO-213 | A2 | S | B1 | C—F | C—F | O | LIIO-214 | A2 | S | B17 | C—F | C—H | O |
| LIIO-215 | A2 | S | B25 | C—F | C—F | O | LIIO-216 | A2 | S | B57 | C—F | C—F | O |
| LIIO-217 | A2 | S | B70 | C—F | C—F | O | LIIO-218 | A2 | S | B72 | C—F | C—F | O |
| LIIO-219 | A2 | S | B1 | C—F | C—F | S | LIIO-220 | A2 | S | B17 | C—F | C—F | S |
| LIIO-221 | A2 | S | B25 | C—F | C—F | S | LIIO-222 | A2 | S | B57 | C—F | C—F | S |
| LIIO-223 | A2 | S | B70 | C—F | C—F | S | LIIO-224 | A2 | S | B72 | C—F | C—F | S |
| LIIO-225 | A2 | S | B1 | C—H | N | O | LIIO-226 | A2 | S | B17 | C—H | N | O |
| LIIO-227 | A2 | S | B25 | C—H | N | O | LIIO-228 | A2 | S | B57 | C—H | N | O |
| LIIO-229 | A2 | S | B70 | C—H | N | O | LIIO-230 | A2 | S | B72 | C—H | N | O |
| LIIO-231 | A2 | S | B1 | C—H | N | S | LIIO-232 | A2 | S | B17 | C—H | N | S |
| LIIO-233 | A2 | S | B25 | C—H | N | S | LIIO-234 | A2 | S | B57 | C—H | N | S |
| LIIO-235 | A2 | S | B70 | C—H | N | S | LIIO-236 | A2 | S | B72 | C—H | N | S |
| LIIO-237 | A2 | S | B1 | N | N | O | LIIO-238 | A2 | S | B17 | N | N | O |
| LIIO-239 | A2 | S | B25 | N | N | O | LIIO-240 | A2 | S | B57 | N | N | O |
| LIIO-241 | A2 | S | B70 | N | N | O | LIIO-242 | A2 | S | B72 | N | N | O |
| LIIO-243 | A2 | S | B1 | N | N | S | LIIO-244 | A2 | S | B17 | N | N | S |
| LIIO-245 | A2 | S | B25 | N | N | S | LIIO-246 | A2 | S | B57 | N | N | S |
| LIIO-247 | A2 | S | B70 | N | N | S | LIIO-248 | A2 | S | B72 | N | N | S |
| LIIO-249 | A2 | Se | B57 | C—H | C—H | O | LIIO-250 | A2 | Se | B70 | C—H | C—H | O |
| LIIO-251 | A2 | Se | B57 | C—H | C—H | S | LIIO-252 | A2 | Se | B70 | C—H | C—H | S |
| LIIO-253 | A2 | Se | B57 | C—F | C—F | O | LIIO-254 | A2 | Se | B70 | C—F | C—F | O |
| LIIO-255 | A2 | Se | B57 | C—F | C—F | S | LIIO-256 | A2 | Se | B70 | C—F | C—F | S |
| LIIO-257 | A2 | Se | B57 | C—H | N | O | LIIO-258 | A2 | Se | B70 | C—H | N | O |
| LIIO-259 | A2 | Se | B57 | C—H | N | S | LIIO-260 | A2 | Se | B70 | C—H | N | S |
| LIIO-261 | A2 | Se | B57 | N | N | O | LIIO-262 | A2 | Se | B70 | N | N | O |
| LIIO-263 | A2 | Se | B57 | N | N | S | LIIO-264 | A2 | Se | B70 | N | N | S |
| LIIO-265 | A2 | NMe | B70 | C—H | C—H | O | LIIO-266 | A2 | NMe | B70 | C—H | C—H | S |
| LIIO-267 | A2 | NMe | B57 | C—F | C—F | O | LIIO-268 | A2 | NMe | B70 | C—F | C—F | O |
| LIIO-269 | A2 | NMe | B57 | C—F | C—F | S | LIIO-270 | A2 | NMe | B70 | C—F | C—F | S |
| LIIO-271 | A2 | NMe | B70 | C—H | N | O | LIIO-272 | A2 | NMe | B70 | C—H | N | S |
| LIIO-273 | A2 | NMe | B70 | N | N | O | LIIO-274 | A2 | NMe | B70 | N | N | S |
| LIIO-275 | A3 | O | B1 | C—H | C—H | O | LIIO-276 | A3 | O | B17 | C—H | C—H | O |
| LIIO-277 | A3 | O | B25 | C—H | C—H | O | LIIO-278 | A3 | O | B57 | C—H | C—H | O |
| LIIO-279 | A3 | O | B70 | C—H | C—H | O | LIIO-280 | A3 | O | B72 | C—H | C—H | O |
| LIIO-281 | A3 | O | B1 | C—H | C—H | S | LIIO-282 | A3 | O | B17 | C—H | C—H | S |
| LIIO-283 | A3 | O | B25 | C—H | C—H | S | LIIO-284 | A3 | O | B57 | C—H | C—H | S |
| LIIO-285 | A3 | O | B70 | C—H | C—H | S | LIIO-286 | A3 | O | B72 | C—H | C—H | S |
| LIIO-287 | A3 | O | B1 | C—F | C—F | O | LIIO-288 | A3 | O | B17 | C—F | C—H | O |
| LIIO-289 | A3 | O | B25 | C—F | C—F | O | LIIO-290 | A3 | O | B57 | C—F | C—F | O |
| LIIO-291 | A3 | O | B70 | C—F | C—F | O | LIIO-292 | A3 | O | B72 | C—F | C—F | O |
| LIIO-293 | A3 | O | B1 | C—F | C—F | S | LIIO-294 | A3 | O | B17 | C—F | C—F | S |
| LIIO-295 | A3 | O | B25 | C—F | C—F | S | LIIO-296 | A3 | O | B57 | C—F | C—F | S |
| LIIO-297 | A3 | O | B70 | C—F | C—F | S | LIIO-298 | A3 | O | B72 | C—F | C—F | S |
| LIIO-299 | A3 | O | B1 | C—H | N | O | LIIO-300 | A3 | O | B17 | C—H | N | O |
| LIIO-301 | A3 | O | B25 | C—H | N | O | LIIO-302 | A3 | O | B57 | C—H | N | O |
| LIIO-303 | A3 | O | B70 | C—H | N | O | LIIO-304 | A3 | O | B72 | C—H | N | O |
| LIIO-305 | A3 | O | B1 | C—H | N | S | LIIO-306 | A3 | O | B17 | C—H | N | S |
| LIIO-307 | A3 | O | B25 | C—H | N | S | LIIO-308 | A3 | O | B57 | C—H | N | S |
| LIIO-309 | A3 | O | B70 | C—H | N | S | LIIO-310 | A3 | O | B72 | C—H | N | S |
| LIIO-311 | A3 | O | B1 | N | N | O | LIIO-312 | A3 | O | B17 | N | N | O |
| LIIO-313 | A3 | O | B25 | N | N | O | LIIO-314 | A3 | O | B57 | N | N | O |
| LIIO-315 | A3 | O | B70 | N | N | O | LIIO-316 | A3 | O | B72 | N | N | O |
| LIIO-317 | A3 | O | B1 | N | N | S | LIIO-318 | A3 | O | B17 | N | N | S |
| LIIO-319 | A3 | O | B25 | N | N | S | LIIO-320 | A3 | O | B57 | N | N | S |
| LIIO-321 | A3 | O | B70 | N | N | S | LIIO-322 | A3 | O | B72 | N | N | S |
| LIIO-323 | A3 | S | B1 | C—H | C—H | O | LIIO-324 | A3 | S | B17 | C—H | C—H | O |
| LIIO-325 | A3 | S | B25 | C—H | C—H | O | LIIO-326 | A3 | S | B57 | C—H | C—H | O |
| LIIO-327 | A3 | S | B70 | C—H | C—H | O | LIIO-328 | A3 | S | B72 | C—H | C—H | O |
| LIIO-329 | A3 | S | B1 | C—H | C—H | S | LIIO-330 | A3 | S | B17 | C—H | C—H | S |
| LIIO-331 | A3 | S | B25 | C—H | C—H | S | LIIO-332 | A3 | S | B57 | C—H | C—H | S |
| LIIO-333 | A3 | S | B70 | C—H | C—H | S | LIIO-334 | A3 | S | B72 | C—H | C—H | S |
| LIIO-335 | A3 | S | B1 | C—F | C—F | O | LIIO-336 | A3 | S | B17 | C—F | C—H | O |
| LIIO-337 | A3 | S | B25 | C—F | C—F | O | LIIO-338 | A3 | S | B57 | C—F | C—F | O |
| LIIO-339 | A3 | S | B70 | C—F | C—F | O | LIIO-340 | A3 | S | B72 | C—F | C—F | O |
| LIIO-341 | A3 | S | B1 | C—F | C—F | S | LIIO-342 | A3 | S | B17 | C—F | C—F | S |
| LIIO-343 | A3 | S | B25 | C—F | C—F | S | LIIO-344 | A3 | S | B57 | C—F | C—F | S |
| LIIO-345 | A3 | S | B70 | C—F | C—F | S | LIIO-346 | A3 | S | B71 | C—F | C—F | S |
| LIIO-347 | A3 | S | B1 | C—H | N | O | LIIO-348 | A3 | S | B17 | C—H | N | O |
| LIIO-349 | A3 | S | B25 | C—H | N | O | LIIO-350 | A3 | S | B57 | C—H | N | O |
| LIIO-351 | A3 | S | B70 | C—H | N | O | LIIO-352 | A3 | S | B72 | C—H | N | O |
| LIIO-353 | A3 | S | B1 | C—H | N | S | LIIO-354 | A3 | S | B17 | C—H | N | S |
| LIIO-355 | A3 | S | B25 | C—H | N | S | LIIO-356 | A3 | S | B57 | C—H | N | S |
| LIIO-357 | A3 | S | B70 | C—H | N | S | LIIO-358 | A3 | S | B72 | C—H | N | S |
| LIIO-359 | A3 | S | B1 | N | N | O | LIIO-360 | A3 | S | B17 | N | N | O |
| LIIO-361 | A3 | S | B25 | N | N | O | LIIO-362 | A3 | S | B57 | N | N | O |
| LIIO-363 | A3 | S | B70 | N | N | O | LIIO-364 | A3 | S | B72 | N | N | O |
| LIIO-365 | A3 | S | B1 | N | N | S | LIIO-366 | A3 | S | B17 | N | N | S |

-continued

| NO. | X | W | R | $Z_1$ | $Z_2$ | E | NO. | X | W | R | $Z_1$ | $Z_2$ | E |
|---|---|---|---|---|---|---|---|---|---|---|---|---|---|
| LIIO-367 | A3 | S | B25 | N | N | S | LIIO-368 | A3 | S | B57 | N | N | S |
| LIIO-369 | A3 | S | B70 | N | N | S | LIIO-370 | A3 | S | B72 | N | N | S |
| LIIO-371 | A3 | Se | B57 | C—H | C—H | O | LIIO-372 | A3 | Se | B70 | C—H | C—H | O |
| LIIO-373 | A3 | Se | B57 | C—H | C—H | S | LIIO-374 | A3 | Se | B70 | C—H | C—H | S |
| LIIO-375 | A3 | Se | B57 | C—F | C—F | O | LIIO-376 | A3 | Se | B70 | C—F | C—F | O |
| LIIO-377 | A3 | Se | B57 | C—F | C—F | S | LIIO-378 | A3 | Se | B70 | C—F | C—F | S |
| LIIO-379 | A3 | Se | B57 | C—H | N | O | LIIO-380 | A3 | Se | B70 | C—H | N | O |
| LIIO-381 | A3 | Se | B57 | C—H | N | S | LIIO-382 | A3 | Se | B70 | C—H | N | S |
| LIIO-383 | A3 | Se | B57 | N | N | O | LIIO-384 | A3 | Se | B70 | N | N | O |
| LIIO-385 | A3 | Se | B57 | N | N | S | LIIO-386 | A3 | Se | B70 | N | N | S |
| LIIO-387 | A3 | NMe | B70 | C—H | C—H | O | LIIO-388 | A3 | NMe | B70 | C—H | C—H | S |
| LIIO-389 | A3 | NMe | B57 | C—F | C—F | O | LIIO-390 | A3 | NMe | B70 | C—F | C—F | O |
| LIIO-391 | A3 | NMe | B57 | C—F | C—F | S | LIIO-392 | A3 | NMe | B70 | C—F | C—F | S |
| LIIO-393 | A3 | NMe | B70 | C—H | N | O | LIIO-394 | A3 | NMe | B70 | C—H | N | S |
| LIIO-395 | A3 | NMe | B70 | N | N | O | LIIO-396 | A3 | NMe | B70 | N | N | S; | wherein Compound LIIIO-1 to Compound LIIIO-298 have a structure represented by Formula LIIIO:

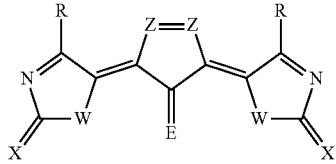

Formula LIIIO in Formula LIIIO, two X are identical, two W are identical, two R are identical, two Z are identical, and X, W, R, E and Z correspond to an atom or a group selected from the following table, respectively:

| NO. | X | W | R | Z | E | NO. | X | W | R | Z | E |
|---|---|---|---|---|---|---|---|---|---|---|---|
| LIIIO-1 | A1 | O | B1 | C—H | O | LIIIO-2 | A1 | O | B17 | C—H | O |
| LIIIO-3 | A1 | O | B25 | C—H | O | LIIIO-4 | A1 | O | B57 | C—H | O |
| LIIIO-5 | A1 | O | B70 | C—H | O | LIIIO-6 | A1 | O | B72 | C—H | O |
| LIIIO-7 | A1 | O | B1 | C—H | S | LIIIO-8 | A1 | O | B17 | C—H | S |
| LIIIO-9 | A1 | O | B25 | C—H | S | LIIIO-10 | A1 | O | B57 | C—H | S |
| LIIIO-11 | A1 | O | B70 | C—H | S | LIIIO-12 | A1 | O | B72 | C—H | S |
| LIIIO-13 | A1 | O | B1 | C—F | O | LIIIO-14 | A1 | O | B17 | C—F | O |
| LIIIO-15 | A1 | O | B25 | C—F | O | LIIIO-16 | A1 | O | B57 | C—F | O |
| LIIIO-17 | A1 | O | B70 | C—F | O | LIIIO-18 | A1 | O | B72 | C—F | O |
| LIIIO-19 | A1 | O | B1 | C—F | S | LIIIO-20 | A1 | O | B17 | C—F | S |
| LIIIO-21 | A1 | O | B25 | C—F | S | LIIIO-22 | A1 | O | B57 | C—F | S |
| LIIIO-23 | A1 | O | B70 | C—F | S | LIIIO-24 | A1 | O | B72 | C—F | S |
| LIIIO-25 | A1 | O | B1 | N | O | LIIIO-26 | A1 | O | B17 | N | O |
| LIIIO-27 | A1 | O | B25 | N | O | LIIIO-28 | A1 | O | B57 | N | O |
| LIIIO-29 | A1 | O | B70 | N | O | LIIIO-30 | A1 | O | B72 | N | O |
| LIIIO-31 | A1 | O | B1 | N | S | LIIIO-32 | A1 | O | B17 | N | S |
| LIIIO-33 | A1 | O | B25 | N | S | LIIIO-34 | A1 | O | B57 | N | S |
| LIIIO-35 | A1 | O | B70 | N | S | LIIIO-36 | A1 | O | B72 | N | S |
| LIIIO-37 | A1 | S | B1 | C—H | O | LIIIO-38 | A1 | S | B17 | C—H | O |
| LIIIO-39 | A1 | S | B25 | C—H | O | LIIIO-40 | A1 | S | B57 | C—H | O |
| LIIIO-41 | A1 | S | B70 | C—H | O | LIIIO-42 | A1 | S | B72 | C—H | O |
| LIIIO-43 | A1 | S | B1 | C—H | S | LIIIO-44 | A1 | S | B17 | C—H | S |
| LIIIO-45 | A1 | S | B25 | C—H | S | LIIIO-46 | A1 | S | B57 | C—H | S |
| LIIIO-47 | A1 | S | B70 | C—H | S | LIIIO-48 | A1 | S | B72 | C—H | S |
| LIIIO-49 | A1 | S | B1 | C—F | O | LIIIO-50 | A1 | S | B17 | C—F | O |
| LIIIO-51 | A1 | S | B25 | C—F | O | LIIIO-52 | A1 | S | B57 | C—F | O |
| LIIIO-53 | A1 | S | B70 | C—F | O | LIIIO-54 | A1 | S | B72 | C—F | O |
| LIIIO-55 | A1 | S | B1 | C—F | S | LIIIO-56 | A1 | S | B17 | C—F | S |
| LIIIO-57 | A1 | S | B25 | C—F | S | LIIIO-58 | A1 | S | B57 | C—F | S |
| LIIIO-59 | A1 | S | B70 | C—F | S | LIIIO-60 | A1 | S | B72 | C—F | S |
| LIIIO-61 | A1 | S | B1 | N | O | LIIIO-62 | A1 | S | B17 | N | O |
| LIIIO-63 | A1 | S | B25 | N | O | LIIIO-64 | A1 | S | B57 | N | O |
| LIIIO-65 | A1 | S | B70 | N | O | LIIIO-66 | A1 | S | B72 | N | O |
| LIIIO-67 | A1 | S | B1 | N | S | LIIIO-68 | A1 | S | B17 | N | S |
| LIIIO-69 | A1 | S | B25 | N | S | LIIIO-70 | A1 | S | B57 | N | S |

-continued

| NO. | X | W | R | Z | E | NO. | X | W | R | Z | E |
|---|---|---|---|---|---|---|---|---|---|---|---|
| LIIIO-71 | A1 | S | B70 | N | S | LIIIO-72 | A1 | S | B72 | N | S |
| LIIIO-73 | A1 | Se | B25 | C—H | O | LIIIO-74 | A1 | Se | B57 | C—H | O |
| LIIIO-75 | A1 | Se | B70 | C—H | O | LIIIO-76 | A1 | Se | B72 | C—H | O |
| LIIIO-77 | A1 | Se | B25 | C—H | S | LIIIO-78 | A1 | Se | B57 | C—H | S |
| LIIIO-79 | A1 | Se | B70 | C—H | S | LIIIO-80 | A1 | Se | B72 | C—H | S |
| LIIIO-81 | A1 | Se | B57 | C—F | O | LIIIO-82 | A1 | Se | B70 | C—F | O |
| LIIIO-83 | A1 | Se | B57 | C—F | S | LIIIO-84 | A1 | Se | B70 | C—F | S |
| LIIIO-85 | A1 | Se | B25 | N | O | LIIIO-86 | A1 | Se | B57 | N | O |
| LIIIO-87 | A1 | Se | B70 | N | O | LIIIO-88 | A1 | Se | B72 | N | O |
| LIIIO-89 | A1 | Se | B25 | N | S | LIIIO-90 | A1 | Se | B57 | N | S |
| LIIIO-91 | A1 | Se | B70 | N | S | LIIIO-92 | A1 | Se | B72 | N | S |
| LIIIO-93 | A1 | NMe | B25 | C—H | O | LIIIO-94 | A1 | NMe | B57 | C—H | O |
| LIIIO-95 | A1 | NMe | B70 | C—H | O | LIIIO-96 | A1 | NMe | B72 | C—H | O |
| LIIIO-97 | A1 | NMe | B25 | C—H | S | LIIIO-98 | A1 | NMe | B57 | C—H | S |
| LIIIO-99 | A1 | NMe | B70 | C—H | S | LIIIO-100 | A1 | NMe | B72 | C—H | S |
| LIIIO-101 | A1 | NMe | B57 | C—F | O | LIIIO-102 | A1 | NMe | B70 | C—F | O |
| LIIIO-103 | A1 | NMe | B57 | C—F | S | LIIIO-104 | A1 | NMe | B70 | C—F | S |
| LIIIO-105 | A1 | NMe | B25 | N | O | LIIIO-106 | A1 | NMe | B57 | N | O |
| LIIIO-107 | A1 | NMe | B70 | N | O | LIIIO-108 | A1 | NMe | B72 | N | O |
| LIIIO-109 | A1 | NMe | B25 | N | S | LIIIO-110 | A1 | NMe | B57 | N | S |
| LIIIO-111 | A1 | NMe | B70 | N | S | LIIIO-112 | A1 | NMe | B72 | N | S |
| LIIIO-113 | A2 | O | B1 | C—H | O | LIIIO-114 | A2 | O | B17 | C—H | O |
| LIIIO-115 | A2 | O | B25 | C—H | O | LIIIO-116 | A2 | O | B57 | C—H | O |
| LIIIO-117 | A2 | O | B70 | C—H | O | LIIIO-118 | A2 | O | B72 | C—H | O |
| LIIIO-119 | A2 | O | B1 | C—H | S | LIIIO-120 | A2 | O | B17 | C—H | S |
| LIIIO-121 | A2 | O | B25 | C—H | S | LIIIO-122 | A2 | O | B57 | C—H | S |
| LIIIO-123 | A2 | O | B70 | C—H | S | LIIIO-124 | A2 | O | B72 | C—H | S |
| LIIIO-125 | A2 | O | B1 | C—F | O | LIIIO-126 | A2 | O | B17 | C—F | O |
| LIIIO-127 | A2 | O | B25 | C—F | O | LIIIO-128 | A2 | O | B57 | C—F | O |
| LIIIO-129 | A2 | O | B70 | C—F | O | LIIIO-130 | A2 | O | B72 | C—F | O |
| LIIIO-131 | A2 | O | B1 | C—F | S | LIIIO-132 | A2 | O | B17 | C—F | S |
| LIIIO-133 | A2 | O | B25 | C—F | S | LIIIO-134 | A2 | O | B57 | C—F | S |
| LIIIO-135 | A2 | O | B70 | C—F | S | LIIIO-136 | A2 | O | B72 | C—F | S |
| LIIIO-137 | A2 | O | B1 | N | O | LIIIO-138 | A2 | O | B17 | N | O |
| LIIIO-139 | A2 | O | B25 | N | O | LIIIO-140 | A2 | O | B57 | N | O |
| LIIIO-141 | A2 | O | B70 | N | O | LIIIO-142 | A2 | O | B72 | N | O |
| LIIIO-143 | A2 | O | B1 | N | S | LIIIO-144 | A2 | O | B17 | N | S |
| LIIIO-145 | A2 | O | B25 | N | S | LIIIO-146 | A2 | O | B57 | N | S |
| LIIIO-147 | A2 | O | B70 | N | S | LIIIO-148 | A2 | O | B72 | N | S |
| LIIIO-149 | A2 | S | B1 | C—H | O | LIIIO-150 | A2 | S | B17 | C—H | O |
| LIIIO-151 | A2 | S | B25 | C—H | O | LIIIO-152 | A2 | S | B57 | C—H | O |
| LIIIO-153 | A2 | S | B70 | C—H | O | LIIIO-154 | A2 | S | B72 | C—H | O |
| LIIIO-155 | A2 | S | B1 | C—H | S | LIIIO-156 | A2 | S | B17 | C—H | S |
| LIIIO-157 | A2 | S | B25 | C—H | S | LIIIO-158 | A2 | S | B57 | C—H | S |
| LIIIO-159 | A2 | S | B70 | C—H | S | LIIIO-160 | A2 | S | B72 | C—H | S |
| LIIIO-161 | A2 | S | B1 | C—F | O | LIIIO-162 | A2 | S | B17 | C—F | O |
| LIIIO-163 | A2 | S | B25 | C—F | O | LIIIO-164 | A2 | S | B57 | C—F | O |
| LIIIO-165 | A2 | S | B70 | C—F | O | LIIIO-166 | A2 | S | B72 | C—F | O |
| LIIIO-167 | A2 | S | B1 | C—F | S | LIIIO-168 | A2 | S | B17 | C—F | S |
| LIIIO-169 | A2 | S | B25 | C—F | S | LIIIO-170 | A2 | S | B57 | C—F | S |
| LIIIO-171 | A2 | S | B70 | C—F | S | LIIIO-172 | A2 | S | B72 | C—F | S |
| LIIIO-173 | A2 | S | B1 | N | O | LIIIO-174 | A2 | S | B17 | N | O |
| LIIIO-175 | A2 | S | B25 | N | O | LIIIO-176 | A2 | S | B57 | N | O |
| LIIIO-177 | A2 | S | B70 | N | O | LIIIO-178 | A2 | S | B72 | N | O |
| LIIIO-179 | A2 | S | B1 | N | S | LIIIO-180 | A2 | S | B17 | N | S |
| LIIIO-181 | A2 | S | B25 | N | S | LIIIO-182 | A2 | S | B57 | N | S |
| LIIIO-183 | A2 | S | B70 | N | S | LIIIO-184 | A2 | S | B72 | N | S |
| LIIIO-185 | A2 | Se | B57 | C—H | O | LIIIO-186 | A2 | Se | B70 | C—H | O |
| LIIIO-187 | A2 | Se | B57 | C—H | S | LIIIO-188 | A2 | Se | B70 | C—H | S |
| LIIIO-189 | A2 | Se | B57 | C—F | O | LIIIO-190 | A2 | Se | B70 | C—F | O |
| LIIIO-191 | A2 | Se | B57 | C—F | S | LIIIO-192 | A2 | Se | B70 | C—F | S |
| LIIIO-193 | A2 | Se | B57 | N | O | LIIIO-194 | A2 | Se | B70 | N | O |
| LIIIO-195 | A2 | Se | B57 | N | S | LIIIO-196 | A2 | Se | B70 | N | S |
| LIIIO-197 | A2 | NMe | B70 | C—H | O | LIIIO-198 | A2 | NMe | B70 | C—H | S |
| LIIIO-199 | A2 | NMe | B57 | C—F | O | LIIIO-200 | A2 | NMe | B70 | C—F | O |
| LIIIO-201 | A2 | NMe | B57 | C—F | S | LIIIO-202 | A2 | NMe | B70 | C—F | S |
| LIIIO-203 | A2 | NMe | B70 | N | O | LIIIO-204 | A2 | NMe | B70 | N | S |
| LIIIO-205 | A3 | O | B1 | C—H | O | LIIIO-206 | A3 | O | B17 | C—H | O |
| LIIIO-207 | A3 | O | B25 | C—H | O | LIIIO-208 | A3 | O | B57 | C—H | O |
| LIIIO-209 | A3 | O | B70 | C—H | O | LIIIO-210 | A3 | O | B72 | C—H | O |
| LIIIO-211 | A3 | O | B1 | C—H | S | LIIIO-212 | A3 | O | B17 | C—H | S |
| LIIIO-213 | A3 | O | B25 | C—H | S | LIIIO-214 | A3 | O | B57 | C—H | S |
| LIIIO-215 | A3 | O | B70 | C—H | S | LIIIO-216 | A3 | O | B72 | C—H | S |
| LIIIO-217 | A3 | O | B1 | C—F | O | LIIIO-218 | A3 | O | B17 | C—F | O |
| LIIIO-219 | A3 | O | B25 | C—F | O | LIIIO-220 | A3 | O | B57 | C—F | O |
| LIIIO-221 | A3 | O | B70 | C—F | O | LIIIO-222 | A3 | O | B72 | C—F | O |
| LIIIO-223 | A3 | O | B1 | C—F | S | LIIIO-224 | A3 | O | B17 | C—F | S |

-continued

| NO. | X | W | R | Z | E | NO. | X | W | R | Z | E |
|---|---|---|---|---|---|---|---|---|---|---|---|
| LIIIO-225 | A3 | O | B25 | C—F | S | LIIIO-226 | A3 | O | B57 | C—F | S |
| LIIIO-227 | A3 | O | B70 | C—F | S | LIIIO-228 | A3 | O | B72 | C—F | S |
| LIIIO-229 | A3 | O | B70 | C—H | S | LIIIO-230 | A3 | O | B72 | C—H | S |
| LIIIO-231 | A3 | O | B1 | N | O | LIIIO-232 | A3 | O | B17 | N | O |
| LIIIO-233 | A3 | O | B25 | N | O | LIIIO-234 | A3 | O | B57 | N | O |
| LIIIO-235 | A3 | O | B70 | N | O | LIIIO-236 | A3 | O | B72 | N | O |
| LIIIO-237 | A3 | O | B1 | N | S | LIIIO-238 | A3 | O | B17 | N | S |
| LIIIO-239 | A3 | O | B25 | N | S | LIIIO-240 | A3 | O | B57 | N | S |
| LIIIO-241 | A3 | O | B70 | N | S | LIIIO-242 | A3 | O | B72 | N | S |
| LIIIO-243 | A3 | S | B1 | C—H | O | LIIIO-244 | A3 | S | B17 | C—H | O |
| LIIIO-245 | A3 | S | B25 | C—H | O | LIIIO-246 | A3 | S | B57 | C—H | O |
| LIIIO-247 | A3 | S | B70 | C—H | O | LIIIO-248 | A3 | S | B72 | C—H | O |
| LIIIO-249 | A3 | S | B1 | C—H | S | LIIIO-250 | A3 | S | B17 | C—H | S |
| LIIIO-251 | A3 | S | B25 | C—H | S | LIIIO-252 | A3 | S | B57 | C—H | S |
| LIIIO-253 | A3 | S | B70 | C—H | S | LIIIO-254 | A3 | S | B72 | C—H | S |
| LIIIO-255 | A3 | S | B1 | C—F | O | LIIIO-256 | A3 | S | B17 | C—F | O |
| LIIIO-257 | A3 | S | B25 | C—F | O | LIIIO-258 | A3 | S | B57 | C—F | O |
| LIIIO-259 | A3 | S | B70 | C—F | O | LIIIO-260 | A3 | S | B72 | C—F | O |
| LIIIO-261 | A3 | S | B1 | C—F | S | LIIIO-262 | A3 | S | B17 | C—F | S |
| LIIIO-263 | A3 | S | B25 | C—F | S | LIIIO-264 | A3 | S | B57 | C—F | S |
| LIIIO-265 | A3 | S | B70 | C—F | S | LIIIO-266 | A3 | S | B72 | C—F | S |
| LIIIO-267 | A3 | S | B1 | N | O | LIIIO-268 | A3 | S | B17 | N | O |
| LIIIO-269 | A3 | S | B25 | N | O | LIIIO-270 | A3 | S | B57 | N | O |
| LIIIO-271 | A3 | S | B70 | N | O | LIIIO-272 | A3 | S | B72 | N | O |
| LIIIO-273 | A3 | S | B1 | N | S | LIIIO-274 | A3 | S | B17 | N | S |
| LIIIO-275 | A3 | S | B25 | N | S | LIIIO-276 | A3 | S | B57 | N | S |
| LIIIO-277 | A3 | S | B70 | N | S | LIIIO-278 | A3 | S | B72 | N | S |
| LIIIO-279 | A3 | Se | B57 | C—H | O | LIIIO-280 | A3 | Se | B70 | C—H | O |
| LIIIO-281 | A3 | Se | B57 | C—H | S | LIIIO-282 | A3 | Se | B70 | C—H | S |
| LIIIO-283 | A3 | Se | B57 | C—F | O | LIIIO-284 | A3 | Se | B70 | C—F | O |
| LIIIO-285 | A3 | Se | B57 | C—F | S | LIIIO-286 | A3 | Se | B70 | C—F | S |
| LIIIO-287 | A3 | Se | B57 | N | O | LIIIO-288 | A3 | Se | B70 | N | O |
| LIIIO-289 | A3 | Se | B57 | N | S | LIIIO-290 | A3 | Se | B70 | N | S |
| LIIIO-291 | A3 | NMe | B70 | C—H | O | LIIIO-292 | A3 | NMe | B70 | C—H | S |
| LIIIO-293 | A3 | NMe | B57 | C—F | O | LIIIO-294 | A3 | NMe | B70 | C—F | O |
| LIIIO-295 | A3 | NMe | B57 | C—F | S | LIIIO-296 | A3 | NMe | B70 | C—F | S |
| LIIIO-297 | A3 | NMe | B70 | N | O | LIIIO-298 | A3 | NMe | B70 | N | S; | wherein Compound LIVO-1 to Compound LIVO-108 have a structure represented by Formula LIVO:

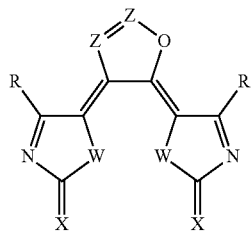

Formula LIVO in Formula LIVO, two X are identical, two W are identical, two R are identical, two Z are identical and are $CR_L$, and X, W, R and $R_L$ correspond to an atom or a group selected from the following table, respectively:

| NO. | X | W | R | $R_L$ | NO. | X | W | R | $R_L$ | NO. | X | W | R | $R_L$ |
|---|---|---|---|---|---|---|---|---|---|---|---|---|---|---|
| LIVO-1 | A1 | O | B1 | H | LIVO-2 | A1 | O | B17 | H | LIVO-3 | A1 | O | B25 | H |
| LIVO-4 | A1 | O | B54 | H | LIVO-5 | A1 | O | B70 | H | LIVO-6 | A1 | O | B72 | H |
| LIVO-7 | A1 | S | B1 | H | LIVO-8 | A1 | S | B17 | H | LIVO-9 | A1 | S | B25 | H |
| LIVO-10 | A1 | S | B54 | H | LIVO-11 | A1 | S | B70 | H | LIVO-12 | A1 | S | B72 | H |
| LIVO-13 | A1 | Se | B54 | H | LIVO-14 | A1 | Se | B70 | H | LIVO-15 | A1 | Se | B72 | H |
| LIVO-16 | A1 | NMe | B54 | H | LIVO-17 | A1 | NMe | B70 | H | LIVO-18 | A1 | NMe | B72 | H |
| LIVO-19 | A1 | O | H | F | LIVO-20 | A1 | O | B17 | F | LIVO-21 | A1 | O | B25 | F |
| LIVO-22 | A1 | O | B54 | F | LIVO-23 | A1 | O | B70 | F | LIVO-24 | A1 | O | B72 | F |
| LIVO-25 | A1 | S | H | F | LIVO-26 | A1 | S | B17 | F | LIVO-27 | A1 | S | B25 | F |
| LIVO-28 | A1 | S | B54 | F | LIVO-29 | A1 | S | B70 | F | LIVO-30 | A1 | S | B72 | F |

-continued

| NO. | X | W | R | $R_L$ | NO. | X | W | R | $R_L$ | NO. | X | W | R | $R_L$ |
|---|---|---|---|---|---|---|---|---|---|---|---|---|---|---|
| LIVO-31 | A1 | O | H | B6 | LIVO-32 | A1 | O | B17 | B6 | LIVO-33 | A1 | O | B25 | B6 |
| LIVO-34 | A1 | O | B54 | B6 | LIVO-35 | A1 | O | B70 | B6 | LIVO-36 | A1 | O | B72 | B6 |
| LIVO-37 | A1 | S | H | B6 | LIVO-38 | A1 | S | B17 | B6 | LIVO-39 | A1 | S | B25 | B6 |
| LIVO-40 | A1 | S | B54 | B6 | LIVO-41 | A1 | S | B70 | B6 | LIVO-42 | A1 | S | B72 | B6 |
| LIVO-43 | A1 | O | H | B70 | LIVO-44 | A1 | O | B17 | B70 | LIVO-45 | A1 | O | B25 | B70 |
| LIVO-46 | A1 | O | B54 | B70 | LIVO-47 | A1 | O | B70 | B70 | LIVO-48 | A1 | O | B72 | B70 |
| LIVO-49 | A1 | S | H | B70 | LIVO-50 | A1 | S | B17 | B70 | LIVO-51 | A1 | S | B25 | B70 |
| LIVO-52 | A1 | S | B54 | B70 | LIVO-53 | A1 | S | B70 | B70 | LIVO-54 | A1 | S | B72 | B70 |
| LIVO-55 | A2 | O | B1 | H | LIVO-56 | A2 | O | B17 | H | LIVO-57 | A2 | O | B25 | H |
| LIVO-58 | A2 | O | B54 | H | LIVO-59 | A2 | O | B70 | H | LIVO-60 | A2 | O | B72 | H |
| LIVO-61 | A2 | S | B1 | H | LIVO-62 | A2 | S | B17 | H | LIVO-63 | A2 | S | B25 | H |
| LIVO-64 | A2 | S | B54 | H | LIVO-65 | A2 | S | B70 | H | LIVO-66 | A2 | S | B72 | H |
| LIVO-67 | A2 | O | B54 | F | LIVO-68 | A2 | O | B70 | F | LIVO-69 | A2 | O | B72 | F |
| LIVO-70 | A2 | S | B54 | F | LIVO-71 | A2 | S | B70 | F | LIVO-72 | A2 | S | B72 | F |
| LIVO-73 | A2 | O | B54 | B6 | LIVO-74 | A2 | O | B70 | B6 | LIVO-75 | A2 | O | B72 | B6 |
| LIVO-76 | A2 | S | B54 | B6 | LIVO-77 | A2 | S | B70 | B6 | LIVO-78 | A2 | S | B72 | B6 |
| LIVO-79 | A2 | O | B54 | B70 | LIVO-80 | A2 | O | B70 | B70 | LIVO-81 | A2 | O | B72 | B70 |
| LIVO-82 | A3 | O | B1 | H | LIVO-83 | A3 | O | B17 | H | LIVO-84 | A3 | O | B25 | H |
| LIVO-85 | A3 | O | B54 | H | LIVO-86 | A3 | O | B70 | H | LIVO-87 | A3 | O | B72 | H |
| LIVO-88 | A3 | S | B1 | H | LIVO-89 | A3 | S | B17 | H | LIVO-90 | A3 | S | B25 | H |
| LIVO-91 | A3 | S | B54 | H | LIVO-92 | A3 | S | B70 | H | LIVO-93 | A3 | S | B72 | H |
| LIVO-94 | A3 | O | B54 | F | LIVO-95 | A3 | O | B70 | F | LIVO-96 | A3 | O | B72 | F |
| LIVO-97 | A3 | S | B54 | F | LIVO-98 | A3 | S | B70 | F | LIVO-99 | A3 | S | B72 | F |
| LIVO-100 | A3 | O | B54 | B6 | LIVO-101 | A3 | O | B70 | B6 | LIVO-102 | A3 | O | B72 | B6 |
| LIVO-103 | A3 | S | B54 | B6 | LIVO-104 | A3 | S | B70 | B6 | LIVO-105 | A3 | S | B72 | B6 |
| LIVO-106 | A3 | O | B54 | B70 | LIVO-107 | A3 | O | B70 | B70 | LIVO-108 | A3 | O | B72 | B70; | wherein Compound LVO-1 to Compound LVO-108 have a structure represented by Formula LVO:

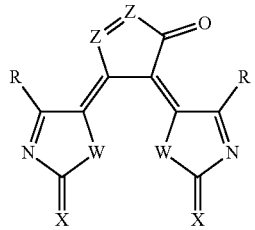

Formula LVO in Formula LVO, two X are identical, two W are identical, two R are identical, two Z are identical and are $CR_L$, and X, W, R and $R_L$ correspond to an atom or a group selected from the following table, respectively:

| NO. | X | W | R | $R_L$ | NO. | X | W | R | $R_L$ | NO. | X | W | R | $R_L$ |
|---|---|---|---|---|---|---|---|---|---|---|---|---|---|---|
| LVO-1 | A1 | O | B1 | H | LVO-2 | A1 | O | B17 | H | LVO-3 | A1 | O | B25 | H |
| LVO-4 | A1 | O | B54 | H | LVO-5 | A1 | O | B70 | H | LVO-6 | A1 | O | B72 | H |
| LVO-7 | A1 | S | B1 | H | LVO-8 | A1 | S | B17 | H | LVO-9 | A1 | S | B25 | H |
| LVO-10 | A1 | S | B54 | H | LVO-11 | A1 | S | B70 | H | LVO-12 | A1 | S | B72 | H |
| LVO-13 | A1 | Se | B54 | H | LVO-14 | A1 | Se | B70 | H | LVO-15 | A1 | Se | B72 | H |
| LVO-16 | A1 | NMe | B54 | H | LVO-17 | A1 | NMe | B70 | H | LVO-18 | A1 | NMe | B72 | H |
| LVO-19 | A1 | O | H | F | LVO-20 | A1 | O | B17 | F | LVO-21 | A1 | O | B25 | F |
| LVO-22 | A1 | O | B54 | F | LVO-23 | A1 | O | B70 | F | LVO-24 | A1 | O | B72 | F |
| LVO-25 | A1 | S | H | F | LVO-26 | A1 | S | B17 | F | LVO-27 | A1 | S | B25 | F |
| LVO-28 | A1 | S | B54 | F | LVO-29 | A1 | S | B70 | F | LVO-30 | A1 | S | B72 | F |
| LVO-31 | A1 | O | H | B6 | LVO-32 | A1 | O | B17 | B6 | LVO-33 | A1 | O | B25 | B6 |
| LVO-34 | A1 | O | B54 | B6 | LVO-35 | A1 | O | B70 | B6 | LVO-36 | A1 | O | B72 | B6 |
| LVO-37 | A1 | S | H | B6 | LVO-38 | A1 | S | B17 | B6 | LVO-39 | A1 | S | B25 | B6 |
| LVO-40 | A1 | S | B54 | B6 | LVO-41 | A1 | S | B70 | B6 | LVO-42 | A1 | S | B72 | B6 |
| LVO-43 | A1 | O | H | B70 | LVO-44 | A1 | O | B17 | B70 | LVO-45 | A1 | O | B25 | B70 |
| LVO-46 | A1 | O | B54 | B70 | LVO-47 | A1 | O | B70 | B70 | LVO-48 | A1 | O | B72 | B70 |
| LVO-49 | A1 | S | H | B70 | LVO-50 | A1 | S | B17 | B70 | LVO-51 | A1 | S | B25 | B70 |
| LVO-52 | A1 | S | B54 | B70 | LVO-53 | A1 | S | B70 | B70 | LVO-54 | A1 | S | B72 | B70 |
| LVO-55 | A2 | O | B1 | H | LVO-56 | A2 | O | B17 | H | LVO-57 | A2 | O | B25 | H |
| LVO-58 | A2 | O | B54 | H | LVO-59 | A2 | O | B70 | H | LVO-60 | A2 | O | B72 | H |
| LVO-61 | A2 | S | B1 | H | LVO-62 | A2 | S | B17 | H | LVO-63 | A2 | S | B25 | H |

-continued

| NO. | X | W | R | R_L | NO. | X | W | R | R_L | NO. | X | W | R | R_L |
|---|---|---|---|---|---|---|---|---|---|---|---|---|---|---|
| LVO-64 | A2 | S | B54 | H | LVO-65 | A2 | S | B70 | H | LVO-66 | A2 | S | B72 | H |
| LVO-67 | A2 | O | B54 | F | LVO-68 | A2 | O | B70 | F | LVO-69 | A2 | O | B72 | F |
| LVO-70 | A2 | S | B54 | F | LVO-71 | A2 | S | B70 | F | LVO-72 | A2 | S | B72 | F |
| LVO-73 | A2 | O | B54 | B6 | LVO-74 | A2 | O | B70 | B6 | LVO-75 | A2 | O | B72 | B6 |
| LVO-76 | A2 | S | B54 | B6 | LVO-77 | A2 | S | B70 | B6 | LVO-78 | A2 | S | B72 | B6 |
| LVO-79 | A2 | O | B54 | B70 | LVO-80 | A2 | O | B70 | B70 | LVO-81 | A2 | O | B72 | B70 |
| LVO-82 | A3 | O | B1 | H | LVO-83 | A3 | O | B17 | H | LVO-84 | A3 | O | B25 | H |
| LVO-85 | A3 | O | B54 | H | LVO-86 | A3 | O | B70 | H | LVO-87 | A3 | O | B72 | H |
| LVO-88 | A3 | S | B1 | H | LVO-89 | A3 | S | B17 | H | LVO-90 | A3 | S | B25 | H |
| LVO-91 | A3 | S | B54 | H | LVO-92 | A3 | S | B70 | H | LVO-93 | A3 | S | B72 | H |
| LVO-94 | A3 | O | B54 | F | LVO-95 | A3 | O | B70 | F | LVO-96 | A3 | O | B72 | F |
| LVO-97 | A3 | S | B54 | F | LVO-98 | A3 | S | B70 | F | LVO-99 | A3 | S | B72 | F |
| LVO-100 | A3 | O | B54 | B6 | LVO-101 | A3 | O | B70 | B6 | LVO-102 | A3 | O | B72 | B6 |
| LVO-103 | A3 | S | B54 | B6 | LVO-104 | A3 | S | B70 | B6 | LVO-105 | A3 | S | B72 | B6 |
| LVO-106 | A3 | O | B54 | B70 | LVO-107 | A3 | O | B70 | B70 | LVO-108 | A3 | O | B72 | B70; | wherein Compound LVIO-1 to Compound LVIO-298 have a structure represented by Formula LVIO:

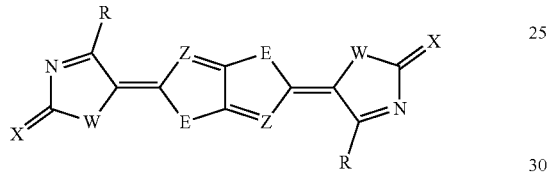

Formula LVIO in Formula LVIO, two X are identical, two W are identical, two R are identical, two Z are identical, two E are identical, and X, W, R, E and Z correspond to an atom or a group selected from the following table, respectively:

| NO. | X | W | R | Z | E | NO. | X | W | R | Z | E |
|---|---|---|---|---|---|---|---|---|---|---|---|
| LVIO-1 | A1 | O | B1 | C—H | O | LVIO-2 | A1 | O | B17 | C—H | O |
| LVIO-3 | A1 | O | B25 | C—H | O | LVIO-4 | A1 | O | B57 | C—H | O |
| LVIO-5 | A1 | O | B70 | C—H | O | LVIO-6 | A1 | O | B72 | C—H | O |
| LVIO-7 | A1 | O | B1 | C—H | S | LVIO-8 | A1 | O | B17 | C—H | S |
| LVIO-9 | A1 | O | B25 | C—H | S | LVIO-10 | A1 | O | B57 | C—H | S |
| LVIO-11 | A1 | O | B70 | C—H | S | LVIO-12 | A1 | O | B72 | C—H | S |
| LVIO-13 | A1 | O | B1 | C—F | O | LVIO-14 | A1 | O | B17 | C—F | O |
| LVIO-15 | A1 | O | B25 | C—F | O | LVIO-16 | A1 | O | B57 | C—F | O |
| LVIO-17 | A1 | O | B70 | C—F | O | LVIO-18 | A1 | O | B72 | C—F | O |
| LVIO-19 | A1 | O | B1 | C—F | S | LVIO-20 | A1 | O | B17 | C—F | S |
| LVIO-21 | A1 | O | B25 | C—F | S | LVIO-22 | A1 | O | B57 | C—F | S |
| LVIO-23 | A1 | O | B70 | C—F | S | LVIO-24 | A1 | O | B72 | C—F | S |
| LVIO-25 | A1 | O | B1 | N | O | LVIO-26 | A1 | O | B17 | N | O |
| LVIO-27 | A1 | O | B25 | N | O | LVIO-28 | A1 | O | B57 | N | O |
| LVIO-29 | A1 | O | B70 | N | O | LVIO-30 | A1 | O | B72 | N | O |
| LVIO-31 | A1 | O | B1 | N | S | LVIO-32 | A1 | O | B17 | N | S |
| LVIO-33 | A1 | O | B25 | N | S | LVIO-34 | A1 | O | B57 | N | S |
| LVIO-35 | A1 | O | B70 | N | S | LVIO-36 | A1 | O | B72 | N | S |
| LVIO-37 | A1 | S | B1 | C—H | O | LVIO-38 | A1 | S | B17 | C—H | O |
| LVIO-39 | A1 | S | B25 | C—H | O | LVIO-40 | A1 | S | B57 | C—H | O |
| LVIO-41 | A1 | S | B70 | C—H | O | LVIO-42 | A1 | S | B72 | C—H | O |
| LVIO-43 | A1 | S | B1 | C—H | S | LVIO-44 | A1 | S | B17 | C—H | S |
| LVIO-45 | A1 | S | B25 | C—H | S | LVIO-46 | A1 | S | B57 | C—H | S |
| LVIO-47 | A1 | S | B70 | C—H | S | LVIO-48 | A1 | S | B72 | C—H | S |
| LVIO-49 | A1 | S | B1 | C—F | O | LVIO-50 | A1 | S | B17 | C—F | O |
| LVIO-51 | A1 | S | B25 | C—F | O | LVIO-52 | A1 | S | B57 | C—F | O |
| LVIO-53 | A1 | S | B70 | C—F | O | LVIO-54 | A1 | S | B72 | C—F | O |
| LVIO-55 | A1 | S | B1 | C—F | S | LVIO-56 | A1 | S | B17 | C—F | S |
| LVIO-57 | A1 | S | B25 | C—F | S | LVIO-58 | A1 | S | B57 | C—F | S |
| LVIO-59 | A1 | S | B70 | C—F | S | LVIO-60 | A1 | S | B72 | C—F | S |
| LVIO-61 | A1 | S | B1 | N | O | LVIO-62 | A1 | S | B17 | N | O |
| LVIO-63 | A1 | S | B25 | N | O | LVIO-64 | A1 | S | B57 | N | O |
| LVIO-65 | A1 | S | B70 | N | O | LVIO-66 | A1 | S | B72 | N | O |

-continued

| NO. | X | W | R | Z | E | NO. | X | W | R | Z | E |
|---|---|---|---|---|---|---|---|---|---|---|---|
| LVIO-67 | A1 | S | B1 | N | S | LVIO-68 | A1 | S | B17 | N | S |
| LVIO-69 | A1 | S | B25 | N | S | LVIO-70 | A1 | S | B57 | N | S |
| LVIO-71 | A1 | S | B70 | N | S | LVIO-72 | A1 | S | B72 | N | S |
| LVIO-73 | A1 | Se | B25 | C—H | O | LVIO-74 | A1 | Se | B57 | C—H | O |
| LVIO-75 | A1 | Se | B70 | C—H | O | LVIO-76 | A1 | Se | B72 | C—H | O |
| LVIO-77 | A1 | Se | B25 | C—H | S | LVIO-78 | A1 | Se | B57 | C—H | S |
| LVIO-79 | A1 | Se | B70 | C—H | S | LVIO-80 | A1 | Se | B72 | C—H | S |
| LVIO-81 | A1 | Se | B57 | C—F | O | LVIO-82 | A1 | Se | B70 | C—F | O |
| LVIO-83 | A1 | Se | B57 | C—F | S | LVIO-84 | A1 | Se | B70 | C—F | S |
| LVIO-85 | A1 | Se | B25 | N | O | LVIO-86 | A1 | Se | B57 | N | O |
| LVIO-87 | A1 | Se | B70 | N | O | LVIO-88 | A1 | Se | B72 | N | O |
| LVIO-89 | A1 | Se | B25 | N | S | LVIO-90 | A1 | Se | B57 | N | S |
| LVIO-91 | A1 | Se | B70 | N | S | LVIO-92 | A1 | Se | B72 | N | S |
| LVIO-93 | A1 | NMe | B25 | C—H | O | LVIO-94 | A1 | NMe | B57 | C—H | O |
| LVIO-95 | A1 | NMe | B70 | C—H | O | LVIO-96 | A1 | NMe | B72 | C—H | O |
| LVIO-97 | A1 | NMe | B25 | C—H | S | LVIO-98 | A1 | NMe | B57 | C—H | S |
| LVIO-99 | A1 | NMe | B70 | C—H | S | LVIO-100 | A1 | NMe | B72 | C—H | S |
| LVIO-101 | A1 | NMe | B57 | C—F | O | LVIO-102 | A1 | NMe | B70 | C—F | O |
| LVIO-103 | A1 | NMe | B57 | C—F | S | LVIO-104 | A1 | NMe | B70 | C—F | S |
| LVIO-105 | A1 | NMe | B25 | N | O | LVIO-106 | A1 | NMe | B57 | N | O |
| LVIO-107 | A1 | NMe | B70 | N | O | LVIO-108 | A1 | NMe | B72 | N | O |
| LVIO-109 | A1 | NMe | B25 | N | S | LVIO-110 | A1 | NMe | B57 | N | S |
| LVIO-111 | A1 | NMe | B70 | N | S | LVIO-112 | A1 | NMe | B72 | N | S |
| LVIO-113 | A2 | O | B1 | C—H | O | LVIO-114 | A2 | O | B17 | C—H | O |
| LVIO-115 | A2 | O | B25 | C—H | O | LVIO-116 | A2 | O | B57 | C—H | O |
| LVIO-117 | A2 | O | B70 | C—H | O | LVIO-118 | A2 | O | B72 | C—H | O |
| LVIO-119 | A2 | O | B1 | C—H | S | LVIO-120 | A2 | O | B17 | C—H | S |
| LVIO-121 | A2 | O | B25 | C—H | S | LVIO-122 | A2 | O | B57 | C—H | S |
| LVIO-123 | A2 | O | B70 | C—H | S | LVIO-124 | A2 | O | B72 | C—H | S |
| LVIO-125 | A2 | O | B1 | C—F | O | LVIO-126 | A2 | O | B17 | C—F | O |
| LVIO-127 | A2 | O | B25 | C—F | O | LVIO-128 | A2 | O | B57 | C—F | O |
| LVIO-129 | A2 | O | B70 | C—F | O | LVIO-130 | A2 | O | B72 | C—F | O |
| LVIO-131 | A2 | O | B1 | C—F | S | LVIO-132 | A2 | O | B17 | C—F | S |
| LVIO-133 | A2 | O | B25 | C—F | S | LVIO-134 | A2 | O | B57 | C—F | S |
| LVIO-135 | A2 | O | B70 | C—F | S | LVIO-136 | A2 | O | B72 | C—F | S |
| LVIO-137 | A2 | O | B1 | N | O | LVIO-138 | A2 | O | B17 | N | O |
| LVIO-139 | A2 | O | B25 | N | O | LVIO-140 | A2 | O | B57 | N | O |
| LVIO-141 | A2 | O | B70 | N | O | LVIO-142 | A2 | O | B72 | N | O |
| LVIO-143 | A2 | O | B1 | N | S | LVIO-144 | A2 | O | B17 | N | S |
| LVIO-145 | A2 | O | B25 | N | S | LVIO-146 | A2 | O | B57 | N | S |
| LVIO-147 | A2 | O | B70 | N | S | LVIO-148 | A2 | O | B72 | N | S |
| LVIO-149 | A2 | S | B1 | C—H | O | LVIO-150 | A2 | S | B17 | C—H | O |
| LVIO-151 | A2 | S | B25 | C—H | O | LVIO-152 | A2 | S | B57 | C—H | O |
| LVIO-153 | A2 | S | B70 | C—H | O | LVIO-154 | A2 | S | B72 | C—H | O |
| LVIO-155 | A2 | S | B1 | C—H | S | LVIO-156 | A2 | S | B17 | C—H | S |
| LVIO-157 | A2 | S | B25 | C—H | S | LVIO-158 | A2 | S | B57 | C—H | S |
| LVIO-159 | A2 | S | B70 | C—H | S | LVIO-160 | A2 | S | B72 | C—H | S |
| LVIO-161 | A2 | S | B1 | C—F | O | LVIO-162 | A2 | S | B17 | C—F | O |
| LVIO-163 | A2 | S | B25 | C—F | O | LVIO-164 | A2 | S | B57 | C—F | O |
| LVIO-165 | A2 | S | B70 | C—F | O | LVIO-166 | A2 | S | B72 | C—F | O |
| LVIO-167 | A2 | S | B1 | C—F | S | LVIO-168 | A2 | S | B17 | C—F | S |
| LVIO-169 | A2 | S | B25 | C—F | S | LVIO-170 | A2 | S | B57 | C—F | S |
| LVIO-171 | A2 | S | B70 | C—F | S | LVIO-172 | A2 | S | B72 | C—F | S |
| LVIO-173 | A2 | S | B1 | N | O | LVIO-174 | A2 | S | B17 | N | O |
| LVIO-175 | A2 | S | B25 | N | O | LVIO-176 | A2 | S | B57 | N | O |
| LVIO-177 | A2 | S | B70 | N | O | LVIO-178 | A2 | S | B72 | N | O |
| LVIO-179 | A2 | S | B1 | N | S | LVIO-180 | A2 | S | B17 | N | S |
| LVIO-181 | A2 | S | B25 | N | S | LVIO-182 | A2 | S | B57 | N | S |
| LVIO-183 | A2 | S | B70 | N | S | LVIO-184 | A2 | S | B72 | N | S |
| LVIO-185 | A2 | Se | B57 | C—H | O | LVIO-186 | A2 | Se | B70 | C—H | O |
| LVIO-187 | A2 | Se | B57 | C—H | O | LVIO-188 | A2 | Se | B70 | C—H | O |
| LVIO-189 | A2 | Se | B57 | C—F | O | LVIO-190 | A2 | Se | B70 | C—F | O |
| LVIO-191 | A2 | Se | B57 | C—F | S | LVIO-192 | A2 | Se | B70 | C—F | S |
| LVIO-193 | A2 | Se | B57 | N | O | LVIO-194 | A2 | Se | B70 | N | O |
| LVIO-195 | A2 | Se | B57 | N | S | LVIO-196 | A2 | Se | B70 | N | S |
| LVIO-197 | A2 | NMe | B70 | C—H | S | LVIO-198 | A2 | NMe | B70 | C—H | S |
| LVIO-199 | A2 | NMe | B57 | C—F | O | LVIO-200 | A2 | NMe | B70 | C—F | O |
| LVIO-201 | A2 | NMe | B57 | C—F | S | LVIO-202 | A2 | NMe | B70 | C—F | S |
| LVIO-203 | A2 | NMe | B70 | N | O | LVIO-204 | A2 | NMe | B70 | N | S |
| LVIO-205 | A3 | O | B1 | C—H | O | LVIO-206 | A3 | O | B17 | C—H | O |
| LVIO-207 | A3 | O | B25 | C—H | O | LVIO-208 | A3 | O | B57 | C—H | O |
| LVIO-209 | A3 | O | B70 | C—H | O | LVIO-210 | A3 | O | B72 | C—H | O |
| LVIO-211 | A3 | O | B1 | C—H | S | LVIO-212 | A3 | O | B17 | C—H | S |
| LVIO-213 | A3 | O | B25 | C—H | S | LVIO-214 | A3 | O | B57 | C—H | S |
| LVIO-215 | A3 | O | B70 | C—H | S | LVIO-216 | A3 | O | B72 | C—H | S |
| LVIO-217 | A3 | O | B1 | C—F | O | LVIO-218 | A3 | O | B17 | C—F | O |
| LVIO-219 | A3 | O | B25 | C—F | O | LVIO-220 | A3 | O | B57 | C—F | O |

-continued

| NO. | X | W | R | Z | E | NO. | X | W | R | Z | E |
|---|---|---|---|---|---|---|---|---|---|---|---|
| LVIO-221 | A3 | O | B70 | C—F | O | LVIO-222 | A3 | O | B72 | C—F | O |
| LVIO-223 | A3 | O | B1 | C—F | S | LVIO-224 | A3 | O | B17 | C—F | S |
| LVIO-225 | A3 | O | B25 | C—F | S | LVIO-226 | A3 | O | B57 | C—F | S |
| LVIO-227 | A3 | O | B70 | C—F | S | LVIO-228 | A3 | O | B72 | C—F | S |
| LVIO-229 | A3 | O | B70 | C—H | S | LVIO-230 | A3 | O | B72 | C—H | S |
| LVIO-231 | A3 | O | B1 | N | O | LVIO-232 | A3 | O | B17 | N | O |
| LVIO-233 | A3 | O | B25 | N | O | LVIO-234 | A3 | O | B57 | N | O |
| LVIO-235 | A3 | O | B70 | N | O | LVIO-236 | A3 | O | B72 | N | O |
| LVIO-237 | A3 | O | B1 | N | S | LVIO-238 | A3 | O | B17 | N | S |
| LVIO-239 | A3 | O | B25 | N | S | LVIO-240 | A3 | O | B57 | N | S |
| LVIO-241 | A3 | O | B70 | N | S | LVIO-242 | A3 | O | B72 | N | S |
| LVIO-243 | A3 | S | B1 | C—H | O | LVIO-244 | A3 | S | B17 | C—H | O |
| LVIO-245 | A3 | S | B25 | C—H | O | LVIO-246 | A3 | S | B57 | C—H | O |
| LVIO-247 | A3 | S | B70 | C—H | O | LVIO-248 | A3 | S | B72 | C—H | O |
| LVIO-249 | A3 | S | B1 | C—H | S | LVIO-250 | A3 | S | B17 | C—H | S |
| LVIO-251 | A3 | S | B25 | C—H | S | LVIO-252 | A3 | S | B57 | C—H | S |
| LVIO-253 | A3 | S | B70 | C—H | S | LVIO-254 | A3 | S | B72 | C—H | S |
| LVIO-255 | A3 | S | B1 | C—F | O | LVIO-256 | A3 | S | B17 | C—F | O |
| LVIO-257 | A3 | S | B25 | C—F | O | LVIO-258 | A3 | S | B57 | C—F | O |
| LVIO-259 | A3 | S | B70 | C—F | O | LVIO-260 | A3 | S | B72 | C—F | O |
| LVIO-261 | A3 | S | B1 | C—F | S | LVIO-262 | A3 | S | B17 | C—F | S |
| LVIO-263 | A3 | S | B25 | C—F | S | LVIO-264 | A3 | S | B57 | C—F | S |
| LVIO-265 | A3 | S | B70 | C—F | S | LVIO-266 | A3 | S | B72 | C—F | S |
| LVIO-267 | A3 | S | B1 | N | O | LVIO-268 | A3 | S | B17 | N | O |
| LVIO-269 | A3 | S | B25 | N | O | LVIO-270 | A3 | S | B57 | N | O |
| LVIO-271 | A3 | S | B70 | N | O | LVIO-272 | A3 | S | B72 | N | O |
| LVIO-273 | A3 | S | B1 | N | S | LVIO-274 | A3 | S | B17 | N | S |
| LVIO-275 | A3 | S | B25 | N | S | LVIO-276 | A3 | S | B57 | N | S |
| LVIO-277 | A3 | S | B70 | N | S | LVIO-278 | A3 | S | B72 | N | S |
| LVIO-279 | A3 | Se | B57 | C—H | O | LVIO-280 | A3 | Se | B70 | C—H | O |
| LVIO-281 | A3 | Se | B57 | C—H | S | LVIO-282 | A3 | Se | B70 | C—H | S |
| LVIO-283 | A3 | Se | B57 | C—F | O | LVIO-284 | A3 | Se | B70 | C—F | O |
| LVIO-285 | A3 | Se | B57 | C—F | S | LVIO-286 | A3 | Se | B70 | C—F | S |
| LVIO-287 | A3 | Se | B57 | N | O | LVIO-288 | A3 | Se | B70 | N | O |
| LVIO-289 | A3 | Se | B57 | N | S | LVIO-290 | A3 | Se | B70 | N | S |
| LVIO-291 | A3 | NMe | B70 | C—H | O | LVIO-292 | A3 | NMe | B70 | C—H | S |
| LVIO-293 | A3 | NMe | B57 | C—F | O | LVIO-294 | A3 | NMe | B70 | C—F | O |
| LVIO-295 | A3 | NMe | B57 | C—F | S | LVIO-296 | A3 | NMe | B70 | C—F | S |
| LVIO-297 | A3 | NMe | B70 | N | O | LVIO-298 | A3 | NMe | B70 | N | S; | wherein Compound LVIIO-1 to Compound LVIIO-298 have a structure represented by Formula LVIIO:

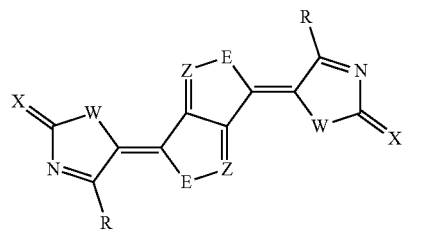

Formula LVIIO in Formula LVIIO, two X are identical, two W are identical, two R are identical, two E are identical, two Z are identical, and X, W, R, E and Z correspond to an atom or a group selected from the following table, respectively:

| NO. | X | W | R | Z | E | NO. | X | W | R | Z | E |
|---|---|---|---|---|---|---|---|---|---|---|---|
| LVIIO-1 | A1 | O | B1 | C—H | O | LVIIO-2 | A1 | O | B17 | C—H | O |
| LVIIO-3 | A1 | O | B25 | C—H | O | LVIIO-4 | A1 | O | B57 | C—H | O |
| LVIIO-5 | A1 | O | B70 | C—H | O | LVIIO-6 | A1 | O | B72 | C—H | O |
| LVIIO-7 | A1 | O | B1 | C—H | S | LVIIO-8 | A1 | O | B17 | C—H | S |
| LVIIO-9 | A1 | O | B25 | C—H | S | LVIIO-10 | A1 | O | B57 | C—H | S |
| LVIIO-11 | A1 | O | B70 | C—H | S | LVIIO-12 | A1 | O | B72 | C—H | S |
| LVIIO-13 | A1 | O | B1 | C—F | O | LVIIO-14 | A1 | O | B17 | C—F | O |

| NO. | X | W | R | Z | E | NO. | X | W | R | Z | E |
|---|---|---|---|---|---|---|---|---|---|---|---|
| LVIIO-15 | A1 | O | B25 | C—F | O | LVIIO-16 | A1 | O | B57 | C—F | O |
| LVIIO-17 | A1 | O | B70 | C—F | O | LVIIO-18 | A1 | O | B72 | C—F | O |
| LVIIO-19 | A1 | O | B1 | C—F | S | LVIIO-20 | A1 | O | B17 | C—F | S |
| LVIIO-21 | A1 | O | B25 | C—F | S | LVIIO-22 | A1 | O | B57 | C—F | S |
| LVIIO-23 | A1 | O | B70 | C—F | S | LVIIO-24 | A1 | O | B72 | C—F | S |
| LVIIO-25 | A1 | O | B1 | N | O | LVIIO-26 | A1 | O | B17 | N | O |
| LVIIO-27 | A1 | O | B25 | N | O | LVIIO-28 | A1 | O | B57 | N | O |
| LVIIO-29 | A1 | O | B70 | N | O | LVIIO-30 | A1 | O | B72 | N | O |
| LVIIO-31 | A1 | O | B1 | N | S | LVIIO-32 | A1 | O | B17 | N | S |
| LVIIO-33 | A1 | O | B25 | N | S | LVIIO-34 | A1 | O | B57 | N | S |
| LVIIO-35 | A1 | O | B70 | N | S | LVIIO-36 | A1 | O | B72 | N | S |
| LVIIO-37 | A1 | S | B1 | C—H | O | LVIIO-38 | A1 | S | B17 | C—H | O |
| LVIIO-39 | A1 | S | B25 | C—H | O | LVIIO-40 | A1 | S | B57 | C—H | O |
| LVIIO-41 | A1 | S | B70 | C—H | O | LVIIO-42 | A1 | S | B72 | C—H | O |
| LVIIO-43 | A1 | S | B1 | C—H | S | LVIIO-44 | A1 | S | B17 | C—H | S |
| LVIIO-45 | A1 | S | B25 | C—H | S | LVIIO-46 | A1 | S | B57 | C—H | S |
| LVIIO-47 | A1 | S | B70 | C—H | S | LVIIO-48 | A1 | S | B72 | C—H | S |
| LVIIO-49 | A1 | S | B1 | C—F | O | LVIIO-50 | A1 | S | B17 | C—F | O |
| LVIIO-51 | A1 | S | B25 | C—F | O | LVIIO-52 | A1 | S | B57 | C—F | O |
| LVIIO-53 | A1 | S | B70 | C—F | O | LVIIO-54 | A1 | S | B72 | C—F | O |
| LVIIO-55 | A1 | S | B1 | C—F | S | LVIIO-56 | A1 | S | B17 | C—F | S |
| LVIIO-57 | A1 | S | B25 | C—F | S | LVIIO-58 | A1 | S | B57 | C—F | S |
| LVIIO-59 | A1 | S | B70 | C—F | S | LVIIO-60 | A1 | S | B72 | C—F | S |
| LVIIO-61 | A1 | S | B1 | N | O | LVIIO-62 | A1 | S | B17 | N | O |
| LVIIO-63 | A1 | S | B25 | N | O | LVIIO-64 | A1 | S | B57 | N | O |
| LVIIO-65 | A1 | S | B70 | N | O | LVIIO-66 | A1 | S | B72 | N | O |
| LVIIO-67 | A1 | S | B1 | N | S | LVIIO-68 | A1 | S | B17 | N | S |
| LVIIO-69 | A1 | S | B25 | N | S | LVIIO-70 | A1 | S | B57 | N | S |
| LVIIO-71 | A1 | S | B70 | N | S | LVIIO-72 | A1 | S | B72 | N | S |
| LVIIO-73 | A1 | Se | B25 | C—H | O | LVIIO-74 | A1 | Se | B57 | C—H | O |
| LVIIO-75 | A1 | Se | B70 | C—H | O | LVIIO-76 | A1 | Se | B72 | C—H | O |
| LVIIO-77 | A1 | Se | B25 | C—H | S | LVIIO-78 | A1 | Se | B57 | C—H | S |
| LVIIO-79 | A1 | Se | B70 | C—H | S | LVIIO-80 | A1 | Se | B72 | C—H | S |
| LVIIO-81 | A1 | Se | B57 | C—F | O | LVIIO-82 | A1 | Se | B70 | C—F | O |
| LVIIO-83 | A1 | Se | B57 | C—F | S | LVIIO-84 | A1 | Se | B70 | C—F | S |
| LVIIO-85 | A1 | Se | B25 | N | O | LVIIO-86 | A1 | Se | B57 | N | O |
| LVIIO-87 | A1 | Se | B70 | N | O | LVIIO-88 | A1 | Se | B72 | N | O |
| LVIIO-89 | A1 | Se | B25 | N | S | LVIIO-90 | A1 | Se | B57 | N | S |
| LVIIO-91 | A1 | Se | B70 | N | S | LVIIO-92 | A1 | Se | B72 | N | S |
| LVIIO-93 | A1 | NMe | B25 | C—H | O | LVIIO-94 | A1 | NMe | B57 | C—H | O |
| LVIIO-95 | A1 | NMe | B70 | C—H | O | LVIIO-96 | A1 | NMe | B72 | C—H | O |
| LVIIO-97 | A1 | NMe | B25 | C—H | S | LVIIO-98 | A1 | NMe | B57 | C—H | S |
| LVIIO-99 | A1 | NMe | B70 | C—H | S | LVIIO-100 | A1 | NMe | B72 | C—H | S |
| LVIIO-101 | A1 | NMe | B57 | C—F | O | LVIIO-102 | A1 | NMe | B70 | C—F | O |
| LVIIO-103 | A1 | NMe | B57 | C—F | S | LVIIO-104 | A1 | NMe | B70 | C—F | S |
| LVIIO-105 | A1 | NMe | B25 | N | O | LVIIO-106 | A1 | NMe | B57 | N | O |
| LVIIO-107 | A1 | NMe | B70 | N | O | LVIIO-108 | A1 | NMe | B72 | N | O |
| LVIIO-109 | A1 | NMe | B25 | N | S | LVIIO-110 | A1 | NMe | B57 | N | S |
| LVIIO-111 | A1 | NMe | B70 | N | S | LVIIO-112 | A1 | NMe | B72 | N | S |
| LVIIO-113 | A2 | O | B1 | C—H | O | LVIIO-114 | A2 | O | B17 | C—H | O |
| LVIIO-115 | A2 | O | B25 | C—H | O | LVIIO-116 | A2 | O | B57 | C—H | O |
| LVIIO-117 | A2 | O | B70 | C—H | O | LVIIO-118 | A2 | O | B72 | C—H | O |
| LVIIO-119 | A2 | O | B1 | C—H | S | LVIIO-120 | A2 | O | B17 | C—H | S |
| LVIIO-121 | A2 | O | B25 | C—H | S | LVIIO-122 | A2 | O | B57 | C—H | S |
| LVIIO-123 | A2 | O | B70 | C—H | S | LVIIO-124 | A2 | O | B72 | C—H | S |
| LVIIO-125 | A2 | O | B1 | C—F | O | LVIIO-126 | A2 | O | B17 | C—F | O |
| LVIIO-127 | A2 | O | B25 | C—F | O | LVIIO-128 | A2 | O | B57 | C—F | O |
| LVIIO-129 | A2 | O | B70 | C—F | O | LVIIO-130 | A2 | O | B72 | C—F | O |
| LVIIO-131 | A2 | O | B1 | C—F | S | LVIIO-132 | A2 | O | B17 | C—F | S |
| LVIIO-133 | A2 | O | B25 | C—F | S | LVIIO-134 | A2 | O | B57 | C—F | S |
| LVIIO-135 | A2 | O | B70 | C—F | S | LVIIO-136 | A2 | O | B72 | C—F | S |
| LVIIO-137 | A2 | O | B1 | N | O | LVIIO-138 | A2 | O | B17 | N | O |
| LVIIO-139 | A2 | O | B25 | N | O | LVIIO-140 | A2 | O | B57 | N | O |
| LVIIO-141 | A2 | O | B70 | N | O | LVIIO-142 | A2 | O | B72 | N | O |
| LVIIO-143 | A2 | O | B1 | N | S | LVIIO-144 | A2 | O | B17 | N | S |
| LVIIO-145 | A2 | O | B25 | N | S | LVIIO-146 | A2 | O | B57 | N | S |
| LVIIO-147 | A2 | O | B70 | N | S | LVIIO-148 | A2 | O | B72 | N | S |
| LVIIO-149 | A2 | S | B1 | C—H | O | LVIIO-150 | A2 | S | B17 | C—H | O |
| LVIIO-151 | A2 | S | B25 | C—H | O | LVIIO-152 | A2 | S | B57 | C—H | O |
| LVIIO-153 | A2 | S | B70 | C—H | O | LVIIO-154 | A2 | S | B72 | C—H | O |
| LVIIO-155 | A2 | S | B1 | C—H | S | LVIIO-156 | A2 | S | B17 | C—H | S |
| LVIIO-157 | A2 | S | B25 | C—H | S | LVIIO-158 | A2 | S | B57 | C—H | S |
| LVIIO-159 | A2 | S | B70 | C—H | S | LVIIO-160 | A2 | S | B72 | C—H | S |
| LVIIO-161 | A2 | S | B1 | C—F | O | LVIIO-162 | A2 | S | B17 | C—F | O |
| LVIIO-163 | A2 | S | B25 | C—F | O | LVIIO-164 | A2 | S | B57 | C—F | O |
| LVIIO-165 | A2 | S | B70 | C—F | O | LVIIO-166 | A2 | S | B72 | C—F | O |
| LVIIO-167 | A2 | S | B1 | C—F | S | LVIIO-168 | A2 | S | B17 | C—F | S |

-continued

| NO. | X | W | R | Z | E | NO. | X | W | R | Z | E |
|---|---|---|---|---|---|---|---|---|---|---|---|
| LVIIO-169 | A2 | S | B25 | C—F | S | LVIIO-170 | A2 | S | B57 | C—F | S |
| LVIIO-171 | A2 | S | B70 | C—F | S | LVIIO-172 | A2 | S | B72 | C—F | S |
| LVIIO-173 | A2 | S | B1 | N | O | LVIIO-174 | A2 | S | B17 | N | O |
| LVIIO-175 | A2 | S | B25 | N | O | LVIIO-176 | A2 | S | B57 | N | O |
| LVIIO-177 | A2 | S | B70 | N | O | LVIIO-178 | A2 | S | B72 | N | O |
| LVIIO-179 | A2 | S | B1 | N | S | LVIIO-180 | A2 | S | B17 | N | S |
| LVIIO-181 | A2 | S | B25 | N | S | LVIIO-182 | A2 | S | B57 | N | S |
| LVIIO-183 | A2 | S | B70 | N | S | LVIIO-184 | A2 | S | B72 | N | S |
| LVIIO-185 | A2 | Se | B57 | C—H | O | LVIIO-186 | A2 | Se | B70 | C—H | O |
| LVIIO-187 | A2 | Se | B57 | C—H | S | LVIIO-188 | A2 | Se | B70 | C—H | S |
| LVIIO-189 | A2 | Se | B57 | C—F | O | LVIIO-190 | A2 | Se | B70 | C—F | O |
| LVIIO-191 | A2 | Se | B57 | C—F | S | LVIIO-192 | A2 | Se | B70 | C—F | S |
| LVIIO-193 | A2 | Se | B57 | N | O | LVIIO-194 | A2 | Se | B70 | N | O |
| LVIIO-195 | A2 | Se | B57 | N | S | LVIIO-196 | A2 | Se | B70 | N | S |
| LVIIO-197 | A2 | NMe | B70 | C—H | O | LVIIO-198 | A2 | NMe | B70 | C—H | S |
| LVIIO-199 | A2 | NMe | B57 | C—F | O | LVIIO-200 | A2 | NMe | B70 | C—F | O |
| LVIIO-201 | A2 | NMe | B57 | C—F | S | LVIIO-202 | A2 | NMe | B70 | C—F | S |
| LVIIO-203 | A2 | NMe | B70 | N | O | LVIIO-204 | A2 | NMe | B70 | N | S |
| LVIIO-205 | A3 | O | B1 | C—H | O | LVIIO-206 | A3 | O | B17 | C—H | O |
| LVIIO-207 | A3 | O | B25 | C—H | O | LVIIO-208 | A3 | O | B57 | C—H | O |
| LVIIO-209 | A3 | O | B70 | C—H | O | LVIIO-210 | A3 | O | B72 | C—H | O |
| LVIIO-211 | A3 | O | B1 | C—H | S | LVIIO-212 | A3 | O | B17 | C—H | S |
| LVIIO-213 | A3 | O | B25 | C—H | S | LVIIO-214 | A3 | O | B57 | C—H | S |
| LVIIO-215 | A3 | O | B70 | C—H | S | LVIIO-216 | A3 | O | B72 | C—H | S |
| LVIIO-217 | A3 | O | B1 | C—F | O | LVIIO-218 | A3 | O | B17 | C—F | O |
| LVIIO-219 | A3 | O | B25 | C—F | O | LVIIO-220 | A3 | O | B57 | C—F | O |
| LVIIO-221 | A3 | O | B70 | C—F | O | LVIIO-222 | A3 | O | B72 | C—F | O |
| LVIIO-223 | A3 | O | B1 | C—F | S | LVIIO-224 | A3 | O | B17 | C—F | S |
| LVIIO-225 | A3 | O | B25 | C—F | S | LVIIO-226 | A3 | O | B57 | C—F | S |
| LVIIO-227 | A3 | O | B70 | C—F | S | LVIIO-228 | A3 | O | B72 | C—F | S |
| LVIIO-229 | A3 | O | B70 | C—H | S | LVIIO-230 | A3 | O | B72 | C—H | S |
| LVIIO-231 | A3 | O | B1 | N | O | LVIIO-232 | A3 | O | B17 | N | O |
| LVIIO-233 | A3 | O | B25 | N | O | LVIIO-234 | A3 | O | B57 | N | O |
| LVIIO-235 | A3 | O | B70 | N | O | LVIIO-236 | A3 | O | B72 | N | O |
| LVIIO-237 | A3 | O | B1 | N | S | LVIIO-238 | A3 | O | B17 | N | S |
| LVIIO-239 | A3 | O | B25 | N | S | LVIIO-240 | A3 | O | B57 | N | S |
| LVIIO-241 | A3 | O | B70 | N | S | LVIIO-242 | A3 | O | B72 | N | S |
| LVIIO-243 | A3 | S | B1 | C—H | O | LVIIO-244 | A3 | S | B17 | C—H | O |
| LVIIO-245 | A3 | S | B25 | C—H | O | LVIIO-246 | A3 | S | B57 | C—H | O |
| LVIIO-247 | A3 | S | B70 | C—H | O | LVIIO-248 | A3 | S | B72 | C—H | O |
| LVIIO-249 | A3 | S | B1 | C—H | S | LVIIO-250 | A3 | S | B17 | C—H | S |
| LVIIO-251 | A3 | S | B25 | C—H | S | LVIIO-252 | A3 | S | B57 | C—H | S |
| LVIIO-253 | A3 | S | B70 | C—H | S | LVIIO-254 | A3 | S | B72 | C—H | S |
| LVIIO-255 | A3 | S | B1 | C—F | O | LVIIO-256 | A3 | S | B17 | C—F | O |
| LVIIO-257 | A3 | S | B25 | C—F | O | LVIIO-258 | A3 | S | B57 | C—F | O |
| LVIIO-259 | A3 | S | B70 | C—F | O | LVIIO-260 | A3 | S | B72 | C—F | O |
| LVIIO-261 | A3 | S | B1 | C—F | S | LVIIO-262 | A3 | S | B17 | C—F | S |
| LVIIO-263 | A3 | S | B25 | C—F | S | LVIIO-264 | A3 | S | B57 | C—F | S |
| LVIIO-265 | A3 | S | B70 | C—F | S | LVIIO-266 | A3 | S | B72 | C—F | S |
| LVIIO-267 | A3 | S | B1 | N | O | LVIIO-268 | A3 | S | B17 | N | O |
| LVIIO-269 | A3 | S | B25 | N | O | LVIIO-270 | A3 | S | B57 | N | O |
| LVIIO-271 | A3 | S | B70 | N | O | LVIIO-272 | A3 | S | B72 | N | O |
| LVIIO-273 | A3 | S | B1 | N | S | LVIIO-274 | A3 | S | B17 | N | S |
| LVIIO-275 | A3 | S | B25 | N | S | LVIIO-276 | A3 | S | B57 | N | S |
| LVIIO-277 | A3 | S | B70 | N | S | LVIIO-278 | A3 | S | B72 | N | S |
| LVIIO-279 | A3 | Se | B57 | C—H | O | LVIIO-280 | A3 | Se | B70 | C—H | O |
| LVIIO-281 | A3 | Se | B57 | C—H | S | LVIIO-282 | A3 | Se | B70 | C—H | S |
| LVIIO-283 | A3 | Se | B57 | C—F | O | LVIIO-284 | A3 | Se | B70 | C—F | O |
| LVIIO-285 | A3 | Se | B57 | C—F | S | LVIIO-286 | A3 | Se | B70 | C—F | S |
| LVIIO-287 | A3 | Se | B57 | N | O | LVIIO-288 | A3 | Se | B70 | N | O |
| LVIIO-289 | A3 | Se | B57 | N | S | LVIIO-290 | A3 | Se | B70 | N | S |
| LVIIO-291 | A3 | NMe | B70 | C—H | O | LVIO-292 | A3 | NMe | B70 | C—H | S |
| LVIIO-293 | A3 | NMe | B57 | C—F | O | LVIIO-294 | A3 | NMe | B70 | C—F | O |
| LVIIO-295 | A3 | NMe | B57 | C—F | S | LVIIO-296 | A3 | NMe | B70 | C—F | S |
| LVIIO-297 | A3 | NMe | B70 | N | O | LVIIO-298 | A3 | NMe | B70 | N | S; | wherein Compound LVIIIO-1 to Compound LVIIIO-108 have a structure represented by Formula LVIIIO:

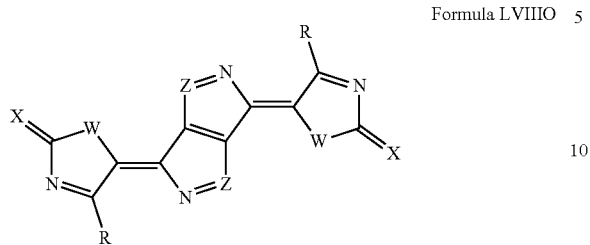

Formula LVIIIO in Formula LVIIIO, two X are identical, two W are identical, two R are identical, two Z are identical and are $CR_L$, and X, W, R and $R_L$ correspond to an atom or a group selected from the following table, respectively:

| NO. | X | W | R | $R_L$ | NO. | X | W | R | $R_L$ | NO. | X | W | R | $R_L$ |
|---|---|---|---|---|---|---|---|---|---|---|---|---|---|---|
| LVIIIO-1 | A1 | O | B1 | H | LVIIIO-2 | A1 | O | B17 | H | LVIIIO-3 | A1 | O | B25 | H |
| LVIIIO-4 | A1 | O | B54 | H | LVIIIO-5 | A1 | O | B70 | H | LVIIIO-6 | A1 | O | B72 | H |
| LVIIIO-7 | A1 | S | B1 | H | LVIIIO-8 | A1 | S | B17 | H | LVIIIO-9 | A1 | S | B25 | H |
| LVIIIO-10 | A1 | S | B54 | H | LVIIIO-11 | A1 | S | B70 | H | LVIIIO-12 | A1 | S | B72 | H |
| LVIIIO-13 | A1 | Se | B54 | H | LVIIIO-14 | A1 | Se | B70 | H | LVIIIO-15 | A1 | Se | B72 | H |
| LVIIIO-16 | A1 | NMe | B54 | H | LVIIIO-17 | A1 | NMe | B70 | H | LVIIIO-18 | A1 | NMe | B72 | H |
| LVIIIO-19 | A1 | O | H | F | LVIIIO-20 | A1 | O | B17 | F | LVIIIO-21 | A1 | O | B25 | F |
| LVIIIO-22 | A1 | O | B54 | F | LVIIIO-23 | A1 | O | B70 | F | LVIIIO-24 | A1 | O | B72 | F |
| LVIIIO-25 | A1 | S | H | F | LVIIIO-26 | A1 | S | B17 | F | LVIIIO-27 | A1 | S | B25 | F |
| LVIIIO-28 | A1 | S | B54 | F | LVIIIO-29 | A1 | S | B70 | F | LVIIIO-30 | A1 | S | B72 | F |
| LVIIIO-31 | A1 | O | H | B6 | LVIIIO-32 | A1 | O | B17 | B6 | LVIIIO-33 | A1 | O | B25 | B6 |
| LVIIIO-34 | A1 | O | B54 | B6 | LVIIIO-35 | A1 | O | B70 | B6 | LVIIIO-36 | A1 | O | B72 | B6 |
| LVIIIO-37 | A1 | S | H | B6 | LVIIIO-38 | A1 | S | B17 | B6 | LVIIIO-39 | A1 | S | B25 | B6 |
| LVIIIO-40 | A1 | S | B54 | B6 | LVIIIO-41 | A1 | S | B70 | B6 | LVIIIO-42 | A1 | S | B72 | B6 |
| LVIIIO-43 | A1 | O | H | B70 | LVIIIO-44 | A1 | O | B17 | B70 | LVIIIO-45 | A1 | O | B25 | B70 |
| LVIIIO-46 | A1 | O | B54 | B70 | LVIIIO-47 | A1 | O | B70 | B70 | LVIIIO-48 | A1 | O | B72 | B70 |
| LVIIIO-49 | A1 | S | H | B70 | LVIIIO-50 | A1 | S | B17 | B70 | LVIIIO-51 | A1 | S | B25 | B70 |
| LVIIIO-52 | A1 | S | B54 | B70 | LVIIIO-53 | A1 | S | B70 | B70 | LVIIIO-54 | A1 | S | B72 | B70 |
| LVIIIO-55 | A2 | O | B1 | H | LVIIIO-56 | A2 | O | B17 | H | LVIIIO-57 | A2 | O | B25 | H |
| LVIIIO-58 | A2 | O | B54 | H | LVIIIO-59 | A2 | O | B70 | H | LVIIIO-60 | A2 | O | B72 | H |
| LVIIIO-61 | A2 | S | B1 | H | LVIIIO-62 | A2 | S | B17 | H | LVIIIO-63 | A2 | S | B25 | H |
| LVIIIO-64 | A2 | S | B54 | H | LVIIIO-65 | A2 | S | B70 | H | LVIIIO-66 | A2 | S | B72 | H |
| LVIIIO-67 | A2 | O | B54 | F | LVIIIO-68 | A2 | O | B70 | F | LVIIIO-69 | A2 | O | B72 | F |
| LVIIIO-70 | A2 | S | B54 | F | LVIIIO-71 | A2 | S | B70 | F | LVIIIO-72 | A2 | S | B72 | F |
| LVIIIO-73 | A2 | O | B54 | B6 | LVIIIO-74 | A2 | O | B70 | B6 | LVIIIO-75 | A2 | O | B72 | B6 |
| LVIIIO-76 | A2 | S | B54 | B6 | LVIIIO-77 | A2 | S | B70 | B6 | LVIIIO-78 | A2 | S | B72 | B6 |
| LVIIIO-79 | A2 | O | B54 | B70 | LVIIIO-80 | A2 | O | B70 | B70 | LVIIIO-81 | A2 | O | B72 | B70 |
| LVIIIO-82 | A3 | O | B1 | H | LVIIIO-83 | A3 | O | B17 | H | LVIIIO-84 | A3 | O | B25 | H |
| LVIIIO-85 | A3 | O | B54 | H | LVIIIO-86 | A3 | O | B70 | H | LVIIIO-87 | A3 | O | B72 | H |
| LVIIIO-88 | A3 | S | B1 | H | LVIIIO-89 | A3 | S | B17 | H | LVIIIO-90 | A3 | S | B25 | H |
| LVIIIO-91 | A3 | S | B54 | H | LVIIIO-92 | A3 | S | B70 | H | LVIIIO-93 | A3 | S | B72 | H |
| LVIIIO-94 | A3 | O | B54 | F | LVIIIO-95 | A3 | O | B70 | F | LVIIIO-96 | A3 | O | B72 | F |
| LVIIIO-97 | A3 | S | B54 | F | LVIIIO-98 | A3 | S | B70 | F | LVIIIO-99 | A3 | S | B72 | F |
| LVIIIO-100 | A3 | O | B54 | B6 | LVIIIO-101 | A3 | O | B70 | B6 | LVIIIO-102 | A3 | O | B72 | B6 |
| LVIIIO-103 | A3 | S | B54 | B6 | LVIIIO-104 | A3 | S | B70 | B6 | LVIIIO-105 | A3 | S | B72 | B6 |
| LVIIIO-106 | A3 | O | B54 | B70 | LVIIIO-107 | A3 | O | B70 | B70 | LVIIIO-108 | A3 | O | B72 | B70; | wherein Compound LIXO-1 to Compound LIXO-298 have a structure represented by Formula LIXO:

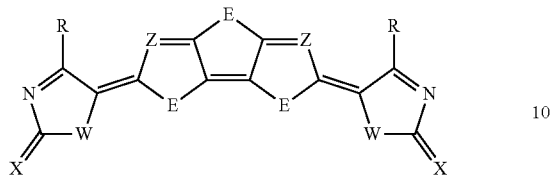

Formula LIXO in Formula LIXO, two X are identical, two W are identical, two R are identical, three E are identical, two Z are identical, and X, W, R, E and Z correspond to an atom or a group selected from the following table, respectively:

| NO. | X | W | R | Z | E | NO. | X | W | R | Z | E |
|---|---|---|---|---|---|---|---|---|---|---|---|
| LIXO-1 | A1 | O | B1 | C—H | O | LIXO-2 | A1 | O | B17 | C—H | O |
| LIXO-3 | A1 | O | B25 | C—H | O | LIXO-4 | A1 | O | B57 | C—H | O |
| LIXO-5 | A1 | O | B70 | C—H | O | LIXO-6 | A1 | O | B72 | C—H | O |
| LIXO-7 | A1 | O | B1 | C—H | S | LIXO-8 | A1 | O | B17 | C—H | S |
| LIXO-9 | A1 | O | B25 | C—H | S | LIXO-10 | A1 | O | B57 | C—H | S |
| LIXO-11 | A1 | O | B70 | C—H | S | LIXO-12 | A1 | O | B72 | C—H | S |
| LIXO-13 | A1 | O | B1 | C—F | O | LIXO-14 | A1 | O | B17 | C—F | O |
| LIXO-15 | A1 | O | B25 | C—F | O | LIXO-16 | A1 | O | B57 | C—F | O |
| LIXO-17 | A1 | O | B70 | C—F | O | LIXO-18 | A1 | O | B72 | C—F | O |
| LIXO-19 | A1 | O | B1 | C—F | S | LIXO-20 | A1 | O | B17 | C—F | S |
| LIXO-21 | A1 | O | B25 | C—F | S | LIXO-22 | A1 | O | B57 | C—F | S |
| LIXO-23 | A1 | O | B70 | C—F | S | LIXO-24 | A1 | O | B72 | C—F | S |
| LIXO-25 | A1 | O | B1 | N | O | LIXO-26 | A1 | O | B17 | N | O |
| LIXO-27 | A1 | O | B25 | N | O | LIXO-28 | A1 | O | B57 | N | O |
| LIXO-29 | A1 | O | B70 | N | O | LIXO-30 | A1 | O | B72 | N | O |
| LIXO-31 | A1 | O | B1 | N | S | LIXO-32 | A1 | O | B17 | N | S |
| LIXO-33 | A1 | O | B25 | N | S | LIXO-34 | A1 | O | B57 | N | S |
| LIXO-35 | A1 | O | B70 | N | S | LIXO-36 | A1 | O | B72 | N | S |
| LIXO-37 | A1 | S | B1 | C—H | O | LIXO-38 | A1 | S | B17 | C—H | O |
| LIXO-39 | A1 | S | B25 | C—H | O | LIXO-40 | A1 | S | B57 | C—H | O |
| LIXO-41 | A1 | S | B70 | C—H | O | LIXO-42 | A1 | S | B72 | C—H | O |
| LIXO-43 | A1 | S | B1 | C—H | S | LIXO-44 | A1 | S | B17 | C—H | S |
| LIXO-45 | A1 | S | B25 | C—H | S | LIXO-46 | A1 | S | B57 | C—H | S |
| LIXO-47 | A1 | S | B70 | C—H | S | LIXO-48 | A1 | S | B72 | C—H | S |
| LIXO-49 | A1 | S | B1 | C—F | O | LIXO-50 | A1 | S | B17 | C—F | O |
| LIXO-51 | A1 | S | B25 | C—F | O | LIXO-52 | A1 | S | B57 | C—F | O |
| LIXO-53 | A1 | S | B70 | C—F | O | LIXO-54 | A1 | S | B72 | C—F | O |
| LIXO-55 | A1 | S | B1 | C—F | S | LIXO-56 | A1 | S | B17 | C—F | S |
| LIXO-57 | A1 | S | B25 | C—F | S | LIXO-58 | A1 | S | B57 | C—F | S |
| LIXO-59 | A1 | S | B70 | C—F | S | LIXO-60 | A1 | S | B72 | C—F | S |
| LIXO-61 | A1 | S | B1 | N | O | LIXO-62 | A1 | S | B17 | N | O |
| LIXO-63 | A1 | S | B25 | N | O | LIXO-64 | A1 | S | B57 | N | O |
| LIXO-65 | A1 | S | B70 | N | O | LIXO-66 | A1 | S | B72 | N | O |
| LIXO-67 | A1 | S | B1 | N | S | LIXO-68 | A1 | S | B17 | N | S |
| LIXO-69 | A1 | S | B25 | N | S | LIXO-70 | A1 | S | B57 | N | S |
| LIXO-71 | A1 | S | B70 | N | S | LIXO-72 | A1 | S | B72 | N | S |
| LIXO-73 | A1 | Se | B25 | C—H | O | LIXO-74 | A1 | Se | B57 | C—H | O |
| LIXO-75 | A1 | Se | B70 | C—H | O | LIXO-76 | A1 | Se | B72 | C—H | O |
| LIXO-77 | A1 | Se | B25 | C—H | S | LIXO-78 | A1 | Se | B57 | C—H | S |
| LIXO-79 | A1 | Se | B70 | C—H | S | LIXO-80 | A1 | Se | B72 | C—H | S |
| LIXO-81 | A1 | Se | B57 | C—F | O | LIXO-82 | A1 | Se | B70 | C—F | O |
| LIXO-83 | A1 | Se | B57 | C—F | S | LIXO-84 | A1 | Se | B70 | C—F | S |
| LIXO-85 | A1 | Se | B25 | N | O | LIXO-86 | A1 | Se | B57 | N | O |
| LIXO-87 | A1 | Se | B70 | N | O | LIXO-88 | A1 | Se | B72 | N | O |
| LIXO-89 | A1 | Se | B25 | N | S | LIXO-90 | A1 | Se | B57 | N | S |
| LIXO-91 | A1 | Se | B70 | N | S | LIXO-92 | A1 | Se | B72 | N | S |
| LIXO-93 | A1 | NMe | B25 | C—H | O | LIXO-94 | A1 | NMe | B57 | C—H | O |
| LIXO-95 | A1 | NMe | B70 | C—H | O | LIXO-96 | A1 | NMe | B72 | C—H | O |
| LIXO-97 | A1 | NMe | B25 | C—H | S | LIXO-98 | A1 | NMe | B57 | C—H | S |
| LIXO-99 | A1 | NMe | B70 | C—H | S | LIXO-100 | A1 | NMe | B72 | C—H | S |
| LIXO-101 | A1 | NMe | B57 | C—F | O | LIXO-102 | A1 | NMe | B70 | C—F | O |
| LIXO-103 | A1 | NMe | B57 | C—F | S | LIXO-104 | A1 | NMe | B70 | C—F | S |
| LIXO-105 | A1 | NMe | B25 | N | O | LIXO-106 | A1 | NMe | B57 | N | O |
| LIXO-107 | A1 | NMe | B70 | N | O | LIXO-108 | A1 | NMe | B72 | N | O |
| LIXO-109 | A1 | NMe | B25 | N | S | LIXO-110 | A1 | NMe | B57 | N | S |

-continued

| NO. | X | W | R | Z | E | NO. | X | W | R | Z | E |
|---|---|---|---|---|---|---|---|---|---|---|---|
| LIXO-111 | A1 | NMe | B70 | N | S | LIXO-112 | A1 | NMe | B72 | N | S |
| LIXO-113 | A2 | O | B1 | C—H | O | LIXO-114 | A2 | O | B17 | C—H | O |
| LIXO-115 | A2 | O | B25 | C—H | O | LIXO-116 | A2 | O | B57 | C—H | O |
| LIXO-117 | A2 | O | B70 | C—H | O | LIXO-118 | A2 | O | B72 | C—H | O |
| LIXO-119 | A2 | O | B1 | C—H | S | LIXO-120 | A2 | O | B17 | C—H | S |
| LIXO-121 | A2 | O | B25 | C—H | S | LIXO-122 | A2 | O | B57 | C—H | S |
| LIXO-123 | A2 | O | B70 | C—H | S | LIXO-124 | A2 | O | B72 | C—H | S |
| LIXO-125 | A2 | O | B1 | C—F | O | LIXO-126 | A2 | O | B17 | C—F | O |
| LIXO-127 | A2 | O | B25 | C—F | O | LIXO-128 | A2 | O | B57 | C—F | O |
| LIXO-129 | A2 | O | B70 | C—F | O | LIXO-130 | A2 | O | B72 | C—F | O |
| LIXO-131 | A2 | O | B1 | C—F | S | LIXO-132 | A2 | O | B17 | C—F | S |
| LIXO-133 | A2 | O | B25 | C—F | S | LIXO-134 | A2 | O | B57 | C—F | S |
| LIXO-135 | A2 | O | B70 | C—F | S | LIXO-136 | A2 | O | B72 | C—F | S |
| LIXO-137 | A2 | O | B1 | N | O | LIXO-138 | A2 | O | B17 | N | O |
| LIXO-139 | A2 | O | B25 | N | O | LIXO-140 | A2 | O | B57 | N | O |
| LIXO-141 | A2 | O | B70 | N | O | LIXO-142 | A2 | O | B72 | N | O |
| LIXO-143 | A2 | O | B1 | N | S | LIXO-144 | A2 | O | B17 | N | S |
| LIXO-145 | A2 | O | B25 | N | S | LIXO-146 | A2 | O | B57 | N | S |
| LIXO-147 | A2 | O | B70 | N | S | LIXO-148 | A2 | O | B72 | N | S |
| LIXO-149 | A2 | S | B1 | C—H | O | LIXO-150 | A2 | S | B17 | C—H | O |
| LIXO-151 | A2 | S | B25 | C—H | O | LIXO-152 | A2 | S | B57 | C—H | O |
| LIXO-153 | A2 | S | B70 | C—H | O | LIXO-154 | A2 | S | B72 | C—H | O |
| LIXO-155 | A2 | S | B1 | C—H | S | LIXO-156 | A2 | S | B17 | C—H | S |
| LIXO-157 | A2 | S | B25 | C—H | S | LIXO-158 | A2 | S | B57 | C—H | S |
| LIXO-159 | A2 | S | B70 | C—H | S | LIXO-160 | A2 | S | B72 | C—H | S |
| LIXO-161 | A2 | S | B1 | C—F | O | LIXO-162 | A2 | S | B17 | C—F | O |
| LIXO-163 | A2 | S | B25 | C—F | O | LIXO-164 | A2 | S | B57 | C—F | O |
| LIXO-165 | A2 | S | B70 | C—F | O | LIXO-166 | A2 | S | B72 | C—F | O |
| LIXO-167 | A2 | S | B1 | C—F | S | LIXO-168 | A2 | S | B17 | C—F | S |
| LIXO-169 | A2 | S | B25 | C—F | S | LIXO-170 | A2 | S | B57 | C—F | S |
| LIXO-171 | A2 | S | B70 | C—F | S | LIXO-172 | A2 | S | B72 | C—F | S |
| LIXO-173 | A2 | S | B1 | N | O | LIXO-174 | A2 | S | B17 | N | O |
| LIXO-175 | A2 | S | B25 | N | O | LIXO-176 | A2 | S | B57 | N | O |
| LIXO-177 | A2 | S | B70 | N | O | LIXO-178 | A2 | S | B72 | N | O |
| LIXO-179 | A2 | S | B1 | N | S | LIXO-180 | A2 | S | B17 | N | S |
| LIXO-181 | A2 | S | B25 | N | S | LIXO-182 | A2 | S | B57 | N | S |
| LIXO-183 | A2 | S | B70 | N | S | LIXO-184 | A2 | S | B72 | N | S |
| LIXO-185 | A2 | Se | B57 | C—H | O | LIXO-186 | A2 | Se | B70 | C—H | O |
| LIXO-187 | A2 | Se | B57 | C—H | S | LIXO-188 | A2 | Se | B70 | C—H | S |
| LIXO-189 | A2 | Se | B57 | C—F | O | LIXO-190 | A2 | Se | B70 | C—F | O |
| LIXO-191 | A2 | Se | B57 | C—F | S | LIXO-192 | A2 | Se | B70 | C—F | S |
| LIXO-193 | A2 | Se | B57 | N | O | LIXO-194 | A2 | Se | B70 | N | O |
| LIXO-195 | A2 | Se | B57 | N | S | LIXO-196 | A2 | Se | B70 | N | S |
| LIXO-197 | A2 | NMe | B70 | C—H | O | LIXO-198 | A2 | NMe | B70 | C—H | S |
| LIXO-199 | A2 | NMe | B57 | C—F | O | LIXO-200 | A2 | NMe | B70 | C—F | O |
| LIXO-201 | A2 | NMe | B57 | C—F | S | LIXO-202 | A2 | NMe | B70 | C—F | S |
| LIXO-203 | A2 | NMe | B70 | N | O | LIXO-204 | A2 | NMe | B70 | N | S |
| LIXO-205 | A3 | O | B1 | C—H | O | LIXO-206 | A3 | O | B17 | C—H | O |
| LIXO-207 | A3 | O | B25 | C—H | O | LIXO-208 | A3 | O | B57 | C—H | O |
| LIXO-209 | A3 | O | B70 | C—H | O | LIXO-210 | A3 | O | B72 | C—H | O |
| LIXO-211 | A3 | O | B1 | C—H | S | LIXO-212 | A3 | O | B17 | C—H | S |
| LIXO-213 | A3 | O | B25 | C—H | S | LIXO-214 | A3 | O | B57 | C—H | S |
| LIXO-215 | A3 | O | B70 | C—H | S | LIXO-216 | A3 | O | B72 | C—H | S |
| LIXO-217 | A3 | O | B1 | C—F | O | LIXO-218 | A3 | O | B17 | C—F | O |
| LIXO-219 | A3 | O | B25 | C—F | O | LIXO-220 | A3 | O | B57 | C—F | O |
| LIXO-221 | A3 | O | B70 | C—F | O | LIXO-222 | A3 | O | B72 | C—F | O |
| LIXO-223 | A3 | O | B1 | C—F | S | LIXO-224 | A3 | O | B17 | C—F | S |
| LIXO-225 | A3 | O | B25 | C—F | S | LIXO-226 | A3 | O | B57 | C—F | S |
| LIXO-227 | A3 | O | B70 | C—F | S | LIXO-228 | A3 | O | B72 | C—F | S |
| LIXO-229 | A3 | O | B70 | C—H | S | LIXO-230 | A3 | O | B72 | C—H | S |
| LIXO-231 | A3 | O | B1 | N | O | LIXO-232 | A3 | O | B17 | N | O |
| LIXO-233 | A3 | O | B25 | N | O | LIXO-234 | A3 | O | B57 | N | O |
| LIXO-235 | A3 | O | B70 | N | O | LIXO-236 | A3 | O | B72 | N | O |
| LIXO-237 | A3 | O | B1 | N | S | LIXO-238 | A3 | O | B17 | N | S |
| LIXO-239 | A3 | O | B25 | N | S | LIXO-240 | A3 | O | B57 | N | S |
| LIXO-241 | A3 | O | B70 | N | S | LIXO-242 | A3 | O | B72 | N | S |
| LIXO-243 | A3 | S | B1 | C—H | O | LIXO-244 | A3 | S | B17 | C—H | O |
| LIXO-245 | A3 | S | B25 | C—H | O | LIXO-246 | A3 | S | B57 | C—H | O |
| LIXO-247 | A3 | S | B70 | C—H | O | LIXO-248 | A3 | S | B72 | C—H | O |
| LIXO-249 | A3 | S | B1 | C—H | S | LIXO-250 | A3 | S | B17 | C—H | S |
| LIXO-251 | A3 | S | B25 | C—H | S | LIXO-252 | A3 | S | B57 | C—H | S |
| LIXO-253 | A3 | S | B70 | C—H | S | LIXO-254 | A3 | S | B72 | C—H | S |
| LIXO-255 | A3 | S | B1 | C—F | O | LIXO-256 | A3 | S | B17 | C—F | O |
| LIXO-257 | A3 | S | B25 | C—F | O | LIXO-258 | A3 | S | B57 | C—F | O |
| LIXO-259 | A3 | S | B70 | C—F | O | LIXO-260 | A3 | S | B72 | C—F | O |
| LIXO-261 | A3 | S | B1 | C—F | S | LIXO-262 | A3 | S | B17 | C—F | S |
| LIXO-263 | A3 | S | B25 | C—F | S | LIXO-264 | A3 | S | B57 | C—F | S |

-continued

| NO. | X | W | R | Z | E | NO. | X | W | R | Z | E |
|---|---|---|---|---|---|---|---|---|---|---|---|
| LIXO-265 | A3 | S | B70 | C—F | S | LIXO-266 | A3 | S | B72 | C—F | S |
| LIXO-267 | A3 | S | B1 | N | O | LIXO-268 | A3 | S | B17 | N | O |
| LIXO-269 | A3 | S | B25 | N | O | LIXO-270 | A3 | S | B57 | N | O |
| LIXO-271 | A3 | S | B70 | N | O | LIXO-272 | A3 | S | B72 | N | O |
| LIXO-273 | A3 | S | B1 | N | S | LIXO-274 | A3 | S | B17 | N | S |
| LIXO-275 | A3 | S | B25 | N | S | LIXO-276 | A3 | S | B57 | N | S |
| LIXO-277 | A3 | S | B70 | N | S | LIXO-278 | A3 | S | B72 | N | S |
| LIXO-279 | A3 | Se | B57 | C—H | O | LIXO-280 | A3 | Se | B70 | C—H | O |
| LIXO-281 | A3 | Se | B57 | C—H | S | LIXO-282 | A3 | Se | B70 | C—H | S |
| LIXO-283 | A3 | Se | B57 | C—F | O | LIXO-284 | A3 | Se | B70 | C—F | O |
| LIXO-285 | A3 | Se | B57 | C—F | S | LIXO-286 | A3 | Se | B70 | C—F | S |
| LIXO-287 | A3 | Se | B57 | N | O | LIXO-288 | A3 | Se | B70 | N | O |
| LIXO-289 | A3 | Se | B57 | N | S | LIXO-290 | A3 | Se | B70 | N | S |
| LIXO-291 | A3 | NMe | B70 | C—H | O | LIXO-292 | A3 | NMe | B70 | C—H | S |
| LIXO-293 | A3 | NMe | B57 | C—F | O | LIXO-294 | A3 | NMe | B70 | C—F | O |
| LIXO-295 | A3 | NMe | B57 | C—F | S | LIXO-296 | A3 | NMe | B70 | C—F | S |
| LIXO-297 | A3 | NMe | B70 | N | O | LIXO-298 | A3 | NMe | B70 | N | S; | wherein Compound LXO-1 to Compound LXO-298 have a structure represented by Formula LXO:

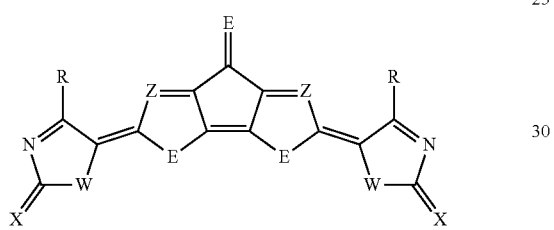

Formula LXO in Formula LXO, two X are identical, two W are identical, two R are identical, three E are identical, two Z are identical, and X, W, R, E and Z correspond to an atom or a group selected from the following table, respectively:

| NO. | X | W | R | Z | E | NO. | X | W | R | Z | E |
|---|---|---|---|---|---|---|---|---|---|---|---|
| LXO-1 | A1 | O | B1 | C—H | O | LXO-2 | A1 | O | B17 | C—H | O |
| LXO-3 | A1 | O | B25 | C—H | O | LXO-4 | A1 | O | B57 | C—H | O |
| LXO-5 | A1 | O | B70 | C—H | O | LXO-6 | A1 | O | B72 | C—H | O |
| LXO-7 | A1 | O | B1 | C—H | S | LXO-8 | A1 | O | B17 | C—H | S |
| LXO-9 | A1 | O | B25 | C—H | S | LXO-10 | A1 | O | B57 | C—H | S |
| LXO-11 | A1 | O | B70 | C—H | S | LXO-12 | A1 | O | B72 | C—H | S |
| LXO-13 | A1 | O | B1 | C—F | O | LXO-14 | A1 | O | B17 | C—F | O |
| LXO-15 | A1 | O | B25 | C—F | O | LXO-16 | A1 | O | B57 | C—F | O |
| LXO-17 | A1 | O | B70 | C—F | O | LXO-18 | A1 | O | B72 | C—F | O |
| LXO-19 | A1 | O | B1 | C—F | S | LXO-20 | A1 | O | B17 | C—F | S |
| LXO-21 | A1 | O | B25 | C—F | S | LXO-22 | A1 | O | B57 | C—F | S |
| LXO-23 | A1 | O | B70 | C—F | S | LXO-24 | A1 | O | B72 | C—F | S |
| LXO-25 | A1 | O | B1 | N | O | LXO-26 | A1 | O | B17 | N | O |
| LXO-27 | A1 | O | B25 | N | O | LXO-28 | A1 | O | B57 | N | O |
| LXO-29 | A1 | O | B70 | N | O | LXO-30 | A1 | O | B72 | N | O |
| LXO-31 | A1 | O | B1 | N | S | LXO-32 | A1 | O | B17 | N | S |
| LXO-33 | A1 | O | B25 | N | S | LXO-34 | A1 | O | B57 | N | S |
| LXO-35 | A1 | O | B70 | N | S | LXO-36 | A1 | O | B72 | N | S |
| LXO-37 | A1 | S | B1 | C—H | O | LXO-38 | A1 | S | B17 | C—H | O |
| LXO-39 | A1 | S | B25 | C—H | O | LXO-40 | A1 | S | B57 | C—H | O |
| LXO-41 | A1 | S | B70 | C—H | O | LXO-42 | A1 | S | B72 | C—H | O |
| LXO-43 | A1 | S | B1 | C—H | S | LXO-44 | A1 | S | B17 | C—H | S |
| LXO-45 | A1 | S | B25 | C—H | S | LXO-46 | A1 | S | B57 | C—H | S |
| LXO-47 | A1 | S | B70 | C—H | S | LXO-48 | A1 | S | B72 | C—H | S |
| LXO-49 | A1 | S | B1 | C—F | O | LXO-50 | A1 | S | B17 | C—F | O |
| LXO-51 | A1 | S | B25 | C—F | O | LXO-52 | A1 | S | B57 | C—F | O |
| LXO-53 | A1 | S | B70 | C—F | O | LXO-54 | A1 | S | B72 | C—F | O |
| LXO-55 | A1 | S | B1 | C—F | S | LXO-56 | A1 | S | B17 | C—F | S |
| LXO-57 | A1 | S | B25 | C—F | S | LXO-58 | A1 | S | B57 | C—F | S |

-continued

| NO. | X | W | R | Z | E | NO. | X | W | R | Z | E |
|---|---|---|---|---|---|---|---|---|---|---|---|
| LXO-59 | A1 | S | B70 | C—F | S | LXO-60 | A1 | S | B72 | C—F | S |
| LXO-61 | A1 | S | B1 | N | O | LXO-62 | A1 | S | B17 | N | O |
| LXO-63 | A1 | S | B25 | N | O | LXO-64 | A1 | S | B57 | N | O |
| LXO-65 | A1 | S | B70 | N | O | LXO-66 | A1 | S | B72 | N | O |
| LXO-67 | A1 | S | B1 | N | S | LXO-68 | A1 | S | B17 | N | S |
| LXO-69 | A1 | S | B25 | N | S | LXO-70 | A1 | S | B57 | N | S |
| LXO-71 | A1 | S | B70 | N | S | LXO-72 | A1 | S | B72 | N | S |
| LXO-73 | A1 | Se | B25 | C—H | O | LXO-74 | A1 | Se | B57 | C—H | O |
| LXO-75 | A1 | Se | B70 | C—H | O | LXO-76 | A1 | Se | B72 | C—H | O |
| LXO-77 | A1 | Se | B25 | C—H | S | LXO-78 | A1 | Se | B57 | C—H | S |
| LXO-79 | A1 | Se | B70 | C—H | S | LXO-80 | A1 | Se | B72 | C—H | S |
| LXO-81 | A1 | Se | B57 | C—F | O | LXO-82 | A1 | Se | B70 | C—F | O |
| LXO-83 | A1 | Se | B57 | C—F | S | LXO-84 | A1 | Se | B70 | C—F | S |
| LXO-85 | A1 | Se | B25 | N | O | LXO-86 | A1 | Se | B57 | N | O |
| LXO-87 | A1 | Se | B70 | N | O | LXO-88 | A1 | Se | B72 | N | O |
| LXO-89 | A1 | Se | B25 | N | S | LXO-90 | A1 | Se | B57 | N | S |
| LXO-91 | A1 | Se | B70 | N | S | LXO-92 | A1 | Se | B72 | N | S |
| LXO-93 | A1 | NMe | B25 | C—H | O | LXO-94 | A1 | NMe | B57 | C—H | O |
| LXO-95 | A1 | NMe | B70 | C—H | O | LXO-96 | A1 | NMe | B72 | C—H | O |
| LXO-97 | A1 | NMe | B25 | C—H | S | LXO-98 | A1 | NMe | B57 | C—H | S |
| LXO-99 | A1 | NMe | B70 | C—H | S | LXO-100 | A1 | NMe | B72 | C—H | S |
| LXO-101 | A1 | NMe | B57 | C—F | O | LXO-102 | A1 | NMe | B70 | C—F | O |
| LXO-103 | A1 | NMe | B57 | C—F | S | LXO-104 | A1 | NMe | B70 | C—F | S |
| LXO-105 | A1 | NMe | B25 | N | O | LXO-106 | A1 | NMe | B57 | N | O |
| LXO-107 | A1 | NMe | B70 | N | O | LXO-108 | A1 | NMe | B72 | N | O |
| LXO-109 | A1 | NMe | B25 | N | S | LXO-110 | A1 | NMe | B57 | N | S |
| LXO-111 | A1 | NMe | B70 | N | S | LXO-112 | A1 | NMe | B72 | N | S |
| LXO-113 | A2 | O | B1 | C—H | O | LXO-114 | A2 | O | B17 | C—H | O |
| LXO-115 | A2 | O | B25 | C—H | O | LXO-116 | A2 | O | B57 | C—H | O |
| LXO-117 | A2 | O | B70 | C—H | O | LXO-118 | A2 | O | B72 | C—H | O |
| LXO-119 | A2 | O | B1 | C—H | S | LXO-120 | A2 | O | B17 | C—H | S |
| LXO-121 | A2 | O | B25 | C—H | S | LXO-122 | A2 | O | B57 | C—H | S |
| LXO-123 | A2 | O | B70 | C—H | S | LXO-124 | A2 | O | B72 | C—H | S |
| LXO-125 | A2 | O | B1 | C—F | O | LXO-126 | A2 | O | B17 | C—F | O |
| LXO-127 | A2 | O | B25 | C—F | O | LXO-128 | A2 | O | B57 | C—F | O |
| LXO-129 | A2 | O | B70 | C—F | O | LXO-130 | A2 | O | B72 | C—F | O |
| LXO-131 | A2 | O | B1 | C—F | S | LXO-132 | A2 | O | B17 | C—F | S |
| LXO-133 | A2 | O | B25 | C—F | S | LXO-134 | A2 | O | B57 | C—F | S |
| LXO-135 | A2 | O | B70 | C—F | S | LXO-136 | A2 | O | B72 | C—F | S |
| LXO-137 | A2 | O | B1 | N | O | LXO-138 | A2 | O | B17 | N | O |
| LXO-139 | A2 | O | B25 | N | O | LXO-140 | A2 | O | B57 | N | O |
| LXO-141 | A2 | O | B70 | N | O | LXO-142 | A2 | O | B72 | N | O |
| LXO-143 | A2 | O | B1 | N | S | LXO-144 | A2 | O | B17 | N | S |
| LXO-145 | A2 | O | B25 | N | S | LXO-146 | A2 | O | B57 | N | S |
| LXO-147 | A2 | O | B70 | N | S | LXO-148 | A2 | O | B72 | N | S |
| LXO-149 | A2 | S | B1 | C—H | O | LXO-150 | A2 | S | B17 | C—H | O |
| LXO-151 | A2 | S | B25 | C—H | O | LXO-152 | A2 | S | B57 | C—H | O |
| LXO-153 | A2 | S | B70 | C—H | O | LXO-154 | A2 | S | B72 | C—H | O |
| LXO-155 | A2 | S | B1 | C—H | S | LXO-156 | A2 | S | B17 | C—H | S |
| LXO-157 | A2 | S | B25 | C—H | S | LXO-158 | A2 | S | B57 | C—H | S |
| LXO-159 | A2 | S | B70 | C—H | S | LXO-160 | A2 | S | B72 | C—H | S |
| LXO-161 | A2 | S | B1 | C—F | O | LXO-162 | A2 | S | B17 | C—F | O |
| LXO-163 | A2 | S | B25 | C—F | O | LXO-164 | A2 | S | B57 | C—F | O |
| LXO-165 | A2 | S | B70 | C—F | O | LXO-166 | A2 | S | B72 | C—F | O |
| LXO-167 | A2 | S | B1 | C—F | S | LXO-168 | A2 | S | B17 | C—F | S |
| LXO-169 | A2 | S | B25 | C—F | S | LXO-170 | A2 | S | B57 | C—F | S |
| LXO-171 | A2 | S | B70 | C—F | S | LXO-172 | A2 | S | B72 | C—F | S |
| LXO-173 | A2 | S | B1 | N | O | LXO-174 | A2 | S | B17 | N | O |
| LXO-175 | A2 | S | B25 | N | O | LXO-176 | A2 | S | B57 | N | O |
| LXO-177 | A2 | S | B70 | N | O | LXO-178 | A2 | S | B72 | N | O |
| LXO-179 | A2 | S | B1 | N | S | LXO-180 | A2 | S | B17 | N | S |
| LXO-181 | A2 | S | B25 | N | S | LXO-182 | A2 | S | B57 | N | S |
| LXO-183 | A2 | S | B70 | N | S | LXO-184 | A2 | S | B72 | N | S |
| LXO-185 | A2 | Se | B57 | C—H | O | LXO-186 | A2 | Se | B70 | C—H | O |
| LXO-187 | A2 | Se | B57 | C—H | S | LXO-188 | A2 | Se | B70 | C—H | S |
| LXO-189 | A2 | Se | B57 | C—F | O | LXO-190 | A2 | Se | B70 | C—F | O |
| LXO-191 | A2 | Se | B57 | C—F | S | LXO-192 | A2 | Se | B70 | C—F | S |
| LXO-193 | A2 | Se | B57 | N | O | LXO-194 | A2 | Se | B70 | N | O |
| LXO-195 | A2 | Se | B57 | N | S | LXO-196 | A2 | Se | B70 | N | S |
| LXO-197 | A2 | NMe | B70 | C—H | O | LXO-198 | A2 | NMe | B70 | C—H | S |
| LXO-199 | A2 | NMe | B57 | C—F | O | LXO-200 | A2 | NMe | B70 | C—F | O |
| LXO-201 | A2 | NMe | B57 | C—F | S | LXO-202 | A2 | NMe | B70 | C—F | S |
| LXO-203 | A2 | NMe | B70 | N | O | LXO-204 | A2 | NMe | B70 | N | S |
| LXO-205 | A3 | O | B1 | C—H | O | LXO-206 | A3 | O | B17 | C—H | O |
| LXO-207 | A3 | O | B25 | C—H | O | LXO-208 | A3 | O | B57 | C—H | O |
| LXO-209 | A3 | O | B70 | C—H | O | LXO-210 | A3 | O | B72 | C—H | O |
| LXO-211 | A3 | O | B1 | C—H | S | LXO-212 | A3 | O | B17 | C—H | S |

-continued

| NO. | X | W | R | Z | E | NO. | X | W | R | Z | E |
|---|---|---|---|---|---|---|---|---|---|---|---|
| LXO-213 | A3 | O | B25 | C—H | S | LXO-214 | A3 | O | B57 | C—H | S |
| LXO-215 | A3 | O | B70 | C—H | S | LXO-216 | A3 | O | B72 | C—H | S |
| LXO-217 | A3 | O | B1 | C—F | O | LXO-218 | A3 | O | B17 | C—F | O |
| LXO-219 | A3 | O | B25 | C—F | O | LXO-220 | A3 | O | B57 | C—F | O |
| LXO-221 | A3 | O | B70 | C—F | O | LXO-222 | A3 | O | B72 | C—F | O |
| LXO-223 | A3 | O | B1 | C—F | S | LXO-224 | A3 | O | B17 | C—F | S |
| LXO-225 | A3 | O | B25 | C—F | S | LXO-226 | A3 | O | B57 | C—F | S |
| LXO-227 | A3 | O | B70 | C—F | S | LXO-228 | A3 | O | B72 | C—F | S |
| LXO-229 | A3 | O | B70 | C—H | S | LXO-230 | A3 | O | B72 | C—H | S |
| LXO-231 | A3 | O | B1 | N | O | LXO-232 | A3 | O | B17 | N | O |
| LXO-233 | A3 | O | B25 | N | O | LXO-234 | A3 | O | B57 | N | O |
| LXO-235 | A3 | O | B70 | N | O | LXO-236 | A3 | O | B72 | N | O |
| LXO-237 | A3 | O | B1 | N | S | LXO-238 | A3 | O | B17 | N | S |
| LXO-239 | A3 | O | B25 | N | S | LXO-240 | A3 | O | B57 | N | S |
| LXO-241 | A3 | O | B70 | N | S | LXO-242 | A3 | O | B72 | N | S |
| LXO-243 | A3 | S | B1 | C—H | O | LXO-244 | A3 | S | B17 | C—H | O |
| LXO-245 | A3 | S | B25 | C—H | O | LXO-246 | A3 | S | B57 | C—H | O |
| LXO-247 | A3 | S | B70 | C—H | O | LXO-248 | A3 | S | B72 | C—H | O |
| LXO-249 | A3 | S | B1 | C—H | S | LXO-250 | A3 | S | B17 | C—H | S |
| LXO-251 | A3 | S | B25 | C—H | S | LXO-252 | A3 | S | B57 | C—H | S |
| LXO-253 | A3 | S | B70 | C—H | S | LXO-254 | A3 | S | B72 | C—H | S |
| LXO-255 | A3 | S | B1 | C—F | O | LXO-256 | A3 | S | B17 | C—F | O |
| LXO-257 | A3 | S | B25 | C—F | O | LXO-258 | A3 | S | B57 | C—F | O |
| LXO-259 | A3 | S | B70 | C—F | O | LXO-260 | A3 | S | B72 | C—F | O |
| LXO-261 | A3 | S | B1 | C—F | S | LXO-262 | A3 | S | B17 | C—F | S |
| LXO-263 | A3 | S | B25 | C—F | S | LXO-264 | A3 | S | B57 | C—F | S |
| LXO-265 | A3 | S | B70 | C—F | S | LXO-266 | A3 | S | B72 | C—F | S |
| LXO-267 | A3 | S | B1 | N | O | LXO-268 | A3 | S | B17 | N | O |
| LXO-269 | A3 | S | B25 | N | O | LXO-270 | A3 | S | B57 | N | O |
| LXO-271 | A3 | S | B70 | N | O | LXO-272 | A3 | S | B72 | N | O |
| LXO-273 | A3 | S | B1 | N | S | LXO-274 | A3 | S | B17 | N | S |
| LXO-275 | A3 | S | B25 | N | S | LXO-276 | A3 | S | B57 | N | S |
| LXO-277 | A3 | S | B70 | N | S | LXO-278 | A3 | S | B72 | N | S |
| LXO-279 | A3 | Se | B57 | C—H | O | LXO-280 | A3 | Se | B70 | C—H | O |
| LXO-281 | A3 | Se | B57 | C—H | S | LXO-282 | A3 | Se | B70 | C—H | S |
| LXO-283 | A3 | Se | B57 | C—F | O | LXO-284 | A3 | Se | B70 | C—F | O |
| LXO-285 | A3 | Se | B57 | C—F | S | LXO-286 | A3 | Se | B70 | C—F | S |
| LXO-287 | A3 | Se | B57 | N | O | LXO-288 | A3 | Se | B70 | N | O |
| LXO-289 | A3 | Se | B57 | N | S | LXO-290 | A3 | Se | B70 | N | S |
| LXO-291 | A3 | NMe | B70 | C—H | O | LXO-292 | A3 | NMe | B70 | C—H | S |
| LXO-293 | A3 | NMe | B57 | C—F | O | LXO-294 | A3 | NMe | B70 | C—F | O |
| LXO-295 | A3 | NMe | B57 | C—F | S | LXO-296 | A3 | NMe | B70 | C—F | S |
| LXO-297 | A3 | NMe | B70 | N | O | LXO-298 | A3 | NMe | B70 | N | S; | wherein Compound LXIO-1 to Compound LXIO-66 have a structure represented by Formula LXIO:

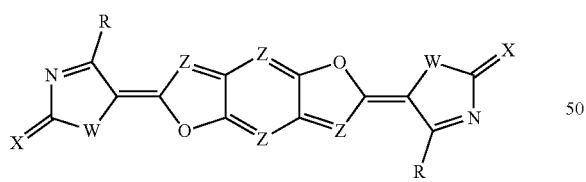

Formula LXIO in Formula LXIO, two X are identical, two W are identical, two R are identical, four Z are identical and are $CR_L$, and X, W, R and $R_L$ correspond to an atom or a group selected from the following table, respectively:

| NO. | X | W | R | $R_L$ | NO. | X | W | R | $R_L$ | NO. | X | W | R | $R_L$ |
|---|---|---|---|---|---|---|---|---|---|---|---|---|---|---|
| LXIO-1 | A1 | O | B1 | H | LXIO-2 | A1 | O | B17 | H | LXIO-3 | A1 | O | B25 | H |
| LXIO-4 | A1 | O | B54 | H | LXIO-5 | A1 | O | B70 | H | LXIO-6 | A1 | O | B72 | H |
| LXIO-7 | A1 | S | B1 | H | LXIO-8 | A1 | S | B17 | H | LXIO-9 | A1 | S | B25 | H |
| LXIO-10 | A1 | S | B54 | H | LXIO-11 | A1 | S | B70 | H | LXIO-12 | A1 | S | B72 | H |
| LXIO-13 | A1 | Se | B54 | H | LXIO-14 | A1 | Se | B70 | H | LXIO-15 | A1 | Se | B72 | H |
| LXIO-16 | A1 | NMe | B54 | H | LXIO-17 | A1 | NMe | B70 | H | LXIO-18 | A1 | NMe | B72 | H |

-continued

| NO. | X | W | R | $R_L$ | NO. | X | W | R | $R_L$ | NO. | X | W | R | $R_L$ |
|---|---|---|---|---|---|---|---|---|---|---|---|---|---|---|
| LXIO-19 | A1 | O | H | F | LXIO-20 | A1 | O | B17 | F | LXIO-21 | A1 | O | B25 | F |
| LXIO-22 | A1 | O | B54 | F | LXIO-23 | A1 | O | B70 | F | LXIO-24 | A1 | O | B72 | F |
| LXIO-25 | A1 | S | H | F | LXIO-26 | A1 | S | B17 | F | LXIO-27 | A1 | S | B25 | F |
| LXIO-28 | A1 | S | B54 | F | LXIO-29 | A1 | S | B70 | F | LXIO-30 | A1 | S | B72 | F |
| LXIO-31 | A2 | O | B1 | H | LXIO-32 | A2 | O | B17 | H | LXIO-33 | A2 | O | B25 | H |
| LXIO-34 | A2 | O | B54 | H | LXIO-35 | A2 | O | B70 | H | LXIO-36 | A2 | O | B72 | H |
| LXIO-37 | A2 | S | B1 | H | LXIO-38 | A2 | S | B17 | H | LXIO-39 | A2 | S | B25 | H |
| LXIO-40 | A2 | S | B54 | H | LXIO-41 | A2 | S | B70 | H | LXIO-42 | A2 | S | B72 | H |
| LXIO-43 | A2 | O | B54 | F | LXIO-44 | A2 | O | B70 | F | LXIO-45 | A2 | O | B72 | F |
| LXIO-46 | A2 | S | B54 | F | LXIO-47 | A2 | S | B70 | F | LXIO-48 | A2 | S | B72 | F |
| LXIO-49 | A3 | O | B1 | H | LXIO-50 | A3 | O | B17 | H | LXIO-51 | A3 | O | B25 | H |
| LXIO-52 | A3 | O | B54 | H | LXIO-53 | A3 | O | B70 | H | LXIO-54 | A3 | O | B72 | H |
| LXIO-55 | A3 | S | B1 | H | LXIO-56 | A3 | S | B17 | H | LXIO-57 | A3 | S | B25 | H |
| LXIO-58 | A3 | S | B54 | H | LXIO-59 | A3 | S | B70 | H | LXIO-60 | A3 | S | B72 | H |
| LXIO-61 | A3 | O | B54 | F | LXIO-62 | A3 | O | B70 | F | LXIO-63 | A3 | O | B72 | F |
| LXIO-64 | A3 | S | B54 | F | LXIO-65 | A3 | S | B70 | F | LXIO-66 | A3 | S | B72 | F; | wherein Compound LXIA-1 to Compound LXIA-42 have a structure represented by Formula LXIA:

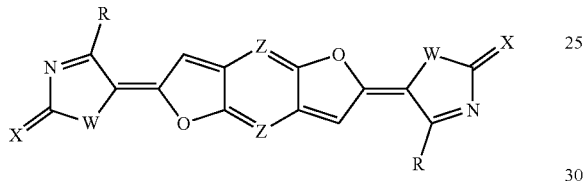

Formula LXIA in Formula LXIA, two X are identical, two W are identical, two R are identical, two Z are identical and are $CR_L$, and X, W, R and $R_L$ correspond to an atom or a group selected from the following table, respectively:

| NO. | X | W | R | $R_L$ | NO. | X | W | R | $R_L$ | NO. | X | W | R | $R_L$ |
|---|---|---|---|---|---|---|---|---|---|---|---|---|---|---|
| LXIA-1 | A1 | O | H | B6 | LXIA-2 | A1 | O | B17 | B6 | LXIA-3 | A1 | O | B25 | B6 |
| LXIA-4 | A1 | O | B54 | B6 | LXIA-5 | A1 | O | B70 | B6 | LXIA-6 | A1 | O | B72 | B6 |
| LXIA-7 | A1 | S | H | B6 | LXIA-8 | A1 | S | B17 | B6 | LXIA-9 | A1 | S | B25 | B6 |
| LXIA-10 | A1 | S | B54 | B6 | LXIA-11 | A1 | S | B70 | B6 | LXIA-12 | A1 | S | B72 | B6 |
| LXIA-13 | A1 | O | H | B70 | LXIA-14 | A1 | O | B17 | B70 | LXIA-15 | A1 | O | B25 | B70 |
| LXIA-16 | A1 | O | B54 | B70 | LXIA-17 | A1 | O | B70 | B70 | LXIA-18 | A1 | O | B72 | B70 |
| LXIA-19 | A1 | S | H | B70 | LXIA-20 | A1 | S | B17 | B70 | LXIA-21 | A1 | S | B25 | B70 |
| LXIA-22 | A1 | S | B54 | B70 | LXIA-23 | A1 | S | B70 | B70 | LXIA-24 | A1 | S | B72 | B70 |
| LXIA-25 | A2 | O | B54 | B6 | LXIA-26 | A2 | O | B70 | B6 | LXIA-27 | A2 | O | B72 | B6 |
| LXIA-28 | A2 | S | B54 | B6 | LXIA-29 | A2 | S | B70 | B6 | LXIA-30 | A2 | S | B72 | B6 |
| LXIA-31 | A2 | O | B54 | B70 | LXIA-32 | A2 | O | B70 | B70 | LXIA-33 | A2 | O | B72 | B70 |
| LXIA-34 | A3 | O | B54 | B6 | LXIA-35 | A3 | O | B70 | B6 | LXIA-36 | A3 | O | B72 | B6 |
| LXIA-37 | A3 | S | B54 | B6 | LXIA-38 | A3 | S | B70 | B6 | LXIA-39 | A3 | S | B72 | B6 |
| LXIA-40 | A3 | O | B54 | B70 | LXIA-41 | A3 | O | B70 | B70 | LXIA-42 | A3 | O | B72 | B70; | wherein Compound LXIIO-1 to Compound LXIIO-66 have a structure represented by Formula LXIIO:

Formula LXIIO

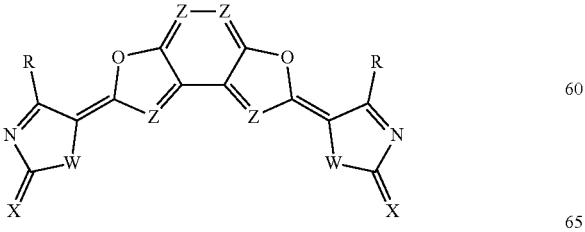

in Formula LXIIO, two X are identical, two W are identical, two R are identical, four Z are identical and are $CR_L$, and X, W, R and $R_L$ correspond to an atom or a group selected from the following table, respectively:

| NO. | X | W | R | $R_L$ | NO. | X | W | R | $R_L$ | NO. | X | W | R | $R_L$ |
|---|---|---|---|---|---|---|---|---|---|---|---|---|---|---|
| LXIIO-1 | A1 | O | B1 | H | LXIIO-2 | A1 | O | B17 | H | LXIIO-3 | A1 | O | B25 | H |
| LXIIO-4 | A1 | O | B54 | H | LXIIO-5 | A1 | O | B70 | H | LXIIO-6 | A1 | O | B72 | H |
| LXIIO-7 | A1 | S | B1 | H | LXIIO-8 | A1 | S | B17 | H | LXIIO-9 | A1 | S | B25 | H |
| LXIIO-10 | A1 | S | B54 | H | LXIIO-11 | A1 | S | B70 | H | LXIIO-12 | A1 | S | B72 | H |
| LXIIO-13 | A1 | Se | B54 | H | LXIIO-14 | A1 | Se | B70 | H | LXIIO-15 | A1 | Se | B72 | H |
| LXIIO-16 | A1 | NMe | B54 | H | LXIIO-17 | A1 | NMe | B70 | H | LXIIO-18 | A1 | NMe | B72 | H |
| LXIIO-19 | A1 | O | H | F | LXIIO-20 | A1 | O | B17 | F | LXIIO-21 | A1 | O | B25 | F |
| LXIIO-22 | A1 | O | B54 | F | LXIIO-23 | A1 | O | B70 | F | LXIIO-24 | A1 | O | B72 | F |
| LXIIO-25 | A1 | S | H | F | LXIIO-26 | A1 | S | B17 | F | LXIIO-27 | A1 | S | B25 | F |
| LXIIO-28 | A1 | S | B54 | F | LXIIO-29 | A1 | S | B70 | F | LXIIO-30 | A1 | S | B72 | F |
| LXIIO-31 | A2 | O | B1 | H | LXIIO-32 | A2 | O | B17 | H | LXIIO-33 | A2 | O | B25 | H |
| LXIIO-34 | A2 | O | B54 | H | LXIIO-35 | A2 | O | B70 | H | LXIIO-36 | A2 | O | B72 | H |
| LXIIO-37 | A2 | S | B1 | H | LXIIO-38 | A2 | S | B17 | H | LXIIO-39 | A2 | S | B25 | H |
| LXIIO-40 | A2 | S | B54 | H | LXIIO-41 | A2 | S | B70 | H | LXIIO-42 | A2 | S | B72 | H |
| LXIIO-43 | A2 | O | B54 | F | LXIIO-44 | A2 | O | B70 | F | LXIIO-45 | A2 | O | B72 | F |
| LXIIO-46 | A2 | S | B54 | F | LXIIO-47 | A2 | S | B70 | F | LXIIO-48 | A2 | S | B72 | F |
| LXIIO-49 | A3 | O | B1 | H | LXIIO-50 | A3 | O | B17 | H | LXIIO-51 | A3 | O | B25 | H |
| LXIIO-52 | A3 | O | B54 | H | LXIIO-53 | A3 | O | B70 | H | LXIIO-54 | A3 | O | B72 | H |
| LXIIO-55 | A3 | S | B1 | H | LXIIO-56 | A3 | S | B17 | H | LXIIO-57 | A3 | S | B25 | H |
| LXIIO-58 | A3 | S | B54 | H | LXIIO-59 | A3 | S | B70 | H | LXIIO-60 | A3 | S | B72 | H |
| LXIIO-61 | A3 | O | B54 | F | LXIIO-62 | A3 | O | B70 | F | LXIIO-63 | A3 | O | B72 | F |
| LXIIO-64 | A3 | S | B54 | F | LXIIO-65 | A3 | S | B70 | F | LXIIO-66 | A3 | S | B72 | F; | wherein Compound LXIIA-1 to Compound LXIIA-42 have a structure represented by Formula LXIIA:

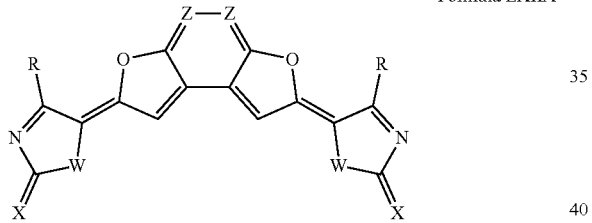

Formula LXIIA in Formula LXIIA, two X are identical, two W are identical, two R are identical, two Z are identical and are $CR_L$, and X, W, R and $R_L$ correspond to an atom or a group selected from the following table, respectively:

| NO. | X | W | R | $R_L$ | NO. | X | W | R | $R_L$ | NO. | X | W | R | $R_L$ |
|---|---|---|---|---|---|---|---|---|---|---|---|---|---|---|
| LXIIA-1 | A1 | O | H | B6 | LXIIA-2 | A1 | O | B17 | B6 | LXIIA-3 | A1 | O | B25 | B6 |
| LXIIA-4 | A1 | O | B54 | B6 | LXIIA-5 | A1 | O | B70 | B6 | LXIIA-6 | A1 | O | B72 | B6 |
| LXIIA-7 | A1 | S | H | B6 | LXIIA-8 | A1 | S | B17 | B6 | LXIIA-9 | A1 | S | B25 | B6 |
| LXIIA-10 | A1 | S | B54 | B6 | LXIIA-11 | A1 | S | B70 | B6 | LXIIA-12 | A1 | S | B72 | B6 |
| LXIIA-13 | A1 | O | H | B70 | LXIIA-14 | A1 | O | B17 | B70 | LXIIA-15 | A1 | O | B25 | B70 |
| LXIIA-16 | A1 | O | B54 | B70 | LXIIA-17 | A1 | O | B70 | B70 | LXIIA-18 | A1 | O | B72 | B70 |
| LXIIA-19 | A1 | S | H | B70 | LXIIA-20 | A1 | S | B17 | B70 | LXIIA-21 | A1 | S | B25 | B70 |
| LXIIA-22 | A1 | S | B54 | B70 | LXIIA-23 | A1 | S | B70 | B70 | LXIIA-24 | A1 | S | B72 | B70 |
| LXIIA-25 | A2 | O | B54 | B6 | LXIIA-26 | A2 | O | B70 | B6 | LXIIA-27 | A2 | O | B72 | B6 |
| LXIIA-28 | A2 | S | B54 | B6 | LXIIA-29 | A2 | S | B70 | B6 | LXIA-30 | A2 | S | B72 | B6 |
| LXIIA-31 | A2 | O | B54 | B70 | LXIIA-32 | A2 | O | B70 | B70 | LXIIA-33 | A2 | O | B72 | B70 |
| LXIIA-34 | A3 | O | B54 | B6 | LXIIA-35 | A3 | O | B70 | B6 | LXIIA-36 | A3 | O | B72 | B6 |
| LXIIA-37 | A3 | S | B54 | B6 | LXIIA-38 | A3 | S | B70 | B6 | LXIIA-39 | A3 | S | B72 | B6 |
| LXIIA-40 | A3 | O | B54 | B70 | LXIIA-41 | A3 | O | B70 | B70 | LXIIA-42 | A3 | O | B72 | B70; | wherein Compound LXIIIO-1 to Compound LXIIIO-66 have a structure represented by Formula LXIIIO:

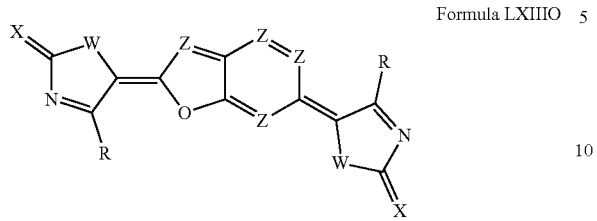

Formula LXIIIO in Formula LXIIIO, two X are identical, two W are identical, two R are identical, four Z are identical and are $CR_L$, and X, W, R and $R_L$ correspond to an atom or a group selected from the following table, respectively:

| NO. | X | W | R | $R_L$ | NO. | X | W | R | $R_L$ | NO. | X | W | R | $R_L$ |
|---|---|---|---|---|---|---|---|---|---|---|---|---|---|---|
| LXIIIO-1 | A1 | O | B1 | H | LXIIIO-2 | A1 | O | B17 | H | LXIIIO-3 | A1 | O | B25 | H |
| LXIIIO-4 | A1 | O | B54 | H | LXIIIO-5 | A1 | O | B70 | H | LXIIIO-6 | A1 | O | B72 | H |
| LXIIIO-7 | A1 | S | B1 | H | LXIIIO-8 | A1 | S | B17 | H | LXIIIO-9 | A1 | S | B25 | H |
| LXIIIO-10 | A1 | S | B54 | H | LXIIIO-11 | A1 | S | B70 | H | LXIIIO-12 | A1 | S | B72 | H |
| LXIIIO-13 | A1 | Se | B54 | H | LXIIIO-14 | A1 | Se | B70 | H | LXIIIO-15 | A1 | Se | B72 | H |
| LXIIIO-16 | A1 | NMe | B54 | H | LXIIIO-17 | A1 | NMe | B70 | H | LXIIIO-18 | A1 | NMe | B72 | H |
| LXIIIO-19 | A1 | O | H | F | LXIIIO-20 | A1 | O | B17 | F | LXIIIO-21 | A1 | O | B25 | F |
| LXIIIO-22 | A1 | O | B54 | F | LXIIIO-23 | A1 | O | B70 | F | LXIIIO-24 | A1 | O | B72 | F |
| LXIIIO-25 | A1 | S | H | F | LXIIIO-26 | A1 | S | B17 | F | LXIIIO-27 | A1 | S | B25 | F |
| LXIIIO-28 | A1 | S | B54 | F | LXIIIO-29 | A1 | S | B70 | F | LXIIIO-30 | A1 | S | B72 | F |
| LXIIIO-31 | A2 | O | B1 | H | LXIIIO-32 | A2 | O | B17 | H | LXIIIO-33 | A2 | O | B25 | H |
| LXIIIO-34 | A2 | O | B54 | H | LXIIIO-35 | A2 | O | B70 | H | LXIIIO-36 | A2 | O | B72 | H |
| LXIIIO-37 | A2 | S | B1 | H | LXIIIO-38 | A2 | S | B17 | H | LXIIIO-39 | A2 | S | B25 | H |
| LXIIIO-40 | A2 | S | B54 | H | LXIIIO-41 | A2 | S | B70 | H | LXIIIO-42 | A2 | S | B72 | H |
| LXIIIO-43 | A2 | O | B54 | F | LXIIIO-44 | A2 | O | B70 | F | LXIIIO-45 | A2 | O | B72 | F |
| LXIIIO-46 | A2 | S | B54 | F | LXIIIO-47 | A2 | S | B70 | F | LXIIIO-48 | A2 | S | B72 | F |
| LXIIIO-49 | A3 | O | B1 | H | LXIIIO-50 | A3 | O | B17 | H | LXIIIO-51 | A3 | O | B25 | H |
| LXIIIO-52 | A3 | O | B54 | H | LXIIIO-53 | A3 | O | B70 | H | LXIIIO-54 | A3 | O | B72 | H |
| LXIIIO-55 | A3 | S | B1 | H | LXIIIO-56 | A3 | S | B17 | H | LXIIIO-57 | A3 | S | B25 | H |
| LXIIIO-58 | A3 | S | B54 | H | LXIIIO-59 | A3 | S | B70 | H | LXIIIO-60 | A3 | S | B72 | H |
| LXIIIO-61 | A3 | O | B54 | F | LXIIIO-62 | A3 | O | B70 | F | LXIIIO-63 | A3 | O | B72 | F |
| LXIIIO-64 | A3 | S | B54 | F | LXIIIO-65 | A3 | S | B70 | F | LXIIIO-66 | A3 | S | B72 | F; | wherein Compound LXIIIA-1 to Compound LXIIIA-42 have a structure represented by Formula LXIIIA:

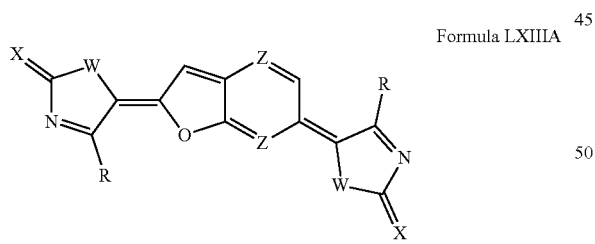

Formula LXIIIA in Formula LXIIIA, two X are identical, two W are identical, two R are identical, two Z are identical and are $CR_L$, and X, W, R and $R_L$ correspond to an atom or a group selected from the following table, respectively:

| NO. | X | W | R | $R_L$ | NO. | X | W | R | $R_L$ | NO. | X | W | R | $R_L$ |
|---|---|---|---|---|---|---|---|---|---|---|---|---|---|---|
| LXIIIA-1 | A1 | O | H | B6 | LXIIIA-2 | A1 | O | B17 | B6 | LXIIIA-3 | A1 | O | B25 | B6 |
| LXIIIA-4 | A1 | O | B54 | B6 | LXIIIA-5 | A1 | O | B70 | B6 | LXIIIA-6 | A1 | O | B72 | B6 |
| LXIIIA-7 | A1 | S | H | B6 | LXIIIA-8 | A1 | S | B17 | B6 | LXIIIA-9 | A1 | S | B25 | B6 |
| LXIIIA-10 | A1 | S | B54 | B6 | LXIIIA-11 | A1 | S | B70 | B6 | LXIIIA-12 | A1 | S | B72 | B6 |
| LXIIIA-13 | A1 | O | H | B70 | LXIIIA-14 | A1 | O | B17 | B70 | LXIIIA-15 | A1 | O | B25 | B70 |

-continued

| NO. | X | W | R | R$_L$ | NO. | X | W | R | R$_L$ | NO. | X | W | R | R$_L$ |
|---|---|---|---|---|---|---|---|---|---|---|---|---|---|---|
| LXIIIA-16 | A1 | O | B54 | B70 | LXIIIA-17 | A1 | O | B70 | B70 | LXIIIA-18 | A1 | O | B72 | B70 |
| LXIIIA-19 | A1 | S | H | B70 | LXIIIA-20 | A1 | S | B17 | B70 | LXIIIA-21 | A1 | S | B25 | B70 |
| LXIIIA-22 | A1 | S | B54 | B70 | LXIIIA-23 | A1 | S | B70 | B70 | LXIIIA-24 | A1 | S | B72 | B70 |
| LXIIIA-25 | A2 | O | B54 | B6 | LXIIIA-26 | A2 | O | B70 | B6 | LXIIIA-27 | A2 | O | B72 | B6 |
| LXIIIA-28 | A2 | S | B54 | B6 | LXIIIA-29 | A2 | S | B70 | B6 | LXIIIA-30 | A2 | S | B72 | B6 |
| LXIIIA-31 | A2 | O | B54 | B70 | LXIIIA-32 | A2 | O | B70 | B70 | LXIIIA-33 | A2 | O | B72 | B70 |
| LXIIIA-34 | A3 | O | B54 | B6 | LXIIIA-35 | A3 | O | B70 | B6 | LXIIIA-36 | A3 | O | B72 | B6 |
| LXIIIA-37 | A3 | S | B54 | B6 | LXIIIA-38 | A3 | S | B70 | B6 | LXIIIA-39 | A3 | S | B72 | B6 |
| LXIIIA-40 | A3 | O | B54 | B70 | LXIIIA-41 | A3 | O | B70 | B70 | LXIIIA-42 | A3 | O | B72 | B70; | wherein Compound LXIVO-1 to Compound LXIVO-66 have a structure represented by Formula LXIVO:

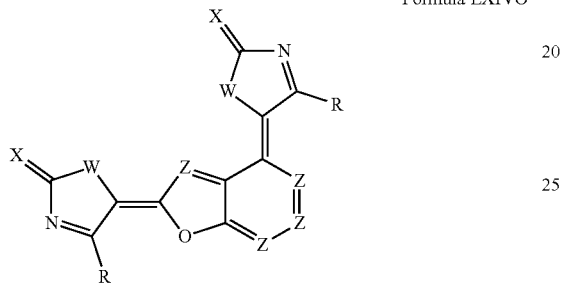

Formula LXIVO in Formula LXIVO, two X are identical, two W are identical, two R are identical, four Z are identical and are CR$_L$, and X, W, R, and R$_L$ correspond to an atom or a group selected from the following table, respectively:

| NO. | X | W | R | R$_L$ | NO. | X | W | R | R$_L$ | NO. | X | W | R | R$_L$ |
|---|---|---|---|---|---|---|---|---|---|---|---|---|---|---|
| LXIVO-1 | A1 | O | B1 | H | LXIVO-2 | A1 | O | B17 | H | LXIVO-3 | A1 | O | B25 | H |
| LXIVO-4 | A1 | O | B54 | H | LXIVO-5 | A1 | O | B70 | H | LXIVO-6 | A1 | O | B72 | H |
| LXIVO-7 | A1 | S | B1 | H | LXIVO-8 | A1 | S | B17 | H | LXIVO-9 | A1 | S | B25 | H |
| LXIVO-10 | A1 | S | B54 | H | LXIVO-11 | A1 | S | B70 | H | LXIVO-12 | A1 | S | B72 | H |
| LXIVO-13 | A1 | Se | B54 | H | LXIVO-14 | A1 | Se | B70 | H | LXIVO-15 | A1 | Se | B72 | H |
| LXIVO-16 | A1 | NMe | B54 | H | LXIVO-17 | A1 | NMe | B70 | H | LXIVO-18 | A1 | NMe | B72 | H |
| LXIVO-19 | A1 | O | H | F | LXIVO-20 | A1 | O | B17 | F | LXIVO-21 | A1 | O | B25 | F |
| LXIVO-22 | A1 | O | B54 | F | LXIVO-23 | A1 | O | B70 | F | LXIVO-24 | A1 | O | B72 | F |
| LXIVO-25 | A1 | S | H | F | LXIVO-26 | A1 | S | B17 | F | LXIVO-27 | A1 | S | B25 | F |
| LXIVO-28 | A1 | S | B54 | F | LXIVO-29 | A1 | S | B70 | F | LXIVO-30 | A1 | S | B72 | F |
| LXIVO-31 | A2 | O | B1 | H | LXIVO-32 | A2 | O | B17 | H | LXIVO-33 | A2 | O | B25 | H |
| LXIVO-34 | A2 | O | B54 | H | LXIVO-35 | A2 | O | B70 | H | LXIVO-36 | A2 | O | B72 | H |
| LXIVO-37 | A2 | S | B1 | H | LXIVO-38 | A2 | S | B17 | H | LXIVO-39 | A2 | S | B25 | H |
| LXIVO-40 | A2 | S | B54 | H | LXIVO-41 | A2 | S | B70 | H | LXIVO-42 | A2 | S | B72 | H |
| LXIVO-43 | A2 | O | B54 | F | LXIVO-44 | A2 | O | B70 | F | LXIVO-45 | A2 | O | B72 | F |
| LXIVO-46 | A2 | S | B54 | F | LXIVO-47 | A2 | S | B70 | F | LXIVO-48 | A2 | S | B72 | F |
| LXIVO-49 | A3 | O | Bi | H | LXIVO-50 | A3 | O | B17 | H | LXIVO-51 | A3 | O | B25 | H |
| LXIVO-52 | A3 | O | B54 | H | LXIVO-53 | A3 | O | B70 | H | LXIVO-54 | A3 | O | B72 | H |
| LXIVO-55 | A3 | S | B1 | H | LXIVO-56 | A3 | S | B17 | H | LXIVO-57 | A3 | S | B25 | H |
| LXIVO-58 | A3 | S | B54 | H | LXIVO-59 | A3 | S | B70 | H | LXIVO-60 | A3 | S | B72 | H |
| LXIVO-61 | A3 | O | B54 | F | LXIVO-62 | A3 | O | B70 | F | LXIVO-63 | A3 | O | B72 | F |
| LXIVO-64 | A3 | S | B54 | F | LXIVO-65 | A3 | S | B70 | F | LXIVO-66 | A3 | S | B72 | F; | wherein Compound LXIVA-1 to Compound LXIVA-42 have a structure represented by Formula LXIVA:

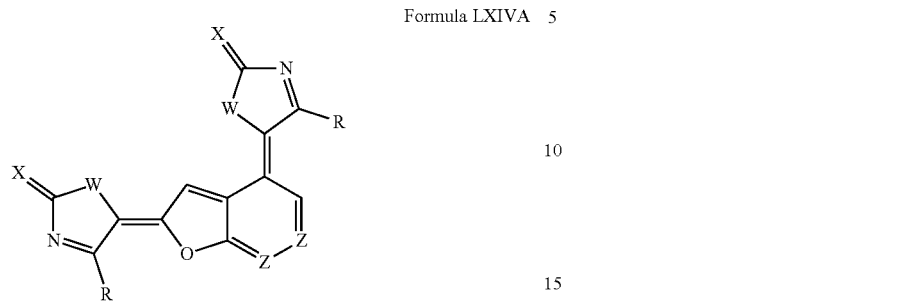

Formula LXIVA in Formula LXIVA, two X are identical, two W are identical, two R are identical, two Z are identical and are $CR_L$, and X, W, R, and $R_L$ correspond to an atom or a group selected from the following table, respectively:

| NO. | X | W | R | $R_L$ | NO. | X | W | R | $R_L$ | NO. | X | W | R | $R_L$ |
|---|---|---|---|---|---|---|---|---|---|---|---|---|---|---|
| LXIVA-1 | A1 | O | H | B6 | LXIVA-2 | A1 | O | B17 | B6 | LXIVA-3 | A1 | O | B25 | B6 |
| LXIVA-4 | A1 | O | B54 | B6 | LXIVA-5 | A1 | O | B70 | B6 | LXIVA-6 | A1 | O | B72 | B6 |
| LXIVA-7 | A1 | S | H | B6 | LXIVA-8 | A1 | S | B17 | B6 | LXIVA-9 | A1 | S | B25 | B6 |
| LXIVA-10 | A1 | S | B54 | B6 | LXIVA-11 | A1 | S | B70 | B6 | LXIVA-12 | A1 | S | B72 | B6 |
| LXIVA-13 | A1 | O | H | B70 | LXIVA-14 | A1 | O | B17 | B70 | LXIVA-15 | A1 | O | B25 | B70 |
| LXIVA-16 | A1 | O | B54 | B70 | LXIVA-17 | A1 | O | B70 | B70 | LXIVA-18 | A1 | O | B72 | B70 |
| LXIVA-19 | A1 | S | H | B70 | LXIVA-20 | A1 | S | B17 | B70 | LXIVA-21 | A1 | S | B25 | B70 |
| LXIVA-22 | A1 | S | B54 | B70 | LXIVA-23 | A1 | S | B70 | B70 | LXIVA-24 | A1 | S | B72 | B70 |
| LXIVA-25 | A2 | O | B54 | B6 | LXIVA-26 | A2 | O | B70 | B6 | LXIVA-27 | A2 | O | B72 | B6 |
| LXIVA-28 | A2 | S | B54 | B6 | LXIVA-29 | A2 | S | B70 | B6 | LXIVA-30 | A2 | S | B72 | B6 |
| LXIVA-31 | A2 | O | B54 | B70 | LXIVA-32 | A2 | O | B70 | B70 | LXIVA-33 | A2 | O | B72 | B70 |
| LXIVA-34 | A3 | O | B54 | B6 | LXIVA-35 | A3 | O | B70 | B6 | LXIVA-36 | A3 | O | B72 | B6 |
| LXIVA-37 | A3 | S | B54 | B6 | LXIVA-38 | A3 | S | B70 | B6 | LXIVA-39 | A3 | S | B72 | B6 |
| LXIVA-40 | A3 | O | B54 | B70 | LXIVA-41 | A3 | O | B70 | B70 | LXIVA-42 | A3 | O | B72 | B70; | wherein Compound LXVO-1 to Compound LXVO-66 have a structure represented by Formula LXVO:

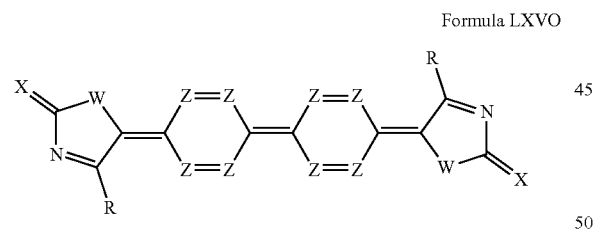

Formula LXVO in Formula LXVO, two X are identical, two W are identical, two R are identical, eight Z are identical and are $CR_L$, and X, W, R, and $R_L$ correspond to an atom or a group selected from the following table, respectively:

| NO. | X | W | R | $R_L$ | NO. | X | W | R | $R_L$ | NO. | X | W | R | $R_L$ |
|---|---|---|---|---|---|---|---|---|---|---|---|---|---|---|
| LXVO-1 | A1 | O | B1 | H | LXVO-2 | A1 | O | B17 | H | LXVO-3 | A1 | O | B25 | H |
| LXVO-4 | A1 | O | B54 | H | LXVO-5 | A1 | O | B70 | H | LXVO-6 | A1 | O | B72 | H |
| LXVO-7 | A1 | S | B1 | H | LXVO-8 | A1 | S | B17 | H | LXVO-9 | A1 | S | B25 | H |
| LXVO-10 | A1 | S | B54 | H | LXVO-11 | A1 | S | B70 | H | LXVO-12 | A1 | S | B72 | H |
| LXVO-13 | A1 | Se | B54 | H | LXVO-14 | A1 | Se | B70 | H | LXVO-15 | A1 | Se | B72 | H |
| LXVO-16 | A1 | NMe | B54 | H | LXVO-17 | A1 | NMe | B70 | H | LXVO-18 | A1 | NMe | B72 | H |
| LXVO-19 | A1 | O | H | F | LXVO-20 | A1 | O | B16 | F | LXVO-21 | A1 | O | B25 | F |
| LXVO-22 | A1 | O | B54 | F | LXVO-23 | A1 | O | B70 | F | LXVO-24 | A1 | O | B72 | F |
| LXVO-25 | A1 | S | H | F | LXVO-26 | A1 | S | B17 | F | LXVO-27 | A1 | S | B25 | F |
| LXVO-28 | A1 | S | B54 | F | LXVO-29 | A1 | S | B70 | F | LXVO-30 | A1 | S | B72 | F |

-continued

| NO. | X | W | R | $R_L$ | NO. | X | W | R | $R_L$ | NO. | X | W | R | $R_L$ |
|---|---|---|---|---|---|---|---|---|---|---|---|---|---|---|
| LXVO-31 | A2 | O | B1 | H | LXVO-32 | A2 | O | B17 | H | LXVO-33 | A2 | O | B25 | H |
| LXVO-34 | A2 | O | B54 | H | LXVO-35 | A2 | O | B70 | H | LXVO-36 | A2 | O | B72 | H |
| LXVO-37 | A2 | S | B1 | H | LXVO-38 | A2 | S | B17 | H | LXVO-39 | A2 | S | B25 | H |
| LXVO-40 | A2 | S | B54 | H | LXVO-41 | A2 | S | B70 | H | LXVO-42 | A2 | S | B72 | H |
| LXVO-43 | A2 | O | B54 | F | LXVO-44 | A2 | O | B70 | F | LXVO-45 | A2 | O | B72 | F |
| LXVO-46 | A2 | S | B54 | F | LXVO-47 | A2 | S | B70 | F | LXVO-48 | A2 | S | B72 | F |
| LXVO-49 | A3 | O | B1 | H | LXVO-50 | A3 | O | B17 | H | LXVO-51 | A3 | O | B25 | H |
| LXVO-52 | A3 | O | B54 | H | LXVO-53 | A3 | O | B70 | H | LXVO-54 | A3 | O | B72 | H |
| LXVO-55 | A3 | S | B1 | H | LXVO-56 | A3 | S | B17 | H | LXVO-57 | A3 | S | B25 | H |
| LXVO-58 | A3 | S | B54 | H | LXVO-59 | A3 | S | B70 | H | LXVO-60 | A3 | S | B72 | H |
| LXVO-61 | A3 | O | B54 | F | LXVO-62 | A3 | O | B70 | F | LXVO-63 | A3 | O | B72 | F |
| LXVO-64 | A3 | S | B54 | F | LXVO-65 | A3 | S | B70 | F | LXVO-66 | A3 | S | B72 | F; | wherein Compound LXVA-1 to Compound LXVA-42 have a structure represented by Formula LXVA:

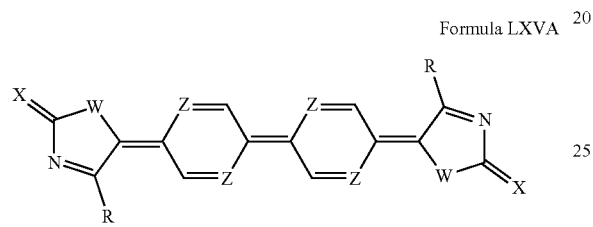

Formula LXVA in Formula LXVA, two X are identical, two W are identical, two R are identical, four Z are identical and are $CR_L$, and X, W, R, and $R_L$ correspond to an atom or a group selected from the following table, respectively:

| NO. | X | W | R | $R_L$ | NO. | X | W | R | $R_L$ | NO. | X | W | R | $R_L$ |
|---|---|---|---|---|---|---|---|---|---|---|---|---|---|---|
| LXVA-1 | A1 | O | H | B6 | LXVA-2 | A1 | O | B17 | B6 | LXVA-3 | A1 | O | B25 | B6 |
| LXVA-4 | A1 | O | B54 | B6 | LXVA-5 | A1 | O | B70 | B6 | LXVA-6 | A1 | O | B72 | B6 |
| LXVA-7 | A1 | S | H | B6 | LXVA-8 | A1 | S | B17 | B6 | LXVA-9 | A1 | S | B25 | B6 |
| LXVA-10 | A1 | S | B54 | B6 | LXVA-11 | A1 | S | B70 | B6 | LXVA-12 | A1 | S | B72 | B6 |
| LXVA-13 | A1 | O | H | B70 | LXVA-14 | A1 | O | B17 | B70 | LXVA-15 | A1 | O | B25 | B70 |
| LXVA-16 | A1 | O | B54 | B70 | LXVA-17 | A1 | O | B70 | B70 | LXVA-18 | A1 | O | B72 | B70 |
| LXVA-19 | A1 | S | H | B70 | LXVA-20 | A1 | S | B17 | B70 | LXVA-21 | A1 | S | B25 | B70 |
| LXVA-22 | A1 | S | B54 | B70 | LXVA-23 | A1 | S | B70 | B70 | LXVA-24 | A1 | S | B72 | B70 |
| LXVA-25 | A2 | O | B54 | B6 | LXVA-26 | A2 | O | B70 | B6 | LXVA-27 | A2 | O | B72 | B6 |
| LXVA-28 | A2 | S | B54 | B6 | LXVA-29 | A2 | S | B70 | B6 | LXVA-30 | A2 | S | B72 | B6 |
| LXVA-31 | A2 | O | B54 | B70 | LXVA-32 | A2 | O | B70 | B70 | LXVA-33 | A2 | O | B72 | B70 |
| LXVA-34 | A3 | O | B54 | B6 | LXVA-35 | A3 | O | B70 | B6 | LXVA-36 | A3 | O | B72 | B6 |
| LXVA-37 | A3 | S | B54 | B6 | LXVA-38 | A3 | S | B70 | B6 | LXVA-39 | A3 | S | B72 | B6 |
| LXVA-40 | A3 | O | B54 | B70 | LXVA-41 | A3 | O | B70 | B70 | LXVA-42 | A3 | O | B72 | B70; | wherein Compound LXVI-1 to Compound LXVIO-66 have a structure represented by Formula LXVIO:

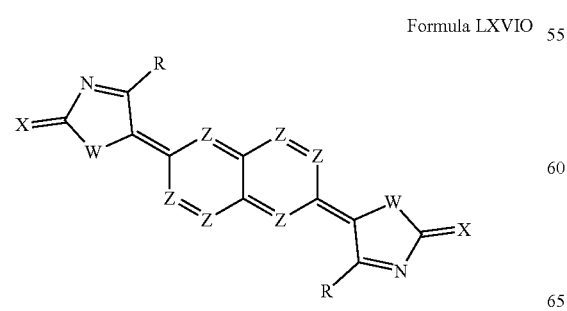

Formula LXVIO in Formula LXVIO, two X are identical, two W are identical, two R are identical, six Z are identical and are $CR_L$, and X, W, R, and $R_L$ correspond to an atom or a group selected from the following table, respectively:

| NO. | X | W | R | $R_L$ | NO. | X | W | R | $R_L$ | NO. | X | W | R | $R_L$ |
|---|---|---|---|---|---|---|---|---|---|---|---|---|---|---|
| LXVIO-1 | A1 | O | B1 | H | LXVIO-2 | A1 | O | B17 | H | LXVIO-3 | A1 | O | B54 | H |
| LXVIO-4 | A1 | O | B57 | H | LXVIO-5 | A1 | O | B70 | H | LXVIO-6 | A1 | O | B72 | H |
| LXVIO-7 | A1 | S | B1 | H | LXVIO-8 | A1 | S | B17 | H | LXVIO-9 | A1 | S | B25 | H |
| LXVIO-10 | A1 | S | B54 | H | LXVIO-11 | A1 | S | B70 | H | LXVIO-12 | A1 | S | B72 | H |
| LXVIO-13 | A1 | Se | B54 | H | LXVIO-14 | A1 | Se | B70 | H | LXVIO-15 | A1 | Se | B72 | H |
| LXVIO-16 | A1 | NMe | B54 | H | LXVIO-17 | A1 | NMe | B70 | H | LXVIO-18 | A1 | NMe | B72 | H |
| LXVIO-19 | A1 | O | H | F | LXVIO-20 | A1 | O | B16 | F | LXVIO-21 | A1 | O | B54 | F |
| LXVIO-22 | A1 | O | B57 | F | LXVIO-23 | A1 | O | B70 | F | LXVIO-24 | A1 | O | B72 | F |
| LXVIO-25 | A1 | S | H | F | LXVIO-26 | A1 | S | B17 | F | LXVIO-27 | A1 | S | B25 | F |
| LXVIO-28 | A1 | S | B54 | F | LXVIO-29 | A1 | S | B70 | F | LXVIO-30 | A1 | S | B72 | F |
| LXVIO-31 | A2 | O | B1 | H | LXVIO-32 | A2 | O | B17 | H | LXVIO-33 | A2 | O | B25 | H |
| LXVIO-34 | A2 | O | B54 | H | LXVIO-35 | A2 | O | B70 | H | LXVIO-36 | A2 | O | B72 | H |
| LXVIO-37 | A2 | S | B1 | H | LXVIO-38 | A2 | S | B17 | H | LXVIO-39 | A2 | S | B25 | H |
| LXVIO-40 | A2 | S | B54 | H | LXVIO-41 | A2 | S | B70 | H | LXVIO-42 | A2 | S | B72 | H |
| LXVIO-43 | A2 | O | B54 | F | LXVIO-44 | A2 | O | B70 | F | LXVIO-45 | A2 | O | B72 | F |
| LXVIO-46 | A2 | S | B54 | F | LXVIO-47 | A2 | S | B70 | F | LXVIO-48 | A2 | S | B72 | F |
| LXVIO-49 | A3 | O | B1 | H | LXVIO-50 | A3 | O | B17 | H | LXVIO-51 | A3 | O | B25 | H |
| LXVIO-52 | A3 | O | B54 | H | LXVIO-53 | A3 | O | B70 | H | LXVIO-54 | A3 | O | B72 | H |
| LXVIO-55 | A3 | S | B1 | H | LXVIO-56 | A3 | S | B17 | H | LXVIO-57 | A3 | S | B25 | H |
| LXVIO-58 | A3 | S | B54 | H | LXVIO-59 | A3 | S | B70 | H | LXVIO-60 | A3 | S | B72 | H |
| LXVIO-61 | A3 | O | B54 | F | LXVIO-62 | A3 | O | B70 | F | LXVIO-63 | A3 | O | B72 | F |
| LXVIO-64 | A3 | S | B54 | F | LXVIO-65 | A3 | S | B70 | F | LXVIO-66 | A3 | S | B72 | F; | wherein Compound LXVIA-1 to Compound LXVIA-42 have a structure represented by Formula LXVIA:

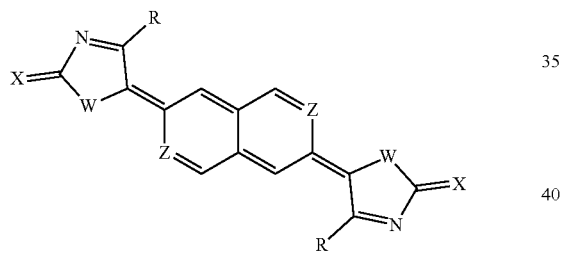

Formula LXVIA in Formula LXVIA, two X are identical, two W are identical, two R are identical, two Z are identical and are $CR_L$, and X, W, R, and $R_L$ correspond to an atom or a group selected from the following table, respectively:

| NO. | X | W | R | $R_L$ | NO. | X | W | R | $R_L$ | NO. | X | W | R | $R_L$ |
|---|---|---|---|---|---|---|---|---|---|---|---|---|---|---|
| LXVIA-1 | A1 | O | H | B6 | LXVIA-2 | A1 | O | B17 | B6 | LXVIA-3 | A1 | O | B25 | B6 |
| LXVIA-4 | A1 | O | B54 | B6 | LXVIA-5 | A1 | O | B70 | B6 | LXVIA-6 | A1 | O | B72 | B6 |
| LXVIA-7 | A1 | S | H | B6 | LXVIA-8 | A1 | S | B17 | B6 | LXVIA-9 | A1 | S | B25 | B6 |
| LXVIA-10 | A1 | S | B54 | B6 | LXVIA-11 | A1 | S | B70 | B6 | LXVIA-12 | A1 | S | B72 | B6 |
| LXVIA-13 | A1 | O | H | B70 | LXVIA-14 | A1 | O | B17 | B70 | LXVIA-15 | A1 | O | B25 | B70 |
| LXVIA-16 | A1 | O | B54 | B70 | LXVIA-17 | A1 | O | B70 | B70 | LXVIA-18 | A1 | O | B72 | B70 |
| LXVIA-19 | A1 | S | H | B70 | LXVIA-20 | A1 | S | B17 | B70 | LXVIA-21 | A1 | S | B25 | B70 |
| LXVIA-22 | A1 | S | B54 | B70 | LXVIA-23 | A1 | S | B70 | B70 | LXVIA-24 | A1 | S | B72 | B70 |
| LXVIA-25 | A2 | O | B54 | B6 | LXVIA-26 | A2 | O | B70 | B6 | LXVIA-27 | A2 | O | B72 | B6 |
| LXVIA-28 | A2 | S | B54 | B6 | LXVIA-29 | A2 | S | B70 | B6 | LXVIA-30 | A2 | S | B72 | B6 |
| LXVIA-31 | A2 | O | B54 | B70 | LXVIA-32 | A2 | O | B70 | B70 | LXVIA-33 | A2 | O | B72 | B70 |
| LXVIA-34 | A3 | O | B54 | B6 | LXVIA-35 | A3 | O | B70 | B6 | LXVIA-36 | A3 | O | B72 | B6 |
| LXVIA-37 | A3 | S | B54 | B6 | LXVIA-38 | A3 | S | B70 | B6 | LXVIA-39 | A3 | S | B72 | B6 |
| LXVIA-40 | A3 | O | B54 | B70 | LXVIA-41 | A3 | O | B70 | B70 | LXVIA-42 | A3 | O | B72 | B70; | wherein Compound LXVII-1 to Compound LXVIIO-66 have a structure represented by Formula LXVIIO:

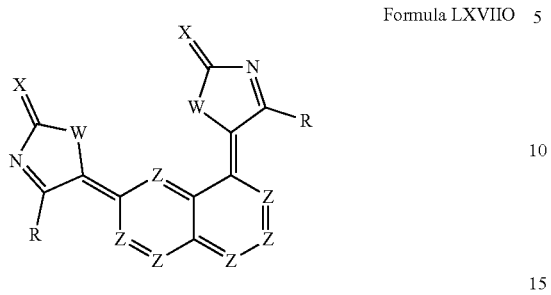

Formula LXVIIO in Formula LXVIIO, two X are identical, two W are identical, two R are identical, six Z are identical and are $CR_L$, and X, W, R, and $R_L$ correspond to an atom or a group selected from the following table, respectively:

| NO. | X | W | R | $R_L$ | NO. | X | W | R | $R_L$ | NO. | X | W | R | $R_L$ |
|---|---|---|---|---|---|---|---|---|---|---|---|---|---|---|
| LXVIIO-1 | A1 | O | B1 | H | LXVIIO-2 | A1 | O | B17 | H | LXVIIO-3 | A1 | O | B25 | H |
| LXVIIO-4 | A1 | O | B54 | H | LXVIIO-5 | A1 | O | B70 | H | LXVIIO-6 | A1 | O | B72 | H |
| LXVIIO-7 | A1 | S | B1 | H | LXVIIO-8 | A1 | S | B17 | H | LXVIIO-9 | A1 | S | B25 | H |
| LXVIIO-10 | A1 | S | B54 | H | LXVIIO-11 | A1 | S | B70 | H | LXVII-12 | A1 | S | B72 | H |
| LXVIIO-13 | A1 | Se | B54 | H | LXVIIO-14 | A1 | Se | B70 | H | LXVIIO-15 | A1 | Se | B72 | H |
| LXVIIO-16 | A1 | NMe | B54 | H | LXVIIO-17 | A1 | NMe | B70 | H | LXVIIO-18 | A1 | NMe | B72 | H |
| LXVIIO-19 | A1 | O | H | F | LXVIIO-20 | A1 | O | B17 | F | LXVIIO-21 | A1 | O | B25 | F |
| LXVIIO-22 | A1 | O | B54 | F | LXVIIO-23 | A1 | O | B70 | F | LXVIIO-24 | A1 | O | B72 | F |
| LXVIIO-25 | A1 | S | H | F | LXVIIO-26 | A1 | S | B17 | F | LXVIIO-27 | A1 | S | B25 | F |
| LXVIIO-28 | A1 | S | B54 | F | LXVIIO-29 | A1 | S | B70 | F | LXVIIO-30 | A1 | S | B72 | F |
| LXVIIO-31 | A2 | O | B1 | H | LXVIIO-32 | A2 | O | B17 | H | LXVIIO-33 | A2 | O | B25 | H |
| LXVIIO-34 | A2 | O | B54 | H | LXVIIO-35 | A2 | O | B70 | H | LXVIIO-36 | A2 | O | B72 | H |
| LXVIIO-37 | A2 | S | B1 | H | LXVIIO-38 | A2 | S | B17 | H | LXVIIO-39 | A2 | S | B25 | H |
| LXVIIO-40 | A2 | S | B54 | H | LXVIIO-41 | A2 | S | B70 | H | LXVIIO-42 | A2 | S | B72 | H |
| LXVIIO-43 | A2 | O | B54 | F | LXVIIO-44 | A2 | O | B70 | F | LXVIIO-45 | A2 | O | B72 | F |
| LXVIIO-46 | A2 | S | B54 | F | LXVIIO-47 | A2 | S | B70 | F | LXVIIO-48 | A2 | S | B72 | F |
| LXVIIO-49 | A3 | O | B1 | H | LXVIIO-50 | A3 | O | B17 | H | LXVIIO-51 | A3 | O | B25 | H |
| LXVIIO-52 | A3 | O | B54 | H | LXVIIO-53 | A3 | O | B70 | H | LXVIIO-54 | A3 | O | B72 | H |
| LXVIIO-55 | A3 | S | B1 | H | LXVIIO-56 | A3 | S | B17 | H | LXVIIO-57 | A3 | S | B25 | H |
| LXVIIO-58 | A3 | S | B54 | H | LXVIIO-59 | A3 | S | B70 | H | LXVIIO-60 | A3 | S | B72 | H |
| LXVIIO-61 | A3 | O | B54 | F | LXVIIO-62 | A3 | O | B70 | F | LXVIIO-63 | A3 | O | B72 | F |
| LXVIIO-64 | A3 | S | B54 | F | LXVIIO-65 | A3 | S | B70 | F | LXVIIO-66 | A3 | S | B72 | F; | wherein Compound LXVIIA-1 to Compound LXVIIA-42 have a structure represented by Formula LXVIIA:

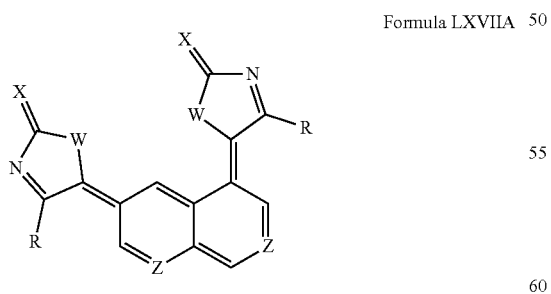

Formula LXVIIA in Formula LXVIIA, two X are identical, two W are identical, two R are identical, two Z are identical and are $CR_L$, and X, W, R, and $R_L$ correspond to an atom or a group selected from the following table, respectively:

| NO. | X | W | R | $R_L$ | No. | X | W | R | $R_L$ | NO. | X | W | R | $R_L$ |
|---|---|---|---|---|---|---|---|---|---|---|---|---|---|---|
| LXVIIA-1 | A1 | O | H | B6 | LXVIIA-2 | A1 | O | B17 | B6 | LXVIIA-3 | A1 | O | B25 | B6 |
| LXVIIA-4 | A1 | O | B54 | B6 | LXVIIA-5 | A1 | O | B70 | B6 | LXVIIA-6 | A1 | O | B72 | B6 |
| LXVIIA-7 | A1 | S | H | B6 | LXVIIA-8 | A1 | S | B17 | B6 | LXVIIA-9 | A1 | S | B25 | B6 |
| LXVIIA-10 | A1 | S | B54 | B6 | LXVIIA-11 | A1 | S | B70 | B6 | LXVIIA-12 | A1 | S | B72 | B6 |
| LXVIIA-13 | A1 | O | H | B70 | LXVIIA-14 | A1 | O | B17 | B70 | LXVIIA-15 | A1 | O | B25 | B70 |
| LXVIIA-16 | A1 | O | B54 | B70 | LXVIIA-17 | A1 | O | B70 | B70 | LXVIIA-18 | A1 | O | B72 | B70 |
| LXVIIA-19 | A1 | S | H | B70 | LXVIIA-20 | A1 | S | B17 | B70 | LXVIIA-21 | A1 | S | B25 | B70 |
| LXVIIA-22 | A1 | S | B54 | B70 | LXVIIA-23 | A1 | S | B70 | B70 | LXVIIA-24 | A1 | S | B72 | B70 |
| LXVIIA-25 | A2 | O | B54 | B6 | LXVIIA-26 | A2 | O | B70 | B6 | LXVIIA-27 | A2 | O | B72 | B6 |
| LXVIIA-28 | A2 | S | B54 | B6 | LXVIIA-29 | A2 | S | B70 | B6 | LXVIIA-30 | A2 | S | B72 | B6 |
| LXVIIA-31 | A2 | O | B54 | B70 | LXVIIA-32 | A2 | O | B70 | B70 | LXVIIA-33 | A2 | O | B72 | B70 |
| LXVIIA-34 | A3 | O | B54 | B6 | LXVIIA-35 | A3 | O | B70 | B6 | LXVIIA-36 | A3 | O | B72 | B6 |
| LXVIIA-37 | A3 | S | B54 | B6 | LXVIIA-38 | A3 | S | B70 | B6 | LXVIIA-39 | A3 | S | B72 | B6 |
| LXVIIA-40 | A3 | O | B54 | B70 | LXVIIA-41 | A3 | O | B70 | B70 | LXVIIA-42 | A3 | O | B72 | B70; | wherein Compound LXVIIIO-1 to Compound LXVIIIO-66 have a structure represented by Formula LXVIIIO:

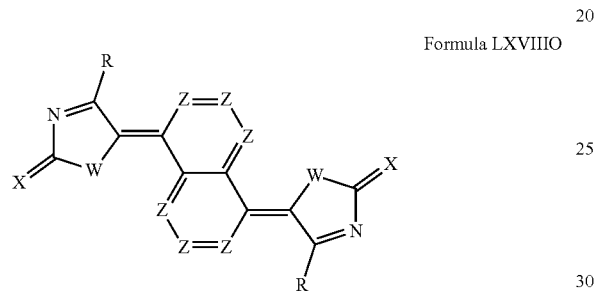

Formula LXVIIIO in Formula LXVIIIO, two X are identical, two W are identical, two R are identical, six Z are identical and are $CR_L$, and X, W, R, and $R_L$ correspond to an atom or a group selected from the following table, respectively:

| NO. | X | W | R | $R_L$ | NO. | X | W | R | $R_L$ | NO. | X | W | R | $R_L$ |
|---|---|---|---|---|---|---|---|---|---|---|---|---|---|---|
| LXVIIIO-1 | A1 | O | H | H | LXVIIIO-2 | A1 | O | B16 | H | LXVIIIO-3 | A1 | O | B54 | H |
| LXVIIIO-4 | A1 | O | B57 | H | LXVIIIO-5 | A1 | O | B70 | H | LXVIIIO-6 | A1 | O | B72 | H |
| LXVIIIO-7 | A1 | S | B1 | H | LXVIIIO-8 | A1 | S | B17 | H | LXVIIIO-9 | A1 | S | B25 | H |
| LXVIIIO-10 | A1 | S | B54 | H | LXVIIIO-11 | A1 | S | B70 | H | LXVIIIO-12 | A1 | S | B72 | H |
| LXVIIIO-13 | A1 | Se | B54 | H | LXVIIIO-14 | A1 | Se | B70 | H | LXVIIIO-15 | A1 | Se | B72 | H |
| LXVIIIO-16 | A1 | NMe | B54 | H | LXVIIIO-17 | A1 | NMe | B70 | H | LXVIIIO-18 | A1 | NMe | B72 | H |
| LXVIIIO-19 | A1 | O | H | F | LXVIIIO-20 | A1 | O | B16 | F | LXVIIIO-21 | A1 | O | B54 | F |
| LXVIIIO-22 | A1 | O | B57 | F | LXVIIIO-23 | A1 | O | B70 | F | LXVIIIO-24 | A1 | O | B72 | F |
| LXVIIIO-25 | A1 | S | H | F | LXVIIIO-26 | A1 | S | B17 | F | LXVIIIO-27 | A1 | S | B25 | F |
| LXVIIIO-28 | A1 | S | B54 | F | LXVIIIO-29 | A1 | S | B70 | F | LXVIIIO-30 | A1 | S | B72 | F |
| LXVIIIO-31 | A2 | O | B1 | H | LXVIIIO-32 | A2 | O | B17 | H | LXVIIIO-33 | A2 | O | B25 | H |
| LXVIIIO-34 | A2 | O | B54 | H | LXVIIIO-35 | A2 | O | B70 | H | LXVIIIO-36 | A2 | O | B72 | H |
| LXVIIIO-37 | A2 | S | B1 | H | LXVIIIO-38 | A2 | S | B17 | H | LXVIIIO-39 | A2 | S | B25 | H |
| LXVIIIO-40 | A2 | S | B54 | H | LXVIIIO-41 | A2 | S | B70 | H | LXVIIIO-42 | A2 | S | B72 | H |
| LXVIIIO-43 | A2 | O | B54 | F | LXVIIIO-44 | A2 | O | B70 | F | LXVIIIO-45 | A2 | O | B72 | F |
| LXVIIIO-46 | A2 | S | B54 | F | LXVIIIO-47 | A2 | S | B70 | F | LXVIIIO-48 | A2 | S | B72 | F |
| LXVIIIO-49 | A3 | O | B1 | H | LXVIIIO-50 | A3 | O | B17 | H | LXVIIIO-51 | A3 | O | B25 | H |
| LXVIIIO-52 | A3 | O | B54 | H | LXVIIIO-53 | A3 | O | B70 | H | LXVIIIO-54 | A3 | O | B72 | H |
| LXVIIIO-55 | A3 | S | B1 | H | LXVIIIO-56 | A3 | S | B17 | H | LXVIIIO-57 | A3 | S | B25 | H |
| LXVIIIO-58 | A3 | S | B54 | H | LXVIIIO-59 | A3 | S | B70 | H | LXVIIIO-60 | A3 | S | B72 | H |
| LXVIIIO-61 | A3 | O | B54 | F | LXVIIIO-62 | A3 | O | B70 | F | LXVIIIO-63 | A3 | O | B72 | F |
| LXVIIIO-64 | A3 | S | B54 | F | LXVIIIO-65 | A3 | S | B70 | F | LXVIIIO-66 | A3 | S | B72 | F; | wherein Compound LXVIIIA-1 to Compound LXVIIIA-42 have a structure represented by Formula LXVIIIA:

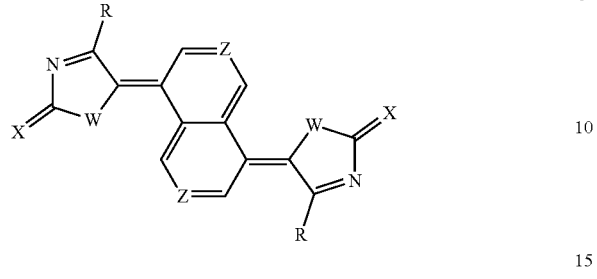

Formula LXVIIIA in Formula LXVIIIA, two X are identical, two W are identical, two R are identical, two Z are identical and are $CR_L$, and X, W, R, and $R_L$ correspond to an atom or a group selected from the following table, respectively:

| NO. | X | W | R | $R_L$ | NO. | X | W | R | $R_L$ | NO. | X | W | R | $R_L$ |
|---|---|---|---|---|---|---|---|---|---|---|---|---|---|---|
| LXVIIIA-1 | A1 | O | H | B6 | LXVIIIA-2 | A1 | O | B17 | B6 | LXVIIIA-3 | A1 | O | B25 | B6 |
| LXVIIIA-4 | A1 | O | B54 | B6 | LXVIIIA-5 | A1 | O | B70 | B6 | LXVIIIA-6 | A1 | O | B72 | B6 |
| LXVIIIA-7 | A1 | S | H | B6 | LXVIIIA-8 | A1 | S | B17 | B6 | LXVIIIA-9 | A1 | S | B25 | B6 |
| LXVIIIA-10 | A1 | S | B54 | B6 | LXVIIIA-11 | A1 | S | B70 | B6 | LXVIIIA-12 | A1 | S | B72 | B6 |
| LXVIIIA-13 | A1 | O | H | B70 | LXVIIIA-14 | A1 | O | B17 | B70 | LXVIIIA-15 | A1 | O | B25 | B70 |
| LXVIIIA-16 | A1 | O | B54 | B70 | LXVIIIA-17 | A1 | O | B70 | B70 | LXVIIIA-18 | A1 | O | B72 | B70 |
| LXVIIIA-19 | A1 | S | H | B70 | LXVIIIA-20 | A1 | S | B17 | B70 | LXVIIIA-21 | A1 | S | B25 | B70 |
| LXVIIIA-22 | A1 | S | B54 | B70 | LXVIIIA-23 | A1 | S | B70 | B70 | LXVIIIA-24 | A1 | S | B72 | B70 |
| LXVIIIA-25 | A2 | O | B54 | B6 | LXVIIIA-26 | A2 | O | B70 | B6 | LXVIIIA-27 | A2 | O | B72 | B6 |
| LXVIIIA-28 | A2 | S | B54 | B6 | LXVIIIA-29 | A2 | S | B70 | B6 | LXVIIIA-30 | A2 | S | B72 | B6 |
| LXVIIIA-31 | A2 | O | B54 | B70 | LXVIIIA-32 | A2 | O | B70 | B70 | LXVIIIA-33 | A2 | O | B72 | B70 |
| LXVIIIA-34 | A3 | O | B54 | B6 | LXVIIIA-35 | A3 | O | B70 | B6 | LXVIIIA-36 | A3 | O | B72 | B6 |
| LXVIIIA-37 | A3 | S | B54 | B6 | LXVIIIA-38 | A3 | S | B70 | B6 | LXVIIIA-39 | A3 | S | B72 | B6 |
| LXVIIIA-40 | A3 | O | B54 | B70 | LXVIIIA-41 | A3 | O | B70 | B70 | LXVIIIA-42 | A3 | O | B72 | B70; | wherein Compound LXIXO-1 to Compound LXIXO-66 have a structure represented by Formula LXIXO:

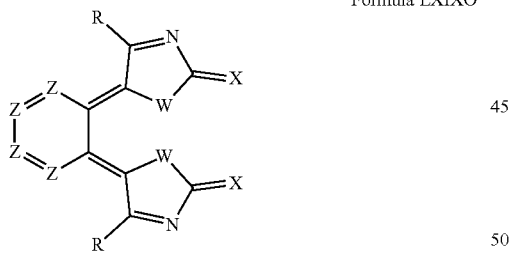

Formula LXIXO in Formula LXIXO, two X are identical, two W are identical, two R are identical, four Z are identical and are $CR_L$, and X, W, R, and $R_L$ correspond to an atom or a group selected from the following table, respectively:

| NO. | X | W | R | $R_L$ | NO. | X | W | R | $R_L$ | NO. | X | W | R | $R_L$ |
|---|---|---|---|---|---|---|---|---|---|---|---|---|---|---|
| LXIXO-1 | A1 | O | H | H | LXIXO-2 | A1 | O | B17 | H | LXIXO-3 | A1 | O | B54 | H |
| LXIXO-4 | A1 | O | B57 | H | LXIXO-5 | A1 | O | B70 | H | LXIXO-6 | A1 | O | B72 | H |
| LXIXO-7 | A1 | S | B1 | H | LXIXO-8 | A1 | S | B17 | H | LXIXO-9 | A1 | S | B25 | H |
| LXIXO-10 | A1 | S | B54 | H | LXIXO-11 | A1 | S | B70 | H | LXIXO-12 | A1 | S | B72 | H |
| LXIXO-13 | A1 | Se | B54 | H | LXIXO-14 | A1 | Se | B70 | H | LXIXO-15 | A1 | Se | B72 | H |
| LXIXO-16 | A1 | NMe | B54 | H | LXIXO-17 | A1 | NMe | B70 | H | LXIXO-18 | A1 | NMe | B72 | H |
| LXIXO-19 | A1 | O | H | F | LXIXO-20 | A1 | O | B17 | F | LXIXO-21 | A1 | O | B54 | F |
| LXIXO-22 | A1 | O | B57 | F | LXIXO-23 | A1 | O | B70 | F | LXIXO-24 | A1 | O | B72 | F |
| LXIXO-25 | A1 | S | H | F | LXIXO-26 | A1 | S | B17 | F | LXIXO-27 | A1 | S | B25 | F |

-continued

| NO. | X | W | R | $R_L$ | NO. | X | W | R | $R_L$ | NO. | X | W | R | $R_L$ |
|---|---|---|---|---|---|---|---|---|---|---|---|---|---|---|
| LXIXO-28 | A1 | S | B54 | F | LXIXO-29 | A1 | S | B70 | F | LXIXO-30 | A1 | S | B72 | F |
| LXIXO-31 | A2 | O | B1 | H | LXIXO-32 | A2 | O | B17 | H | LXIXO-33 | A2 | O | B25 | H |
| LXIXO-34 | A2 | O | B54 | H | LXIXO-35 | A2 | O | B70 | H | LXIXO-36 | A2 | O | B72 | H |
| LXIXO-37 | A2 | S | B1 | H | LXIXO-38 | A2 | S | B17 | H | LXIXO-39 | A2 | S | B25 | H |
| LXIXO-40 | A2 | S | B54 | H | LXIXO-41 | A2 | S | B70 | H | LXIXO-42 | A2 | S | B72 | H |
| LXIXO-43 | A2 | O | B54 | F | LXIXO-44 | A2 | O | B70 | F | LXIXO-45 | A2 | O | B72 | F |
| LXIXO-46 | A2 | S | B54 | F | LXIXO-47 | A2 | S | B70 | F | LXIXO-48 | A2 | S | B72 | F |
| LXIXO-49 | A3 | O | B1 | H | LXIXO-50 | A3 | O | B17 | H | LXIXO-51 | A3 | O | B25 | H |
| LXIXO-52 | A3 | O | B54 | H | LXIXO-53 | A3 | O | B70 | H | LXIXO-54 | A3 | O | B72 | H |
| LXIXO-55 | A3 | S | B1 | H | LXIXO-56 | A3 | S | B17 | H | LXIXO-57 | A3 | S | B25 | H |
| LXIXO-58 | A3 | S | B54 | H | LXIXO-59 | A3 | S | B70 | H | LXIXO-60 | A3 | S | B72 | H |
| LXIXO-61 | A3 | O | B54 | F | LXIXO-62 | A3 | O | B70 | F | LXIXO-63 | A3 | O | B72 | F |
| LXIXO-64 | A3 | S | B54 | F | LXIXO-65 | A3 | S | B70 | F | LXIXO-66 | A3 | S | B72 | F; | wherein Compound LXIXA-1 to Compound LXIXA-42 have a structure represented by Formula LXIXA:

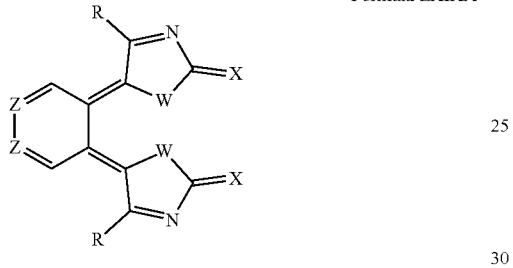

Formula LXIXA in Formula LXIXA, two X are identical, two W are identical, two R are identical, two Z are identical and are $CR_L$, and X, W, R, and $R_L$ correspond to an atom or a group selected from the following table, respectively:

| NO. | X | W | R | $R_L$ | NO. | X | W | R | $R_L$ | NO. | X | W | R | $R_L$ |
|---|---|---|---|---|---|---|---|---|---|---|---|---|---|---|
| LXIXA-1 | A1 | O | H | B6 | LXIXA-2 | A1 | O | B17 | B6 | LXIXA-3 | A1 | O | B25 | B6 |
| LXIXA-4 | A1 | O | B54 | B6 | LXIXA-5 | A1 | O | B70 | B6 | LXIXA-6 | A1 | O | B72 | B6 |
| LXIXA-7 | A1 | S | H | B6 | LXIXA-8 | A1 | S | B17 | B6 | LXIXA-9 | A1 | S | B25 | B6 |
| LXIXA-10 | A1 | S | B54 | B6 | LXIXA-11 | A1 | S | B70 | B6 | LXIXA-12 | A1 | S | B72 | B6 |
| LXIXA-13 | A1 | O | H | B70 | LXIXA-14 | A1 | O | B17 | B70 | LXIXA-15 | A1 | O | B25 | B70 |
| LXIXA-16 | A1 | O | B54 | B70 | LXIXA-17 | A1 | O | B70 | B70 | LXIXA-18 | A1 | O | B72 | B70 |
| LXIXA-19 | A1 | S | H | B70 | LXIXA-20 | A1 | S | B17 | B70 | LXIXA-21 | A1 | S | B25 | B70 |
| LXIXA-22 | A1 | S | B54 | B70 | LXIXA-23 | A1 | S | B70 | B70 | LXIXA-24 | A1 | S | B72 | B70 |
| LXIXA-25 | A2 | O | B54 | B6 | LXIXA-26 | A2 | O | B70 | B6 | LXIXA-27 | A2 | O | B72 | B6 |
| LXIXA-28 | A2 | S | B54 | B6 | LXIXA-29 | A2 | S | B70 | B6 | LXIXA-30 | A2 | S | B72 | B6 |
| LXIXA-31 | A2 | O | B54 | B70 | LXIXA-32 | A2 | O | B70 | B70 | LXIXA-33 | A2 | O | B72 | B70 |
| LXIXA-34 | A3 | O | B54 | B6 | LXIXA-35 | A3 | O | B70 | B6 | LXIXA-36 | A3 | O | B72 | B6 |
| LXIXA-37 | A3 | S | B54 | B6 | LXIXA-38 | A3 | S | B70 | B6 | LXIXA-39 | A3 | S | B72 | B6 |
| LXIXA-40 | A3 | O | B54 | B70 | LXIXA-41 | A3 | O | B70 | B70 | LXIXA-42 | A3 | O | B72 | B70; | wherein Compound LXXO-1 to Compound LXXO-66 have a structure represented by Formula LXXO:

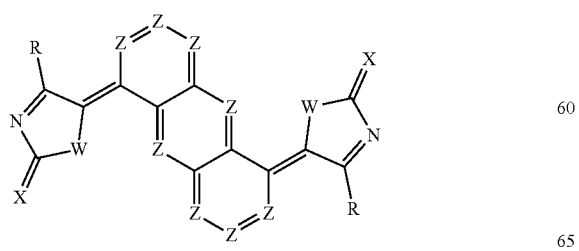

Formula LXXO in Formula LXXO, two X are identical, two W are identical, two R are identical, eight Z are identical and are $CR_L$, and X, W, R, and $R_L$ correspond to an atom or a group selected from the following table, respectively:

| NO. | X | W | R | $R_L$ | NO. | X | W | R | $R_L$ | NO. | X | W | R | $R_L$ |
|---|---|---|---|---|---|---|---|---|---|---|---|---|---|---|
| LXXO-1 | A1 | O | H | H | LXXO-2 | A1 | O | B17 | H | LXXO-3 | A1 | O | B54 | H |
| LXXO-4 | A1 | O | B57 | H | LXXO-5 | A1 | O | B70 | H | LXXO-6 | A1 | O | B72 | H |
| LXXO-7 | A1 | S | B1 | H | LXXO-8 | A1 | S | B17 | H | LXXO-9 | A1 | S | B25 | H |
| LXXO-10 | A1 | S | B54 | H | LXXO-11 | A1 | S | B70 | H | LXXO-12 | A1 | S | B72 | H |
| LXXO-13 | A1 | Se | B54 | H | LXXO-14 | A1 | Se | B70 | H | LXXO-15 | A1 | Se | B72 | H |
| LXXO-16 | A1 | NMe | B54 | H | LXXO-17 | A1 | NMe | B70 | H | LXXO-18 | A1 | NMe | B72 | H |
| LXXO-19 | A1 | O | H | F | LXXO-20 | A1 | O | B17 | F | LXXO-21 | A1 | O | B54 | F |
| LXXO-22 | A1 | O | B57 | F | LXXO-23 | A1 | O | B70 | F | LXXO-24 | A1 | O | B72 | F |
| LXXO-25 | A1 | S | H | F | LXXO-26 | A1 | S | B17 | F | LXXO-27 | A1 | S | B25 | F |
| LXXO-28 | A1 | S | B54 | F | LXXO-29 | A1 | S | B70 | F | LXXO-30 | A1 | S | B72 | F |
| LXXO-31 | A2 | O | B1 | H | LXXO-32 | A2 | O | B17 | H | LXXO-33 | A2 | O | B25 | H |
| LXXO-34 | A2 | O | B54 | H | LXXO-35 | A2 | O | B70 | H | LXXO-36 | A2 | O | B72 | H |
| LXXO-37 | A2 | S | B1 | H | LXXO-38 | A2 | S | B17 | H | LXXO-39 | A2 | S | B25 | H |
| LXXO-40 | A2 | S | B54 | H | LXXO-41 | A2 | S | B70 | H | LXXO-42 | A2 | S | B72 | H |
| LXXO-43 | A2 | O | B54 | F | LXXO-44 | A2 | O | B70 | F | LXXO-45 | A2 | O | B72 | F |
| LXXO-46 | A2 | S | B54 | F | LXXO-47 | A2 | S | B70 | F | LXXO-48 | A2 | S | B72 | F |
| LXXO-49 | A3 | O | B1 | H | LXXO-50 | A3 | O | B17 | H | LXXO-51 | A3 | O | B25 | H |
| LXXO-52 | A3 | O | B54 | H | LXXO-53 | A3 | O | B70 | H | LXXO-54 | A3 | O | B72 | H |
| LXXO-55 | A3 | S | B1 | H | LXXO-56 | A3 | S | B17 | H | LXXO-57 | A3 | S | B25 | H |
| LXXO-58 | A3 | S | B54 | H | LXXO-59 | A3 | S | B70 | H | LXXO-60 | A3 | S | B72 | H |
| LXXO-61 | A3 | O | B54 | F | LXXO-62 | A3 | O | B70 | F | LXXO-63 | A3 | O | B72 | F |
| LXXO-64 | A3 | S | B54 | F | LXXO-65 | A3 | S | B70 | F | LXXO-66 | A3 | S | B72 | F; | wherein Compound LXXA-1 to Compound LXXA-42 have a structure represented by Formula LXXA:

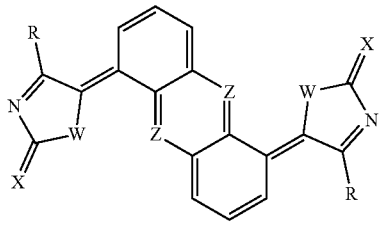

Formula LXXA in Formula LXXA, two X are identical, two W are identical, two R are identical, two Z are identical and are $CR_L$, and X, W, R, and $R_L$ correspond to an atom or a group selected from the following table, respectively:

| NO. | X | W | R | $R_L$ | NO. | X | W | R | $R_L$ | NO. | X | W | R | $R_L$ |
|---|---|---|---|---|---|---|---|---|---|---|---|---|---|---|
| LXXA-1 | A1 | O | H | B6 | LXXA-2 | A1 | O | B17 | B6 | LXXA-3 | A1 | O | B25 | B6 |
| LXXA-4 | A1 | O | B54 | B6 | LXXA-5 | A1 | O | B70 | B6 | LXXA-6 | A1 | O | B72 | B6 |
| LXXA-7 | A1 | S | H | B6 | LXXA-8 | A1 | S | B17 | B6 | LXXA-9 | A1 | S | B25 | B6 |
| LXXA-10 | A1 | S | B54 | B6 | LXXA-11 | A1 | S | B70 | B6 | LXXA-12 | A1 | S | B72 | B6 |
| LXXA-13 | A1 | O | H | B70 | LXXA-14 | A1 | O | B17 | B70 | LXXA-15 | A1 | O | B25 | B70 |
| LXXA-16 | A1 | O | B54 | B70 | LXXA-17 | A1 | O | B70 | B70 | LXXA-18 | A1 | O | B72 | B70 |
| LXXA-19 | A1 | S | H | B70 | LXXA-20 | A1 | S | B17 | B70 | LXXA-21 | A1 | S | B25 | B70 |
| LXXA-22 | A1 | S | B54 | B70 | LXXA-23 | A1 | S | B70 | B70 | LXXA-24 | A1 | S | B72 | B70 |
| LXXA-25 | A2 | O | B54 | B6 | LXXA-26 | A2 | O | B70 | B6 | LXXA-27 | A2 | O | B72 | B6 |
| LXXA-28 | A2 | S | B54 | B6 | LXXA-29 | A2 | S | B70 | B6 | LXXA-30 | A2 | S | B72 | B6 |
| LXXA-31 | A2 | O | B54 | B70 | LXXA-32 | A2 | O | B70 | B70 | LXXA-33 | A2 | O | B72 | B70 |
| LXXA-34 | A3 | O | B54 | B6 | LXXA-35 | A3 | O | B70 | B6 | LXXA-36 | A3 | O | B72 | B6 |
| LXXA-37 | A3 | S | B54 | B6 | LXXA-38 | A3 | S | B70 | B6 | LXXA-39 | A3 | S | B72 | B6 |
| LXXA-40 | A3 | O | B54 | B70 | LXXA-41 | A3 | O | B70 | B70 | LXXA-42 | A3 | O | B72 | B70; | wherein Compound LXXIO-1 to Compound LXXIO-66 have a structure represented by Formula LXXIO:

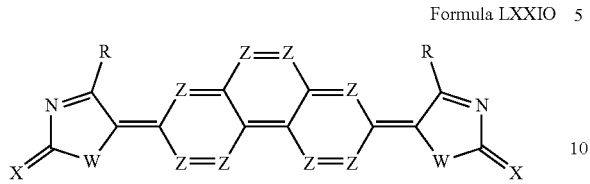

Formula LXXIO in Formula LXXIO, two X are identical, two W are identical, two R are identical, eight Z are identical and are $CR_L$, and X, W, R, and $R_L$ correspond to an atom or a group selected from the following table, respectively:

| NO. | X | W | R | $R_L$ | NO. | X | W | R | $R_L$ | NO. | X | W | R | $R_L$ |
|---|---|---|---|---|---|---|---|---|---|---|---|---|---|---|
| LXXIO-1 | A1 | O | B1 | H | LXXIO-2 | A1 | O | B17 | H | LXXIO-3 | A1 | O | B25 | H |
| LXXIO-4 | A1 | O | B54 | H | LXXIO-5 | A1 | O | B70 | H | LXXIO-6 | A1 | O | B72 | H |
| LXXIO-7 | A1 | S | B1 | H | LXXIO-8 | A1 | S | B17 | H | LXXIO-9 | A1 | S | B25 | H |
| LXXIO-10 | A1 | S | B54 | H | LXXIO-11 | A1 | S | B70 | H | LXXIO-12 | A1 | S | B72 | H |
| LXXIO-13 | A1 | Se | B54 | H | LXXIO-14 | A1 | Se | B70 | H | LXXIO-15 | A1 | Se | B72 | H |
| LXXIO-16 | A1 | NMe | B54 | H | LXXIO-17 | A1 | NMe | B70 | H | LXXIO-18 | A1 | NMe | B72 | H |
| LXXIO-19 | A1 | O | H | F | LXXIO-20 | A1 | O | B17 | F | LXXIO-21 | A1 | O | B25 | F |
| LXXIO-22 | A1 | O | B54 | F | LXXIO-23 | A1 | O | B70 | F | LXXIO-24 | A1 | O | B72 | F |
| LXXIO-25 | A1 | S | H | F | LXXIO-26 | A1 | S | B17 | F | LXXIO-27 | A1 | S | B25 | F |
| LXXIO-28 | A1 | S | B54 | F | LXXIO-29 | A1 | S | B70 | F | LXXIO-30 | A1 | S | B72 | F |
| LXXIO-31 | A2 | O | B1 | H | LXXIO-32 | A2 | O | B17 | H | LXXIO-33 | A2 | O | B25 | H |
| LXXIO-34 | A2 | O | B54 | H | LXXIO-35 | A2 | O | B70 | H | LXXIO-36 | A2 | O | B72 | H |
| LXXIO-37 | A2 | S | B1 | H | LXXIO-38 | A2 | S | B17 | H | LXXIO-39 | A2 | S | B25 | H |
| LXXIO-40 | A2 | S | B54 | H | LXXIO-41 | A2 | S | B70 | H | LXXIO-42 | A2 | S | B72 | H |
| LXXIO-43 | A2 | O | B54 | F | LXXIO-44 | A2 | O | B70 | F | LXXIO-45 | A2 | O | B72 | F |
| LXXIO-46 | A2 | S | B54 | F | LXXIO-47 | A2 | S | B70 | F | LXXIO-48 | A2 | S | B72 | F |
| LXXIO-49 | A3 | O | B1 | H | LXXIO-50 | A3 | O | B17 | H | LXXIO-51 | A3 | O | B25 | H |
| LXXIO-52 | A3 | O | B54 | H | LXXIO-53 | A3 | O | B70 | H | LXXIO-54 | A3 | O | B72 | H |
| LXXIO-55 | A3 | S | B1 | H | LXXIO-56 | A3 | S | B17 | H | LXXIO-57 | A3 | S | B25 | H |
| LXXIO-58 | A3 | S | B54 | H | LXXIO-59 | A3 | S | B70 | H | LXXIO-60 | A3 | S | B72 | H |
| LXXIO-61 | A3 | O | B54 | F | LXXIO-62 | A3 | O | B70 | F | LXXIO-63 | A3 | O | B72 | F |
| LXXIO-64 | A3 | S | B54 | F | LXXIO-65 | A3 | S | B70 | F | LXXIO-66 | A3 | S | B72 | F; | wherein Compound LXXIA-1 to Compound LXXIA-42 have a structure represented by Formula LXXIA:

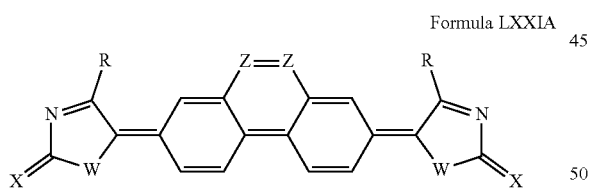

Formula LXXIA in Formula LXXIA, two X are identical, two W are identical, two R are identical, two Z are identical and are $CR_L$, and X, W, R, and $R_L$ correspond to an atom or a group selected from the following table, respectively:

| NO. | X | W | R | $R_L$ | NO. | X | W | R | $R_L$ | NO. | X | W | R | $R_L$ |
|---|---|---|---|---|---|---|---|---|---|---|---|---|---|---|
| LXXIA-1 | A1 | O | H | B6 | LXXIA-2 | A1 | O | B17 | B6 | LXXIA-3 | A1 | O | B25 | B6 |
| LXXIA-4 | A1 | O | B54 | B6 | LXXIA-5 | A1 | O | B70 | B6 | LXXIA-6 | A1 | O | B72 | B6 |
| LXXIA-7 | A1 | S | H | B6 | LXXIA-8 | A1 | S | B17 | B6 | LXXIA-9 | A1 | S | B25 | B6 |
| LXXIA-10 | A1 | S | B54 | B6 | LXXIA-11 | A1 | S | B70 | B6 | LXXIA-12 | A1 | S | B72 | B6 |
| LXXIA-13 | A1 | O | H | B70 | LXXIA-14 | A1 | O | B17 | B70 | LXXIA-15 | A1 | O | B25 | B70 |
| LXXIA-16 | A1 | O | B54 | B70 | LXXIA-17 | A1 | O | B70 | B70 | LXXIA-18 | A1 | O | B72 | B70 |
| LXXIA-19 | A1 | S | H | B70 | LXXIA-20 | A1 | S | B17 | B70 | LXXIA-21 | A1 | S | B25 | B70 |
| LXXIA-22 | A1 | S | B54 | B70 | LXXIA-23 | A1 | S | B70 | B70 | LXXIA-24 | A1 | S | B72 | B70 |
| LXXIA-25 | A2 | O | B54 | B6 | LXXIA-26 | A2 | O | B70 | B6 | LXXIA-27 | A2 | O | B72 | B6 |

-continued

| NO. | X | W | R | $R_L$ | NO. | X | W | R | $R_L$ | NO. | X | W | R | $R_L$ |
|---|---|---|---|---|---|---|---|---|---|---|---|---|---|---|
| LXXIA-28 | A2 | S | B54 | B6 | LXXIA-29 | A2 | S | B70 | B6 | LXXIA-30 | A2 | S | B72 | B6 |
| LXXIA-31 | A2 | O | B54 | B70 | LXXIA-32 | A2 | O | B70 | B70 | LXXIA-33 | A2 | O | B72 | B70 |
| LXXIA-34 | A3 | O | B54 | B6 | LXXIA-35 | A3 | O | B70 | B6 | LXXIA-36 | A3 | O | B72 | B6 |
| LXXIA-37 | A3 | S | B54 | B6 | LXXIA-38 | A3 | S | B70 | B6 | LXXIA-39 | A3 | S | B72 | B6 |
| LXXIA-40 | A3 | O | B54 | B70 | LXXIA-41 | A3 | O | B70 | B70 | LXXIA-42 | A3 | O | B72 | B70; | wherein Compound LXXIIO-1 to Compound LXXIIO-66 have a structure represented by Formula LXXIIO:

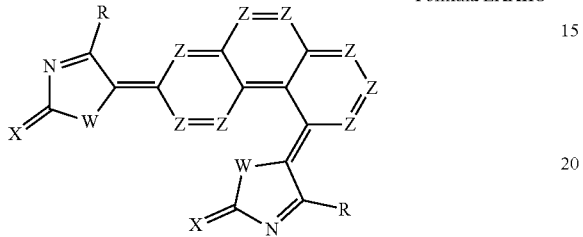

Formula LXXIIO in Formula LXXIIO, two X are identical, two W are identical, two R are identical, eight Z are identical and are $CR_L$, and X, W, R, and $R_L$ correspond to an atom or a group selected from the following table, respectively:

| NO. | X | W | R | $R_L$ | NO. | X | W | R | $R_L$ | NO. | X | W | R | $R_L$ |
|---|---|---|---|---|---|---|---|---|---|---|---|---|---|---|
| LXXIIO-1 | A1 | O | B1 | H | LXXIIO-2 | A1 | O | B17 | H | LXXIIO-3 | A1 | O | B25 | H |
| LXXIIO-4 | A1 | O | B54 | H | LXXIIO-5 | A1 | O | B70 | H | LXXIIO-6 | A1 | O | B72 | H |
| LXXIIO-7 | A1 | S | B1 | H | LXXIIO-8 | A1 | S | B17 | H | LXXIIO-9 | A1 | S | B25 | H |
| LXXIIO-10 | A1 | S | B54 | H | LXXIIO-11 | A1 | S | B70 | H | LXXIIO-12 | A1 | S | B72 | H |
| LXXIIO-13 | A1 | Se | B54 | H | LXXIIO-14 | A1 | Se | B70 | H | LXXIIO-15 | A1 | Se | B72 | H |
| LXXIIO-16 | A1 | NMe | B54 | H | LXXIIO-17 | A1 | NMe | B70 | H | LXXIIO-18 | A1 | NMe | B72 | H |
| LXXIIO-19 | A1 | O | H | F | LXXIIO-20 | A1 | O | B17 | F | LXXIIO-21 | A1 | O | B25 | F |
| LXXIIO-22 | A1 | O | B54 | F | LXXIIO-23 | A1 | O | B70 | F | LXXIIO-24 | A1 | O | B72 | F |
| LXXIIO-25 | A1 | S | H | F | LXXIIO-26 | A1 | S | B17 | F | LXXIIO-27 | A1 | S | B25 | F |
| LXXIIO-28 | A1 | S | B54 | F | LXXIIO-29 | A1 | S | B70 | F | LXXIIO-30 | A1 | S | B72 | F |
| LXXIIO-31 | A2 | O | B1 | H | LXXIIO-32 | A2 | O | B17 | H | LXXIIO-33 | A2 | O | B25 | H |
| LXXIIO-34 | A2 | O | B54 | H | LXXIIO-35 | A2 | O | B70 | H | LXXIIO-36 | A2 | O | B72 | H |
| LXXIIO-37 | A2 | S | B1 | H | LXXIIO-38 | A2 | S | B17 | H | LXXIIO-39 | A2 | S | B25 | H |
| LXXIIO-40 | A2 | S | B54 | H | LXXIIO-41 | A2 | S | B70 | H | LXXIIO-42 | A2 | S | B72 | H |
| LXXIIO-43 | A2 | O | B54 | F | LXXIIO-44 | A2 | O | B70 | F | LXXIIO-45 | A2 | O | B72 | F |
| LXXIIO-46 | A2 | S | B54 | F | LXXIIO-47 | A2 | S | B70 | F | LXXIIO-48 | A2 | S | B72 | F |
| LXXIIO-49 | A3 | O | B1 | H | LXXIIO-50 | A3 | O | B17 | H | LXXIIO-51 | A3 | O | B25 | H |
| LXXIIO-52 | A3 | O | B54 | H | LXXIIO-53 | A3 | O | B70 | H | LXXIIO-54 | A3 | O | B72 | H |
| LXXIIO-55 | A3 | S | B1 | H | LXXIIO-56 | A3 | S | B17 | H | LXXIIO-57 | A3 | S | B25 | H |
| LXXIIO-58 | A3 | S | B54 | H | LXXIIO-59 | A3 | S | B70 | H | LXXIIO-60 | A3 | S | B72 | H |
| LXXIIO-61 | A3 | O | B54 | F | LXXIIO-62 | A3 | O | B70 | F | LXXIIO-63 | A3 | O | B72 | F |
| LXXIIO-64 | A3 | S | B54 | F | LXXIIO-65 | A3 | S | B70 | F | LXXIIO-66 | A3 | S | B72 | F; | wherein Compound LXXIIA-1 to Compound LXXIIA-42 have a structure represented by Formula LXXIIA:

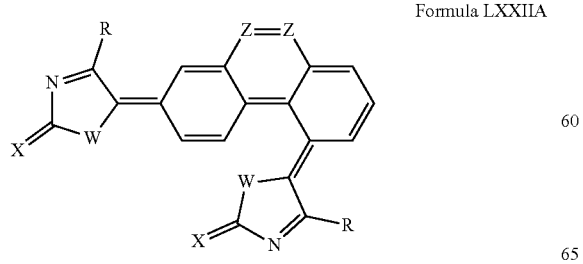

Formula LXXIIA in Formula LXXIIA, two X are identical, two W are identical, two R are identical, two Z are identical and are $CR_L$, and X, W, R, and $R_L$ correspond to an atom or a group selected from the following table, respectively:

| NO. | X | W | R | $R_L$ | NO. | X | W | R | $R_L$ | NO. | X | W | R | $R_L$ |
|---|---|---|---|---|---|---|---|---|---|---|---|---|---|---|
| LXXIIA-1 | A1 | O | H | B6 | LXXIIA-2 | A1 | O | B17 | B6 | LXXIIA-3 | A1 | O | B25 | B6 |
| LXXIIA-4 | A1 | O | B54 | B6 | LXXIIA-5 | A1 | O | B70 | B6 | LXXIIA-6 | A1 | O | B72 | B6 |
| LXXIIA-7 | A1 | S | H | B6 | LXXIIA-8 | A1 | S | B17 | B6 | LXXIIA-9 | A1 | S | B25 | B6 |
| LXXIIA-10 | A1 | S | B54 | B6 | LXXIIA-11 | A1 | S | B70 | B6 | LXXIIA-12 | A1 | S | B72 | B6 |
| LXXIIA-13 | A1 | O | H | B70 | LXXIIA-14 | A1 | O | B17 | B70 | LXXIIA-15 | A1 | O | B25 | B70 |
| LXXIIA-16 | A1 | O | B54 | B70 | LXXIIA-17 | A1 | O | B70 | B70 | LXXIIA-18 | A1 | O | B72 | B70 |
| LXXIIA-19 | A1 | S | H | B70 | LXXIIA-20 | A1 | S | B17 | B70 | LXXIIA-21 | A1 | S | B25 | B70 |
| LXXIIA-22 | A1 | S | B54 | B70 | LXXIIA-23 | A1 | S | B70 | B70 | LXXIIA-24 | A1 | S | B72 | B70 |
| LXXIIA-25 | A2 | O | B54 | B6 | LXXIIA-26 | A2 | O | B70 | B6 | LXXIIA-27 | A2 | O | B72 | B6 |
| LXXIIA-28 | A2 | S | B54 | B6 | LXXIIA-29 | A2 | S | B70 | B6 | LXXIIA-30 | A2 | S | B72 | B6 |
| LXXIIA-31 | A2 | O | B54 | B70 | LXXIIA-32 | A2 | O | B70 | B70 | LXXIIA-33 | A2 | O | B72 | B70 |
| LXXIIA-34 | A3 | O | B54 | B6 | LXXIIA-35 | A3 | O | B70 | B6 | LXXIIA-36 | A3 | O | B72 | B6 |
| LXXIIA-37 | A3 | S | B54 | B6 | LXXIIA-38 | A3 | S | B70 | B6 | LXXIIA-39 | A3 | S | B72 | B6 |
| LXXIIA-40 | A3 | O | B54 | B70 | LXXIIA-41 | A3 | O | B70 | B70 | LXXIIA-42 | A3 | O | B72 | B70; | wherein Compound LXXIIIO-1 to Compound LXXIIIO-66 have a structure represented by Formula LXXIIIO:

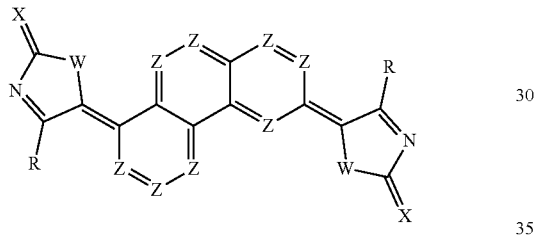

Formula LXXIIIO in Formula LXXIIIO, two X are identical, two W are identical, two R are identical, eight Z are identical and are $CR_L$, and X, W, R, and $R_L$ correspond to an atom or a group selected from the following table, respectively:

| NO. | X | W | R | $R_L$ | NO. | X | W | R | $R_L$ | NO. | X | W | R | $R_L$ |
|---|---|---|---|---|---|---|---|---|---|---|---|---|---|---|
| LXXIIIO-1 | A1 | O | B1 | H | LXXIIIO-2 | A1 | O | B17 | H | LXXIIIO-3 | A1 | O | B25 | H |
| LXXIIIO-4 | A1 | O | B54 | H | LXXIIIO-5 | A1 | O | B70 | H | LXXIIIO-6 | A1 | O | B72 | H |
| LXXIIIO-7 | A1 | S | B1 | H | LXXIIIO-8 | A1 | S | B17 | H | LXXIIIO-9 | A1 | S | B25 | H |
| LXXIIIO-10 | A1 | S | B54 | H | LXXIIIO-11 | A1 | S | B70 | H | LXXIIIO-12 | A1 | S | B72 | H |
| LXXIIIO-13 | A1 | Se | B54 | H | LXXIIIO-14 | A1 | Se | B70 | H | LXXIIIO-15 | A1 | Se | B72 | H |
| LXXIIIO-16 | A1 | NMe | B54 | H | LXXIIIO-17 | A1 | NMe | B70 | H | LXXIIIO-18 | A1 | NMe | B72 | H |
| LXXIIIO-19 | A1 | O | H | F | LXXIIIO-20 | A1 | O | B17 | F | LXXIIIO-21 | A1 | O | B25 | F |
| LXXIIIO-22 | A1 | O | B54 | F | LXXIIIO-23 | A1 | O | B70 | F | LXXIIIO-24 | A1 | O | B72 | F |
| LXXIIIO-25 | A1 | S | H | F | LXXIIIO-26 | A1 | S | B17 | F | LXXIIIO-27 | A1 | S | B25 | F |
| LXXIIIO-28 | A1 | S | B54 | F | LXXIIIO-29 | A1 | S | B70 | F | LXXIIIO-30 | A1 | S | B72 | F |
| LXXIIIO-31 | A2 | O | B1 | H | LXXIIIO-32 | A2 | O | B17 | H | LXXIIIO-33 | A2 | O | B25 | H |
| LXXIIIO-34 | A2 | O | B54 | H | LXXIIIO-35 | A2 | O | B70 | H | LXXIIIO-36 | A2 | O | B72 | H |
| LXXIIIO-37 | A2 | S | B1 | H | LXXIIIO-38 | A2 | S | B17 | H | LXXIIIO-39 | A2 | S | B25 | H |
| LXXIIIO-40 | A2 | S | B54 | H | LXXIIIO-41 | A2 | S | B70 | H | LXXIIIO-42 | A2 | S | B72 | H |
| LXXIIIO-43 | A2 | O | B54 | F | LXXIIIO-44 | A2 | O | B70 | F | LXXIIIO-45 | A2 | O | B72 | F |
| LXXIIIO-46 | A2 | S | B54 | F | LXXIIIO-47 | A2 | S | B70 | F | LXXIIIO-48 | A2 | S | B72 | F |
| LXXIIIO-49 | A3 | O | B1 | H | LXXIIIO-50 | A3 | O | B17 | H | LXXIIIO-51 | A3 | O | B25 | H |
| LXXIIIO-52 | A3 | O | B54 | H | LXXIIIO-53 | A3 | O | B70 | H | LXXIIIO-54 | A3 | O | B72 | H |
| LXXIIIO-55 | A3 | S | B1 | H | LXXIIIO-56 | A3 | S | B17 | H | LXXIIIO-57 | A3 | S | B25 | H |
| LXXIIIO-58 | A3 | S | B54 | H | LXXIIIO-59 | A3 | S | B70 | H | LXXIIIO-60 | A3 | S | B72 | H |
| LXXIIIO-61 | A3 | O | B54 | F | LXXIIIO-62 | A3 | O | B70 | F | LXXIIIO-63 | A3 | O | B72 | F |
| LXXIIIO-64 | A3 | S | B54 | F | LXXIIIO-65 | A3 | S | B70 | F | LXXIIIO-66 | A3 | S | B72 | F; | wherein Compound LXXIIIA-1 to Compound LXXIIIA-42 have a structure represented by Formula LXXIIIA:

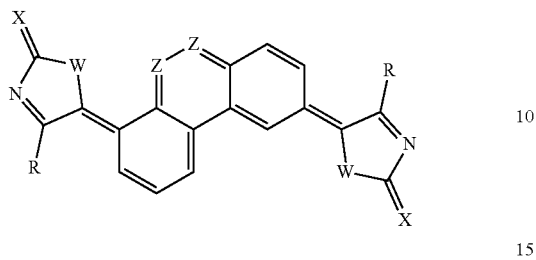

Formula LXXIIIA in Formula LXXIIIA, two X are identical, two W are identical, two R are identical, two Z are identical and are $CR_L$, and X, W, R, and $R_L$ correspond to an atom or a group selected from the following table, respectively:

| NO. | X | W | R | $R_L$ | NO. | X | W | R | $R_L$ | NO. | X | W | R | $R_L$ |
|---|---|---|---|---|---|---|---|---|---|---|---|---|---|---|
| LXXIIIA-1 | A1 | O | H | B6 | LXXIIIA-2 | A1 | O | B17 | B6 | LXXIIIA-3 | A1 | O | B25 | B6 |
| LXXIIIA-4 | A1 | O | B54 | B6 | LXXIIIA-5 | A1 | O | B70 | B6 | LXXIIIA-6 | A1 | O | B72 | B6 |
| LXXIIIA-7 | A1 | S | H | B6 | LXXIIIA-8 | A1 | S | B17 | B6 | LXXIIIA-9 | A1 | S | B25 | B6 |
| LXXIIIA-10 | A1 | S | B54 | B6 | LXXIIIA-11 | A1 | S | B70 | B6 | LXXIIIA-12 | A1 | S | B72 | B6 |
| LXXIIIA-13 | A1 | O | H | B70 | LXXIIIA-14 | A1 | O | B17 | B70 | LXXIIIA-15 | A1 | O | B25 | B70 |
| LXXIIIA-16 | A1 | O | B54 | B70 | LXXIIIA-17 | A1 | O | B70 | B70 | LXXIIIA-18 | A1 | O | B72 | B70 |
| LXXIIIA-19 | A1 | S | H | B70 | LXXIIIA-20 | A1 | S | B17 | B70 | LXXIIIA-21 | A1 | S | B25 | B70 |
| LXXIIIA-22 | A1 | S | B54 | B70 | LXXIIIA-23 | A1 | S | B70 | B70 | LXXIIIA-24 | A1 | S | B72 | B70 |
| LXXIIIA-25 | A2 | O | B54 | B6 | LXXIIIA-26 | A2 | O | B70 | B6 | LXXIIIA-27 | A2 | O | B72 | B6 |
| LXXIIIA-28 | A2 | S | B54 | B6 | LXXIIIA-29 | A2 | S | B70 | B6 | LXXIIIA-30 | A2 | S | B72 | B6 |
| LXXIIIA-31 | A2 | O | B54 | B70 | LXXIIIA-32 | A2 | O | B70 | B70 | LXXIIIA-33 | A2 | O | B72 | B70 |
| LXXIIIA-34 | A3 | O | B54 | B6 | LXXIIIA-35 | A3 | O | B70 | B6 | LXXIIIA-36 | A3 | O | B72 | B6 |
| LXXIIIA-37 | A3 | S | B54 | B6 | LXXIIIA-38 | A3 | S | B70 | B6 | LXXIIIA-39 | A3 | S | B72 | B6 |
| LXXIIIA-40 | A3 | O | B54 | B70 | LXXIIIA-41 | A3 | O | B70 | B70 | LXXIIIA-42 | A3 | O | B72 | B70; | wherein Compound LXXIVO-1 to Compound LXXIVO-66 have a structure represented by Formula LXXIVO:

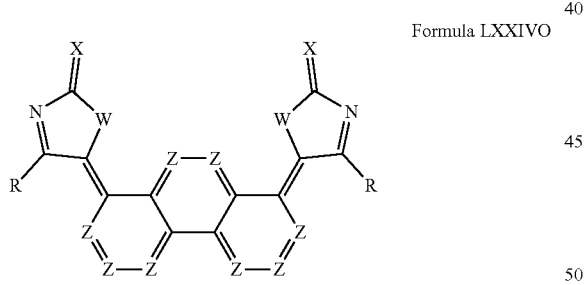

Formula LXXIVO in Formula LXXIVO, two X are identical, two W are identical, two R are identical, eight Z are identical and are $CR_L$, and X, W, R, and $R_L$ correspond to an atom or a group selected from the following table, respectively:

| NO. | X | W | R | $R_L$ | NO. | X | W | R | $R_L$ | NO. | X | W | R | $R_L$ |
|---|---|---|---|---|---|---|---|---|---|---|---|---|---|---|
| LXXIVO-1 | A1 | O | B1 | H | LXXIVO-2 | A1 | O | B17 | H | LXXIVO-3 | A1 | O | B25 | H |
| LXXIVO-4 | A1 | O | B54 | H | LXXIVO-5 | A1 | O | B70 | H | LXXIVO-6 | A1 | O | B72 | H |
| LXXIVO-7 | A1 | S | B1 | H | LXXIVO-8 | A1 | S | B17 | H | LXXIVO-9 | A1 | S | B25 | H |
| LXXIVO-10 | A1 | S | B54 | H | LXXIVO-11 | A1 | S | B70 | H | LXXIVO-12 | A1 | S | B72 | H |
| LXXIVO-13 | A1 | Se | B54 | H | LXXIVO-14 | A1 | Se | B70 | H | LXXIVO-15 | A1 | Se | B72 | H |
| LXXIVO-16 | A1 | NMe | B54 | H | LXXIVO-17 | A1 | NMe | B70 | H | LXXIVO-18 | A1 | NMe | B72 | H |
| LXXIVO-19 | A1 | O | H | F | LXXIVO-20 | A1 | O | B17 | F | LXXIVO-21 | A1 | O | B25 | F |
| LXXIVO-22 | A1 | O | B54 | F | LXXIVO-23 | A1 | O | B70 | F | LXXIVO-24 | A1 | O | B72 | F |
| LXXIVO-25 | A1 | S | H | F | LXXIVO-26 | A1 | S | B17 | F | LXXIVO-27 | A1 | S | B25 | F |

-continued

| NO. | X | W | R | $R_L$ | NO. | X | W | R | $R_L$ | NO. | X | W | R | $R_L$ |
|---|---|---|---|---|---|---|---|---|---|---|---|---|---|---|
| LXXIVO-28 | A1 | S | B54 | F | LXXIVO-29 | A1 | S | B70 | F | LXXIVO-30 | A1 | S | B72 | F |
| LXXIVO-31 | A2 | O | B1 | H | LXXIVO-32 | A2 | O | B17 | H | LXXIVO-33 | A2 | O | B25 | H |
| LXXIVO-34 | A2 | O | B54 | H | LXXIVO-35 | A2 | O | B70 | H | LXXIVO-36 | A2 | O | B72 | H |
| LXXIVO-37 | A2 | S | B1 | H | LXXIVO-38 | A2 | S | B17 | H | LXXIVO-39 | A2 | S | B25 | H |
| LXXIVO-40 | A2 | S | B54 | H | LXXIVO-41 | A2 | S | B70 | H | LXXIVO-42 | A2 | S | B72 | H |
| LXXIVO-43 | A2 | O | B54 | F | LXXIVO-44 | A2 | O | B70 | F | LXXIVO-45 | A2 | O | B72 | F |
| LXXIVO-46 | A2 | S | B54 | F | LXXIVO-47 | A2 | S | B70 | F | LXXIVO-48 | A2 | S | B72 | F |
| LXXIVO-49 | A3 | O | B1 | H | LXXIVO-50 | A3 | O | B17 | H | LXXIVO-51 | A3 | O | B25 | H |
| LXXIVO-52 | A3 | O | B54 | H | LXXIVO-53 | A3 | O | B70 | H | LXXIVO-54 | A3 | O | B72 | H |
| LXXIVO-55 | A3 | S | B1 | H | LXXIVO-56 | A3 | S | B17 | H | LXXIVO-57 | A3 | S | B25 | H |
| LXXIVO-58 | A3 | S | B54 | H | LXXIVO-59 | A3 | S | B70 | H | LXXIVO-60 | A3 | S | B72 | H |
| LXXIVO-61 | A3 | O | B54 | F | LXXIVO-62 | A3 | O | B70 | F | LXXIVO-63 | A3 | O | B72 | F |
| LXXIVO-64 | A3 | S | B54 | F | LXXIVO-65 | A3 | S | B70 | F | LXXIVO-66 | A3 | S | B72 | F; | wherein Compound LXXIVA-1 to Compound LXXIVA-42 have a structure represented by Formula LXXIVA:

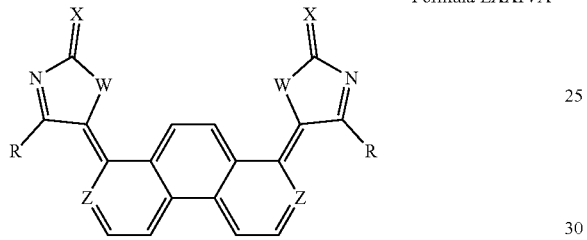

Formula LXXIVA in Formula LXXIVA, two X are identical, two W are identical, two R are identical, two Z are identical and are $CR_L$, and X, W, R, and $R_L$ correspond to an atom or a group selected from the following table, respectively:

| NO. | X | W | R | $R_L$ | NO. | X | W | R | $R_L$ | NO. | X | W | R | $R_L$ |
|---|---|---|---|---|---|---|---|---|---|---|---|---|---|---|
| LXXIVA-1 | A1 | O | H | B6 | LXXIVA-2 | A1 | O | B17 | B6 | LXXIVA-3 | A1 | O | B25 | B6 |
| LXXIVA-4 | A1 | O | B54 | B6 | LXXIVA-5 | A1 | O | B70 | B6 | LXXIVA-6 | A1 | O | B72 | B6 |
| LXXIVA-7 | A1 | S | H | B6 | LXXIVA-8 | A1 | S | B17 | B6 | LXXIVA-9 | A1 | S | B25 | B6 |
| LXXIVA-10 | A1 | S | B54 | B6 | LXXIVA-11 | A1 | S | B70 | B6 | LXXIVA-12 | A1 | S | B72 | B6 |
| LXXIVA-13 | A1 | O | H | B70 | LXXIVA-14 | A1 | O | B17 | B70 | LXXIVA-15 | A1 | O | B25 | B70 |
| LXXIVA-16 | A1 | O | B54 | B70 | LXXIVA-17 | A1 | O | B70 | B70 | LXXIVA-18 | A1 | O | B72 | B70 |
| LXXIVA-19 | A1 | S | H | B70 | LXXIVA-20 | A1 | S | B17 | B70 | LXXIVA-21 | A1 | S | B25 | B70 |
| LXXIVA-22 | A1 | S | B54 | B70 | LXXIVA-23 | A1 | S | B70 | B70 | LXXIVA-24 | A1 | S | B72 | B70 |
| LXXIVA-25 | A2 | O | B54 | B6 | LXXIVA-26 | A2 | O | B70 | B6 | LXXIVA-27 | A2 | O | B72 | B6 |
| LXXIVA-28 | A2 | S | B54 | B6 | LXXIVA-29 | A2 | S | B70 | B6 | LXXIVA-30 | A2 | S | B72 | B6 |
| LXXIVA-31 | A2 | O | B54 | B70 | LXXIVA-32 | A2 | O | B70 | B70 | LXXIVA-33 | A2 | O | B72 | B70 |
| LXXIVA-34 | A3 | O | B54 | B6 | LXXIVA-35 | A3 | O | B70 | B6 | LXXIVA-36 | A3 | O | B72 | B6 |
| LXXIVA-37 | A3 | S | B54 | B6 | LXXIVA-38 | A3 | S | B70 | B6 | LXXIVA-39 | A3 | S | B72 | B6 |
| LXXIVA-40 | A3 | O | B54 | B70 | LXXIVA-41 | A3 | O | B70 | B70 | LXXIVA-42 | A3 | O | B72 | B70; | wherein Compound LXXVO-1 to Compound LXXVO-66 have a structure represented by Formula LXXVO:

Formula LXXVO

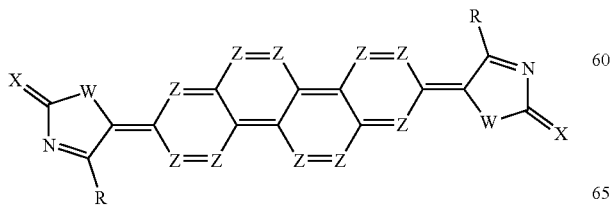

in Formula LXXVO, two X are identical, two W are identical, two R are identical, ten Z are identical and are CR$_L$, and X, W, R, and R$_L$ correspond to an atom or a group selected from the following table, respectively:

| NO. | X | W | R | R$_L$ | NO. | X | W | R | R$_L$ | NO. | X | W | R | R$_L$ |
|---|---|---|---|---|---|---|---|---|---|---|---|---|---|---|
| LXXVO-1 | A1 | O | B1 | H | LXXVO-2 | A1 | O | B17 | H | LXXVO-3 | A1 | O | B25 | H |
| LXXVO-4 | A1 | O | B54 | H | LXXVO-5 | A1 | O | B70 | H | LXXVO-6 | A1 | O | B72 | H |
| LXXVO-7 | A1 | S | B1 | H | LXXVO-8 | A1 | S | B17 | H | LXXVO-9 | A1 | S | B25 | H |
| LXXVO-10 | A1 | S | B54 | H | LXXVO-11 | A1 | S | B70 | H | LXXVO-12 | A1 | S | B72 | H |
| LXXVO-13 | A1 | Se | B54 | H | LXXVO-14 | A1 | Se | B70 | H | LXXVO-15 | A1 | Se | B72 | H |
| LXXVO-16 | A1 | NMe | B54 | H | LXXVO-17 | A1 | NMe | B70 | H | LXXVO-18 | A1 | NMe | B72 | H |
| LXXVO-19 | A1 | O | H | F | LXXVO-20 | A1 | O | B17 | F | LXXVO-21 | A1 | O | B25 | F |
| LXXVO-22 | A1 | O | B54 | F | LXXVO-23 | A1 | O | B70 | F | LXXVO-24 | A1 | O | B72 | F |
| LXXVO-25 | A1 | S | H | F | LXXVO-26 | A1 | S | B17 | F | LXXVO-27 | A1 | S | B25 | F |
| LXXVO-28 | A1 | S | B54 | F | LXXVO-29 | A1 | S | B70 | F | LXXVO-30 | A1 | S | B72 | F |
| LXXVO-31 | A2 | O | B1 | H | LXXVO-32 | A2 | O | B17 | H | LXXVO-33 | A2 | O | B25 | H |
| LXXVO-34 | A2 | O | B54 | H | LXXVO-35 | A2 | O | B70 | H | LXXVO-36 | A2 | O | B72 | H |
| LXXVO-37 | A2 | S | B1 | H | LXXVO-38 | A2 | S | B17 | H | LXXVO-39 | A2 | S | B25 | H |
| LXXVO-40 | A2 | S | B54 | H | LXXVO-41 | A2 | S | B70 | H | LXXVO-42 | A2 | S | B72 | H |
| LXXVO-43 | A2 | O | B54 | F | LXXVO-44 | A2 | O | B70 | F | LXXVO-45 | A2 | O | B72 | F |
| LXXVO-46 | A2 | S | B54 | F | LXXVO-47 | A2 | S | B70 | F | LXXVO-48 | A2 | S | B72 | F |
| LXXVO-49 | A3 | O | B1 | H | LXXVO-50 | A3 | O | B17 | H | LXXVO-51 | A3 | O | B25 | H |
| LXXVO-52 | A3 | O | B54 | H | LXXVO-53 | A3 | O | B70 | H | LXXVO-54 | A3 | O | B72 | H |
| LXXVO-55 | A3 | S | B1 | H | LXXVO-56 | A3 | S | B17 | H | LXXVO-57 | A3 | S | B25 | H |
| LXXVO-58 | A3 | S | B54 | H | LXXVO-59 | A3 | S | B70 | H | LXXVO-60 | A3 | S | B72 | H |
| LXXVO-61 | A3 | O | B54 | F | LXXVO-62 | A3 | O | B70 | F | LXXVO-63 | A3 | O | B72 | F |
| LXXVO-64 | A3 | S | B54 | F | LXXVO-65 | A3 | S | B70 | F | LXXVO-66 | A3 | S | B72 | F; | wherein Compound LXXVA-1 to Compound LXXVA-42 have a structure represented by Formula LXXVA:

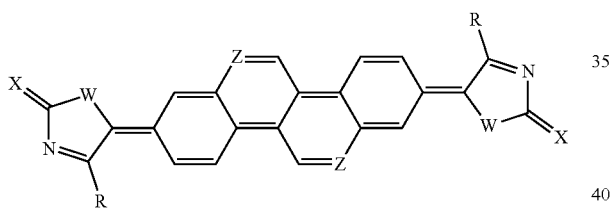

Formula LXXVO in Formula LXXVA, two X are identical, two W are identical, two R are identical, two Z are identical and are CR$_L$, and X, W, R, and R$_L$ correspond to an atom or a group selected from the following table, respectively:

| NO. | X | W | R | R$_L$ | NO. | X | W | R | R$_L$ | NO. | X | W | R | R$_L$ |
|---|---|---|---|---|---|---|---|---|---|---|---|---|---|---|
| LXXVA-1 | A1 | O | H | B6 | LXXVA-2 | A1 | O | B17 | B6 | LXXVA-3 | A1 | O | B25 | B6 |
| LXXVA-4 | A1 | O | B54 | B6 | LXXVA-5 | A1 | O | B70 | B6 | LXXVA-6 | A1 | O | B72 | B6 |
| LXXVA-7 | A1 | S | H | B6 | LXXVA-8 | A1 | S | B17 | B6 | LXXVA-9 | A1 | S | B25 | B6 |
| LXXVA-10 | A1 | S | B54 | B6 | LXXVA-11 | A1 | S | B70 | B6 | LXXVA-12 | A1 | S | B72 | B6 |
| LXXVA-13 | A1 | O | H | B70 | LXXVA-14 | A1 | O | B17 | B70 | LXXVA-15 | A1 | O | B25 | B70 |
| LXXVA-16 | A1 | O | B54 | B70 | LXXVA-17 | A1 | O | B70 | B70 | LXXVA-18 | A1 | O | B72 | B70 |
| LXXVA-19 | A1 | S | H | B70 | LXXVA-20 | A1 | S | B17 | B70 | LXXVA-21 | A1 | S | B25 | B70 |
| LXXVA-22 | A1 | S | B54 | B70 | LXXVA-23 | A1 | S | B70 | B70 | LXXVA-24 | A1 | S | B72 | B70 |
| LXXVA-25 | A2 | O | B54 | B6 | LXXVA-26 | A2 | O | B70 | B6 | LXXVA-27 | A2 | O | B72 | B6 |
| LXXVA-28 | A2 | S | B54 | B6 | LXXVA-29 | A2 | S | B70 | B6 | LXXVA-30 | A2 | S | B72 | B6 |
| LXXVA-31 | A2 | O | B54 | B70 | LXXVA-32 | A2 | O | B70 | B70 | LXXVA-33 | A2 | O | B72 | B70 |
| LXXVA-34 | A3 | O | B54 | B6 | LXXVA-35 | A3 | O | B70 | B6 | LXXVA-36 | A3 | O | B72 | B6 |
| LXXVA-37 | A3 | S | B54 | B6 | LXXVA-38 | A3 | S | B70 | B6 | LXXVA-39 | A3 | S | B72 | B6 |
| LXXVA-40 | A3 | O | B54 | B70 | LXXVA-41 | A3 | O | B70 | B70 | LXXVA-42 | A3 | O | B72 | B70; | wherein Compound LXXVI-1 to Compound LXXVIO-66 have a structure represented by Formula LXXVIO:

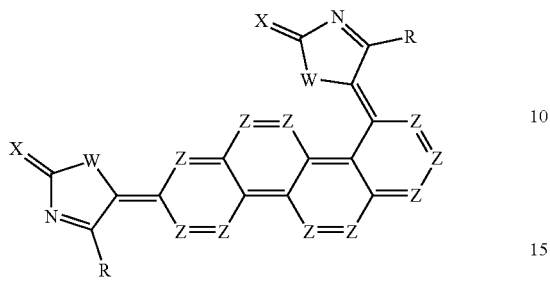

Formula LXXVIO in Formula LXXVIO, two X are identical, two W are identical, two R are identical, ten Z are identical and are $CR_L$, and X, W, R, and $R_L$ correspond to an atom or a group selected from the following table, respectively:

| NO. | X | W | R | $R_L$ | NO. | X | W | R | $R_L$ | NO. | X | W | R | $R_L$ |
|---|---|---|---|---|---|---|---|---|---|---|---|---|---|---|
| LXXVIO-1 | A1 | O | B1 | H | LXXVIO-2 | A1 | O | B17 | H | LXXVIO-3 | A1 | O | B25 | H |
| LXXVIO-4 | A1 | O | B54 | H | LXXVIO-5 | A1 | O | B70 | H | LXXVIO-6 | A1 | O | B72 | H |
| LXXVIO-7 | A1 | S | B1 | H | LXXVIO-8 | A1 | S | B17 | H | LXXVIO-9 | A1 | S | B25 | H |
| LXXVIO-10 | A1 | S | B54 | H | LXXVIO-11 | A1 | S | B70 | H | LXXVIO-12 | A1 | S | B72 | H |
| LXXVIO-13 | A1 | Se | B54 | H | LXXVIO-14 | A1 | Se | B70 | H | LXXVIO-15 | A1 | Se | B72 | H |
| LXXVIO-16 | A1 | NMe | B54 | H | LXXVIO-17 | A1 | NMe | B70 | H | LXXVIO-18 | A1 | NMe | B72 | H |
| LXXVIO-19 | A1 | O | H | F | LXXVIO-20 | A1 | O | B17 | F | LXXVIO-21 | A1 | O | B25 | F |
| LXXVIO-22 | A1 | O | B54 | F | LXXVIO-23 | A1 | O | B70 | F | LXXVIO-24 | A1 | O | B72 | F |
| LXXVIO-25 | A1 | S | H | F | LXXVIO-26 | A1 | S | B17 | F | LXXVIO-27 | A1 | S | B25 | F |
| LXXVIO-28 | A1 | S | B54 | F | LXXVIO-29 | A1 | S | B70 | F | LXXVIO-30 | A1 | S | B72 | F |
| LXXVIO-31 | A2 | O | B1 | H | LXXVIO-32 | A2 | O | B17 | H | LXXVIO-33 | A2 | O | B25 | H |
| LXXVIO-34 | A2 | O | B54 | H | LXXVIO-35 | A2 | O | B70 | H | LXXVIO-36 | A2 | O | B72 | H |
| LXXVIO-37 | A2 | S | B1 | H | LXXVIO-38 | A2 | S | B17 | H | LXXVIO-39 | A2 | S | B25 | H |
| LXXVIO-40 | A2 | S | B54 | H | LXXVIO-41 | A2 | S | B70 | H | LXXVIO-42 | A2 | S | B72 | H |
| LXXVIO-43 | A2 | O | B54 | F | LXXVIO-44 | A2 | O | B70 | F | LXXVIO-45 | A2 | O | B72 | F |
| LXXVIO-46 | A2 | S | B54 | F | LXXVIO-47 | A2 | S | B70 | F | LXXVIO-48 | A2 | S | B72 | F |
| LXXVIO-49 | A3 | O | B1 | H | LXXVIO-50 | A3 | O | B17 | H | LXXVIO-51 | A3 | O | B25 | H |
| LXXVIO-52 | A3 | O | B54 | H | LXXVIO-53 | A3 | O | B70 | H | LXXVIO-54 | A3 | O | B72 | H |
| LXXVIO-55 | A3 | S | B1 | H | LXXVIO-56 | A3 | S | B17 | H | LXXVIO-57 | A3 | S | B25 | H |
| LXXVIO-58 | A3 | S | B54 | H | LXXVIO-59 | A3 | S | B70 | H | LXXVIO-60 | A3 | S | B72 | H |
| LXXVIO-61 | A3 | O | B54 | F | LXXVIO-62 | A3 | O | B70 | F | LXXVIO-63 | A3 | O | B72 | F |
| LXXVIO-64 | A3 | S | B54 | F | LXXVIO-65 | A3 | S | B70 | F | LXXVIO-66 | A3 | S | B72 | F; | wherein Compound LXXVIA-1 to Compound LXXVIA-42 have a structure represented by Formula LXXVIA:

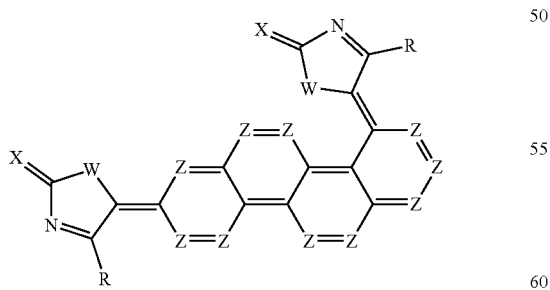

Formula LXXVIO in Formula LXXVIA, two X are identical, two W are identical, two R are identical, ten Z are identical and are $CR_L$, and X, W, R, and $R_L$ correspond to an atom or a group selected from the following table, respectively:

| NO. | X | W | R | R_L | NO. | X | W | R | R_L | NO. | X | W | R | R_L |
|---|---|---|---|---|---|---|---|---|---|---|---|---|---|---|
| LXXVIA-1 | A1 | O | H | B6 | LXXVIA-2 | A1 | O | B17 | B6 | LXXVIA-3 | A1 | O | B25 | B6 |
| LXXVIA-4 | A1 | O | B54 | B6 | LXXVIA-5 | A1 | O | B70 | B6 | LXXVIA-6 | A1 | O | B72 | B6 |
| LXXVIA-7 | A1 | S | H | B6 | LXXVIA-8 | A1 | S | B17 | B6 | LXXVIA-9 | A1 | S | B25 | B6 |
| LXXVIA-10 | A1 | S | B54 | B6 | LXXVIA-11 | A1 | S | B70 | B6 | LXXVIA-12 | A1 | S | B72 | B6 |
| LXXVIA-13 | A1 | O | H | B70 | LXXVIA-14 | A1 | O | B17 | B70 | LXXVIA-15 | A1 | O | B25 | B70 |
| LXXVIA-16 | A1 | O | B54 | B70 | LXXVIA-17 | A1 | O | B70 | B70 | LXXVIA-18 | A1 | O | B72 | B70 |
| LXXVIA-19 | A1 | S | H | B70 | LXXVIA-20 | A1 | S | B17 | B70 | LXXVIA-21 | A1 | S | B25 | B70 |
| LXXVIA-22 | A1 | S | B54 | B70 | LXXVIA-23 | A1 | S | B70 | B70 | LXXVIA-24 | A1 | S | B72 | B70 |
| LXXVIA-25 | A2 | O | B54 | B6 | LXXVIA-26 | A2 | O | B70 | B6 | LXXVIA-27 | A2 | O | B72 | B6 |
| LXXVIA-28 | A2 | S | B54 | B6 | LXXVIA-29 | A2 | S | B70 | B6 | LXXVIA-30 | A2 | S | B72 | B6 |
| LXXVIA-31 | A2 | O | B54 | B70 | LXXVIA-32 | A2 | O | B70 | B70 | LXXVIA-33 | A2 | O | B72 | B70 |
| LXXVIA-34 | A3 | O | B54 | B6 | LXXVIA-35 | A3 | O | B70 | B6 | LXXVIA-36 | A3 | O | B72 | B6 |
| LXXVIA-37 | A3 | S | B54 | B6 | LXXVIA-38 | A3 | S | B70 | B6 | LXXVIA-39 | A3 | S | B72 | B6 |
| LXXVIA-40 | A3 | O | B54 | B70 | LXXVIA-41 | A3 | O | B70 | B70 | LXXVIA-42 | A3 | O | B72 | B70; | wherein Compound LXXVIIO-1 to Compound LXXVIIO-66 have a structure represented by Formula LXXVIIO:

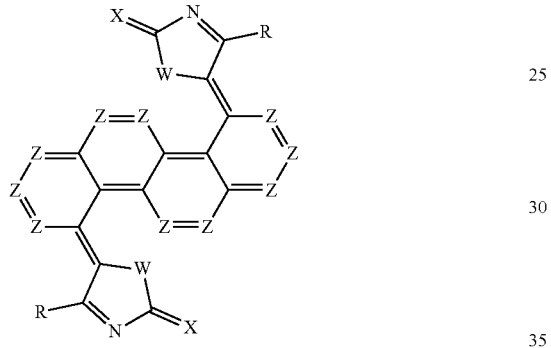

Formula LXXVIIO in Formula LXXVIIO, two X are identical, two W are identical, two R are identical, ten Z are identical and are $CR_L$, and X, W, R, and $R_L$ correspond to an atom or a group selected from the following table, respectively:

| NO. | X | W | R | R_L | NO. | X | W | R | R_L | NO. | X | W | R | R_L |
|---|---|---|---|---|---|---|---|---|---|---|---|---|---|---|
| LXXVIIO-1 | A1 | O | B1 | H | LXXVIIO-2 | A1 | O | B17 | H | LXXVIIO-3 | A1 | O | B25 | H |
| LXXVIIO-4 | A1 | O | B54 | H | LXXVIIO-5 | A1 | O | B70 | H | LXXVIIO-6 | A1 | O | B72 | H |
| LXXVIIO-7 | A1 | S | B1 | H | LXXVIIO-8 | A1 | S | B17 | H | LXXVIIO-9 | A1 | S | B25 | H |
| LXXVIIO-10 | A1 | S | B54 | H | LXXVIIO-11 | A1 | S | B70 | H | LXXVIIO-12 | A1 | S | B72 | H |
| LXXVIIO-13 | A1 | Se | B54 | H | LXXVIIO-14 | A1 | Se | B70 | H | LXXVIIO-15 | A1 | Se | B72 | H |
| LXXVIIO-16 | A1 | NMe | B54 | H | LXXVIIO-17 | A1 | NMe | B70 | H | LXXVIIO-18 | A1 | NMe | B72 | H |
| LXXVIIO-19 | A1 | O | H | F | LXXVIIO-20 | A1 | O | B17 | F | LXXVIIO-21 | A1 | O | B25 | F |
| LXXVIIO-22 | A1 | O | B54 | F | LXXVIIO-23 | A1 | O | B70 | F | LXXVIIO-24 | A1 | O | B72 | F |
| LXXVIIO-25 | A1 | S | H | F | LXXVIIO-26 | A1 | S | B17 | F | LXXVIIO-27 | A1 | S | B25 | F |
| LXXVIIO-28 | A1 | S | B54 | F | LXXVIIO-29 | A1 | S | B70 | F | LXXVIIO-30 | A1 | S | B72 | F |
| LXXVIIO-31 | A2 | O | B1 | H | LXXVIIO-32 | A2 | O | B17 | H | LXXVIIO-33 | A2 | O | B25 | H |
| LXXVIIO-34 | A2 | O | B54 | H | LXXVIIO-35 | A2 | O | B70 | H | LXXVIIO-36 | A2 | O | B72 | H |
| LXXVIIO-37 | A2 | S | B1 | H | LXXVIIO-38 | A2 | S | B17 | H | LXXVIIO-39 | A2 | S | B25 | H |
| LXXVIIO-40 | A2 | S | B54 | H | LXXVIIO-41 | A2 | S | B70 | H | LXXVIIO-42 | A2 | S | B72 | H |
| LXXVIIO-43 | A2 | O | B54 | F | LXXVIIO-44 | A2 | O | B70 | F | LXXVIIO-45 | A2 | O | B72 | F |
| LXXVIIO-46 | A2 | S | B54 | F | LXXVIIO-47 | A2 | S | B70 | F | LXXVIIO-48 | A2 | S | B72 | F |
| LXXVIIO-49 | A3 | O | B1 | H | LXXVIIO-50 | A3 | O | B17 | H | LXXVIIO-51 | A3 | O | B25 | H |
| LXXVIIO-52 | A3 | O | B54 | H | LXXVIIO-53 | A3 | O | B70 | H | LXXVIIO-54 | A3 | O | B72 | H |
| LXXVIIO-55 | A3 | S | B1 | H | LXXVIIO-56 | A3 | S | B17 | H | LXXVIIO-57 | A3 | S | B25 | H |
| LXXVIIO-58 | A3 | S | B54 | H | LXXVIIO-59 | A3 | S | B70 | H | LXXVIIO-60 | A3 | S | B72 | H |
| LXXVIIO-61 | A3 | O | B54 | F | LXXVIIO-62 | A3 | O | B70 | F | LXXVIIO-63 | A3 | O | B72 | F |
| LXXVIIO-64 | A3 | S | B54 | F | LXXVIIO-65 | A3 | S | B70 | F | LXXVIIO-66 | A3 | S | B72 | F; | wherein Compound LXXVIIA-1 to Compound LXXVIIA-42 have a structure represented by Formula LXXVIIA:

Formula LXXVIIA

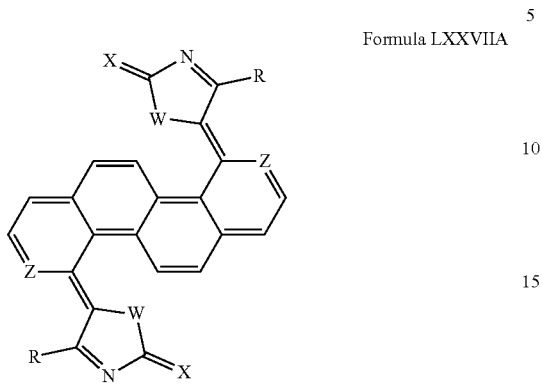

in Formula LXXVIIA, two X are identical, two W are identical, two R are identical, two Z are identical and are $CR_L$, and X, W, R, and $R_L$ correspond to an atom or a group selected from the following table, respectively:

| NO. | X | W | R | $R_L$ | NO. | X | W | R | $R_L$ | NO. | X | W | R | $R_L$ |
|---|---|---|---|---|---|---|---|---|---|---|---|---|---|---|
| LXXVIIA-1 | A1 | O | H | B6 | LXXVIIA-2 | A1 | O | B17 | B6 | LXXVIIA-3 | A1 | O | B25 | B6 |
| LXXVIIA-4 | A1 | O | B54 | B6 | LXXVIIA-5 | A1 | O | B70 | B6 | LXXVIIA-6 | A1 | O | B72 | B6 |
| LXXVIIA-7 | A1 | S | H | B6 | LXXVIIA-8 | A1 | S | B17 | B6 | LXXVIIA-9 | A1 | S | B25 | B6 |
| LXXVIIA-10 | A1 | S | B54 | B6 | LXXVIIA-11 | A1 | S | B70 | B6 | LXXVIIA-12 | A1 | S | B72 | B6 |
| LXXVIIA-13 | A1 | O | H | B70 | LXXVIIA-14 | A1 | O | B17 | B70 | LXXVIIA-15 | A1 | O | B25 | B70 |
| LXXVIIA-16 | A1 | O | B54 | B70 | LXXVIIA-17 | A1 | O | B70 | B70 | LXXVIIA-18 | A1 | O | B72 | B70 |
| LXXVIIA-19 | A1 | S | H | B70 | LXXVIIA-20 | A1 | S | B17 | B70 | LXXVIIA-21 | A1 | S | B25 | B70 |
| LXXVIIA-22 | A1 | S | B54 | B70 | LXXVIIA-23 | A1 | S | B70 | B70 | LXXVIIA-24 | A1 | S | B72 | B70 |
| LXXVIIA-25 | A2 | O | B54 | B6 | LXXVIIA-26 | A2 | O | B70 | B6 | LXXVIIA-27 | A2 | O | B72 | B6 |
| LXXVIIA-28 | A2 | S | B54 | B6 | LXXVIIA-29 | A2 | S | B70 | B6 | LXXVIIA-30 | A2 | S | B72 | B6 |
| LXXVIIA-31 | A2 | O | B54 | B70 | LXXVIIA-32 | A2 | O | B70 | B70 | LXXVIIA-33 | A2 | O | B72 | B70 |
| LXXVIIA-34 | A3 | O | B54 | B6 | LXXVIIA-35 | A3 | O | B70 | B6 | LXXVIIA-36 | A3 | O | B72 | B6 |
| LXXVIIA-37 | A3 | S | B54 | B6 | LXXVIIA-38 | A3 | S | B70 | B6 | LXXVIIA-39 | A3 | S | B72 | B6 |
| LXXVIIA-40 | A3 | O | B54 | B70 | LXXVIIA-41 | A3 | O | B70 | B70 | LXXVIIA-42 | A3 | O | B72 | B70; | wherein Compound LXXVIIIO-1 to Compound LXXVIIIO-66 have a structure represented by Formula LXXVIIIO:

Formula LXXVIIIO

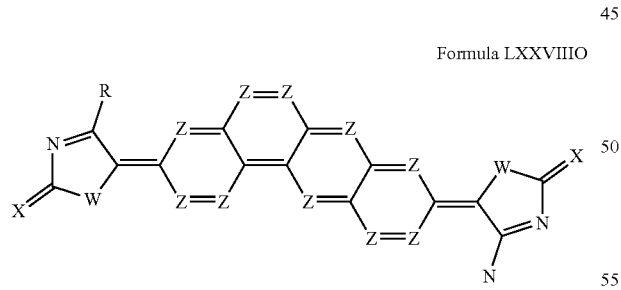

in Formula LXXVIIIO, two X are identical, two W are identical, two R are identical, ten Z are identical and are $CR_L$, and X, W, R, and $R_L$ correspond to an atom or a group selected from the following table, respectively:

| NO. | X | W | R | $R_L$ | NO. | X | W | R | $R_L$ | NO. | X | W | R | $R_L$ |
|---|---|---|---|---|---|---|---|---|---|---|---|---|---|---|
| LXXVIIIO-1 | A1 | O | B1 | H | LXXVIIIO-2 | A1 | O | B17 | H | LXXVIIIO-3 | A1 | O | B25 | H |
| LXXVIIIO-4 | A1 | O | B54 | H | LXXVIIIO-5 | A1 | O | B70 | H | LXXVIIIO-6 | A1 | O | B72 | H |
| LXXVIIIO-7 | A1 | S | B1 | H | LXXVIIIO-8 | A1 | S | B17 | H | LXXVIIIO-9 | A1 | S | B25 | H |

-continued

| NO. | X | W | R | $R_L$ | NO. | X | W | R | $R_L$ | NO. | X | W | R | $R_L$ |
|---|---|---|---|---|---|---|---|---|---|---|---|---|---|---|
| LXXVIIIO-10 | A1 | S | B54 | H | LXXVIIIO-11 | A1 | S | B70 | H | LXXVIIIO-12 | A1 | S | B72 | H |
| LXXVIIIO-13 | A1 | Se | B54 | H | LXXVIIIO-14 | A1 | Se | B70 | H | LXXVIIIO-15 | A1 | Se | B72 | H |
| LXXVIIIO-16 | A1 | NMe | B54 | H | LXXVIIIO-17 | A1 | NMe | B70 | H | LXXVIIIO-18 | A1 | NMe | B72 | H |
| LXXVIIIO-19 | A1 | O | H | F | LXXVIIIO-20 | A1 | O | B17 | F | LXXVIIIO-21 | A1 | O | B25 | F |
| LXXVIIIO-22 | A1 | O | B54 | F | LXXVIIIO-23 | A1 | O | B70 | F | LXXVIIIO-24 | A1 | O | B72 | F |
| LXXVIIIO-25 | A1 | S | H | F | LXXVIIIO-26 | A1 | S | B17 | F | LXXVIIIO-27 | A1 | S | B25 | F |
| LXXVIIIO-28 | A1 | S | B54 | F | LXXVIIIO-29 | A1 | S | B70 | F | LXXVIIIO-30 | A1 | S | B72 | F |
| LXXVIIIO-31 | A2 | O | B1 | H | LXXVIIIO-32 | A2 | O | B17 | H | LXXVIIIO-33 | A2 | O | B25 | H |
| LXXVIIIO-34 | A2 | O | B54 | H | LXXVIIIO-35 | A2 | O | B70 | H | LXXVIIIO-36 | A2 | O | B72 | H |
| LXXVIIIO-37 | A2 | S | B1 | H | LXXVIIIO-38 | A2 | S | B17 | H | LXXVIIIO-39 | A2 | S | B25 | H |
| LXXVIIIO-40 | A2 | S | B54 | H | LXXVIIIO-41 | A2 | S | B70 | H | LXXVIIIO-42 | A2 | S | B72 | H |
| LXXVIIIO-43 | A2 | O | B54 | F | LXXVIIIO-44 | A2 | O | B70 | F | LXXVIIIO-45 | A2 | O | B72 | F |
| LXXVIIIO-46 | A2 | S | B54 | F | LXXVIIIO-47 | A2 | S | B70 | F | LXXVIIIO-48 | A2 | S | B72 | F |
| LXXVIIIO-49 | A3 | O | B1 | H | LXXVIIIO-50 | A3 | O | B17 | H | LXXVIIIO-51 | A3 | O | B25 | H |
| LXXVIIIO-52 | A3 | O | B54 | H | LXXVIIIO-53 | A3 | O | B70 | H | LXXVIIIO-54 | A3 | O | B72 | H |
| LXXVIIIO-55 | A3 | S | B1 | H | LXXVIIIO-56 | A3 | S | B17 | H | LXXVIIIO-57 | A3 | S | B25 | H |
| LXXVIIIO-58 | A3 | S | B54 | H | LXXVIIIO-59 | A3 | S | B70 | H | LXXVIIIO-60 | A3 | S | B72 | H |
| LXXVIIIO-61 | A3 | O | B54 | F | LXXVIIIO-62 | A3 | O | B70 | F | LXXVIIIO-63 | A3 | O | B72 | F |
| LXXVIIIO-64 | A3 | S | B54 | F | LXXVIIIO-65 | A3 | S | B70 | F | LXXVIIIO-66 | A3 | S | B72 | F; | wherein Compound LXXVIIIA-1 to Compound LXXVIIIA-42 have a structure represented by Formula LXXVIIIA:

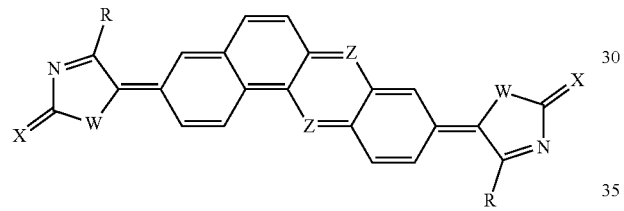

Formula LXXVIIIA in Formula LXXVIIIA, two X are identical, two W are identical, two R are identical, two Z are identical and are $CR_L$, and X, W, R, and $R_L$ correspond to an atom or a group selected from the following table, respectively:

| NO. | X | W | R | $R_L$ | NO. | X | W | R | $R_L$ | NO. | X | W | R | $R_L$ |
|---|---|---|---|---|---|---|---|---|---|---|---|---|---|---|
| LXXVIIIA-1 | A1 | O | H | B6 | LXXVIIIA-2 | A1 | O | B17 | B6 | LXXVIIIA-3 | A1 | O | B25 | B6 |
| LXXVIIIA-4 | A1 | O | B54 | B6 | LXXVIIIA-5 | A1 | O | B70 | B6 | LXXVIIIA-6 | A1 | O | B72 | B6 |
| LXXVIIIA-7 | A1 | S | H | B6 | LXXVIIIA-8 | A1 | S | B17 | B6 | LXXVIIIA-9 | A1 | S | B25 | B6 |
| LXXVIIIA-10 | A1 | S | B54 | B6 | LXXVIIIA-11 | A1 | S | B70 | B6 | LXXVIIIA-12 | A1 | S | B72 | B6 |
| LXXVIIIA-13 | A1 | O | H | B70 | LXXVIIIA-14 | A1 | O | B17 | B70 | LXXVIIIA-15 | A1 | O | B25 | B70 |
| LXXVIIIA-16 | A1 | O | B54 | B70 | LXXVIIIA-17 | A1 | O | B70 | B70 | LXXVIIIA-18 | A1 | O | B72 | B70 |
| LXXVIIIA-19 | A1 | S | H | B70 | LXXVIIIA-20 | A1 | S | B17 | B70 | LXXVIIIA-21 | A1 | S | B25 | B70 |
| LXXVIIIA-22 | A1 | S | B54 | B70 | LXXVIIIA-23 | A1 | S | B70 | B70 | LXXVIIIA-24 | A1 | S | B72 | B70 |
| LXXVIIIA-25 | A2 | O | B54 | B6 | LXXVIIIA-26 | A2 | O | B70 | B6 | LXXVIIIA-27 | A2 | O | B72 | B6 |
| LXXVIIIA-28 | A2 | S | B54 | B6 | LXXVIIIA-29 | A2 | S | B70 | B6 | LXXVIIIA-30 | A2 | S | B72 | B6 |
| LXXVIIIA-31 | A2 | O | B54 | B70 | LXXVIIIA-32 | A2 | O | B70 | B70 | LXXVIIIA-33 | A2 | O | B72 | B70 |
| LXXVIIIA-34 | A3 | O | B54 | B6 | LXXVIIIA-35 | A3 | O | B70 | B6 | LXXVIIIA-36 | A3 | O | B72 | B6 |
| LXXVIIIA-37 | A3 | S | B54 | B6 | LXXVIIIA-38 | A3 | S | B70 | B6 | LXXVIIIA-39 | A3 | S | B72 | B6 |
| LXXVIIIA-40 | A3 | O | B54 | B70 | LXXVIIIA-41 | A3 | O | B70 | B70 | LXXVIIIA-42 | A3 | O | B72 | B70; | wherein Compound LXXIXO-1 to Compound LXXIXO-66 have a structure represented by Formula LXXIXO:

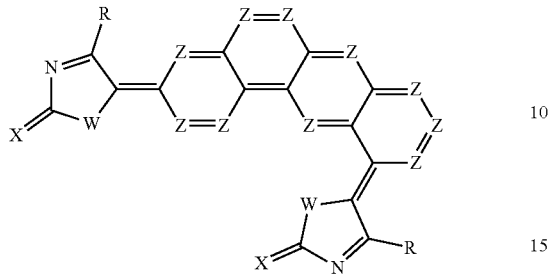

Formula LXXIXO in Formula LXXIXO, two X are identical, two W are identical, two R are identical, ten Z are identical and are $CR_L$, and X, W, R, and $R_L$ correspond to an atom or a group selected from the following table, respectively:

| NO. | X | W | R | $R_L$ | NO. | X | W | R | $R_L$ | NO. | X | W | R | $R_L$ |
|---|---|---|---|---|---|---|---|---|---|---|---|---|---|---|
| LXXIXO-1 | A1 | O | B1 | H | LXXIXO-2 | A1 | O | B17 | H | LXXIXO-3 | A1 | O | B25 | H |
| LXXIXO-4 | A1 | O | B54 | H | LXXIXO-5 | A1 | O | B70 | H | LXXIXO-6 | A1 | O | B72 | H |
| LXXIXO-7 | A1 | S | B1 | H | LXXIXO-8 | A1 | S | B17 | H | LXXIXO-9 | A1 | S | B25 | H |
| LXXIXO-10 | A1 | S | B54 | H | LXXIXO-11 | A1 | S | B70 | H | LXXIXO-12 | A1 | S | B72 | H |
| LXXIXO-13 | A1 | Se | B54 | H | LXXIXO-14 | A1 | Se | B70 | H | LXXIXO-15 | A1 | Se | B72 | H |
| LXXIXO-16 | A1 | NMe | B54 | H | LXXIXO-17 | A1 | NMe | B70 | H | LXXIXO-18 | A1 | NMe | B72 | H |
| LXXIXO-19 | A1 | O | H | F | LXXIXO-20 | A1 | O | B17 | F | LXXIXO-21 | A1 | O | B25 | F |
| LXXIXO-22 | A1 | O | B54 | F | LXXIXO-23 | A1 | O | B70 | F | LXXIXO-24 | A1 | O | B72 | F |
| LXXIXO-25 | A1 | S | H | F | LXXIXO-26 | A1 | S | B17 | F | LXXIXO-27 | A1 | S | B25 | F |
| LXXIXO-28 | A1 | S | B54 | F | LXXIXO-29 | A1 | S | B70 | F | LXXIXO-30 | A1 | S | B72 | F |
| LXXIXO-31 | A2 | O | B1 | H | LXXIXO-32 | A2 | O | B17 | H | LXXIXO-33 | A2 | O | B25 | H |
| LXXIXO-34 | A2 | O | B54 | H | LXXIXO-35 | A2 | O | B70 | H | LXXIXO-36 | A2 | O | B72 | H |
| LXXIXO-37 | A2 | S | B1 | H | LXXIXO-38 | A2 | S | B17 | H | LXXIXO-39 | A2 | S | B25 | H |
| LXXIXO-40 | A2 | S | B54 | H | LXXIXO-41 | A2 | S | B70 | H | LXXIXO-42 | A2 | S | B72 | H |
| LXXIXO-43 | A2 | O | B54 | F | LXXIXO-44 | A2 | O | B70 | F | LXXIXO-45 | A2 | O | B72 | F |
| LXXIXO-46 | A2 | S | B54 | F | LXXIXO-47 | A2 | S | B70 | F | LXXIXO-48 | A2 | S | B72 | F |
| LXXIXO-49 | A3 | O | B1 | H | LXXIXO-50 | A3 | O | B17 | H | LXXIXO-51 | A3 | O | B25 | H |
| LXXIXO-52 | A3 | O | B54 | H | LXXIXO-53 | A3 | O | B70 | H | LXXIXO-54 | A3 | O | B72 | H |
| LXXIXO-55 | A3 | S | B1 | H | LXXIXO-56 | A3 | S | B17 | H | LXXIXO-57 | A3 | S | B25 | H |
| LXXIXO-58 | A3 | S | B54 | H | LXXIXO-59 | A3 | S | B70 | H | LXXIXO-60 | A3 | S | B72 | H |
| LXXIXO-61 | A3 | O | B54 | F | LXXIXO-62 | A3 | O | B70 | F | LXXIXO-63 | A3 | O | B72 | F |
| LXXIXO-64 | A3 | S | B54 | F | LXXIXO-65 | A3 | S | B70 | F | LXXIXO-66 | A3 | S | B72 | F; | wherein Compound LXXIXA-1 to Compound LXXIXA-42 have a structure represented by Formula LXXIXA:

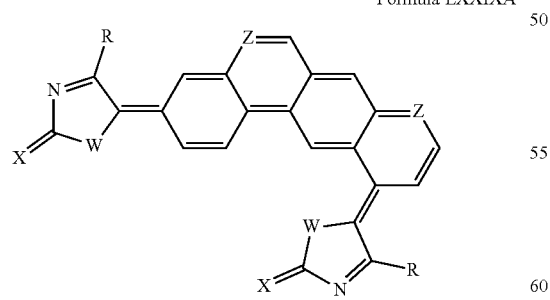

Formula LXXIXA in Formula LXXIXA, two X are identical, two W are identical, two R are identical, two Z are identical and are $CR_L$, and X, W, R, and $R_L$ correspond to an atom or a group selected from the following table, respectively:

| NO. | X | W | R | R_L | NO. | X | W | R | R_L | NO. | X | W | R | R_L |
|---|---|---|---|---|---|---|---|---|---|---|---|---|---|---|
| LXXIXA-1 | A1 | O | H | B6 | LXXIXA-2 | A1 | O | B17 | B6 | LXXIXA-3 | A1 | O | B25 | B6 |
| LXXIXA-4 | A1 | O | B54 | B6 | LXXIXA-5 | A1 | O | B70 | B6 | LXXIXA-6 | A1 | O | B72 | B6 |
| LXXIXA-7 | A1 | S | H | B6 | LXXIXA-8 | A1 | S | B17 | B6 | LXXIXA-9 | A1 | S | B25 | B6 |
| LXXIXA-10 | A1 | S | B54 | B6 | LXXIXA-11 | A1 | S | B70 | B6 | LXXIXA-12 | A1 | S | B72 | B6 |
| LXXIXA-13 | A1 | O | H | B70 | LXXIXA-14 | A1 | O | B17 | B70 | LXXIXA-15 | A1 | O | B25 | B70 |
| LXXIXA-16 | A1 | O | B54 | B70 | LXXIXA-17 | A1 | O | B70 | B70 | LXXIXA-18 | A1 | O | B72 | B70 |
| LXXIXA-19 | A1 | S | H | B70 | LXXIXA-20 | A1 | S | B17 | B70 | LXXIXA-21 | A1 | S | B25 | B70 |
| LXXIXA-22 | A1 | S | B54 | B70 | LXXIXA-23 | A1 | S | B70 | B70 | LXXIXA-24 | A1 | S | B72 | B70 |
| LXXIXA-25 | A2 | O | B54 | B6 | LXXIXA-26 | A2 | O | B70 | B6 | LXXIXA-27 | A2 | O | B72 | B6 |
| LXXIXA-28 | A2 | S | B54 | B6 | LXXIXA-29 | A2 | S | B70 | B6 | LXXIXA-30 | A2 | S | B72 | B6 |
| LXXIXA-31 | A2 | O | B54 | B70 | LXXIXA-32 | A2 | O | B70 | B70 | LXXIXA-33 | A2 | O | B72 | B70 |
| LXXIXA-34 | A3 | O | B54 | B6 | LXXIXA-35 | A3 | O | B70 | B6 | LXXIXA-36 | A3 | O | B72 | B6 |
| LXXIXA-37 | A3 | S | B54 | B6 | LXXIXA-38 | A3 | S | B70 | B6 | LXXIXA-39 | A3 | S | B72 | B6 |
| LXXIXA-40 | A3 | O | B54 | B70 | LXXIXA-41 | A3 | O | B70 | B70 | LXXIXA-42 | A3 | O | B72 | B70; | wherein Compound LXXXO-1 to Compound LXXXO-66 have a structure represented by Formula LXXXO:

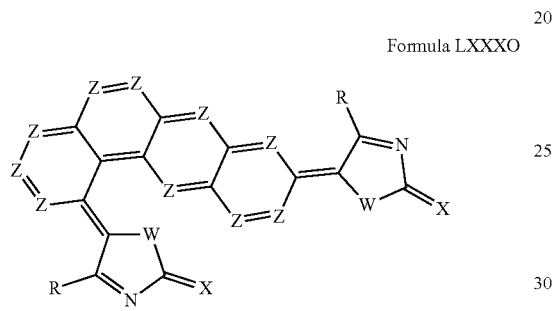

Formula LXXXO in Formula LXXXO, two X are identical, two W are identical, two R are identical, ten Z are identical and are $CR_L$, and X, W, R, and $R_L$ correspond to an atom or a group selected from the following table, respectively:

| NO. | X | W | R | R_L | NO. | X | W | R | R_L | NO. | X | W | R | R_L |
|---|---|---|---|---|---|---|---|---|---|---|---|---|---|---|
| LXXXO-1 | A1 | O | B1 | H | LXXXO-2 | A1 | O | B17 | H | LXXXO-3 | A1 | O | B25 | H |
| LXXXO-4 | A1 | O | B54 | H | LXXXO-5 | A1 | O | B70 | H | LXXXO-6 | A1 | O | B72 | H |
| LXXXO-7 | A1 | S | B1 | H | LXXXO-8 | A1 | S | B17 | H | LXXXO-9 | A1 | S | B25 | H |
| LXXXO-10 | A1 | S | B54 | H | LXXXO-11 | A1 | S | B70 | H | LXXXO-12 | A1 | S | B72 | H |
| LXXXO-13 | A1 | Se | B54 | H | LXXXO-14 | A1 | Se | B70 | H | LXXXO-15 | A1 | Se | B72 | H |
| LXXXO-16 | A1 | NMe | B54 | H | LXXXO-17 | A1 | NMe | B70 | H | LXXXO-18 | A1 | NMe | B72 | H |
| LXXXO-19 | A1 | O | H | F | LXXXO-20 | A1 | O | B17 | F | LXXXO-21 | A1 | O | B25 | F |
| LXXXO-22 | A1 | O | B54 | F | LXXXO-23 | A1 | O | B70 | F | LXXXO-24 | A1 | O | B72 | F |
| LXXXO-25 | A1 | S | H | F | LXXXO-26 | A1 | S | B17 | F | LXXXO-27 | A1 | S | B25 | F |
| LXXXO-28 | A1 | S | B54 | F | LXXXO-29 | A1 | S | B70 | F | LXXXO-30 | A1 | S | B72 | F |
| LXXXO-31 | A2 | O | B1 | H | LXXXO-32 | A2 | O | B17 | H | LXXXO-33 | A2 | O | B25 | H |
| LXXXO-34 | A2 | O | B54 | H | LXXXO-35 | A2 | O | B70 | H | LXXXO-36 | A2 | O | B72 | H |
| LXXXO-37 | A2 | S | B1 | H | LXXXO-38 | A2 | S | B17 | H | LXXXO-39 | A2 | S | B25 | H |
| LXXXO-40 | A2 | S | B54 | H | LXXXO-41 | A2 | S | B70 | H | LXXXO-42 | A2 | S | B72 | H |
| LXXXO-43 | A2 | O | B54 | F | LXXXO-44 | A2 | O | B70 | F | LXXXO-45 | A2 | O | B72 | F |
| LXXXO-46 | A2 | S | B54 | F | LXXXO-47 | A2 | S | B70 | F | LXXXO-48 | A2 | S | B72 | F |
| LXXXO-49 | A3 | O | B1 | H | LXXXO-50 | A3 | O | B17 | H | LXXXO-51 | A3 | O | B25 | H |
| LXXXO-52 | A3 | O | B54 | H | LXXXO-53 | A3 | O | B70 | H | LXXXO-54 | A3 | O | B72 | H |
| LXXXO-55 | A3 | S | B1 | H | LXXXO-56 | A3 | S | B17 | H | LXXXO-57 | A3 | S | B25 | H |
| LXXXO-58 | A3 | S | B54 | H | LXXXO-59 | A3 | S | B70 | H | LXXXO-60 | A3 | S | B72 | H |
| LXXXO-61 | A3 | O | B54 | F | LXXXO-62 | A3 | O | B70 | F | LXXXO-63 | A3 | O | B72 | F |
| LXXXO-64 | A3 | S | B54 | F | LXXXO-65 | A3 | S | B70 | F | LXXXO-66 | A3 | S | B72 | F; | wherein Compound LXXXA-1 to Compound LXXXA-42 have a structure represented by Formula LXXXA:

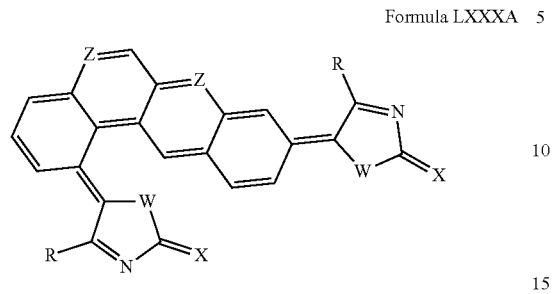

Formula LXXXA in Formula LXXXA, two X are identical, two W are identical, two R are identical, two Z are identical and are $CR_L$, and X, W, R, and $R_L$ correspond to an atom or a group selected from the following table, respectively:

| NO. | X | W | R | $R_L$ | NO. | X | W | R | $R_L$ | NO. | X | W | R | $R_L$ |
|---|---|---|---|---|---|---|---|---|---|---|---|---|---|---|
| LXXXA-1 | A1 | O | H | B6 | LXXXA-2 | A1 | O | B17 | B6 | LXXXA-3 | A1 | O | B25 | B6 |
| LXXXA-4 | A1 | O | B54 | B6 | LXXXA-5 | A1 | O | B70 | B6 | LXXXA-6 | A1 | O | B72 | B6 |
| LXXXA-7 | A1 | S | H | B6 | LXXXA-8 | A1 | S | B17 | B6 | LXXXA-9 | A1 | S | B25 | B6 |
| LXXXA-10 | A1 | S | B54 | B6 | LXXXA-11 | A1 | S | B70 | B6 | LXXXA-12 | A1 | S | B72 | B6 |
| LXXXA-13 | A1 | O | H | B70 | LXXXA-14 | A1 | O | B17 | B70 | LXXXA-15 | A1 | O | B25 | B70 |
| LXXXA-16 | A1 | O | B54 | B70 | LXXXA-17 | A1 | O | B70 | B70 | LXXXA-18 | A1 | O | B72 | B70 |
| LXXXA-19 | A1 | S | H | B70 | LXXXA-20 | A1 | S | B17 | B70 | LXXXA-21 | A1 | S | B25 | B70 |
| LXXXA-22 | A1 | S | B54 | B70 | LXXXA-23 | A1 | S | B70 | B70 | LXXXA-24 | A1 | S | B72 | B70 |
| LXXXA-25 | A2 | O | B54 | B6 | LXXXA-26 | A2 | O | B70 | B6 | LXXXA-27 | A2 | O | B72 | B6 |
| LXXXA-28 | A2 | S | B54 | B6 | LXXXA-29 | A2 | S | B70 | B6 | LXXXA-30 | A2 | S | B72 | B6 |
| LXXXA-31 | A2 | O | B54 | B70 | LXXXA-32 | A2 | O | B70 | B70 | LXXXA-33 | A2 | O | B72 | B70 |
| LXXXA-34 | A3 | O | B54 | B6 | LXXXA-35 | A3 | O | B70 | B6 | LXXXA-36 | A3 | O | B72 | B6 |
| LXXXA-37 | A3 | S | B54 | B6 | LXXXA-38 | A3 | S | B70 | B6 | LXXXA-39 | A3 | S | B72 | B6 |
| LXXXA-40 | A3 | O | B54 | B70 | LXXXA-41 | A3 | O | B70 | B70 | LXXXA-42 | A3 | O | B72 | B70; | wherein Compound LXXXIO-1 to Compound LXXXIO-66 have a structure represented by Formula LXXXIO:

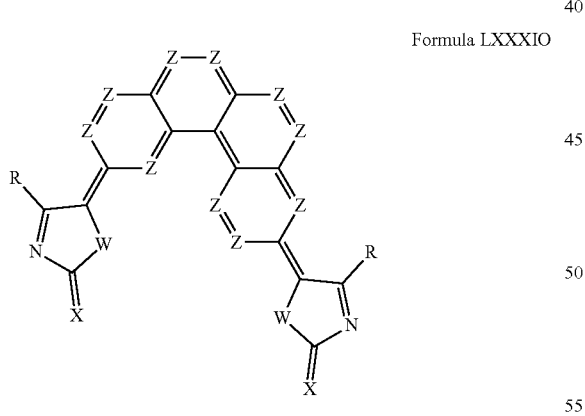

Formula LXXXIO in Formula LXXXIO, two X are identical, two W are identical, two R are identical, ten Z are identical and are $CR_L$, and X, W, R, and $R_L$ correspond to an atom or a group selected from the following table, respectively:

| NO. | X | W | R | $R_L$ | NO. | X | W | R | $R_L$ | NO. | X | W | R | $R_L$ |
|---|---|---|---|---|---|---|---|---|---|---|---|---|---|---|
| LXXXIO-1 | A1 | O | B1 | H | LXXXIO-2 | A1 | O | B17 | H | LXXXIO-3 | A1 | O | B25 | H |
| LXXXIO-4 | A1 | O | B54 | H | LXXXIO-5 | A1 | O | B70 | H | LXXXIO-6 | A1 | O | B72 | H |
| LXXXIO-7 | A1 | S | B1 | H | LXXXIO-8 | A1 | S | B17 | H | LXXXIO-9 | A1 | S | B25 | H |
| LXXXIO-10 | A1 | S | B54 | H | LXXXIO-11 | A1 | S | B70 | H | LXXXIO-12 | A1 | S | B72 | H |

| NO. | X | W | R | R$_L$ | NO. | X | W | R | R$_L$ | NO. | X | W | R | R$_L$ |
|---|---|---|---|---|---|---|---|---|---|---|---|---|---|---|
| LXXXIO-13 | A1 | Se | B54 | H | LXXXIO-14 | A1 | Se | B70 | H | LXXXIO-15 | A1 | Se | B72 | H |
| LXXXIO-16 | A1 | NMe | B54 | H | LXXXIO-17 | A1 | NMe | B70 | H | LXXXIO-18 | A1 | NMe | B72 | H |
| LXXXIO-19 | A1 | O | H | F | LXXXIO-20 | A1 | O | B17 | F | LXXXIO-21 | A1 | O | B25 | F |
| LXXXIO-22 | A1 | O | B54 | F | LXXXIO-23 | A1 | O | B70 | F | LXXXIO-24 | A1 | O | B72 | F |
| LXXXIO-25 | A1 | S | H | F | LXXXIO-26 | A1 | S | B17 | F | LXXXIO-27 | A1 | S | B25 | F |
| LXXXIO-28 | A1 | S | B54 | F | LXXXIO-29 | A1 | S | B70 | F | LXXXIO-30 | A1 | S | B72 | F |
| LXXXIO-31 | A2 | O | B1 | H | LXXXIO-32 | A2 | O | B17 | H | LXXXIO-33 | A2 | O | B25 | H |
| LXXXIO-34 | A2 | O | B54 | H | LXXXIO-35 | A2 | O | B70 | H | LXXXIO-36 | A2 | O | B72 | H |
| LXXXIO-37 | A2 | S | B1 | H | LXXXIO-38 | A2 | S | B17 | H | LXXXIO-39 | A2 | S | B25 | H |
| LXXXIO-40 | A2 | S | B54 | H | LXXXIO-41 | A2 | S | B70 | H | LXXXIO-42 | A2 | S | B72 | H |
| LXXXIO-43 | A2 | O | B54 | F | LXXXIO-44 | A2 | O | B70 | F | LXXXIO-45 | A2 | O | B72 | F |
| LXXXIO-46 | A2 | S | B54 | F | LXXXIO-47 | A2 | S | B70 | F | LXXXIO-48 | A2 | S | B72 | F |
| LXXXIO-49 | A3 | O | B1 | H | LXXXIO-50 | A3 | O | B17 | H | LXXXIO-51 | A3 | O | B25 | H |
| LXXXIO-52 | A3 | O | B54 | H | LXXXIO-53 | A3 | O | B70 | H | LXXXIO-54 | A3 | O | B72 | H |
| LXXXIO-55 | A3 | S | B1 | H | LXXXIO-56 | A3 | S | B17 | H | LXXXIO-57 | A3 | S | B25 | H |
| LXXXIO-58 | A3 | S | B54 | H | LXXXIO-59 | A3 | S | B70 | H | LXXXIO-60 | A3 | S | B72 | H |
| LXXXIO-61 | A3 | O | B54 | F | LXXXIO-62 | A3 | O | B70 | F | LXXXIO-63 | A3 | O | B72 | F |
| LXXXIO-64 | A3 | S | B54 | F | LXXXIO-65 | A3 | S | B70 | F | LXXXIO-66 | A3 | S | B72 | F; | wherein Compound LXXXIA-1 to Compound LXXXIA-42 have a structure represented by Formula LXXXIA:

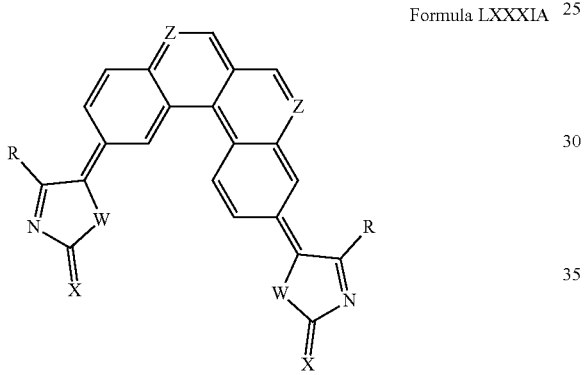

Formula LXXXIA in Formula LXXXIA, two X are identical, two W are identical, two R are identical, two Z are identical and are CR$_L$, and X, W, R, and R$_L$ correspond to an atom or a group selected from the following table, respectively:

| NO. | X | W | R | R$_L$ | NO. | X | W | R | R$_L$ | NO. | X | W | R | R$_L$ |
|---|---|---|---|---|---|---|---|---|---|---|---|---|---|---|
| LXXXIA-1 | A1 | O | H | B6 | LXXXIA-2 | A1 | O | B17 | B6 | LXXXIA-3 | A1 | O | B25 | B6 |
| LXXXIA-4 | A1 | O | B54 | B6 | LXXXIA-5 | A1 | O | B70 | B6 | LXXXIA-6 | A1 | O | B72 | B6 |
| LXXXIA-7 | A1 | S | H | B6 | LXXXIA-8 | A1 | S | B17 | B6 | LXXXIA-9 | A1 | S | B25 | B6 |
| LXXXIA-10 | A1 | S | B54 | B6 | LXXXIA-11 | A1 | S | B70 | B6 | LXXXIA-12 | A1 | S | B72 | B6 |
| LXXXIA-13 | A1 | O | H | B70 | LXXXIA-14 | A1 | O | B17 | B70 | LXXXIA-15 | A1 | O | B25 | B70 |
| LXXXIA-16 | A1 | O | B54 | B70 | LXXXIA-17 | A1 | O | B70 | B70 | LXXXIA-18 | A1 | O | B72 | B70 |
| LXXXIA-19 | A1 | S | H | B70 | LXXXIA-20 | A1 | S | B17 | B70 | LXXXIA-21 | A1 | S | B25 | B70 |
| LXXXIA-22 | A1 | S | B54 | B70 | LXXXIA-23 | A1 | S | B70 | B70 | LXXXIA-24 | A1 | S | B72 | B70 |
| LXXXIA-25 | A2 | O | B54 | B6 | LXXXIA-26 | A2 | O | B70 | B6 | LXXXIA-27 | A2 | O | B72 | B6 |
| LXXXIA-28 | A2 | S | B54 | B6 | LXXXIA-29 | A2 | S | B70 | B6 | LXXXIA-30 | A2 | S | B72 | B6 |
| LXXXIA-31 | A2 | O | B54 | B70 | LXXXIA-32 | A2 | O | B70 | B70 | LXXXIA-33 | A2 | O | B72 | B70 |
| LXXXIA-34 | A3 | O | B54 | B6 | LXXXIA-35 | A3 | O | B70 | B6 | LXXXIA-36 | A3 | O | B72 | B6 |
| LXXXIA-37 | A3 | S | B54 | B6 | LXXXIA-38 | A3 | S | B70 | B6 | LXXXIA-39 | A3 | S | B72 | B6 |
| LXXXIA-40 | A3 | O | B54 | B70 | LXXXIA-41 | A3 | O | B70 | B70 | LXXXIA-42 | A3 | O | B72 | B70; | wherein Compound LXXXIIO-1 to Compound LXXXIIO-66 have a structure represented by Formula LXXXIIO:

Formula LXXXIIO

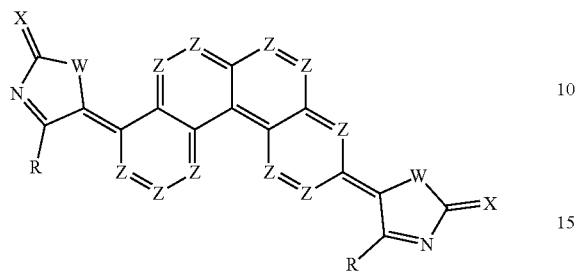

in Formula LXXXIIO two X are identical two W are identical two R are identical ten Z are identical and are $CR_L$, and X, W, R, and $R_L$ correspond to an atom or a group selected from the following table, respectively:

| NO. | X | W | R | $R_L$ | NO. | X | W | R | $R_L$ | NO. | X | W | R | $R_L$ |
|---|---|---|---|---|---|---|---|---|---|---|---|---|---|---|
| LXXXIIO-1 | A1 | O | B1 | H | LXXXIIO-2 | A1 | O | B17 | H | LXXXIIO-3 | A1 | O | B25 | H |
| LXXXIIO-4 | A1 | O | B54 | H | LXXXIIO-5 | A1 | O | B70 | H | LXXXIIO-6 | A1 | O | B72 | H |
| LXXXIIO-7 | A1 | S | B1 | H | LXXXIIO-8 | A1 | S | B17 | H | LXXXIIO-9 | A1 | S | B25 | H |
| LXXXIIO-10 | A1 | S | B54 | H | LXXXIIO-11 | A1 | S | B70 | H | LXXXIIO-12 | A1 | S | B72 | H |
| LXXXIIO-13 | A1 | Se | B54 | H | LXXXIIO-14 | A1 | Se | B70 | H | LXXXIIO-15 | A1 | Se | B72 | H |
| LXXXIIO-16 | A1 | NMe | B54 | H | LXXXIIO-17 | A1 | NMe | B70 | H | LXXXIIO-18 | A1 | NMe | B72 | H |
| LXXXIIO-19 | A1 | O | H | F | LXXXIIO-20 | A1 | O | B17 | F | LXXXIIO-21 | A1 | O | B25 | F |
| LXXXIIO-22 | A1 | O | B54 | F | LXXXIIO-23 | A1 | O | B70 | F | LXXXIIO-24 | A1 | O | B72 | F |
| LXXXIIO-25 | A1 | S | H | F | LXXXIIO-26 | A1 | S | B17 | F | LXXXIIO-27 | A1 | S | B25 | F |
| LXXXIIO-28 | A1 | S | B54 | F | LXXXIIO-29 | A1 | S | B70 | F | LXXXIIO-30 | A1 | S | B72 | F |
| LXXXIIO-31 | A2 | O | B1 | H | LXXXIIO-32 | A2 | O | B17 | H | LXXXIIO-33 | A2 | O | B25 | H |
| LXXXIIO-34 | A2 | O | B54 | H | LXXXIIO-35 | A2 | O | B70 | H | LXXXIIO-36 | A2 | O | B72 | H |
| LXXXIIO-37 | A2 | S | B1 | H | LXXXIIO-38 | A2 | S | B17 | H | LXXXIIO-39 | A2 | S | B25 | H |
| LXXXIIO-40 | A2 | S | B54 | H | LXXXIIO-41 | A2 | S | B70 | H | LXXXIIO-42 | A2 | S | B72 | H |
| LXXXIIO-43 | A2 | O | B54 | F | LXXXIIO-44 | A2 | O | B70 | F | LXXXIIO-45 | A2 | O | B72 | F |
| LXXXIIO-46 | A2 | S | B54 | F | LXXXIIO-47 | A2 | S | B70 | F | LXXXIIO-48 | A2 | S | B72 | F |
| LXXXIIO-49 | A3 | O | B1 | H | LXXXIIO-50 | A3 | O | B17 | H | LXXXIIO-51 | A3 | O | B25 | H |
| LXXXIIO-52 | A3 | O | B54 | H | LXXXIIO-53 | A3 | O | B70 | H | LXXXIIO-54 | A3 | O | B72 | H |
| LXXXIIO-55 | A3 | S | B1 | H | LXXXIIO-56 | A3 | S | B17 | H | LXXXIIO-57 | A3 | S | B25 | H |
| LXXXIIO-58 | A3 | S | B54 | H | LXXXIIO-59 | A3 | S | B70 | H | LXXXIIO-60 | A3 | S | B72 | H |
| LXXXIIO-61 | A3 | O | B54 | F | LXXXIIO-62 | A3 | O | B70 | F | LXXXIIO-63 | A3 | O | B72 | F |
| LXXXIIO-64 | A3 | S | B54 | F | LXXXIIO-65 | A3 | S | B70 | F | LXXXIIO-66 | A3 | S | B72 | F; | wherein Compound LXXXIIA-1 to Compound LXXXIIA-42 have a structure represented by Formula LXXXIIA:

Formula LXXXIIA

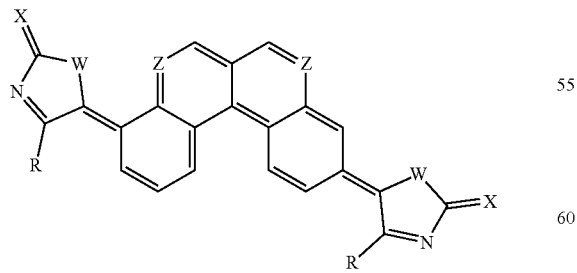

in Formula LXXXIIA, two X are identical, two W are identical, two R are identical, two Z are identical and are $CR_L$, and X, W, R, and $R_L$ correspond to an atom or a group selected from the following table, respectively:

| NO. | X | W | R | R_L | NO. | X | W | R | R_L | NO. | X | W | R | R_L |
|---|---|---|---|---|---|---|---|---|---|---|---|---|---|---|
| LXXXIIA-1 | A1 | O | H | B6 | LXXXIIA-2 | A1 | O | B17 | B6 | LXXXIIA-3 | A1 | O | B25 | B6 |
| LXXXIIA-4 | A1 | O | B54 | B6 | LXXXIIA-5 | A1 | O | B70 | B6 | LXXXIIA-6 | A1 | O | B72 | B6 |
| LXXXIIA-7 | A1 | S | H | B6 | LXXXIIA-8 | A1 | S | B17 | B6 | LXXXIIA-9 | A1 | S | B25 | B6 |
| LXXXIIA-10 | A1 | S | B54 | B6 | LXXXIIA-11 | A1 | S | B70 | B6 | LXXXIIA-12 | A1 | S | B72 | B6 |
| LXXXIIA-13 | A1 | O | H | B70 | LXXXIIA-14 | A1 | O | B17 | B70 | LXXXIIA-15 | A1 | O | B25 | B70 |
| LXXXIIA-16 | A1 | O | B54 | B70 | LXXXIIA-17 | A1 | O | B70 | B70 | LXXXIIA-18 | A1 | O | B72 | B70 |
| LXXXIIA-19 | A1 | S | H | B70 | LXXXIIA-20 | A1 | S | B17 | B70 | LXXXIIA-21 | A1 | S | B25 | B70 |
| LXXXIIA-22 | A1 | S | B54 | B70 | LXXXIIA-23 | A1 | S | B70 | B70 | LXXXIIA-24 | A1 | S | B72 | B70 |
| LXXXIIA-25 | A2 | O | B54 | B6 | LXXXIIA-26 | A2 | O | B70 | B6 | LXXXIIA-27 | A2 | O | B72 | B6 |
| LXXXIIA-28 | A2 | S | B54 | B6 | LXXXIIA-29 | A2 | S | B70 | B6 | LXXXIIA-30 | A2 | S | B72 | B6 |
| LXXXIIA-31 | A2 | O | B54 | B70 | LXXXIIA-32 | A2 | O | B70 | B70 | LXXXIIA-33 | A2 | O | B72 | B70 |
| LXXXIIA-34 | A3 | O | B54 | B6 | LXXXIIA-35 | A3 | O | B70 | B6 | LXXXIIA-36 | A3 | O | B72 | B6 |
| LXXXIIA-37 | A3 | S | B54 | B6 | LXXXIIA-38 | A3 | S | B70 | B6 | LXXXIIA-39 | A3 | S | B72 | B6 |
| LXXXIIA-40 | A3 | O | B54 | B70 | LXXXIIA-41 | A3 | O | B70 | B70 | LXXXIIA-42 | A3 | O | B72 | B70; | wherein Compound LXXXIIIO-1 to Compound LXXXIIIO-66 have a structure represented by Formula LXXXIIIO:

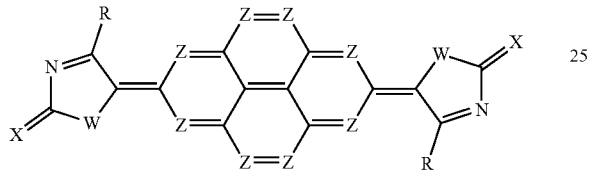

Formula LXXXIIIO in Formula LXXXIIIO, two X are identical, two W are identical, two R are identical, eight Z are identical and are $CR_L$, and X, W, R, and $R_L$ correspond to an atom or a group selected from the following table, respectively:

| NO. | X | W | R | R_L | NO. | X | W | R | R_L | NO. | X | W | R | R_L |
|---|---|---|---|---|---|---|---|---|---|---|---|---|---|---|
| LXXXIIIO-1 | A1 | O | B1 | H | LXXXIIIO-2 | A1 | O | B17 | H | LXXXIIIO-3 | A1 | O | B25 | H |
| LXXXIIIO-4 | A1 | O | B54 | H | LXXXIIIO-5 | A1 | O | B70 | H | LXXXIIIO-6 | A1 | O | B72 | H |
| LXXXIIIO-7 | A1 | S | B1 | H | LXXXIIIO-8 | A1 | S | B17 | H | LXXXIIIO-9 | A1 | S | B25 | H |
| LXXXIIIO-10 | A1 | S | B54 | H | LXXXIIIO-11 | A1 | S | B70 | H | LXXXIIIO-12 | A1 | S | B72 | H |
| LXXXIIIO-13 | A1 | Se | B54 | H | LXXXIIIO-14 | A1 | Se | B70 | H | LXXXIIIO-15 | A1 | Se | B72 | H |
| LXXXIIIO-16 | A1 | NMe | B54 | H | LXXXIIIO-17 | A1 | NMe | B70 | H | LXXXIIIO-18 | A1 | NMe | B72 | H |
| LXXXIIIO-19 | A1 | O | H | F | LXXXIIIO-20 | A1 | O | B17 | F | LXXXIIIO-21 | A1 | O | B25 | F |
| LXXXIIIO-22 | A1 | O | B54 | F | LXXXIIIO-23 | A1 | O | B70 | F | LXXXIIIO-24 | A1 | O | B72 | F |
| LXXXIIIO-25 | A1 | S | H | F | LXXXIIIO-26 | A1 | S | B17 | F | LXXXIIIO-27 | A1 | S | B25 | F |
| LXXXIIIO-28 | A1 | S | B54 | F | LXXXIIIO-29 | A1 | S | B70 | F | LXXXIIIO-30 | A1 | S | B72 | F |
| LXXXIIIO-31 | A2 | O | B1 | H | LXXXIIIO-32 | A2 | O | B17 | H | LXXXIIIO-33 | A2 | O | B25 | H |
| LXXXIIIO-34 | A2 | O | B54 | H | LXXXIIIO-35 | A2 | O | B70 | H | LXXXIIIO-36 | A2 | O | B72 | H |
| LXXXIIIO-37 | A2 | S | B1 | H | LXXXIIIO-38 | A2 | S | B17 | H | LXXXIIIO-39 | A2 | S | B25 | H |
| LXXXIIIO-40 | A2 | S | B54 | H | LXXXIIIO-41 | A2 | S | B70 | H | LXXXIIIO-42 | A2 | S | B72 | H |
| LXXXIIIO-43 | A2 | O | B54 | F | LXXXIIIO-44 | A2 | O | B70 | F | LXXXIIIO-45 | A2 | O | B72 | F |
| LXXXIIIO-46 | A2 | S | B54 | F | LXXXIIIO-47 | A2 | S | B70 | F | LXXXIIIO-48 | A2 | S | B72 | F |
| LXXXIIIO-49 | A3 | O | B1 | H | LXXXIIIO-50 | A3 | O | B17 | H | LXXXIIIO-51 | A3 | O | B25 | H |
| LXXXIIIO-52 | A3 | O | B54 | H | LXXXIIIO-53 | A3 | O | B70 | H | LXXXIIIO-54 | A3 | O | B72 | H |
| LXXXIIIO-55 | A3 | S | B1 | H | LXXXIIIO-56 | A3 | S | B17 | H | LXXXIIIO-57 | A3 | S | B25 | H |
| LXXXIIIO-58 | A3 | S | B54 | H | LXXXIIIO-59 | A3 | S | B70 | H | LXXXIIIO-60 | A3 | S | B72 | H |
| LXXXIIIO-61 | A3 | O | B54 | F | LXXXIIIO-62 | A3 | O | B70 | F | LXXXIIIO-63 | A3 | O | B72 | F |
| LXXXIIIO-64 | A3 | S | B54 | F | LXXXIIIO-65 | A3 | S | B70 | F | LXXXIIIO-66 | A3 | S | B72 | F; | wherein Compound LXXXIIIA-1 to Compound LXXXIIIA-42 have a structure represented by Formula LXXXIIIA:

Formula LXXXIIIA

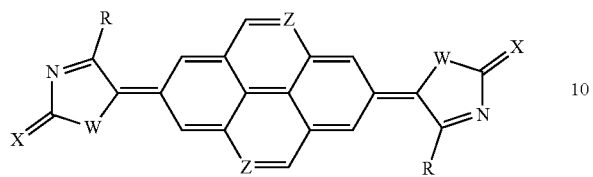

in Formula LXXXIIIA, two X are identical, two W are identical, two R are identical, two Z are identical and are $CR_L$, and X, W, R, and $R_L$ correspond to an atom or a group selected from the following table, respectively:

| NO. | X | W | R | $R_L$ | NO. | X | W | R | $R_L$ | NO. | X | W | R | $R_L$ |
|---|---|---|---|---|---|---|---|---|---|---|---|---|---|---|
| LXXXIIIA-1 | A1 | O | H | B6 | LXXXIIIA-2 | A1 | O | B17 | B6 | LXXXIIIA-3 | A1 | O | B25 | B6 |
| LXXXIIIA-4 | A1 | O | B54 | B6 | LXXXIIIA-5 | A1 | O | B70 | B6 | LXXXIIIA-6 | A1 | O | B72 | B6 |
| LXXXIIIA-7 | A1 | S | H | B6 | LXXXIIIA-8 | A1 | S | B17 | B6 | LXXXIIIA-9 | A1 | S | B25 | B6 |
| LXXXIIIA-10 | A1 | S | B54 | B6 | LXXXIIIA-11 | A1 | S | B70 | B6 | LXXXIIIA-12 | A1 | S | B72 | B6 |
| LXXXIIIA-13 | A1 | O | H | B70 | LXXXIIIA-14 | A1 | O | B17 | B70 | LXXXIIIA-15 | A1 | O | B25 | B70 |
| LXXXIIIA-16 | A1 | O | B54 | B70 | LXXXIIIA-17 | A1 | O | B70 | B70 | LXXXIIIA-18 | A1 | O | B72 | B70 |
| LXXXIIIA-19 | A1 | S | H | B70 | LXXXIIIA-20 | A1 | S | B17 | B70 | LXXXIIIA-21 | A1 | S | B25 | B70 |
| LXXXIIIA-22 | A1 | S | B54 | B70 | LXXXIIIA-23 | A1 | S | B70 | B70 | LXXXIIIA-24 | A1 | S | B72 | B70 |
| LXXXIIIA-25 | A2 | O | B54 | B6 | LXXXIIIA-26 | A2 | O | B70 | B6 | LXXXIIIA-27 | A2 | O | B72 | B6 |
| LXXXIIIA-28 | A2 | S | B54 | B6 | LXXXIIIA-29 | A2 | S | B70 | B6 | LXXXIIIA-30 | A2 | S | B72 | B6 |
| LXXXIIIA-31 | A2 | O | B54 | B70 | LXXXIIIA-32 | A2 | O | B70 | B70 | LXXXIIIA-33 | A2 | O | B72 | B70 |
| LXXXIIIA-34 | A3 | O | B54 | B6 | LXXXIIIA-35 | A3 | O | B70 | B6 | LXXXIIIA-36 | A3 | O | B72 | B6 |
| LXXXIIIA-37 | A3 | S | B54 | B6 | LXXXIIIA-38 | A3 | S | B70 | B6 | LXXXIIIA-39 | A3 | S | B72 | B6 |
| LXXXIIIA-40 | A3 | O | B54 | B70 | LXXXIIIA-41 | A3 | O | B70 | B70 | LXXXIIIA-42 | A3 | O | B72 | B70; | wherein Compound LXXXIVO-1 to Compound LXXXIVO-66 have a structure represented by Formula LXXXIVO:

Formula LXXXIVO

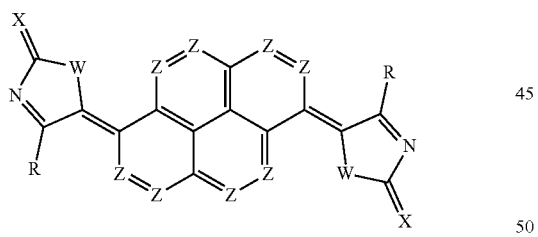

in Formula LXXXIVO, two X are identical, two W are identical, two R are identical, eight Z are identical and are $CR_L$, and X, W, R, and $R_L$ correspond to an atom or a group selected from the following table, respectively:

| NO. | X | W | R | $R_L$ | NO. | X | W | R | $R_L$ | NO. | X | W | R | $R_L$ |
|---|---|---|---|---|---|---|---|---|---|---|---|---|---|---|
| LXXXIVO-1 | A1 | O | B1 | H | LXXXIVO-2 | A1 | O | B17 | H | LXXXIVO-3 | A1 | O | B25 | H |
| LXXXIVO-4 | A1 | O | B54 | H | LXXXIVO-5 | A1 | O | B70 | H | LXXXIVO-6 | A1 | O | B72 | H |
| LXXXIVO-7 | A1 | S | B1 | H | LXXXIVO-8 | A1 | S | B17 | H | LXXXIVO-9 | A1 | S | B25 | H |
| LXXXIVO-10 | A1 | S | B54 | H | LXXXIVO-11 | A1 | S | B70 | H | LXXXIVO-12 | A1 | S | B72 | H |
| LXXXIVO-13 | A1 | Se | B54 | H | LXXXIVO-14 | A1 | Se | B70 | H | LXXXIVO-15 | A1 | Se | B72 | H |
| LXXXIVO-16 | A1 | NMe | B54 | H | LXXXIVO-17 | A1 | NMe | B70 | H | LXXXIVO-18 | A1 | NMe | B72 | H |
| LXXXIVO-19 | A1 | O | H | F | LXXXIVO-20 | A1 | O | B17 | F | LXXXIVO-21 | A1 | O | B25 | F |
| LXXXIVO-22 | A1 | O | B54 | F | LXXXIVO-23 | A1 | O | B70 | F | LXXXIVO-24 | A1 | O | B72 | F |
| LXXXIVO-25 | A1 | S | H | F | LXXXIVO-26 | A1 | S | B17 | F | LXXXIVO-27 | A1 | S | B25 | F |

-continued

| NO. | X | W | R | R$_L$ | NO. | X | W | R | R$_L$ | NO. | X | W | R | R$_L$ |
|---|---|---|---|---|---|---|---|---|---|---|---|---|---|---|
| LXXXIVO-28 | A1 | S | B54 | F | LXXXIVO-29 | A1 | S | B70 | F | LXXXIVO-30 | A1 | S | B72 | F |
| LXXXIVO-31 | A2 | O | B1 | H | LXXXIVO-32 | A2 | O | B17 | H | LXXXIVO-33 | A2 | O | B25 | H |
| LXXXIVO-34 | A2 | O | B54 | H | LXXXIVO-35 | A2 | O | B70 | H | LXXXIVO-36 | A2 | O | B72 | H |
| LXXXIVO-37 | A2 | S | B1 | H | LXXXIVO-38 | A2 | S | B17 | H | LXXXIVO-39 | A2 | S | B25 | H |
| LXXXIVO-40 | A2 | S | B54 | H | LXXXIVO-41 | A2 | S | B70 | H | LXXXIVO-42 | A2 | S | B72 | H |
| LXXXIVO-43 | A2 | O | B54 | F | LXXXIVO-44 | A2 | O | B70 | F | LXXXIVO-45 | A2 | O | B72 | F |
| LXXXIVO-46 | A2 | S | B54 | F | LXXXIVO-47 | A2 | S | B70 | F | LXXXIVO-48 | A2 | S | B72 | F |
| LXXXIVO-49 | A3 | O | B1 | H | LXXXIVO-50 | A3 | O | B17 | H | LXXXIVO-51 | A3 | O | B25 | H |
| LXXXIVO-52 | A3 | O | B54 | H | LXXXIVO-53 | A3 | O | B70 | H | LXXXIVO-54 | A3 | O | B72 | H |
| LXXXIVO-55 | A3 | S | B1 | H | LXXXIVO-56 | A3 | S | B17 | H | LXXXIVO-57 | A3 | S | B25 | H |
| LXXXIVO-58 | A3 | S | B54 | H | LXXXIVO-59 | A3 | S | B70 | H | LXXXIVO-60 | A3 | S | B72 | H |
| LXXXIVO-61 | A3 | O | B54 | F | LXXXIVO-62 | A3 | O | B70 | F | LXXXIVO-63 | A3 | O | B72 | F |
| LXXXIVO-64 | A3 | S | B54 | F | LXXXIVO-65 | A3 | S | B70 | F | LXXXIVO-66 | A3 | S | B72 | F; | wherein Compound LXXXIVA-1 to Compound LXXXIVA-42 have a structure represented by Formula LXXXVIA:

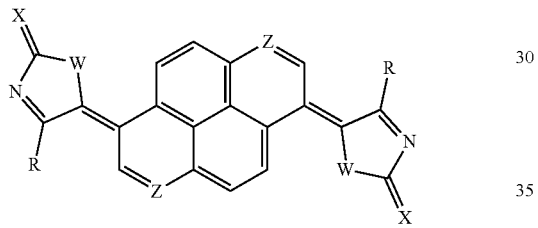

Formula LXXXIVA in Formula LXXXVIA, two X are identical, two W are identical, two R are identical, two Z are identical and are CR$_L$, and X, W, R, and R$_L$ correspond to an atom or a group selected from the following table, respectively:

| NO. | X | W | R | R$_L$ | NO. | X | W | R | R$_L$ | NO. | X | W | R | R$_L$ |
|---|---|---|---|---|---|---|---|---|---|---|---|---|---|---|
| LXXXIVA-1 | A1 | O | H | B6 | LXXXIVA-2 | A1 | O | B17 | B6 | LXXXIVA-3 | A1 | O | B25 | B6 |
| LXXXIVA-4 | A1 | O | B54 | B6 | LXXXIVA-5 | A1 | O | B70 | B6 | LXXXIVA-6 | A1 | O | B72 | B6 |
| LXXXIVA-7 | A1 | S | H | B6 | LXXXIVA-8 | A1 | S | B17 | B6 | LXXXIVA-9 | A1 | S | B25 | B6 |
| LXXXIVA-10 | A1 | S | B54 | B6 | LXXXIVA-11 | A1 | S | B70 | B6 | LXXXIVA-12 | A1 | S | B72 | B6 |
| LXXXIVA-13 | A1 | O | H | B70 | LXXXIVA-14 | A1 | O | B17 | B70 | LXXXIVA-15 | A1 | O | B25 | B70 |
| LXXXIVA-16 | A1 | O | B54 | B70 | LXXXIVA-17 | A1 | O | B70 | B70 | LXXXIVA-18 | A1 | O | B72 | B70 |
| LXXXIVA-19 | A1 | S | H | B70 | LXXXIVA-20 | A1 | S | B17 | B70 | LXXXIVA-21 | A1 | S | B25 | B70 |
| LXXXIVA-22 | A1 | S | B54 | B70 | LXXXIVA-23 | A1 | S | B70 | B70 | LXXXIVA-24 | A1 | S | B72 | B70 |
| LXXXIVA-25 | A2 | O | B54 | B6 | LXXXIVA-26 | A2 | O | B70 | B6 | LXXXIVA-27 | A2 | O | B72 | B6 |
| LXXXIVA-28 | A2 | S | B54 | B6 | LXXXIVA-29 | A2 | S | B70 | B6 | LXXXIVA-30 | A2 | S | B72 | B6 |
| LXXXIVA-31 | A2 | O | B54 | B70 | LXXXIVA-32 | A2 | O | B70 | B70 | LXXXIVA-33 | A2 | O | B72 | B70 |
| LXXXIVA-34 | A3 | O | B54 | B6 | LXXXIVA-35 | A3 | O | B70 | B6 | LXXXIVA-36 | A3 | O | B72 | B6 |
| LXXXIVA-37 | A3 | S | B54 | B6 | LXXXIVA-38 | A3 | S | B70 | B6 | LXXXIVA-39 | A3 | S | B72 | B6 |
| LXXXIVA-40 | A3 | O | B54 | B70 | LXXXIVA-41 | A3 | O | B70 | B70 | LXXXIVA-42 | A3 | O | B72 | B70; | wherein Compound LXXXVO-1 to Compound LXXXVO-66 have a structure represented by Formula LXXXVO:

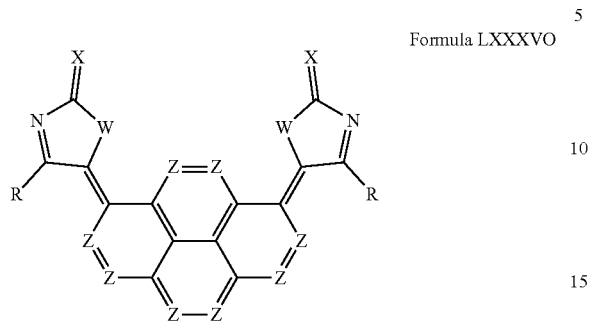

Formula LXXXVO in Formula LXXXVO, two X are identical, two W are identical, two R are identical, eight Z are identical and are $CR_L$, and X, W, R, and $R_L$ correspond to an atom or a group selected from the following table, respectively:

| NO. | X | W | R | $R_L$ | NO. | X | W | R | $R_L$ | NO. | X | W | R | $R_L$ |
|---|---|---|---|---|---|---|---|---|---|---|---|---|---|---|
| LXXXVO-1 | A1 | O | B1 | H | LXXXVO-2 | A1 | O | B17 | H | LXXXVO-3 | A1 | O | B25 | H |
| LXXXVO-4 | A1 | O | B54 | H | LXXXVO-5 | A1 | O | B70 | H | LXXXVO-6 | A1 | O | B72 | H |
| LXXXVO-7 | A1 | S | B1 | H | LXXXVO-8 | A1 | S | B17 | H | LXXXVO-9 | A1 | S | B25 | H |
| LXXXVO-10 | A1 | S | B54 | H | LXXXVO-11 | A1 | S | B70 | H | LXXXVO-12 | A1 | S | B72 | H |
| LXXXVO-13 | A1 | Se | B54 | H | LXXXVO-14 | A1 | Se | B70 | H | LXXXVO-15 | A1 | Se | B72 | H |
| LXXXVO-16 | A1 | NMe | B54 | H | LXXXVO-17 | A1 | NMe | B70 | H | LXXXVO-18 | A1 | NMe | B72 | H |
| LXXXVO-19 | A1 | O | H | F | LXXXVO-20 | A1 | O | B17 | F | LXXXVO-21 | A1 | O | B25 | F |
| LXXXVO-22 | A1 | O | B54 | F | LXXXVO-23 | A1 | O | B70 | F | LXXXVO-24 | A1 | O | B72 | F |
| LXXXVO-25 | A1 | S | H | F | LXXXVO-26 | A1 | S | B17 | F | LXXXVO-27 | A1 | S | B25 | F |
| LXXXVO-28 | A1 | S | B54 | F | LXXXVO-29 | A1 | S | B70 | F | LXXXVO-30 | A1 | S | B72 | F |
| LXXXVO-31 | A2 | O | B1 | H | LXXXVO-32 | A2 | O | B17 | H | LXXXVO-33 | A2 | O | B25 | H |
| LXXXVO-34 | A2 | O | B54 | H | LXXXVO-35 | A2 | O | B70 | H | LXXXVO-36 | A2 | O | B72 | H |
| LXXXVO-37 | A2 | S | B1 | H | LXXXVO-38 | A2 | S | B17 | H | LXXXVO-39 | A2 | S | B25 | H |
| LXXXVO-40 | A2 | S | B54 | H | LXXXVO-41 | A2 | S | B70 | H | LXXXVO-42 | A2 | S | B72 | H |
| LXXXVO-43 | A2 | O | B54 | F | LXXXVO-44 | A2 | O | B70 | F | LXXXVO-45 | A2 | O | B72 | F |
| LXXXVO-46 | A2 | S | B54 | F | LXXXVO-47 | A2 | S | B70 | F | LXXXVO-48 | A2 | S | B72 | F |
| LXXXVO-49 | A3 | O | B1 | H | LXXXVO-50 | A3 | O | B17 | H | LXXXVO-51 | A3 | O | B25 | H |
| LXXXVO-52 | A3 | O | B54 | H | LXXXVO-53 | A3 | O | B70 | H | LXXXVO-54 | A3 | O | B72 | H |
| LXXXVO-55 | A3 | S | B1 | H | LXXXVO-56 | A3 | S | B17 | H | LXXXVO-57 | A3 | S | B25 | H |
| LXXXVO-58 | A3 | S | B54 | H | LXXXVO-59 | A3 | S | B70 | H | LXXXVO-60 | A3 | S | B72 | H |
| LXXXVO-61 | A3 | O | B54 | F | LXXXVO-62 | A3 | O | B70 | F | LXXXVO-63 | A3 | O | B72 | F |
| LXXXVO-64 | A3 | S | B54 | F | LXXXVO-65 | A3 | S | B70 | F | LXXXVO-66 | A3 | S | B72 | F; | wherein Compound LXXXVA-1 to Compound LXXXVA-42 have a structure represented by Formula LXXXVA:

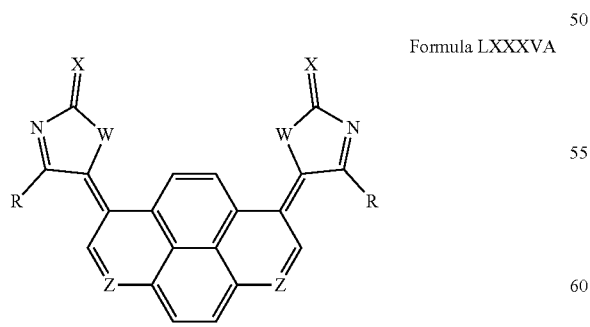

Formula LXXXVA in Formula LXXXVA, two X are identical, two W are identical, two R are identical, two Z are identical and are $CR_L$, and X, W, R, and $R_L$ correspond to an atom or a group selected from the following table, respectively:

| NO. | X | W | R | R$_L$ | NO. | X | W | R | R$_L$ | NO. | X | W | R | R$_L$ |
|---|---|---|---|---|---|---|---|---|---|---|---|---|---|---|
| LXXXVA-1 | A1 | O | H | B6 | LXXXVA-2 | A1 | O | B17 | B6 | LXXXVA-3 | A1 | O | B25 | B6 |
| LXXXVA-4 | A1 | O | B54 | B6 | LXXXVA-5 | A1 | O | B70 | B6 | LXXXVA-6 | A1 | O | B72 | B6 |
| LXXXVA-7 | A1 | S | H | B6 | LXXXVA-8 | A1 | S | B17 | B6 | LXXXVA-9 | A1 | S | B25 | B6 |
| LXXXVA-10 | A1 | S | B54 | B6 | LXXXVA-11 | A1 | S | B70 | B6 | LXXXVA-12 | A1 | S | B72 | B6 |
| LXXXVA-13 | A1 | O | H | B70 | LXXXVA-14 | A1 | O | B17 | B70 | LXXXVA-15 | A1 | O | B25 | B70 |
| LXXXVA-16 | A1 | O | B54 | B70 | LXXXVA-17 | A1 | O | B70 | B70 | LXXXVA-18 | A1 | O | B72 | B70 |
| LXXXVA-19 | A1 | S | H | B70 | LXXXVA-20 | A1 | S | B17 | B70 | LXXXVA-21 | A1 | S | B25 | B70 |
| LXXXVA-22 | A1 | S | B54 | B70 | LXXXVA-23 | A1 | S | B70 | B70 | LXXXVA-24 | A1 | S | B72 | B70 |
| LXXXVA-25 | A2 | O | B54 | B6 | LXXXVA-26 | A2 | O | B70 | B6 | LXXXVA-27 | A2 | O | B72 | B6 |
| LXXXVA-28 | A2 | S | B54 | B6 | LXXXVA-29 | A2 | S | B70 | B6 | LXXXVA-30 | A2 | S | B72 | B6 |
| LXXXVA-31 | A2 | O | B54 | B70 | LXXXVA-32 | A2 | O | B70 | B70 | LXXXVA-33 | A2 | O | B72 | B70 |
| LXXXVA-34 | A3 | O | B54 | B6 | LXXXVA-35 | A3 | O | B70 | B6 | LXXXVA-36 | A3 | O | B72 | B6 |
| LXXXVA-37 | A3 | S | B54 | B6 | LXXXVA-38 | A3 | S | B70 | B6 | LXXXVA-39 | A3 | S | B72 | B6 |
| LXXXVA-40 | A3 | O | B54 | B70 | LXXXVA-41 | A3 | O | B70 | B70 | LXXXVA-42 | A3 | O | B72 | B70; | wherein Compound LVI-IO-1 to Compound LVI-IO-138 have a structure represented by Formula LVI-IO:

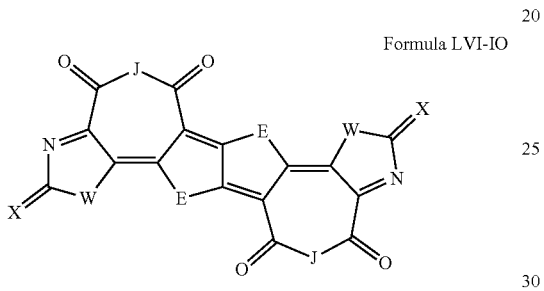

Formula LVI-IO in Formula LVI-IO, two X are identical, two W are identical, two E are identical, two J are identical and are NR$_{NJ}$, and X, W, E, and R$_{NJ}$ correspond to an atom or a group selected from the following table, respectively:

| NO. | X | W | R$_{NJ}$ | E | NO. | X | W | R$_{NJ}$ | E | NO. | X | W | R$_{NJ}$ | E |
|---|---|---|---|---|---|---|---|---|---|---|---|---|---|---|
| LVI-IO-1 | A1 | O | B14 | O | LVI-IO-2 | A1 | O | B16 | O | LVI-IO-3 | A1 | O | H18 | O |
| LVI-IO-4 | A1 | O | B25 | O | LVI-IO-5 | A1 | O | B57 | O | LVI-IO-6 | A1 | O | B58 | O |
| LVI-IO-7 | A1 | O | B70 | O | LVI-IO-8 | A1 | O | B72 | O | LVI-IO-9 | A1 | O | B117 | O |
| LVI-IO-10 | A1 | S | B14 | O | LVI-IO-11 | A1 | S | B16 | O | LVI-IO-12 | A1 | S | B18 | O |
| LVI-IO-13 | A1 | S | B25 | O | LVI-IO-14 | A1 | S | B57 | O | LVI-IO-15 | A1 | S | B58 | O |
| LVI-IO-16 | A1 | S | B70 | O | LVI-IO-17 | A1 | S | B72 | O | LVI-IO-18 | A1 | S | B117 | O |
| LVI-IO-19 | A1 | Se | B25 | O | LVI-IO-20 | A1 | Se | B57 | O | LVI-IO-21 | A1 | Se | B58 | O |
| LVI-IO-22 | A1 | Se | B70 | O | LVI-IO-23 | A1 | Se | B72 | O | LVI-IO-24 | A1 | Se | B117 | O |
| LVI-IO-25 | A2 | O | B14 | O | LVI-IO-26 | A2 | O | B16 | O | LVI-IO-27 | A2 | O | B18 | O |
| LVI-IO-28 | A2 | O | B25 | O | LVI-IO-29 | A2 | O | B57 | O | LVI-IO-30 | A2 | O | B58 | O |
| LVI-IO-31 | A2 | O | B70 | O | LVI-IO-32 | A2 | O | B72 | O | LVI-IO-33 | A2 | O | B117 | O |
| LVI-IO-34 | A2 | S | B25 | O | LVI-IO-35 | A2 | S | B57 | O | LVI-IO-36 | A2 | S | B58 | O |
| LVI-IO-37 | A2 | S | B70 | O | LVI-IO-38 | A2 | S | B72 | O | LVI-IO-39 | A2 | S | B117 | O |
| LVI-IO-40 | A2 | Se | B25 | O | LVI-IO-41 | A2 | Se | B57 | O | LVI-IO-42 | A2 | Se | B58 | O |
| LVI-IO-43 | A3 | O | B14 | O | LVI-IO-44 | A3 | O | B16 | O | LVI-IO-45 | A3 | O | B18 | O |
| LVI-IO-46 | A3 | O | B25 | O | LVI-IO-47 | A3 | O | B57 | O | LVI-IO-48 | A3 | O | B58 | O |
| LVI-IO-49 | A3 | O | B70 | O | LVI-IO-50 | A3 | O | B72 | O | LVI-IO-51 | A3 | O | B117 | O |
| LVI-IO-52 | A3 | S | B25 | O | LVI-IO-53 | A3 | S | B57 | O | LVI-IO-54 | A3 | S | B58 | O |
| LVI-IO-55 | A3 | S | B70 | O | LVI-IO-56 | A3 | S | B72 | O | LVI-IO-57 | A3 | S | B117 | O |
| LVI-IO-58 | A3 | Se | B25 | O | LVI-IO-59 | A3 | Se | B57 | O | LVI-IO-60 | A3 | Se | B58 | O |
| LVI-IO-61 | A1 | O | B14 | S | LVI-IO-62 | A1 | O | B16 | S | LVI-IO-63 | A1 | O | B18 | S |
| LVI-IO-64 | A1 | O | B25 | S | LVI-IO-65 | A1 | O | B57 | S | LVI-IO-66 | A1 | O | B58 | S |
| LVI-IO-67 | A1 | O | B70 | S | LVI-IO-68 | A1 | O | B72 | S | LVI-IO-69 | A1 | O | B117 | S |
| LVI-IO-70 | A1 | S | B14 | S | LVI-IO-71 | A1 | S | B16 | S | LVI-IO-72 | A1 | S | B1 | S |
| LVI-IO-73 | A1 | S | B25 | S | LVI-IO-74 | A1 | S | B57 | S | LVI-IO-75 | A1 | S | B58 | S |
| LVI-IO-76 | A1 | S | B70 | S | LVI-IO-77 | A1 | S | B72 | S | LVI-IO-78 | A1 | S | B117 | S |
| LVI-IO-79 | A1 | Se | B25 | S | LVI-IO-80 | A1 | Se | B57 | S | LVI-IO-81 | A1 | Se | B58 | S |
| LVI-IO-82 | A1 | Se | B70 | S | LVI-IO-83 | A1 | Se | B72 | S | LVI-IO-84 | A1 | Se | B117 | S |
| LVI-IO-85 | A2 | O | B14 | S | LVI-IO-86 | A2 | O | B16 | S | LVI-IO-87 | A2 | O | B18 | S |
| LVI-IO-88 | A2 | O | B25 | S | LVI-IO-89 | A2 | O | B57 | S | LVI-IO-90 | A2 | O | B58 | S |
| LVI-IO-91 | A2 | O | B70 | S | LVI-IO-92 | A2 | O | B72 | S | LVI-IO-93 | A2 | O | B117 | S |
| LVI-IO-94 | A2 | S | B25 | S | LVI-IO-95 | A2 | S | B57 | S | LVI-IO-96 | A2 | S | B58 | S |
| LVI-IO-97 | A2 | S | B70 | S | LVI-IO-98 | A2 | S | B72 | S | LVI-IO-99 | A2 | S | B117 | S |
| LVI-IO-100 | A2 | Se | B25 | S | LVI-IO-101 | A2 | Se | B57 | S | LVI-IO-102 | A2 | Se | B58 | S |
| LVI-IO-103 | A3 | O | B14 | S | LVI-IO-104 | A3 | O | B16 | S | LVI-IO-105 | A3 | O | B18 | S |

-continued

| NO. | X | W | $R_{NJ}$ | E | NO. | X | W | $R_{NJ}$ | E | NO. | X | W | $R_{NJ}$ | E |
|---|---|---|---|---|---|---|---|---|---|---|---|---|---|---|
| LVI-IO-106 | A3 | O | B25 | S | LVI-IO-107 | A3 | O | B57 | S | LVI-IO-108 | A3 | O | B58 | S |
| LVI-IO-109 | A3 | O | B70 | S | LVI-IO-110 | A3 | O | B72 | S | LVI-IO-111 | A3 | O | B117 | S |
| LVI-IO-112 | A3 | S | B25 | S | LVI-IO-113 | A3 | S | B57 | S | LVI-IO-114 | A3 | S | B58 | S |
| LVI-IO-115 | A3 | S | B70 | S | LVI-IO-116 | A3 | S | B72 | S | LVI-IO-117 | A3 | S | B117 | S |
| LVI-IO-118 | A3 | Se | B25 | S | LVI-IO-119 | A3 | Se | B57 | S | LVI-IO-120 | A3 | Se | B58 | S |
| LVI-IO-121 | A1 | O | B14 | Se | LVI-IO-122 | A1 | O | B16 | Se | LVI-IO-123 | A1 | O | B18 | Se |
| LVI-IO-124 | A1 | O | B25 | Se | LVI-IO-125 | A1 | O | B57 | Se | LVI-IO-126 | A1 | O | B58 | Se |
| LVI-IO-127 | A1 | O | B70 | Se | LVI-IO-128 | A1 | O | B72 | Se | LVI-IO-129 | A1 | O | B117 | Se |
| LVI-IO-130 | A1 | S | B14 | Se | LVI-IO-131 | A1 | S | B16 | Se | LVI-IO-132 | A1 | S | B18 | Se |
| LVI-IO-133 | A1 | S | B25 | Se | LVI-IO-134 | A1 | S | B57 | Se | LVI-IO-135 | A1 | S | B58 | Se |
| LVI-IO-136 | A1 | S | B70 | Se | LVI-IO-137 | A1 | S | B72 | Se | LVI-IO-138 | A1 | S | B117 | Se; | wherein Compound LXVI-IO-1 to Compound LXVI-IO-60 have a structure represented by Formula LXVI-IO:

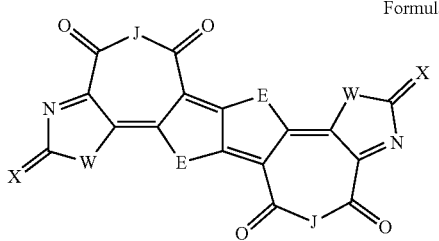

Formula LVI-IO in Formula LXVI-IO, two X are identical, two W are identical, two E are identical, two J are identical and are $NR_{NJ}$, and X, W, E, and $R_{NJ}$ correspond to an atom or a group selected from the following table, respectively:

| NO. | X | W | $R_{NJ}$ | NO. | X | W | $R_{NJ}$ | NO. | X | W | $R_{NJ}$ |
|---|---|---|---|---|---|---|---|---|---|---|---|
| LXVI-IO-1 | A1 | O | B14 | LXVI-IO-2 | A1 | O | B16 | LXVI-IO-3 | A1 | O | B18 |
| LXVI-IO-4 | A1 | O | B25 | LXVI-IO-5 | A1 | O | B57 | LXVI-IO-6 | A1 | O | B58 |
| LXVI-IO-7 | A1 | O | B70 | LXVI-IO-8 | A1 | O | B72 | LXVI-IO-9 | A1 | O | B117 |
| LXVI-IO-10 | A1 | S | B14 | LXVI-IO-11 | A1 | S | B16 | LXVI-IO-12 | A1 | S | B18 |
| LXVI-IO-13 | A1 | S | B25 | LXVI-IO-14 | A1 | S | B57 | LXVI-IO-15 | A1 | S | B58 |
| LXVI-IO-16 | A1 | S | B70 | LXVI-IO-17 | A1 | S | B72 | LXVI-IO-18 | A1 | S | B117 |
| LXVI-IO-19 | A1 | Se | B25 | LXVI-IO-20 | A1 | Se | B57 | LXVI-IO-21 | A1 | Se | B58 |
| LXVI-IO-22 | A1 | Se | B70 | LXVI-IO-23 | A1 | Se | B72 | LXVI-IO-24 | A1 | Se | B117 |
| LXVI-IO-25 | A2 | O | B14 | LXVI-IO-26 | A2 | O | B16 | LXVI-IO-27 | A2 | O | B18 |
| LXVI-IO-28 | A2 | O | B25 | LXVI-IO-29 | A2 | O | B57 | LXVI-IO-30 | A2 | O | B58 |
| LXVI-IO-31 | A2 | O | B70 | LXVI-IO-32 | A2 | O | B72 | LXVI-IO-33 | A2 | O | B117 |
| LXVI-IO-34 | A2 | S | B25 | LXVI-IO-35 | A2 | S | B57 | LXVI-IO-36 | A2 | S | B58 |
| LXVI-IO-37 | A2 | S | B70 | LXVI-IO-38 | A2 | S | B72 | LXVI-IO-39 | A2 | S | B117 |
| LXVI-IO-40 | A2 | Se | B25 | LXVI-IO-41 | A2 | Se | B57 | LXVI-IO-42 | A2 | Se | B58 |
| LXVI-IO-43 | A3 | O | B14 | LXVI-IO-44 | A3 | O | B16 | LXVI-IO-45 | A3 | O | B18 |
| LXVI-IO-46 | A3 | O | B25 | LXVI-IO-47 | A3 | O | B57 | LXVI-IO-48 | A3 | O | B58 |
| LXVI-IO-49 | A3 | O | B70 | LXVI-IO-50 | A3 | O | B72 | LXVI-IO-51 | A3 | O | B117 |
| LXVI-IO-52 | A3 | S | B25 | LXVI-IO-53 | A3 | S | B57 | LXVI-IO-54 | A3 | S | B58 |
| LXVI-IO-55 | A3 | S | B70 | LXVI-IO-56 | A3 | S | B72 | LXVI-IO-57 | A3 | S | B117 |
| LXVI-IO-58 | A3 | Se | B25 | LXVI-IO-59 | A3 | Se | B57 | LXVI-IO-60 | A3 | Se | B58. |

17. An electroluminescent device, comprising:
an anode,
a cathode, and
an organic layer disposed between the anode and the cathode, wherein the organic layer comprises the compound according to claim 1.

18. The electroluminescent device according to claim 17, wherein the organic layer is a hole injection layer or a hole transporting layer, and the hole injection layer or the hole transporting layer is formed by the compound alone;
or the hole injection layer or the hole transporting layer further comprises at least one hole transporting material; wherein the molar doping ratio of the compound to the hole transporting material ranges from 10000:1 to 1:10000; and preferably, the molar ratio of the compound to the hole transporting material ranges from 10:1 to 1:100.

19. The electroluminescent device according to claim 17, wherein the electroluminescent device comprises a plurality of stack layers between the anode and the cathode, and the plurality of stack layers comprise a first emissive layer and a second emissive layer, wherein a first stack layer comprises the first emissive layer, a second stack layer comprises the second emissive layer, and a charge generation layer is disposed between the first stack layer and the second stack layer, wherein the charge generation layer comprises a p-type charge generation layer and an n-type charge generation layer; wherein the p-type charge generation layer comprises the compound;

preferably, the p-type charge generation layer further comprises at least one hole transporting material, wherein the molar doping ratio of the compound to the hole transporting material ranges from 10000:1 to 1:10000;

preferably, wherein the molar doping ratio of the compound to the hole transporting material ranges from 10:1 to 1:100.

20. The electroluminescent device according to claim 19, wherein the hole transporting material comprises a compound having a triarylamine unit, a spirobifluorene compound, a pentacene compound, an oligothiophene compound, an oligomeric phenyl compound, an oligomeric phenylenevinylene compound, an oligomeric fluorene compound, a porphyrin complex or a metal phthalocyanine complex.

21. The electroluminescent device according to claim 20, wherein the charge generation layer further comprises a buffer layer disposed between the p-type charge generation layer and the N-type charge generation layer, and the buffer layer comprises the compound.

22. A compound composition, comprising the compound according to claim 1.

* * * * *